United States Patent
Williams et al.

(10) Patent No.: US 9,562,031 B1
(45) Date of Patent: Feb. 7, 2017

(54) PHENETHYLDIHYDROBENZODIOXOLONES AND METHODS OF USE

(71) Applicant: Sequoia Sciences, Inc., St. Louis, MO (US)

(72) Inventors: Russell B Williams, St. Louis, MO (US); Gary Eldridge, St. Louis, MO (US); Courtney M. Starks, St. Louis, MO (US); Peter Robert Guzzo, Niskayuna, NY (US); Zhongping Huang, Voorheesville, NY (US)

(73) Assignee: Sequoia Sciences, Inc., St. Louis, MO (US)

( * ) Notice: Subject to any disclaimer, the term of this patent is extended or adjusted under 35 U.S.C. 154(b) by 0 days.

(21) Appl. No.: 14/852,524

(22) Filed: Sep. 12, 2015

(51) Int. Cl.
| | | |
|---|---|---|
| *A61K 31/44* | (2006.01) | |
| *C07D 317/46* | (2006.01) | |
| *C07D 405/12* | (2006.01) | |
| *C07D 405/06* | (2006.01) | |

(52) U.S. Cl.
CPC .......... *C07D 317/46* (2013.01); *C07D 405/06* (2013.01); *C07D 405/12* (2013.01)

(58) Field of Classification Search
None
See application file for complete search history.

(56) References Cited

PUBLICATIONS

Drewes, S. et al. Phytochemistry 1997, vol. 44, pp. 437-440.*
Siegfried E. Drewes, et al., Iso-ocobullenone and a neolignan ketone from Ocotea bullata bark, Phytochemistry, 1995, 1505-1508, 38, 6.
Siegfried E. Drewes, et al., Cryptocarya liebertiana and Ocotea bullata—Their phytochemical relationship, Phytochemistry, 1997, 437-440, 44, 3.
Sibylle Zschocke, et al., Stereostructure and anti-inflammatory activity of three diastereomers of ocobullenone from Ocotea bullata, Phytochemistry, 2000, 591-595, 54.
Ericsson David Coy, et al., COX, LOX and platelet aggregation inhibitory properties of Lauraceae neolignans, Bioorganic & Medicinal Chemistry Letters, 2009, 6922-6925, 19.
L. Harinantenaina Rakotondraibe, et al., Neolignans and other metabolites from Ocotea cymosa from the Madagascar rain forest and thier biological activities, Journal of Natural Products, 2015, 431-440, 78.
Kuete et al., Cytotoxicity and modes of action of five Cameroonian medicinal plants against multi-factorial drug resistance of tumor cells, Journal of Ethnopharmacology, 2014, 153, 207-219.
Chen et al., New Cytotoxic tetrahydrofuran- and Dihydrofuran- type lignans from the stem of Beilschmiedia tsangii, Planta Med 2006, 72, 351-357.
Office Action of U.S. Appl. No. 14/851,624 dated May 5, 2016.

* cited by examiner

*Primary Examiner* — Heidi Reese
(74) *Attorney, Agent, or Firm* — Christopher Casieri

(57) ABSTRACT

The present invention generally relates to phenethyldihydrobenzodioxolone compounds and compositions useful for reducing or inhibiting tumor growth. It also relates to methods of use and the preparation of phenethyldihydrobenzodioxolone compounds.

43 Claims, No Drawings

PHENETHYLDIHYDROBENZODIOXOLONES AND METHODS OF USE

BACKGROUND OF THE INVENTION

Field of the Invention

The present invention generally relates to phenethyldihydrobenzodioxolone compounds and compositions useful for reducing or inhibiting tumor growth. It also relates to methods of use and the preparation of phenethyldihydrobenzodioxolone compounds.

Description of the Related Art

Medicines used by oncologists to treat the majority of solid tumors and various other cancers have not significantly changed in the last twenty years. In fact, nitrogen mustards, antifolates, platinums, nucleoside analogues, taxanes, and anthracyclines are all still first-line or primary therapies despite record increases in R&D spending by the NIH and the pharmaceutical industry. Furthermore, large scale genomics efforts have yielded results that have contradicted expectations of a future full of targeted therapies. For the majority of solid tumors, targeted therapies must still be given along with more traditional non-selective chemotherapies. Thus, there is a need for new chemotherapeutic agents for use as both monotherapies and for combination with new targeted therapies.

The taxanes and vinca alkaloids are first-line chemotherapies that have robustly proven the superior benefits of inhibiting microtubules for increasing overall survival of patients with advanced stage cancer. Newer microtubule inhibitors have further demonstrated the clinical superiority of microtubule inhibitors in breast, prostate, and ovarian cancers and lymphoma. Microtubule inhibitors have withstood dozens of head to head competitive clinical trials unequivocally demonstrating that this is a preferred mechanism of action for antitumor agents.

The identification of a new microtubule inhibitor, bifidenone, is reported in patent application Ser. No. 14/851,624, filed Sep. 11, 2015, entitled "Bifidenone Compositions and Methods of Use" incorporated herein in its entirety. Bifidenone has a phenethyldihydrobenzodioxolone ("7,7a-dihydro-7a-phenethylbenzo[d][1,3]dioxol-5(6H)-one") scaffold and inhibits tubulin polymerization. The present invention provides analogues of phenethyldihydrobenzodioxolone compounds.

BRIEF SUMMARY OF INVENTION

The phenethyldihydrobenzodioxolone compounds of the invention have the following chemical scaffold 7,7a-dihydro-7a-phenethylbenzo[d][1,3]dioxol-5(6H)-one.

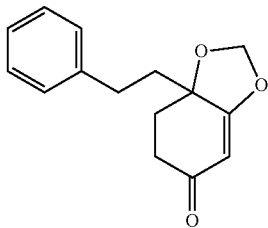

The present invention provides phenethyldihydrobenzodioxolone compounds of the following formula (I)

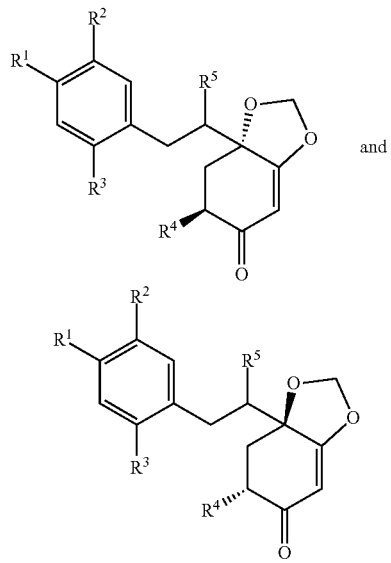

or stereoisomers thereof, wherein $R^1$ is selected from the group consisting of methoxy, ethoxy, —$SCH_3$, —$SCH_2CH_3$, and —$NR^8R^9$; $R^2$ is selected from the group consisting of hydrogen, hydroxyl, alkoxy, amino, aminoalkyl, aminoalkenyl, aminoalkynyl, halide, haloalkyl, hydroxyalkyl, —NHCN, aminocarbonyl, hydroxyaminocarbonyl, alkylaminocarbonyl, acyloxy, nitrile, —$CH_2CN$, lower alkyl, substituted lower alkyl, lower alkenyl, lower alkynyl, —SH, —$SCH_3$, alkoxycarbonyl, alkylcarbonylamino, —NHC(O)—O-lower alkyl, —NHC(O)—O-lower alkenyl, —NHC(O)—O-lower alkynyl, —NHCO-cyclopropyl, —NHCO-haloalkyl, —$NHSO_2CH_3$, —$NHCSNHCH_3$, —$SO_2NH_2$, sulfoximine, —CH=NOH, —$SOCH_3$, —$SO_2CH_3$, —$NHSO_2CH_3$, and —$SO_2NH_2$; $R^3$ is selected from the group consisting of hydrogen, halide, haloalkyl, hydroxyl, amino, methylamino, —$CH_2OH$, methoxy, lower alkyl, lower alkenyl, lower alkynyl, acyloxy, alkylcarbonylamino, —$C(O)OCH_3$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkoxy, alkoxyalkyl, alkoxyalkenyl, alkoxyalkynyl, alkyl ether, alkylthio, alkenylthio, alkynylthio, thioalkyl ether, —$(CH_2)_m$-A, and $C_2$-$C_3$ alkenyl-A; $R^5$ is selected from the group consisting of lower alkyl, lower alkenyl, and haloalkyl; $R^8$ and $R^9$ are independently selected from the group consisting of hydrogen, lower alkyl, substituted lower alkyl, lower alkenyl, substituted lower alkenyl, and cycloalkyl; A is selected from the group consisting of cycloalkyl, cycloalkenyl, heteroaryl, heterocycloalkyl, phenyl, and substituted phenyl, and m is selected from the group consisting of 0, 1, 2, and 3; provided that $R^2$ is not methoxy when $R^1$ is methoxy, $R^3$ is hydrogen, and $R^4$ is 2-propenyl.

Another embodiment of the present invention provides compounds of formula (I), provided that $R^2$ is not hydrogen, hydroxyl, or methoxy when $R^1$ is methoxy, $R^3$ is hydrogen, and $R^4$ is 2-propenyl, propyl, ethyl, or butyl.

Another embodiment of the present invention provides compounds of formula (I), provided that $R^3$ is not hydroxyl or methoxy, when $R^1$ is methoxy, and $R^4$ is 2-propenyl, propyl, ethyl, or butyl.

Another embodiment of the present invention provides compounds of formula (I), provided that $R^2$ is not methoxy when $R^1$ is methoxy and $R^3$ is hydrogen.

Another embodiment of the present invention provides compounds that are the enantiomers of formula (I), or even more particularly the (+)-enantiomers of formula (I).

Compositions containing the compounds described above and a pharmaceutically acceptable carrier are also contemplated by this invention. As demonstrated herein such compositions are useful in reducing or inhibiting tumor growth or for the treatment of cancer.

The compounds, chemical structures, or formulae referred to herein exhibit stereoisomerism, in which such compounds may adopt an R or S configuration at chiral centers. Thus, whether or not the stereochemical configuration is indicated in a particular example, this invention also encompasses any stereoisomeric form, their corresponding enantiomers ((+) and (−) isomers) and diastereomers thereof, and mixtures thereof, and is not limited to any one stereoisomeric form, although some stereoisomeric forms are preferred as indicated herein. The methods for the determination of stereochemistry and the separation of stereoisomers are well-known to those skilled in the art.

In another aspect of the invention, methods of administration for reducing or inhibiting tumor growth comprising contacting the tissue or cell capable of tumor formation with an effective amount of a composition or a compound described above are provided.

In another aspect of the invention, this invention also provides for novel compositions or novel formulations of the compounds of the invention and for methods of administration of these compositions and formulations for reducing or inhibiting tumor growth comprising contacting the tissue or cell capable of tumor formation with an effective amount of a composition or a compound described herein.

In another aspect of the invention, compounds described herein are useful in combination with known anticancer, antitumor, and cytotoxic agents and treatments, including radiation. A preferred combination is with platinum-based anticancer agents.

In another aspect of the invention, novel compounds or intermediates produced during the synthesis of the compounds of the invention are described.

In another aspect of the invention, novel synthetic procedures or processes to produce novel synthetic intermediates are described for the preparation of the compounds of the invention.

In another aspect of the invention, novel synthetic procedures or processes to produce the compounds of the invention are described.

In another aspect, the present invention provides compositions comprising the compounds of the invention covalently attached to a linker compound that is covalently attached to a small molecule, protein, or antibody and a pharmaceutically acceptable carrier or vehicle. The small molecule, protein, or antibody may be conjugated directly to the compounds of the invention, but more preferably by the means of a linker.

Another aspect of this invention relates to methods of administering the compounds of the invention for the treatment of inflammatory disorders such as gout and other related disorders including but not limited to inflammatory arthritis.

In another aspect of the invention, methods of seed, seedling, or plant treatment with the compounds of the invention are provided that produce new varieties with or advantageous or desirable characteristics.

DETAILED DESCRIPTION OF THE INVENTION

The phenethyldihydrobenzodioxolone compounds of the invention have the following chemical scaffold 7,7a-dihydro-7a-phenethylbenzo[d][1,3]dioxol-5(6H)-one.

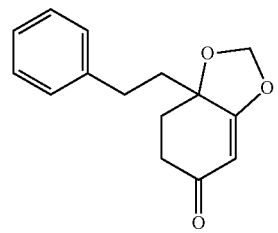 [SMILES: O=C1C=C2OCOC2(CCc2ccccc2)CC1]

The compounds of the present invention are depicted throughout by a drawing of the structure or formula. As indicated, the compounds, chemical structures, or formulae referred to herein exhibit stereoisomerism, in which such compounds may adopt an R or S configuration at chiral centers. Thus, this invention also encompasses any stereoisomeric form, their corresponding enantiomers ((+) and (−) isomers) and diastereomers thereof, and mixtures thereof. However, structures are drawn herein to show relative stereochemistry, and no representation is made to the absolute configuration that corresponds to the (+) or (−) enantiomer unless otherwise indicated.

Accordingly, the formula of the compounds of the invention may be depicted in a variety of ways and still encompass multiple stereoisomeric forms. For one example (although the following description applies to any formula unless otherwise noted), the present invention provides compounds of the formula (II)

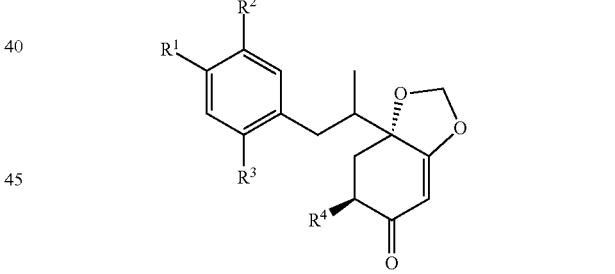

(II)

Formula (II), and all other related compounds described herein and other formula, encompass both of the following diastereomers as detailed in the Examples herein and shown below:

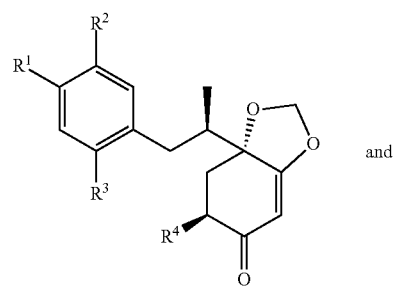

and

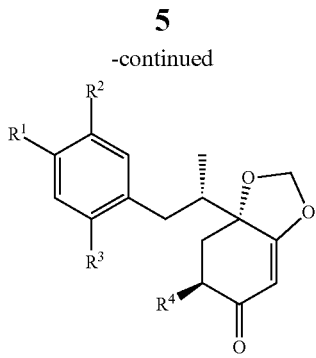

5

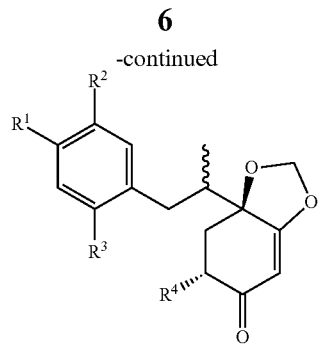

6

Alternatively, the pair of diasteromers may also be depicted as the following:

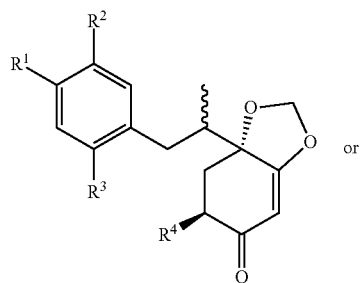

or

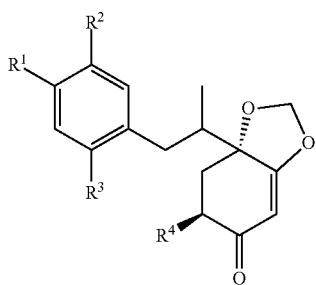

Furthermore and as described herein, the configuration of the stereogenic centers of the compounds of the invention is relative, so the invention (e.g. the compounds of formula (II) or other formula described herein) encompasses the following stereochemical configurations (i.e. enantiomers),

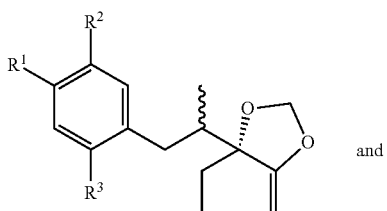

and

Bioavailability and Structure-Activity Relationship

Multiple series of phenethyldihydrobenzodioxolone analogues were synthesized to search for more potent analogues with good bioavailability, and to determine the structure-activity relationship. Analogues were initially screened in antiproliferation assays against M14 and NCI-H460 cancer cells; selected analogues were screened against additional cell lines. Selected active analogues are shown in EXAMPLE II.

The antiproliferative activity of phenethyldihydrobenzodioxolones tolerated a variety of substitutions on the aromatic ring (Table 3-Table 8), and was enhanced by certain specific substitutions. Substitution of a fluorine at the ortho position (for example, compound 2) enhanced antiproliferation activity and maintained plasma bioavailability. Several analogues of compound 2 with the general formula

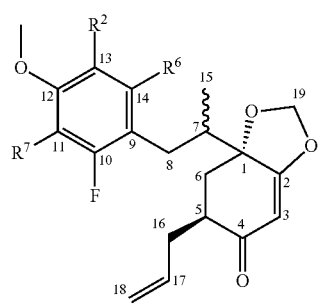

were synthesized (Table 2). Certain substitutions at $R^2$ (e.g. phenyl, tetrazole) abolished antiproliferative activity while other substitutions at $R^2$ maintained or enhanced activity (e.g. amino, aminocarbonyl, nitrile, hydroxyl).

All eight possible stereoisomers of compound 4 were synthesized, and their antiproliferation activity is summarized in Table 1. Structures in Table 1 indicate relative configuration. The sign of optical rotation is listed in the table.

TABLE 1

Stereoisomers of compound 4. Relative configurations are drawn.

| Structure | Compound | Sign of $\alpha_D$ (+ or −) | IC$_{50}$ NCI-H460 (μM) |
|---|---|---|---|
| 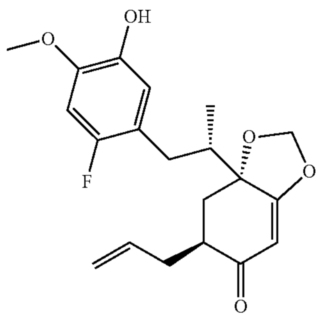 [SMILES: C=CC[C@H]1C[C@]2([C@@H](C)Cc3cc(O)c(OC)cc3F)OCOC2=CC1=O] | 5 | + | 0.033 |
| 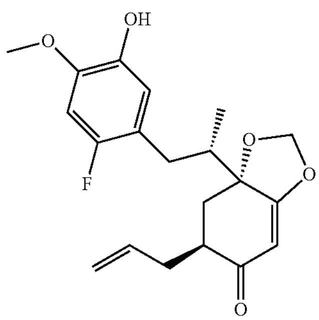 [SMILES: C=CC[C@H]1C[C@]2([C@@H](C)Cc3cc(O)c(OC)cc3F)OCOC2=CC1=O] | SQ 1371 | − | 2.5 |
| 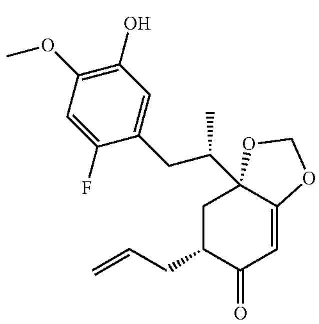 [SMILES: C=CC[C@@H]1C[C@]2([C@@H](C)Cc3cc(O)c(OC)cc3F)OCOC2=CC1=O] | SQ 1389 | + | 2.5 |
| 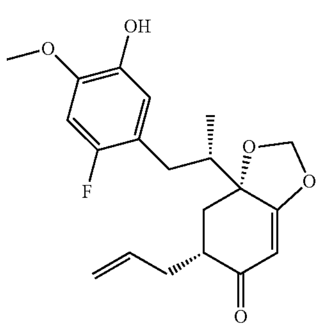 [SMILES: C=CC[C@@H]1C[C@]2([C@@H](C)Cc3cc(O)c(OC)cc3F)OCOC2=CC1=O] | SQ 1375 | − | 2.5 |
| | 4 | + | 0.015 |
| | SQ 1372 | − | 1.9 |
| | SQ 1378 | + | 1.9 |
| | SQ 1400 | − | 2.5 |

Several analogues of the general formula,

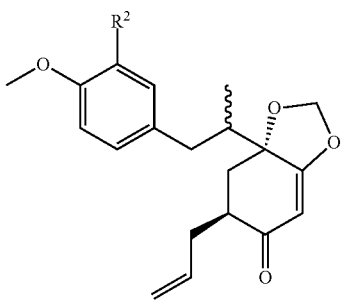

which is without the ortho fluorine were also prepared (Table 4). Certain substitutions at $R^2$ abolished antiproliferative activity (e.g. acetyl, piperidine), while other substitutions at $R^2$ maintained or enhanced activity (e.g. H, fluorine, amino, aminocarbonyl, nitrile, hydroxyl, acetoxy).

Effects of substitution at the para position were investigated by making a series of para position analogues in the absence or presence of fluorines at $R^2$ and $R^3$ in the general formula (Table 5):

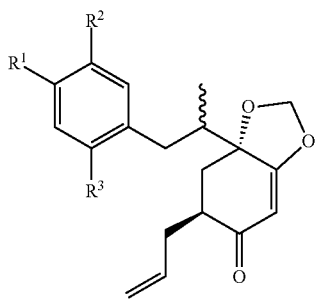

In the absence of fluorines, some para ($R^1$) substituents maintain antiproliferation activity (e.g. ethoxy) while others abolish activity (e.g. acetate, hydroxy). In the presence of fluorine at $R^2$ and or $R^3$, however, the para position appears to tolerate more varied substitution. For example, amines and alkylamines are tolerated.

The antiproliferative activity of phenethyldihydrobenzodioxolone compounds tolerated replacement of the phenyl ring with certain heterocycles and bicyclic systems (Table 8). Additional analogues with different aromatic substitutions were made and are shown in the Examples. Several of these were active, including analogues with chlorine or acetate groups at the ortho position.

While the relative configuration at $R^4$ is important for activity (Table 1), a variety of chemical substituents are tolerated at $R^4$ (Table 7). Tolerated substituents include straight and branched alkanes and alkenes as well as halogen-containing groups and chains with cyclic or aromatic substituents.

The antiproliferative activity of phenethyldihydrobenzodioxolone compounds was diminished somewhat by adding methyl groups to C-15, C-3, or C-19 (Table 8).

The compounds described herein interact with microtubules. They are thus useful in the treatment of a variety of cancers or other abnormal proliferative diseases, including (but not limited to) carcinoma, hematopoietic tumors, and other tumors. Not to be bound by theory, the compounds described herein interact with the colchicine-binding site of tubulin. Such properties may be useful in the treatment of human diseases including gout and familial Mediterranean fever. Compounds described herein may also inhibit tumor angiogenesis. Such anti-angiogenesis properties may be useful in the treatment of certain forms of blindness related to retinal vascularization, arthritis, multiple sclerosis, restenosis, and psoriasis. Compounds described herein may induce apoptosis. Such apoptosis-inducing properties may be useful in the treatment of human diseases with aberrations in apoptosis including (but not limited to) cancer, viral infections, autoimmune diseases, neurodegenerative disorders, and hematological diseases.

Definitions

"Acceptable carrier" refers to a carrier that is not deleterious to the other ingredients of the composition and is not deleterious to material to which it is to be applied.

"Administration" refers to any means of providing a compound or composition to a subject. Non-limiting examples of administration means include oral, topical, rectal, percutaneous, parenteral injection, intravenous, intravenous infusion, intranasal and inhalation delivery.

"Is one that permits" as it relates to a pharmaceutically acceptable carrier that has characteristics that enable the preparation to be used for a given mode of administration of the composition. For example, pharmaceutically acceptable carriers that permit parenteral administration or intravenous infusion to an animal are liquids that are not injurious or lethal to the animals when so injected. Such carriers often comprise sterile water, which may be supplemented with various solutes to increase solubility. Sterile water or sterile water supplemented with solutes is thus a pharmaceutically acceptable carrier that permits parenteral administration.

"Pharmaceutically acceptable carrier" refers to a carrier that is not deleterious to the other ingredients of the composition and is not deleterious to the human or other animal recipient thereof. In the context of the other ingredients of the composition, "not deleterious" means that the carrier will not react with or degrade the other ingredients or otherwise interfere with their efficacy. Interference with the efficacy of an ingredient does not encompass mere dilution of the ingredient. In the context of the animal host, "not deleterious" means that the carrier is not injurious or lethal to the animal.

"Subject in need thereof" refers to living organism that would benefit from either prevention or reductions in the degree of an abnormal proliferative disease. Subjects may include animals or more specifically, mammals or humans.

The term "acyloxy" as used herein by itself or as part of another substituent refers to the group —OC(O)-(lower alkyl), —OC(O)-(lower alkenyl), and —OC(O)-(lower alkynyl), which may also be written as —OC(O)—$C_1$-$C_5$ alkyl, —OC(O)—$C_2$-$C_5$ alkenyl, and —OC(O)—$C_2$-$C_5$ alkynyl, respectively. The term "acyloxy" includes substituted acyloxy and unsubstituted acyloxy. These said lower alkyl, lower alkenyl, and lower alkynyl groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —SH, —SCH$_3$, and —SCH$_2$CH$_3$. In certain embodiments, acyloxy with substituents as described herein may be written as "substituted acyloxy." Examples include, but are not limited to, acetoxy and propionyloxy. More preferably, these said lower alkyl, lower alkenyl, and lower alkynyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$.

The term "alkoxy" as used herein by itself or as part of another substituent, refers to the group —OR, wherein R is a lower alkyl, lower alkenyl, or lower alkynyl group as defined herein, which may also be written as $C_1$-$C_5$ alkyl, $C_2$-$C_5$ alkenyl, and $C_2$-$C_5$ alkynyl, respectively. The term "alkoxy" includes substituted alkoxy and unsubstituted alkoxy. These said R groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —SH, —SCH$_3$, and —SCH$_2$CH$_3$. In certain embodiments, alkoxy with substituents as described herein may be written as "substituted alkoxy." Examples of alkoxy groups include, but are not limited to, methoxy, ethoxy, propoxy, isopropoxy, butoxy, tert-butoxy, —OCHF$_2$, —OCH$_2$Cl, —OCH$_2$CH$_2$CHF$_2$, —OCH$_2$CH$_2$CF$_3$, —OCH$_2$SCH$_3$, —OCH$_2$CH$_2$OCH$_3$, —OCH$_2$CH$_2$NH$_2$. Preferably, these said lower alkyl, lower alkenyl, and lower alkynyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R groups of an alkoxy at $R^4$ are substituted by independent replacement of one of the hydrogen atoms.

The term "alkoxyalkyl" as used herein refers to a lower alkyl group as defined herein with one carbon atom replaced with an oxygen atom. Examples include, but are not limited to, —CH$_2$CH$_2$OCH$_3$ and —CH$_2$OCH$_2$CH$_2$CH$_3$.

The term "alkoxyalkenyl" as used herein refers to a lower alkenyl group as defined herein with one carbon atom replaced with an oxygen atom.

The term "alkoxyalkynyl" as used herein refers to a lower alkynyl group as defined herein with one carbon atom replaced with an oxygen atom.

The term "alkoxycarbonyl" as used herein by itself or as part of another substituent, refers to the group —C(O)-(alkoxy), wherein alkoxy is as defined herein. Examples include, but are not limited to, —C(O)OCH$_3$ and —C(O)OCH$_2$CH$_3$.

The term "alkylcarbonylamino" as used herein refers to the groups —NHC(O)— lower alkyl, —NHC(O)-lower alkenyl, and —NHC(O)-lower alkynyl, which can also be written as —NHC(O)—$C_1$-$C_5$ alkyl, —NHC(O)—$C_2$-$C_5$ alkenyl, and —NHC(O)—$C_2$-$C_5$ alkynyl, respectively. The term "alkylcarbonylamino" includes substituted alkylcarbonylamino and unsubstituted alkylcarbonylamino. These said lower alkyl, lower alkenyl, or lower alkynyl groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, CF$_3$, CCl$_3$, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$—SO$_2$NH$_2$, —C(O)OCH$_3$, —C(O)CH$_3$, —SH, —SCH$_3$, and —SCH$_2$CH$_3$. In certain embodiments, alkylcarbonylamino with substituents as described herein may be written as "substituted alkylcarbonylamino." Examples include, but are not limited to, —NHC(O)CH$_3$, and —NHC(O)CH$_2$CH$_3$. Preferably, the term "alkylcarbonylamino" as used herein refers to substituted and unsubstituted —NHC(O)-lower alkyl and —NHC(O)-lower alkenyl. More preferably, these said lower alkyl, lower alkenyl, and lower alkynyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$.

The term "alkylaminocarbonyl" as used herein by itself or as part of another substituent, refers to the groups —C(O)NH-lower alkyl, —C(O)NH-lower alkenyl and —C(O)NH— lower alkynyl, which can also be written as —C(O)NH—$C_1$-$C_5$ alkyl, —C(O)NH—$C_2$-$C_5$ alkenyl, and —C(O)NH—$C_2$-$C_5$ alkynyl, respectively. The term "alkylaminocarbonyl" includes substituted alkylaminocarbonyl and unsubstituted alkylaminocarbonyl. These said lower alkyl, lower alkenyl, or lower alkynyl groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, CF$_3$, CCl$_3$, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —SH, —SCH$_3$, and —SCH$_2$CH$_3$. In certain embodiments, alkylaminocarbonyl with substituents as described herein may be written as "substituted alkylaminocarbonyl." Examples include, but are not limited to, —C(O)NHCH$_3$ and —C(O)NHCH$_2$CH$_3$. Preferably, the term "alkylaminocarbonyl" as used herein refers to substituted and unsubstituted —C(O)NH—$C_1$-$C_5$ alkyl and —C(O)NH—$C_2$-$C_5$ alkenyl. More preferably, these said lower alkyl, lower alkenyl, and lower alkynyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$.

The phrase "alkyl ether" as used herein refers to ethers of the formula R'OR", wherein R' is a saturated hydrocarbon chain having one, two, or three carbon atoms that are straight or branched, which can also be written as $C_1$-$C_3$ alkyl (straight or branched) and R" is a lower alkyl, lower alkenyl, and lower alkynyl, which said R" can also be written as $C_1$-$C_5$ alkyl, $C_2$-$C_5$ alkenyl, $C_2$-$C_5$ alkynyl, respectively. The term "alkyl ether" includes substituted alkyl ether and unsubstituted alkyl ether. These said R' and R" groups may be optionally substituted by independent replacement of one or two hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, CF$_3$, CCl$_3$, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$—SO$_2$NH$_2$, —C(O)OCH$_3$, —C(O)CH$_3$, —SH, —SCH$_3$, and —SCH$_2$CH$_3$. In certain embodiments, alkyl ether with substituents as described herein may be written as "substituted alkyl ether." Examples of R' include, but are not limited to, methyl, ethyl, propyl, and isopropyl. Examples of R" include, but are not limited to, —CH$_2$CH$_2$SCH$_3$, —CH$_2$CH$_2$OCH$_3$, —CH$_2$CH$_2$NH$_2$. Examples of alkyl ethers include, but are not limited to, —CH$_2$OCH$_2$CH$_2$CH$_3$, —CH$_2$OCH$_2$SCH$_3$, —CH$_2$OCH$_2$CH$_2$OCH$_3$, —CH$_2$OCH$_2$CH$_2$NH$_2$. Preferably, these said R' and R" groups may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R' and R" groups of alkyl ether at R$^4$ are substituted by independent replacement of one of the hydrogen atoms.

The term "aminoalkyl" as used herein refers to lower alkyl with one nitrogen atom replacing one carbon atom in the unbranched or branched chain. Examples include, but are not limited to, —NHCH$_2$CH$_2$CH$_3$, —CH$_2$CH$_2$NHCH$_3$, —CH$_2$N(CH$_3$)$_2$, —N(CH$_3$)$_2$, and —CH$_2$CH$_2$NH$_2$.

The term "aminoalkenyl" as used herein refers to lower alkenyl with one nitrogen atom replacing one carbon atom in the unbranched or branched chain. An example includes, but is not limited to, —NHCH$_2$CHCH$_2$.

The term "aminoalkynyl" as used herein refers to lower alkynyl with one nitrogen atom replacing one carbon atom in the unbranched or branched chain. An example includes, but is not limited to, —NHCH$_2$CH$_2$CCH.

The term "cycloalkyl," as used herein by itself or as part of another substituent, means a saturated carbocyclic ring compound selected from the group consisting of cyclopropyl, cyclobutyl, cyclopentyl, cyclohexyl, norbornane, and adamantane, or written as C$_3$-C$_6$ cycloalkyl (substituted or not) and norbornane, and adamantane; and substitutions to these lower cycloalkyls by independent replacement of one or two of the hydrogen atoms thereon with substituents selected from the group consisting of methyl, ethyl, propyl, ethenyl, propenyl, ethynyl, propynyl, halide, haloalkyl, —O-haloalkyl, amino, methylamino, dimethylamino, ethylamino, diethylamino, hydroxyl, —CH$_2$OH, methoxy, ethoxy, nitrile, —CH$_2$CN, aminocarbonyl, hydroxyaminocarbonyl, methylaminocarbonyl, dimethylaminocarbonyl, methylcarbonylamino, ethylcarbonylamino, —SH, —SCH$_3$, —SCH$_2$CH$_3$, —CH$_2$SCH$_3$.

The term "cycloalkenyl" as used herein by itself or as part of another substituent specifically refers to an unsaturated hydrocarbon ring with five or six carbons or written as C$_5$-C$_6$ cycloalkenyl (substituted or not); and substitutions to these lower cycloalkenyls by independent replacement of one or two of the hydrogen atoms thereon with substituents selected from the group consisting of methyl, ethyl, propyl, ethenyl, propenyl, ethynyl, propynyl, halide, haloalkyl, —O-haloalkyl, amino, methylamino, dimethylamino, ethylamino, diethylamino, hydroxyl, —CH$_2$OH, methoxy, ethoxy, nitrile, —CH$_2$CN, aminocarbonyl, hydroxyaminocarbonyl, methylaminocarbonyl, dimethylaminocarbonyl, methylcarbonylamino, ethylcarbonylamino, —SH, —SCH$_3$, —SCH$_2$CH$_3$, —CH$_2$SCH$_3$.

The terms "halo" and "halogen," as used herein, mean an atom selected from fluorine, chlorine, bromine and iodine and the term "halide" and used herein means the corresponding anion.

The term "haloalkyl" as used herein by itself or as part of another substituent refers to a saturated hydrocarbon chain having one, two, or three carbon atoms wherein one or more hydrogen atoms attached to a carbon atom is replaced with 1, 2, or 3 halide atoms. Examples include, but are not limited to, fluoromethyl, difluoroethyl, and trifluoromethyl.

The term "heteroaryl" as used herein by itself or as part of another substituent refers to heteroaryl selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl; specifically their partially reduced forms as known to those skilled in the art like as tetrahydroisoquinolinyl is to isoquinolinyl; and the term "substituted heteroaryl" as used herein refers to substitutions to these heteroaryls by independent replacement of one, two, or three of the hydrogen atoms thereon with substituents selected from the group consisting of methyl, ethyl, propyl, ethenyl, propenyl, ethynyl, propynyl, halide, haloalkyl, —O-haloalkyl, amino, methylamino, dimethylamino, ethylamino, diethylamino, hydroxyl, —CH$_2$OH, methoxy, ethoxy, nitrile, —CH$_2$CN, aminocarbonyl, hydroxyaminocarbonyl, methylaminocarbonyl, dimethylaminocarbonyl, methylcarbonylamino, ethylcarbonylamino, —SH, —SCH$_3$, —SCH$_2$CH$_3$, —CH$_2$SCH$_3$.

The term "heterocycloalkyl" as used herein by itself or as part of another substituent refers to heterocycloalkyl selected from the group consisting of azetidinyl, [1,3]dioxolane, pyrazolinyl, pyrrolidinyl, 2-pyrrolinyl, 3-pyrrolinyl, tetrahydrofuranyl, dihydrofuranyl, pyranyl, tetrahydropyranyl, dihydropyranyl, tetrahydrothienyl, imidazolinyl, imidazolidinyl, pyrazolidinyl, oxazolidinyl, isoxazolidinyl, thiazolidinyl, isothiazolidinyl, piperidinyl, homopiperidinyl, quinuclidinyl, piperazinyl, morpholinyl, thiamorpholinyl, 1-pyrazolidinyl, azepinyl; and specifically the phrase "substituted heterocycloalkyl" as used herein refers to substitutions to these heterocycloalkyls by independent replacement of one or two of the hydrogen atoms thereon with substituents selected from the group consisting of methyl, ethyl, propyl, ethenyl, propenyl, ethynyl, propynyl, halide, haloalkyl, —O-haloalkyl, amino, methylamino, dimethylamino, ethylamino, diethylamino, hydroxyl, —CH$_2$OH, methoxy, ethoxy, nitrile, —CH$_2$CN, aminocarbonyl, hydroxyaminocarbonyl, methylaminocarbonyl, dimethylaminocarbonyl, methylcarbonylamino, ethylcarbonylamino, —SH, —SCH$_3$, —SCH$_2$CH$_3$, —CH$_2$SCH$_3$. For example, substitutions to pyrrolidinyl may include hydroxyl-pyrrolidinyl, chloropyrrolidinyl, methoxy-pyrrolidinyl, nitrile-pyrrolidinyl, methyl-pyrrolidinyl, and amino-pyrrolidinyl.

The term "heteroatom" as used herein refers to a nitrogen, sulfur, or oxygen atom.

The term "hydroxyalkyl" as used herein by itself or as part of another substituent refers to a saturated hydrocarbon chain having one or two carbon atoms wherein one hydrogen atom attached to a carbon atom is replaced with one hydroxyl. Examples include —CH$_2$OH, —CH$_2$CH$_2$OH and —CH(OH)CH$_3$.

The phrase "lower alkyl" as used herein by itself or as part of another substituent refers to a saturated hydrocarbon chain having one, two, three, four, or five carbon atoms, which can also be written as C$_1$-C$_5$ alkyl. Lower alkyl groups may be optionally substituted with one or more substituents as defined herein to form substituted lower alkyl groups. Lower alkyl groups may be straight or branched. Examples include, but are not limited to, methyl, ethyl, propyl, isopropyl, butyl, isobutyl, tert-butyl, pentyl, and isopentyl. If a lower alkyl group replaces one or two hydrogens on an amino as shown herein for —NR$^8$R$^9$, a terminal hydrogen on the lower alkyl group may be optionally substituted with hydroxyl, halide, or nitrile in this specific case.

The phrase "substituted lower alkyl" as used herein, refers to a lower alkyl group, as previously defined, substituted by independent replacement of one, two, three, or four of the hydrogen atoms thereon with substituents selected from the group consisting of methoxy, ethoxy, propoxy, isopropoxy, gem-dimethyl, cyclopropyl, oxo, sulfoxide, acetoxy, halide, nitrile, hydroxyl, amino, methylamino, dimethylamino, ethylamino, diethylamino, tert-butylamino, aminocarbonyl, methylaminocarbonyl, methylcarbonylamino, —O-haloalkyl, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, CF$_3$, —SH, —SCH$_3$, and —SCH$_2$CH$_3$. More preferably, a lower alkyl group at R$^4$, R$^8$, and R$^9$ is substituted by independent replacement of one of the hydrogen atoms.

The phrase "lower alkenyl" as used herein by itself or as part of another substituent refers to an unsaturated hydrocarbon chain having two, three, four, or five carbon atoms and having one or more carbon-carbon double bonds within the chain, which can also be written as C$_2$-C$_5$ alkenyl. The lower alkenyl groups may be straight or branched and may be optionally substituted with one or more substituents as defined herein to form substituted lower alkenyl groups. Examples of lower alkenyl groups include ethenyl, propenyl and butenyl.

The phrase "substituted lower alkenyl" as used herein, refers to a lower alkenyl group, as previously defined, substituted by independent replacement of one, two, three, or four of the hydrogen atoms thereon with substituents selected from the group consisting of methoxy, ethoxy, propoxy, isopropoxy, gem-dimethyl, cyclopropyl, oxo, sulfoxide, acetoxy, halide, nitrile, hydroxyl, amino, methylamino, dimethylamino, ethylamino, diethylamino, tert-butylamino, aminocarbonyl, methylaminocarbonyl, methylcarbonylamino, —O-haloalkyl, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, CF$_3$, —SH, —SCH$_3$, and —SCH$_2$CH$_3$. More preferably, a lower alkenyl group at R$^4$ is substituted by independent replacement of one of the hydrogen atoms.

The phrase "lower alkynyl" as used herein by itself or as part of another substituent refers to an unsaturated hydrocarbon chain having two, three, four, or five carbon atoms and having one or more carbon-carbon triple bonds within the chain, which can also be written as C$_2$-C$_5$ alkynyl. The lower alkynyl groups may be straight or branched and may be optionally substituted with one or more substituents as defined herein to form substituted lower alkynyl groups. Examples of lower alkynyl groups include ethynyl and propargyl.

The phrase "substituted lower alkynyl" as used herein refers to a lower alkynyl group, as previously defined, substituted by independent replacement of one, two, three, or four of the hydrogen atoms thereon with substituents selected from the group consisting of methoxy, ethoxy, propoxy, isopropoxy, gem-dimethyl, cyclopropyl, oxo, sulfoxide, acetoxy, halide, nitrile, hydroxyl, amino, methylamino, dimethylamino, ethylamino, diethylamino, tert-butylamino, aminocarbonyl, methylaminocarbonyl, methylcarbonylamino, —O-haloalkyl, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, and —SCH$_2$CH$_3$. More preferably, a lower alkynyl group at R$^4$ is substituted by independent replacement of one of the hydrogen atoms.

The term "substituted phenyl", means a phenyl group by itself or as part of another substituent substituted by independent replacement of one, two, or three of the hydrogen atoms thereon with substituents selected from the group consisting of methyl, ethyl, propyl, ethenyl, propenyl, ethynyl, propynyl, halide, haloalkyl, —O-haloalkyl, amino, methylamino, dimethylamino, ethylamino, diethylamino, hydroxyl, —CH$_2$OH, methoxy, ethoxy, nitrile, —CH$_2$CN, aminocarbonyl, hydroxyaminocarbonyl, methylaminocarbonyl, dimethylaminocarbonyl, methylcarbonylamino, ethylcarbonylamino, —SH, —SCH$_3$, —SCH$_2$CH$_3$, and —CH$_2$SCH$_3$.

The term "alkylthio" as used herein by itself or as part of another substituent, refers to a group —SR, wherein R is a lower alkyl group as defined herein, which can also be written as C$_1$-C$_5$ alkyl. The term "alkylthio" includes substituted alkylthio and unsubstituted alkylthio. These said R groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, —O-haloalkyl, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, and —SCH$_2$CH$_3$. In certain embodiments, alkylthio with substituents as described herein may be written as "substituted alkylthio." Examples of alkylthio groups include, but are not limited to, methylthio, ethylthio, propylthio, isopropylthio, tert-butylthio, —SCH$_2$CHF$_2$, —SCH$_2$OCH$_3$, and —SCH$_2$CH$_2$NH$_2$. Preferably, the said lower alkyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R groups of alkylthio at R$^4$ are substituted by independent replacement of one of the hydrogen atoms.

The phrase "thioalkyl ether" as used herein by itself or as part of another substituent refers to the formula R'SR", wherein R' is C$_1$-C$_3$ alkyl (straight or branched) and R" is C$_1$-C$_3$ alkyl, C$_2$-C$_3$ alkenyl, or C$_2$-C$_3$ alkynyl (straight or branched). The term "thioalkyl ether" includes substituted thioalkyl ether and unsubstituted thioalkyl ether. These said R' and R" groups may be optionally substituted by independent replacement of one or two hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, —O-haloalkyl, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, —SCH$_2$CH$_3$. In certain embodiments, thioalkyl ether with substituents as described herein may be written as "substituted thioalkyl ether." Examples of a thioalkyl ether include, but are not limited to, —CH$_2$CH$_2$SCH$_3$, —CH$_2$SCH$_2$CH$_3$, —CH$_2$SCH$_2$CHF$_2$, and —CH$_2$SCH=CHF, —CH$_2$SCH$_2$OCH$_3$, and —CH$_2$SCH$_2$CH$_2$NH$_2$. Preferably, the said R' and R" groups may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R' and R" groups of a thioalkyl ether at R$^4$ are substituted by independent replacement of one of the hydrogen atoms.

The term "alkenylthio" as used herein by itself or as part of another substituent, refers to a group —SR, wherein R is a lower alkenyl group as defined herein, which can also be written as C$_2$-C$_5$ alkenyl. The term "alkenylthio" includes substituted alkenylthio and unsubstituted alkenylthio. These said R groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, —O-haloalkyl, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, and —SCH$_2$CH$_3$. In certain embodiments, alkenylthio with substituents as described herein may be written as "substituted alkenylthio." Examples of alkenylthio groups include, but are not limited to, —SCH=CH$_2$, —SCH=CHF, —SCH$_2$CH$_2$OCH$_3$, and —SCH$_2$CH=CHCl. Preferably, the said lower alkenyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R groups of an alkenylthio at R$^4$ are substituted by independent replacement of one of the hydrogen atoms.

The term "alkynylthio" as used herein by itself or as part of another substituent, refers to a group —SR, wherein R is a lower alkynyl group as defined herein, which can also be written as C$_2$-C$_5$ alkynyl. The term "alkynylthio" includes substituted alkynylthio and unsubstituted alkynylthio. These said R groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, —O-haloalkyl, nitrile, amino, methylamino, dimethylamino, ethylamino, diethylamino, tert-butylamino, aminocarbonyl, methylaminocarbonyl, methylcarbonylamino, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, and —SCH$_2$CH$_3$. In certain embodiments, alkynylthio with substituents as described herein may be written as "substituted alkynylthio." Examples of alkynylthio groups include, but are not limited to, —SCH=CH$_2$, —SCH$_2$C≡CCH$_2$OCH$_3$, and —SCH$_2$CH$_2$CH$_2$Cl. Preferably, the said lower alkynyl may be substituted with substituents selected from the group consisting of methoxy, cyclopropyl, oxo, hydroxyl, halide, nitrile, amino, methylamino, dimethylamino, ethylamino, diethylamino, tert-butylamino, aminocarbonyl, methylaminocarbonyl, methylcarbonylamino, —COOH, —C(O)OCH$_3$, and —C(O)CH$_3$. More preferably, said R groups of an alkynylthio at R$^4$ are substituted by independent replacement of one of the hydrogen atoms.

The term "substituted" as used herein immediately preceding or following a defined chemical group herein (only for which its definition does not include a list of substituents to replace hydrogen atoms) means the group is substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, halide, nitrile, hydroxyl, amino, methylamino, dimethylamino, ethylamino, diethylamino, tert-butylamino, aminocarbonyl, methylaminocarbonyl, methylcarbonylamino, —O—haloalkyl, —CH=NOH, —COOH, —SOCH$_3$, —SO$_2$CH$_3$, —NHSO$_2$CH$_3$, —SO$_2$NH$_2$, —C(O)OCH$_3$, —C(O)CH$_3$, —CF$_3$, —SH, —SCH$_3$, and —SCH$_2$CH$_3$. For example, substituted alkoxyalkyl, substituted alkoxyalkenyl, substituted aminoalkyl, and substituted aminoalkenyl means one, two, or three hydrogens may be independently replaced as defined herein.

The term "unsubstituted" as used herein immediately preceding or following a defined chemical group herein means the group does not have any substituents.

The phrase "amino protecting group," as used herein, means a labile chemical moiety which is known in the art to protect an amino group against undesired reactions during synthetic procedures. Following such procedures, the amino protecting group may be selectively removed. Examples of amino protecting groups include, but are not limited to, tert-butoxycarbonyl, 9-fluorenylmethoxycarbonyl, benzyloxycarbonyl, and the like. The phrase "protected amino," as used herein, means an amino group protected with an amino protecting group as defined above.

The phrase "hydroxyl protecting group," as used herein, means a labile chemical moiety which is known in the art to protect a hydroxyl group against undesired reactions during synthetic procedures. Following such procedures, the hydroxyl protecting group may be selectively removed. Examples of hydroxyl protecting groups include, but are not limited to, methylthiomethyl, tert-butyldimethylsilyl, tert-butyldiphenylsilyl, acyl substituted with an aromatic group, and the like. The phrase "protected hydroxyl," as used herein, means a hydroxyl group protected with a hydroxyl protecting group, as defined above, including benzoyl, acetyl, trimethylsilyl, triethylsilyl, methoxymethyl groups, for example.

Preparation Of Phenethyldihydrobenzodioxolones

The compounds of the invention may be prepared by the techniques described in the examples below. In designing synthetic strategies to prepare analogs of the starting chemical compound, modifications at certain positions of the scaffold of the basic chemical compound prove to be important for modulating antiproliferative activity, while other modifications at positions can improve the bioavailability of the compound. Many of these modifications or optimizations are taught in the literature known to those skilled in the art, including Silverman, R. B., 2004. The Organic Chemistry of Drug Design and Drug Action (Second Edition) Academic Press, San Diego, specifically including Table 2.11 of the reference.

Table 2 below provides examples of the compounds of the invention and does not represent all of the compounds of the invention. Compounds in Table 2 have been synthesized as described in detail below. Reference to specific compounds by number throughout the specification refer to corresponding structure as identified in Table 2.

TABLE 2

Representative Compounds of the Invention.

| Compound | Chemical Structure |
|---|---|
| 2 | 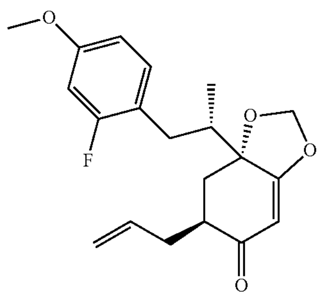 [SMILES: C=CC[C@H]1C[C@]2([C@@H](C)Cc3ccc(OC)cc3F)OCOC2=CC1=O] |
| 3 | 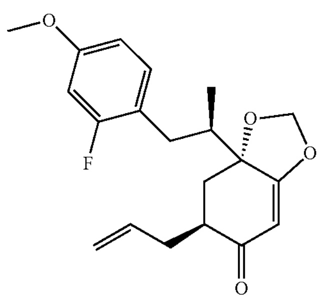 [SMILES: C=CC[C@H]1C[C@]2([C@H](C)Cc3ccc(OC)cc3F)OCOC2=CC1=O] |
| 4 | 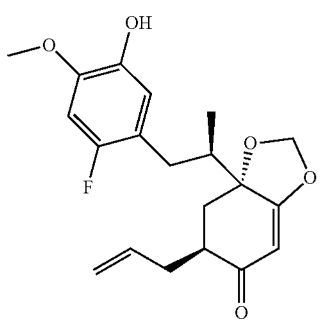 [SMILES: C=CC[C@H]1C[C@]2([C@H](C)Cc3cc(O)c(OC)cc3F)OCOC2=CC1=O] |
| 5 | 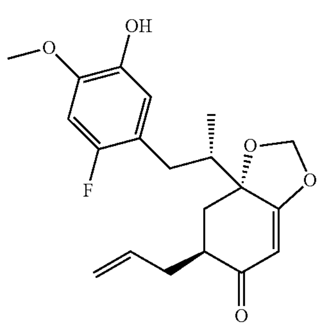 [SMILES: C=CC[C@H]1C[C@]2([C@@H](C)Cc3cc(O)c(OC)cc3F)OCOC2=CC1=O] |
| 6 | |
| 7 | |
| 8 | |
| 9 | |

TABLE 2-continued

Representative Compounds of the Invention.

| Compound | Chemical Structure |
|---|---|
| 10 | 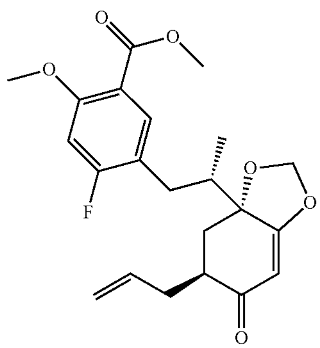 [SMILES: C=CC[C@H]1C[C@]2([C@@H](C)Cc3cc(C(=O)OC)c(OC)cc3F)OCOC2=CC1=O] |
| 11 | 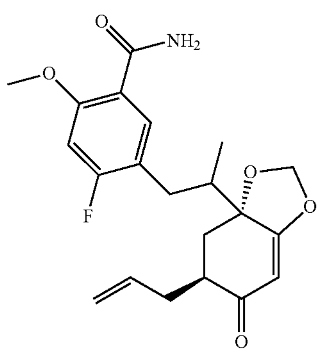 [SMILES: C=CC[C@H]1C[C@]2(C(C)Cc3cc(C(N)=O)c(OC)cc3F)OCOC2=CC1=O] |
| 12 | 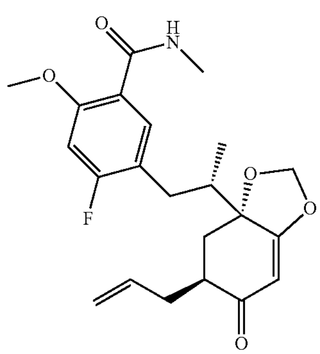 [SMILES: C=CC[C@H]1C[C@]2([C@@H](C)Cc3cc(C(=O)NC)c(OC)cc3F)OCOC2=CC1=O] |
| 13 | 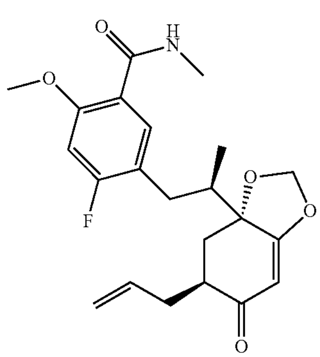 [SMILES: C=CC[C@H]1C[C@]2([C@H](C)Cc3cc(C(=O)NC)c(OC)cc3F)OCOC2=CC1=O] |
| 14 | |
| 15 | |
| 16 | |
| 17 | |

TABLE 2-continued
Representative Compounds of the Invention.
| Compound | Chemical Structure |
|---|---|
| 18 | 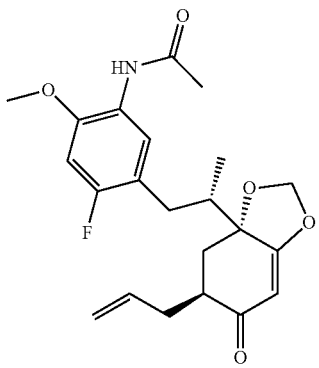 [SMILES: C=CC[C@H]1C[C@]2([C@@H](C)Cc3cc(NC(C)=O)c(OC)cc3F)OCOC2=CC1=O] |
| 19 | 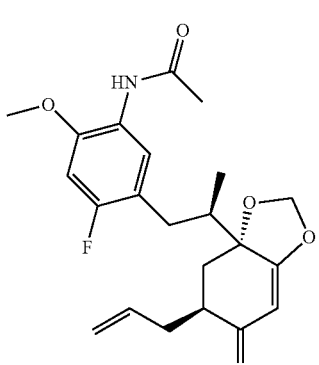 |
| 20 | 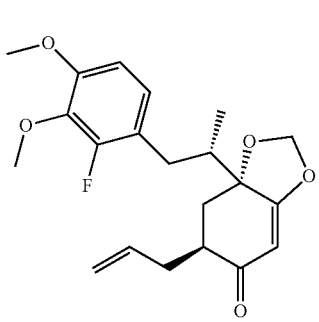 [SMILES: C=CC[C@H]1C[C@]2([C@@H](C)Cc3ccc(OC)c(OC)c3F)OCOC2=CC1=O] |
| 21 | 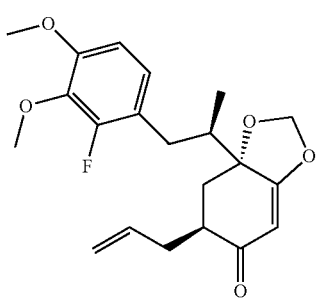 [SMILES: C=CC[C@H]1C[C@]2([C@H](C)Cc3ccc(OC)c(OC)c3F)OCOC2=CC1=O] |
| 22 | 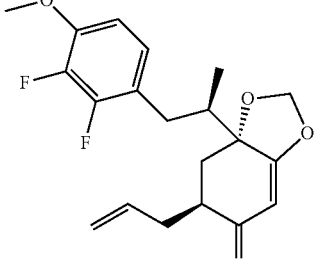 |
| 23 | 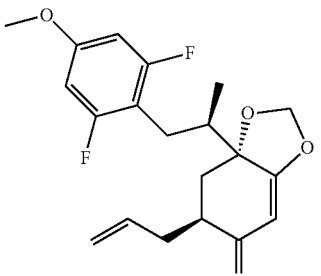 |
| 24 | 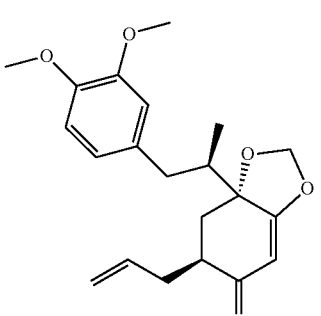 |
| 25 | 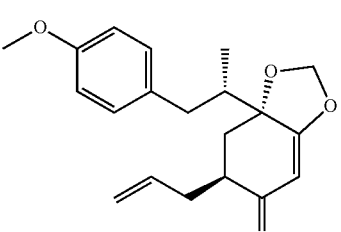 |
| 26 | 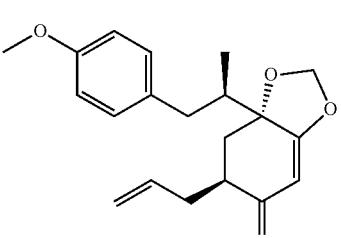 |

TABLE 2-continued

Representative Compounds of the Invention.

| Compound | Chemical Structure |
|---|---|
| 27 | 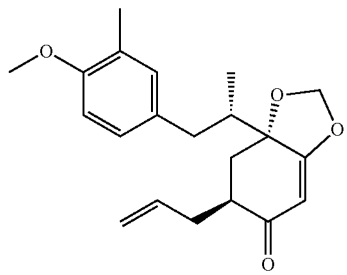 [SMILES: C=CC[C@H]1C[C@]2([C@@H](C)Cc3ccc(OC)c(C)c3)OCOC2=CC1=O] |
| 28 | 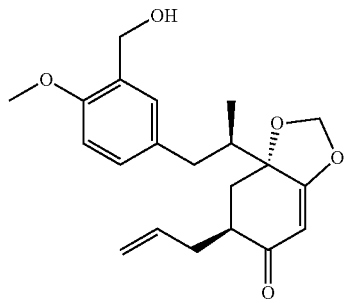 [SMILES: C=CC[C@H]1C[C@]2([C@H](C)Cc3ccc(OC)c(CO)c3)OCOC2=CC1=O] |
| 29 | 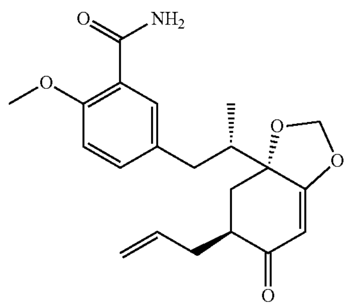 [SMILES: C=CC[C@H]1C[C@]2([C@@H](C)Cc3ccc(OC)c(C(N)=O)c3)OCOC2=CC1=O] |
| 30 | 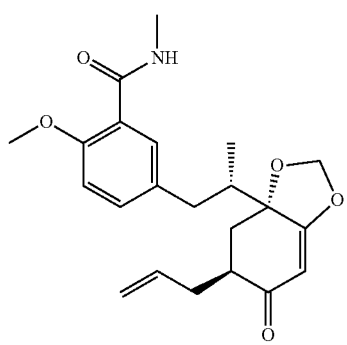 [SMILES: C=CC[C@H]1C[C@]2([C@@H](C)Cc3ccc(OC)c(C(=O)NC)c3)OCOC2=CC1=O] |
| 31 | 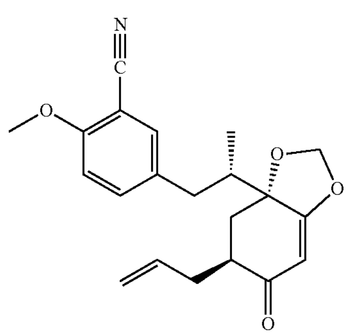 [SMILES: C=CC[C@H]1C[C@]2([C@@H](C)Cc3ccc(OC)c(C#N)c3)OCOC2=CC1=O] |
| 32 | |
| 33 | |
| 34 | |
| 35 | |

TABLE 2-continued

Representative Compounds of the Invention.

| Compound | Chemical Structure |
|----------|-------------------|
| 36 | 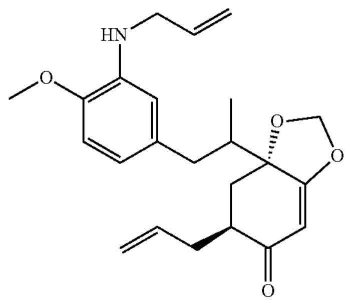 [SMILES: C=CCNc1cc(CC(C)[C@]23C[C@H](CC=C)C(=O)C=C2OCO3)ccc1OC] |
| 37 | 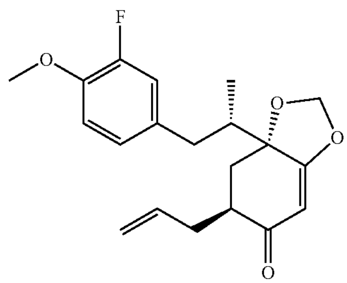 [SMILES: C=CC[C@H]1C[C@]2([C@@H](C)Cc3ccc(OC)c(F)c3)OCOC2=CC1=O] |
| 38 | 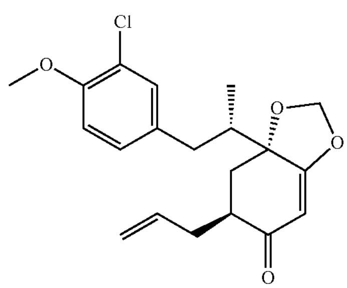 [SMILES: C=CC[C@H]1C[C@]2([C@@H](C)Cc3ccc(OC)c(Cl)c3)OCOC2=CC1=O] |
| 39 | 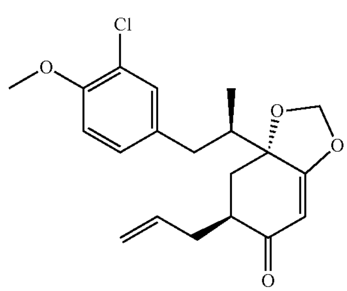 [SMILES: C=CC[C@H]1C[C@]2([C@H](C)Cc3ccc(OC)c(Cl)c3)OCOC2=CC1=O] |
| 40 | 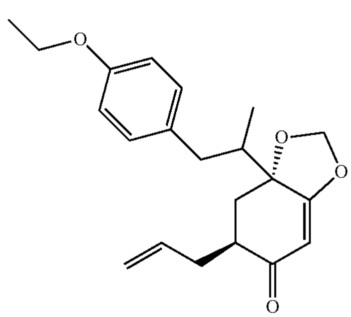 [SMILES: C=CC[C@H]1C[C@]2(C(C)Cc3ccc(OCC)cc3)OCOC2=CC1=O] |
| 41 | 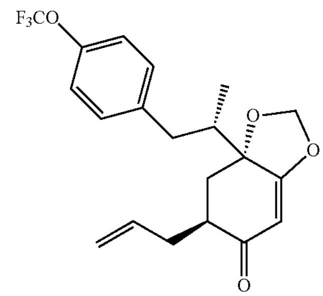 [SMILES: C=CC[C@H]1C[C@]2([C@@H](C)Cc3ccc(OC(F)(F)F)cc3)OCOC2=CC1=O] |
| 42 | 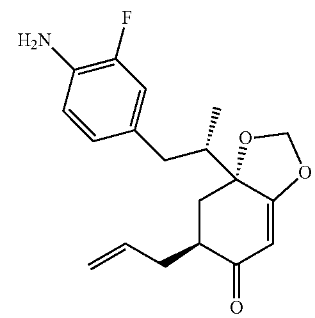 [SMILES: C=CC[C@H]1C[C@]2([C@@H](C)Cc3ccc(N)c(F)c3)OCOC2=CC1=O] |
| 43 | 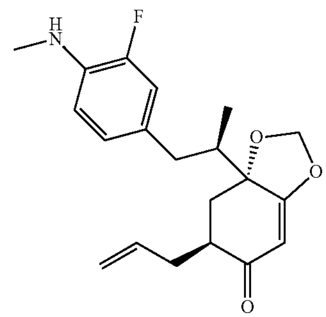 [SMILES: C=CC[C@H]1C[C@]2([C@H](C)Cc3ccc(NC)c(F)c3)OCOC2=CC1=O] |
| 44 | 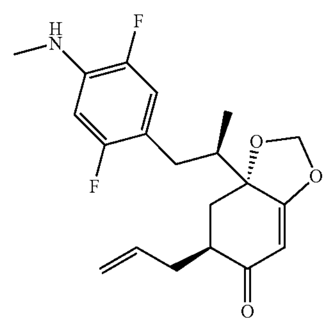 [SMILES: C=CC[C@H]1C[C@]2([C@H](C)Cc3cc(F)c(NC)cc3F)OCOC2=CC1=O] |
| 45 | 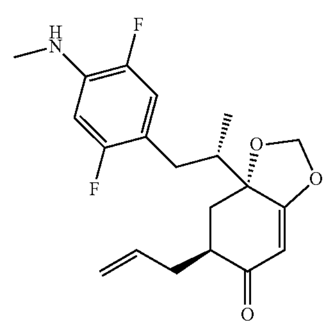 [SMILES: C=CC[C@H]1C[C@]2([C@@H](C)Cc3cc(F)c(NC)cc3F)OCOC2=CC1=O] |

TABLE 2-continued

Representative Compounds of the Invention.

| Compound | Chemical Structure |
|---|---|
| 46 | 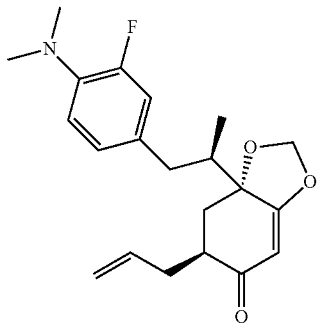 [SMILES: C=CC[C@H]1C[C@]2([C@H](C)Cc3ccc(N(C)C)c(F)c3)OCOC2=CC1=O] |
| 47 | 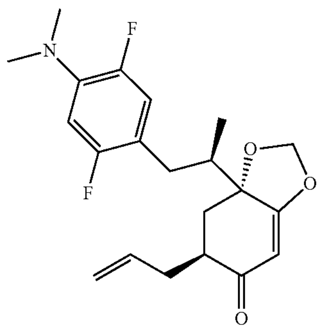 [SMILES: C=CC[C@H]1C[C@]2([C@H](C)Cc3cc(F)c(N(C)C)cc3F)OCOC2=CC1=O] |
| 48 | 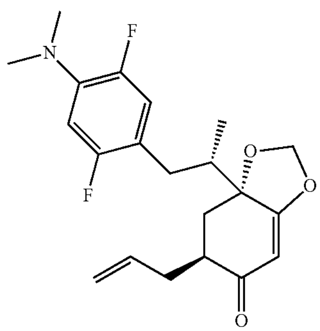 [SMILES: C=CC[C@H]1C[C@]2([C@@H](C)Cc3cc(F)c(N(C)C)cc3F)OCOC2=CC1=O] |
| 49 | 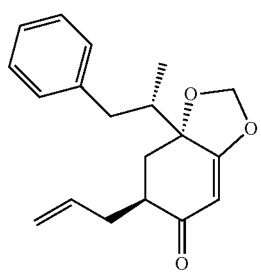 [SMILES: C=CC[C@H]1C[C@]2([C@@H](C)Cc3ccccc3)OCOC2=CC1=O] |
| 50 | 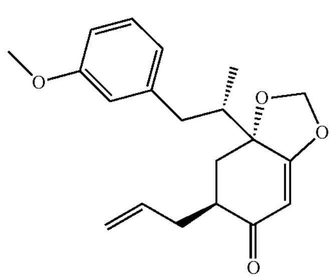 [SMILES: C=CC[C@H]1C[C@]2([C@@H](C)Cc3cccc(OC)c3)OCOC2=CC1=O] |
| 51 | 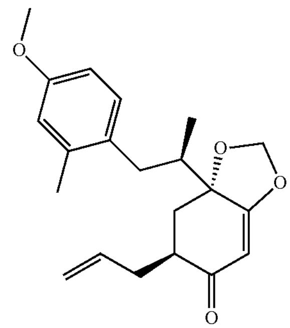 [SMILES: C=CC[C@H]1C[C@]2([C@H](C)Cc3ccc(OC)cc3C)OCOC2=CC1=O] |
| 52 | 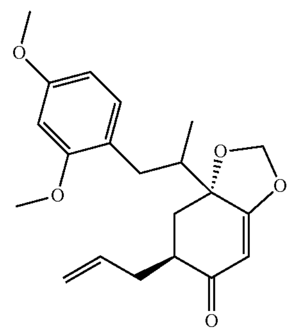 [SMILES: C=CC[C@H]1C[C@]2(C(C)Cc3ccc(OC)cc3OC)OCOC2=CC1=O] |
| 53 | 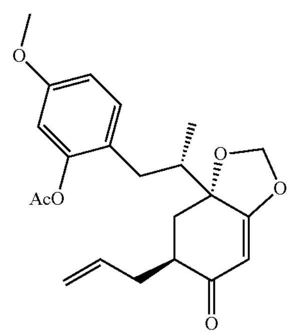 [SMILES: C=CC[C@H]1C[C@]2([C@@H](C)Cc3ccc(OC)cc3OC(C)=O)OCOC2=CC1=O] |
| 54 | 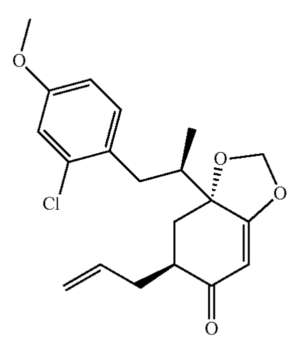 [SMILES: C=CC[C@H]1C[C@]2([C@H](C)Cc3ccc(OC)cc3Cl)OCOC2=CC1=O] |

TABLE 2-continued
Representative Compounds of the Invention.
| Compound | Chemical Structure |
|---|---|
| 55 | 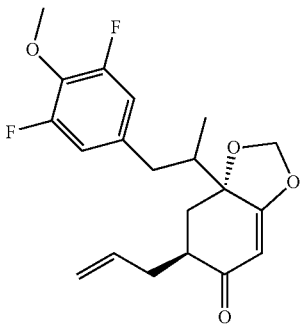 [SMILES: C=CC[C@H]1C[C@]2(C(C)Cc3cc(F)c(OC)c(F)c3)OCOC2=CC1=O] |
| 56 | 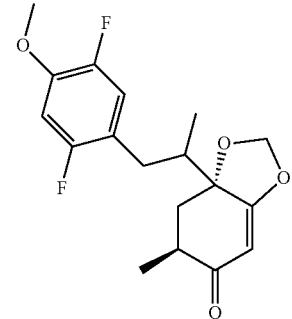 [SMILES: COc1cc(F)c(CC(C)[C@]23C[C@H](C)C(=O)C=C2OCO3)cc1F] |
| 57 | 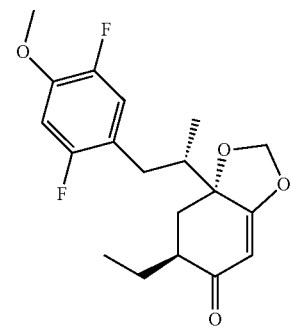 [SMILES: CC[C@H]1C[C@]2([C@@H](C)Cc3cc(F)c(OC)cc3F)OCOC2=CC1=O] |
| 58 | 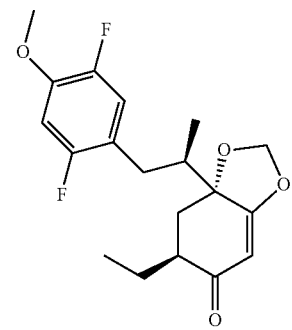 [SMILES: CC[C@H]1C[C@]2([C@H](C)Cc3cc(F)c(OC)cc3F)OCOC2=CC1=O] |
| 59 | 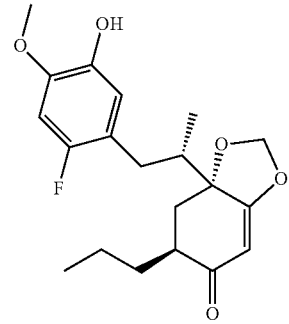 [SMILES: CCC[C@H]1C[C@]2([C@@H](C)Cc3cc(O)c(OC)cc3F)OCOC2=CC1=O] |
| 60 | 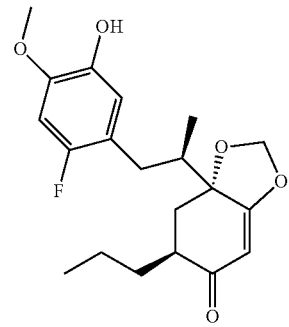 [SMILES: CCC[C@H]1C[C@]2([C@H](C)Cc3cc(O)c(OC)cc3F)OCOC2=CC1=O] |
| 61 | 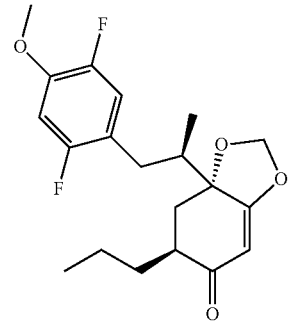 [SMILES: CCC[C@H]1C[C@]2([C@H](C)Cc3cc(F)c(OC)cc3F)OCOC2=CC1=O] |
| 62 | 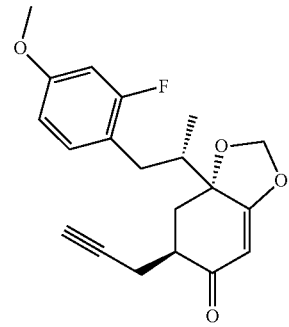 [SMILES: C#CC[C@H]1C[C@]2([C@@H](C)Cc3ccc(OC)cc3F)OCOC2=CC1=O] |

TABLE 2-continued

Representative Compounds of the Invention.

| Compound | Chemical Structure |
|---|---|
| 63 | 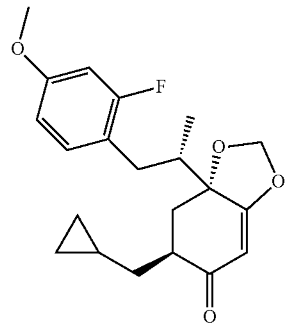 [SMILES: COc1ccc(C[C@H](C)[C@]23C[C@H](CC4CC4)C(=O)C=C2OCO3)c(F)c1] |
| 64 | 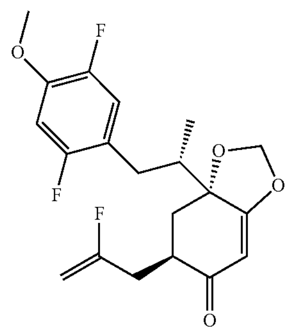 [SMILES: C=C(F)C[C@H]1C[C@]2([C@@H](C)Cc3cc(F)c(OC)cc3F)OCOC2=CC1=O] |
| 65 | 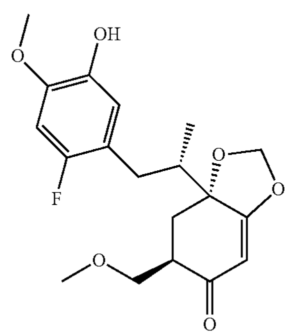 [SMILES: COC[C@H]1C[C@]2([C@@H](C)Cc3cc(O)c(OC)cc3F)OCOC2=CC1=O] |
| 66 | 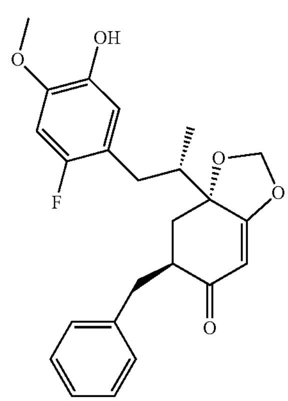 [SMILES: COc1cc(F)c(C[C@H](C)[C@]23C[C@H](Cc4ccccc4)C(=O)C=C2OCO3)cc1O] |
| 67 | |
| 68 | |
| 69 | |
| 70 | |

TABLE 2-continued

Representative Compounds of the Invention.

| Compound | Chemical Structure |
|---|---|
| 71 | |
| 72 | |
| 73 | |
| 74 | |
| 75 | 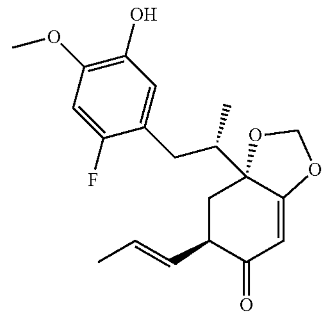 [SMILES: C/C=C/[C@H]1C[C@]2([C@@H](C)Cc3cc(O)c(OC)cc3F)OCOC2=CC1=O] |
| 76 | 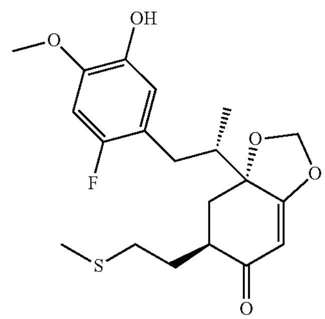 [SMILES: COc1cc(F)c(C[C@H](C)[C@]23C[C@H](CCSC)C(=O)C=C2OCO3)cc1O] |
| 77 | 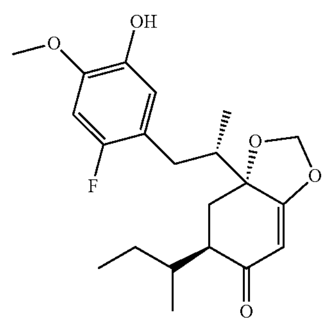 [SMILES: CCC(C)[C@H]1C[C@]2([C@@H](C)Cc3cc(O)c(OC)cc3F)OCOC2=CC1=O] |
| 78 | 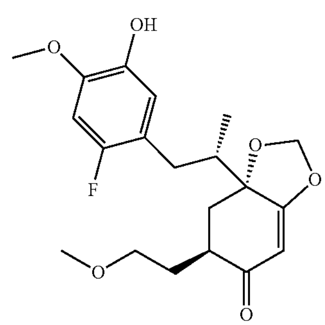 [SMILES: COCC[C@H]1C[C@]2([C@@H](C)Cc3cc(O)c(OC)cc3F)OCOC2=CC1=O] |
| 79 | 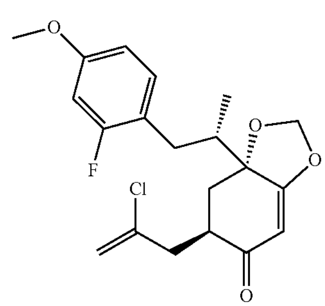 [SMILES: C=C(Cl)C[C@H]1C[C@]2([C@@H](C)Cc3ccc(OC)cc3F)OCOC2=CC1=O] |

TABLE 2-continued
Representative Compounds of the Invention.
| Compound | Chemical Structure |
|---|---|
| 80 | 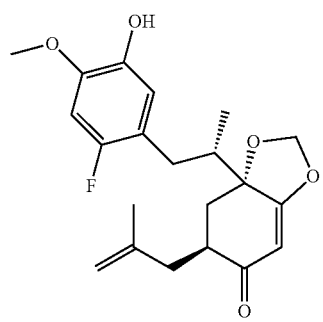 [SMILES: C=C(C)C[C@H]1C[C@]2([C@@H](C)Cc3cc(O)c(OC)cc3F)OCOC2=CC1=O] |
| 81 | 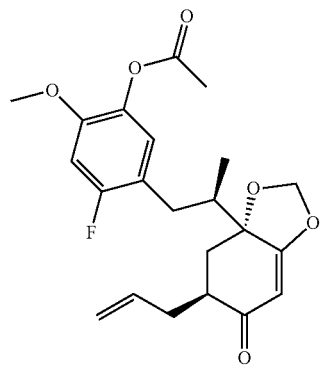 [SMILES: C=CC[C@H]1C[C@]2([C@H](C)Cc3cc(OC(C)=O)c(OC)cc3F)OCOC2=CC1=O] |
| 82 | 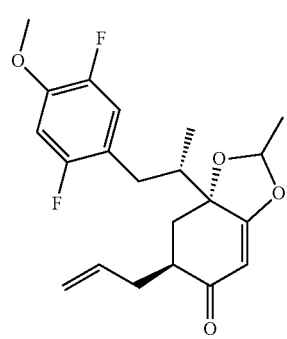 |
| 83 | 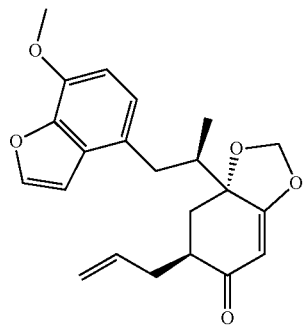 [SMILES: C=CC[C@H]1C[C@]2([C@H](C)Cc3ccc(OC)c4occc34)OCOC2=CC1=O] |
| 84 | 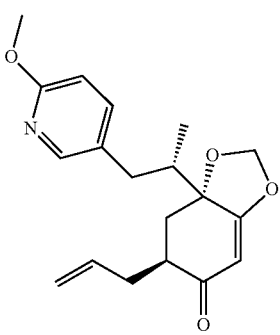 [SMILES: C=CC[C@H]1C[C@]2([C@@H](C)Cc3ccc(OC)nc3)OCOC2=CC1=O] |
| 85 | 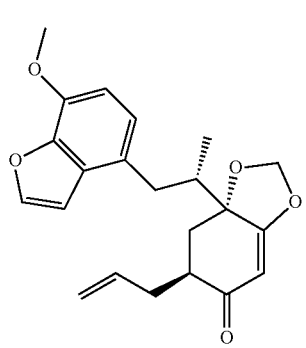 [SMILES: C=CC[C@H]1C[C@]2([C@@H](C)Cc3ccc(OC)c4occc34)OCOC2=CC1=O] |
| 86 | 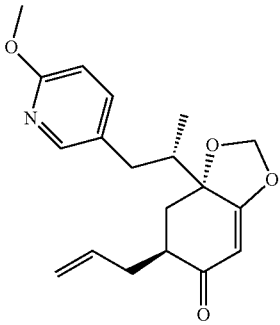 [SMILES: C=CC[C@H]1C[C@]2([C@@H](C)Cc3ccc(OC)nc3)OCOC2=CC1=O] |
| 87 | 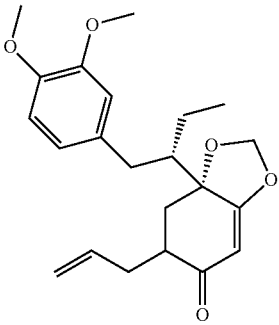 [SMILES: C=CCC1C[C@]2([C@@H](CC)Cc3ccc(OC)c(OC)c3)OCOC2=CC1=O] |

TABLE 2-continued
Representative Compounds of the Invention.
| Compound | Chemical Structure |
|---|---|
| 88 | 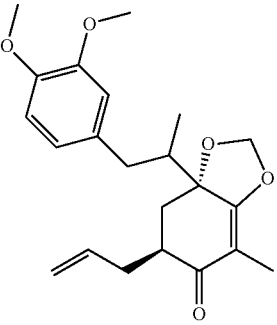 [SMILES: C=CC[C@H]1C[C@]2(C(C)Cc3ccc(OC)c(OC)c3)OCOC2=C(C)C1=O] |
| 89 | 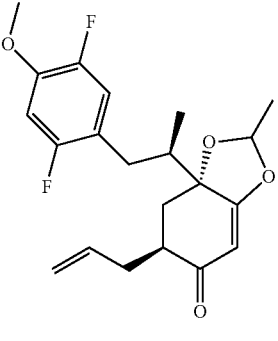 |
| 90 | 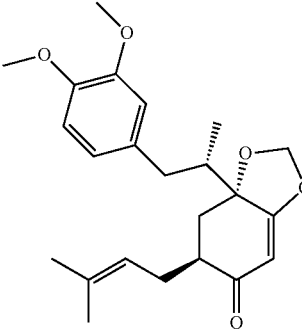 |
| 108 | 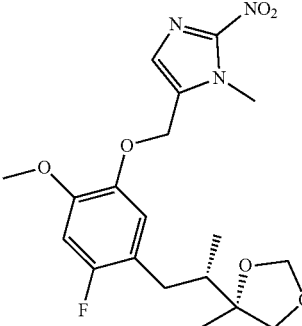 |
| 109 | 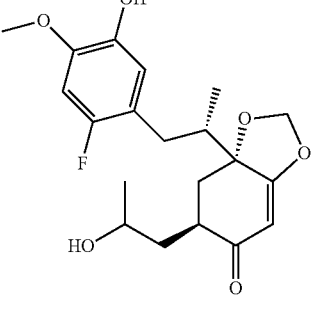 |
| 110 | 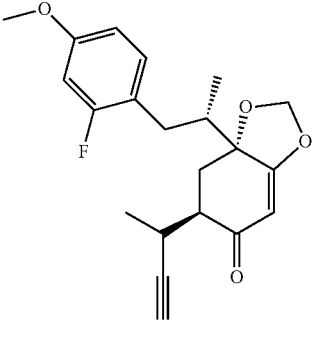 [SMILES: C#CC(C)[C@H]1C[C@]2([C@@H](C)Cc3ccc(OC)cc3F)OCOC2=CC1=O] |
| 111 | 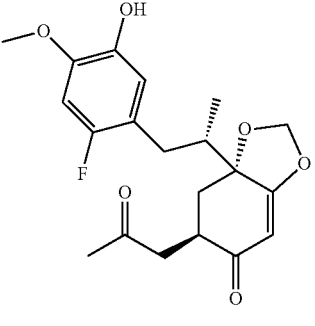 [SMILES: COc1cc(F)c(C[C@H](C)[C@]23C[C@H](CC(C)=O)C(=O)C=C2OCO3)cc1O] |
| 112 | 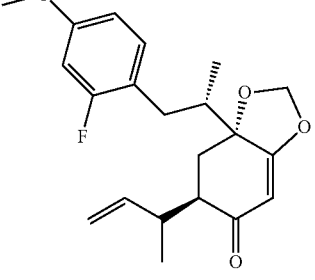 |

TABLE 2-continued

Representative Compounds of the Invention.

| Compound | Chemical Structure |
|---|---|
| 13 | 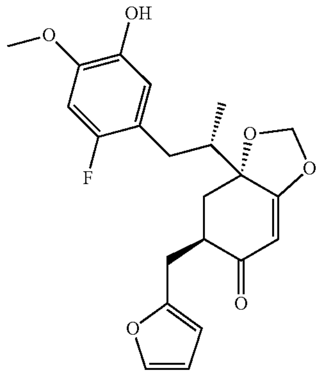 [SMILES: COc1cc(F)c(C[C@H](C)[C@]23C[C@H](Cc4ccco4)C(=O)C=C2OCO3)cc1O] |
| 114 | 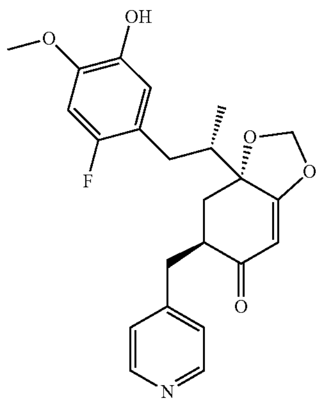 [SMILES: COc1cc(F)c(C[C@H](C)[C@]23C[C@H](Cc4ccncc4)C(=O)C=C2OCO3)cc1O] |
| 115 | 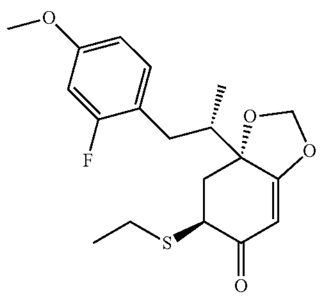 [SMILES: CCS[C@H]1C[C@]2([C@@H](C)Cc3ccc(OC)cc3F)OCOC2=CC1=O] |
| 116 | 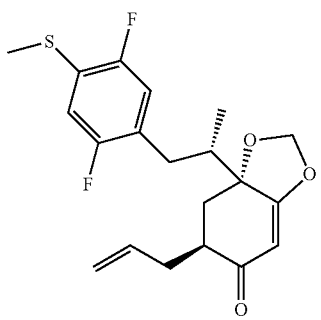 [SMILES: C=CC[C@H]1C[C@]2([C@@H](C)Cc3cc(F)c(SC)cc3F)OCOC2=CC1=O] |

The compounds of the invention described herein may be identified by name instead of, or in addition to, the structure. The name encompasses any stereoisomeric form, its corresponding enantiomers ((+) and (−) isomers) and diastereomers thereof, and mixtures thereof, and is not limited to any one stereoisomeric form. For example, 6-allyl-7a-(1-(2-fluoro-4-methoxyphenyl)propan-2-yl)-7,7a-dihydrobenzo[d][1,3]dioxol-5(6H)-one comprises compounds 2 and 3 above. 6-allyl-7a-(1-(2-fluoro-5-hydroxy-4-methoxyphenyl)propan-2-yl)-7,7a-dihydrobenzo[d][1,3]dioxol-5(6H)-one comprises compounds 4 and 5 above. 6-allyl-7a-(1-(2,5-difluoro-4-methoxyphenyl)propan-2-yl)-7,7a-dihydrobenzo[d][1,3]dioxol-5(6H)-one comprises compounds 6 and 7 above. 6-allyl-7a-(1-(2,5-difluoro-4-(methylamino)phenyl)propan-2-yl)-7,7a-dihydrobenzo[d][1,3]dioxol-5(6H)-one comprises compounds 44 and 45 above.

Compounds of the Invention

The present invention provides compounds of the following chemical formula (I)

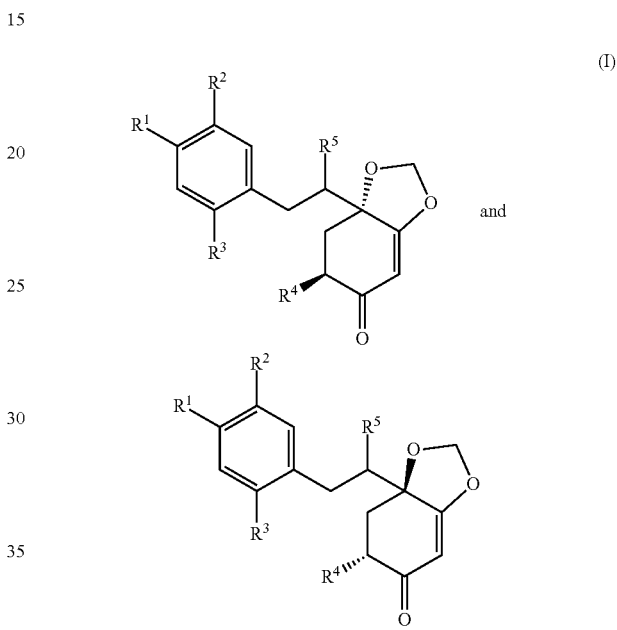

(I)

and or stereoisomers thereof, wherein $R^1$ is selected from the group consisting of methoxy, ethoxy, —SCH$_3$, —SCH$_2$CH$_3$, and —NR$^8$R$^9$; $R^2$ is selected from the group consisting of hydrogen, hydroxyl, alkoxy, amino, aminoalkyl, aminoalkenyl, aminoalkynyl, halide, haloalkyl, hydroxyalkyl, —NHCN, aminocarbonyl, hydroxyaminocarbonyl, alkylaminocarbonyl, acyloxy, nitrile, —CH$_2$CN, lower alkyl, substituted lower alkyl, lower alkenyl, lower alkynyl, —SH, —SCH$_3$, alkoxycarbonyl, alkylcarbonylamino, —NHC(O)—O-lower alkyl, —NHC(O)—O-lower alkenyl, —NHC(O)—O-lower alkynyl, —NHCO-cyclopropyl, —NHCO-haloalkyl, —NHSO$_2$CH$_3$, —NHCSNHCH$_3$, sulfoximine, —CH=NOH, —SOCH$_3$, —SO$_2$CH$_3$, —NHSO$_2$CH$_3$, and —SO$_2$NH$_2$; $R^3$ is selected from the group consisting of hydrogen, halide, haloalkyl, hydroxyl, amino, methylamino, —CH$_2$OH, methoxy, lower alkyl, lower alkenyl, lower alkynyl, acyloxy, alkylcarbonylamino, —C(O)OCH$_3$, nitrile, and —CH$_2$CN; $R^4$ is selected from the group consisting of lower alkyl, substituted lower alkyl, lower alkenyl, substituted lower alkenyl, lower alkynyl, substituted lower alkynyl, alkoxy, alkoxyalkyl, alkoxyalkenyl, alkoxyalkynyl, alkyl ether, alkylthio, alkenylthio, alkynylthio, thioalkyl ether, —(CH$_2$)$_m$-A, and C$_2$-C$_3$ alkenyl-A; $R^5$ is selected from the group consisting of lower alkyl, lower alkenyl, and haloalkyl; $R^8$ and $R^9$ are independently selected from the group consisting of hydrogen, lower alkyl, substituted lower alkyl, lower alkenyl, substituted lower alkenyl, and cycloalkyl; A is selected from the group consisting of cycloalkyl, cycloalkenyl, heteroaryl, heterocycloalkyl, phenyl, and substituted phenyl, and m is selected from the group consisting of 0, 1, 2, and 3; provided that $R^2$ is not methoxy when $R^1$ is methoxy, $R^3$ is hydrogen, and $R^4$ is 2-propenyl.

Another embodiment of the present invention provides compounds of formula (I), provided that $R^2$ is not hydrogen, hydroxyl, or methoxy when $R^1$ is methoxy, $R^3$ is hydrogen, and $R^4$ is 2-propenyl, propyl, ethyl, or butyl.

Another embodiment of the present invention provides compounds of formula (I), provided that $R^3$ is not hydroxyl or methoxy, when $R^1$ is methoxy, and $R^4$ is 2-propenyl, propyl, ethyl, or butyl.

Another embodiment of the present invention provides compounds of formula (I), provided that $R^2$ is not methoxy when $R^1$ is methoxy and $R^3$ is hydrogen.

Another embodiment of the present invention provides compounds of the formula (I), when $R^1$ is selected from the group consisting of methoxy, —$SCH_3$, —$OCF_3$, —$OCHF_2$, —$OCH_2F$, —$OCH_2Cl$, and $OCHCl_2$.

Another embodiment of the present invention provides compounds of the formula (I), when the aminocarbonyl of $R^2$ is replaced with a bioisostere selected from the group of 1,2,4-oxadiazole, 1,3,4-oxadiazole, and 4H-1,2,4-triazole.

Another embodiment of the present invention provides compounds that are the (+)-enantiomers of formula (I).

Another embodiment of the present invention provides compounds of the formula (II)

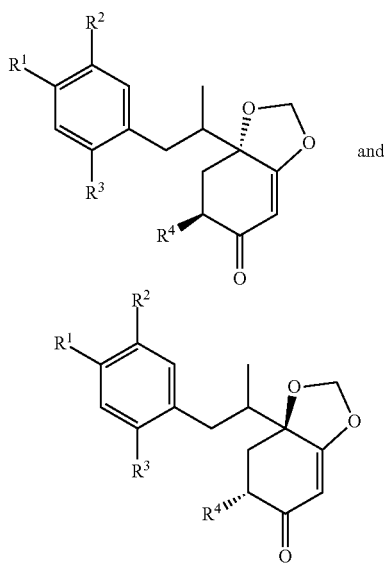

or stereoisomers thereof, wherein $R^1$ is selected from the group consisting of methoxy, ethoxy, —$SCH_3$, —$SCH_2CH_3$, and —$NR^8R^9$; $R^2$ is selected from the group consisting of hydrogen, hydroxyl, alkoxy, amino, aminoalkyl, aminoalkenyl, aminoalkynyl, halide, haloalkyl, hydroxyalkyl, —NHCN, aminocarbonyl, hydroxyaminocarbonyl, alkylaminocarbonyl, acyloxy, nitrile, —$CH_2CN$, lower alkyl, substituted lower alkyl, lower alkenyl, lower alkynyl, —SH, —$SCH_3$, alkoxycarbonyl, alkylcarbonylamino, —NHCO-cyclopropyl, —NHCO-haloalkyl, —$NHSO_2CH_3$, —NHCSNHCH$_3$, sulfoximine, —CH=NOH, —$SOCH_3$, —$SO_2CH_3$, —$NHSO_2CH_3$, and —$SO_2NH_2$; $R^3$ is selected from the group consisting of hydrogen, halide, haloalkyl, hydroxyl, —$CH_2OH$, methoxy, lower alkyl, lower alkenyl, lower alkynyl, acyloxy, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkoxy, alkoxyalkyl, alkoxyalkenyl, alkoxyalkynyl, alkyl ether, alkylthio, alkenylthio, alkynylthio, thioalkyl ether; $R^8$ and $R^9$ are independently selected from the group consisting of hydrogen, lower alkyl, substituted lower alkyl, lower alkenyl, and cycloalkyl; provided that $R^2$ is not methoxy when $R^1$ is methoxy, $R^3$ is hydrogen, and $R^4$ is 2-propenyl.

Another embodiment of the present invention provides compounds of formula (II), provided that $R^2$ is not hydrogen, hydroxyl, or methoxy when $R^1$ is methoxy, $R^3$ is hydrogen, and $R^4$ is 2-propenyl, propyl, ethyl, or butyl.

Another embodiment of the present invention provides compounds of formula (II), provided that $R^3$ is not hydroxyl or methoxy, when $R^1$ is methoxy, and $R^4$ is 2-propenyl, propyl, ethyl, or butyl.

Another embodiment of the present invention provides compounds of formula (II), provided that $R^2$ is not methoxy when $R^1$ is methoxy and $R^3$ is hydrogen.

Another embodiment of the present invention provides compounds that are the (+)-enantiomers of formula (II).

Another embodiment of the present invention provides compounds of formula (II) above wherein $R^1$ is selected from the group consisting of methoxy, —$SCH_3$, and —$NR^8R^9$; wherein $R^2$ is selected from the group consisting of hydrogen, hydroxyl, alkoxy, amino, aminoalkyl, aminoalkenyl, halide, haloalkyl, aminocarbonyl, hydroxyaminocarbonyl, alkylaminocarbonyl, acyloxy, nitrile, —$CH_2CN$, lower alkyl, lower alkenyl, alkoxycarbonyl, and alkylcarbonylamino; $R^3$ is selected from the group consisting of hydrogen, halide, haloalkyl, lower alkyl, ethenyl, ethynyl, acyloxy, —$C(O)OCH_3$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, alkylthio, alkenylthio, alkynylthio, and thioalkyl ether; and $R^8$ and $R^9$ are independently selected from the group consisting of hydrogen and lower alkyl; provided that $R^2$ is not methoxy when $R^1$ is methoxy, $R^3$ is hydrogen, and $R^4$ is 2-propenyl.

Another embodiment of the present invention provides compounds of formula (II) above wherein $R^1$ is selected from the group consisting of methoxy, —$SCH_3$, —$NHCH_3$, —$N(CH_3)_2$; $R^2$ is selected from the group consisting of hydrogen, hydroxyl, unsubstituted alkoxy, amino, aminoalkyl, aminoalkenyl, halide, haloalkyl, aminocarbonyl, hydroxyaminocarbonyl, methylaminocarbonyl, ethylaminocarbonyl, acetoxy, propionyloxy, nitrile, —$CH_2CN$, lower alkyl, ethenyl, ethynyl, alkoxycarbonyl, and alkylcarbonylamino; $R^3$ is selected from the group consisting of hydrogen, halide, haloalkyl, methyl, ethyl, propyl, acetoxy, —$C(O)OCH_3$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, and thioalkyl ether; provided that $R^2$ is not methoxy when $R^1$ is methoxy, $R^3$ is hydrogen, and $R^4$ is 2-propenyl.

Another embodiment of the present invention provides compounds of formula (II) above wherein $R^1$ is selected from the group consisting of methoxy, —$NHCH_3$, and —$N(CH_3)_2$; $R^2$ is selected from the group consisting of hydrogen, hydroxyl, methoxy, ethoxy, amino, —$NHCH_3$, halide, methyl, ethyl, propyl, ethenyl, ethynyl, aminocarbonyl, hydroxyaminocarbonyl, methylaminocarbonyl, acetoxy, propionyloxy, nitrile, —CH₂CN, alkoxycarbonyl, and alkylcarbonylamino; R³ is selected from the group consisting of hydrogen, fluoro, chloro, methyl, ethyl, acetoxy, —C(O)OCH₃, nitrile, and —CH₂CN; R⁴ is selected from the group consisting of substituted lower alkyl, lower alkenyl, substituted lower alkenyl, lower alkynyl, substituted lower alkynyl, and thioalkyl ether; provided that R² is not methoxy when R¹ is methoxy, R³ is hydrogen, and R⁴ is 2-propenyl.

Another embodiment of the present invention provides compounds of the following formula (III)

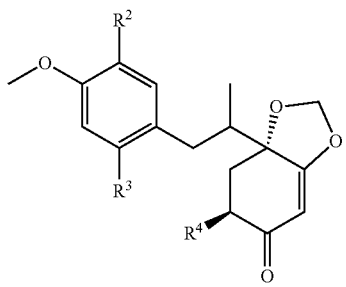

(III)

or stereoisomers thereof, wherein R² is selected from the group consisting of hydrogen, hydroxyl, unsubstituted alkoxy, amino, aminoalkyl, aminoalkenyl, halide, haloalkyl, aminocarbonyl, hydroxyaminocarbonyl, alkylaminocarbonyl, acyloxy, nitrile, —CH₂CN, lower alkyl, lower alkenyl, alkoxycarbonyl, and alkylcarbonylamino; R³ is selected from the group consisting of hydrogen, halide, haloalkyl, lower alkyl, lower alkenyl, acyloxy, —C(O)OCH₃, nitrile, and —CH₂CN; R⁴ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, alkylthio, alkenylthio, alkynylthio, and thioalkyl ether; provided that R² is not methoxy when R³ is hydrogen and R⁴ is 2-propenyl.

Another embodiment of the present invention provides compounds of formula (III), provided that R² is not hydrogen, hydroxyl, or methoxy when R¹ is methoxy, R³ is hydrogen, and R⁴ is 2-propenyl, propyl, ethyl, or butyl.

Another embodiment of the present invention provides compounds of formula (III), provided that R³ is not hydroxyl or methoxy, when R¹ is methoxy, and R⁴ is 2-propenyl, propyl, ethyl, or butyl.

Another embodiment of the present invention provides compounds of formula (III), provided that R² is not methoxy when R¹ is methoxy and R³ is hydrogen.

Another embodiment of the present invention provides compounds that are enantiomers of formula (III).

Another embodiment of the present invention provides compounds that are the (+)-enantiomers of formula (III).

Another embodiment of the present invention provides compounds of the following formula (IV)

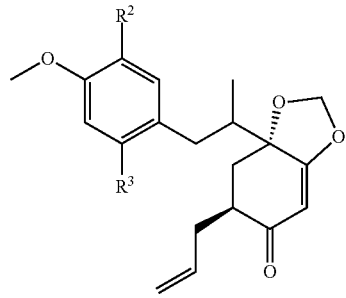

(IV)

or stereoisomers thereof, wherein R² is selected from the group consisting of hydrogen, hydroxyl, unsubstituted alkoxy, amino, aminoalkyl, aminoalkenyl, halide, haloalkyl, aminocarbonyl, hydroxyaminocarbonyl, alkylaminocarbonyl, acyloxy, nitrile, —CH₂CN, lower alkyl, lower alkenyl, alkoxycarbonyl, and alkylcarbonylamino; and R³ is selected from the group consisting of hydrogen, halide, and methyl; provided that R² is not methoxy when R³ is hydrogen.

Another embodiment of the present invention provides compounds of formula (IV), provided that R² is not hydrogen, hydroxyl, or methoxy when R¹ is methoxy and R³ is hydrogen.

Another embodiment of the present invention provides compounds of formula (IV), provided that R³ is not hydroxyl or methoxy, when R¹ is methoxy.

Another embodiment of the present invention provides compounds that are enantiomers of formula (IV).

Another embodiment of the present invention provides compounds that are the (+)-enantiomers of formula (IV).

Another embodiment of the present invention provides compounds of the following formula (V)

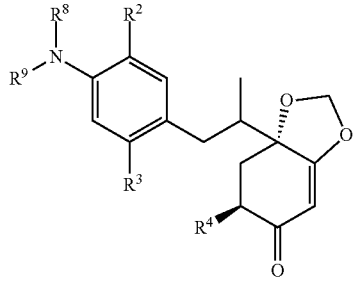

(V)

or stereoisomers thereof, wherein R² is selected from the group consisting of hydrogen, hydroxyl, methoxy, ethoxy, amino, —NHCH₃, fluoro, chloro, methyl, ethyl, ethenyl, ethynyl, haloalkyl, aminocarbonyl, hydroxyaminocarbonyl, methylaminocarbonyl, acetoxy, propionyloxy, nitrile, —CH₂CN, alkoxycarbonyl, and alkylcarbonylamino; R³ is selected from the group consisting of hydrogen, fluoro, chloro, methyl, ethyl, propyl, and haloalkyl; R⁴ is selected from the group consisting of of lower alkyl, substituted lower alkyl, lower alkenyl, substituted lower alkenyl, lower alkynyl, substituted lower alkynyl and thioalkyl ether; and wherein R⁸ and R⁹ are independently selected from the group consisting of hydrogen, methyl, ethyl, propyl, ethenyl, propenyl, and cycloalkyl.

Another embodiment of the present invention provides compounds that are enantiomers of formula (V).

Another embodiment of the present invention provides compounds that are the (+)-enantiomers of formula (V).

Another embodiment of the present invention provides compounds of the following formula (VI)

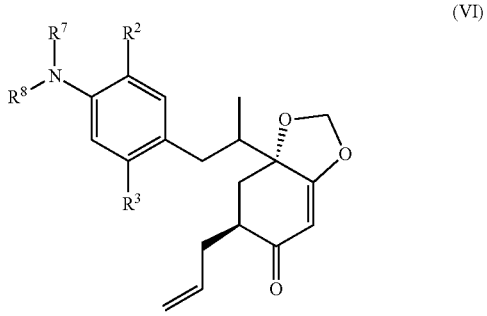

(VI)

or stereoisomers thereof, wherein $R^2$ is selected from the group consisting of hydrogen, fluoro, chloro, methyl, ethyl, propyl, ethenyl, propenyl, and haloalkyl; $R^3$ is selected from the group consisting of hydrogen, halide, methyl, and haloalkyl; and $R^8$ and $R^9$ are independently selected from the group consisting of hydrogen, methyl, ethyl, propyl, ethenyl, propenyl, and cyclopropyl.

Another embodiment of the present invention provides compounds that are enantiomers of formula (VI).

Another embodiment of the present invention provides compounds that are the (+)-enantiomers of formula (VI).

The present invention also provides compounds of the following formula (VII)

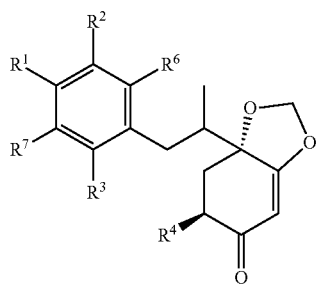

or stereoisomers thereof, wherein $R^1$ is selected from the group consisting of methoxy, ethoxy, —NHCH$_3$, and —N(CH$_3$)$_2$; $R^2$ is selected from the group consisting of hydrogen, hydroxyl, ethoxy, amino, aminoalkyl, aminoalkenyl, fluoro, chloro, aminocarbonyl, hydroxyaminocarbonyl, methylaminocarbonyl, ethylaminocarbonyl, acetoxy, nitrile, lower alkyl, lower alkenyl, lower alkynyl, alkoxycarbonyl, and alkylcarbonylamino; $R^3$ is selected from the group consisting of hydrogen, fluoro, chloro, lower alkyl, lower alkenyl, haloalkyl, acetoxy, —C(O)OCH$_3$, nitrile, and —CH$_2$CN; $R^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, and thioalkyl ether; $R^6$ is selected from the group consisting of hydrogen, halide, methoxy, ethoxy, methyl, ethyl, propyl, nitrile, and acetoxy; $R^7$ is selected from the group consisting of hydrogen, halide, hydroxyl, amino, methoxy, ethoxy, methyl, ethyl, propyl, nitrile, and acetoxy, or pharmaceutically acceptable salts, solvates, or prodrugs thereof; provided that when $R^2$ is hydrogen $R^3$ is not hydrogen and only one of either $R^6$ or $R^7$ are hydrogen; $R^2$, $R^3$, $R^6$, and $R^7$ are all not hydrogen; and $R^2$ is not methoxy when $R^1$ is methoxy, $R^3$ is hydrogen, and $R^4$ is 2-propenyl.

Another embodiment of the present invention provides compounds of formula (VII), provided that $R^2$ is not hydrogen, hydroxyl, or methoxy when $R^1$ is methoxy, $R^3$ is hydrogen, and $R^4$ is 2-propenyl, propyl, ethyl, or butyl.

Another embodiment of the present invention provides compounds of formula (VII), provided that $R^3$ is not hydroxyl or methoxy, when $R^1$ is methoxy, and $R^4$ is 2-propenyl, propyl, ethyl, or butyl.

Another embodiment of the present invention provides compounds of formula (VII), provided that $R^2$ is not methoxy when $R^1$ is methoxy and $R^3$ is hydrogen.

Another embodiment of the present invention provides compounds that are enantiomers of formula (VII).

Another embodiment of the present invention provides compounds that are the (+)-enantiomers of formula (VII).

Compositions And Methods Of Use

Compositions containing the compounds described above and a pharmaceutically acceptable carrier are also contemplated by this invention. As demonstrated herein such compositions are useful in reducing or inhibiting tumor growth or for the treatment of cancer.

This invention also provides methods for reducing or inhibiting tumor growth comprising contacting the tissue or cell capable of tumor formation with an effective amount of a composition or a compound described above.

In another embodiment, compounds described herein are useful in combination with known anticancer, antitumor, and cytotoxic agents and treatments, including radiation. A preferred combination is with platinum-based anticancer agents.

Various pharmaceutical compositions contemplated by the present invention, including the compounds of the invention and the specific examples described herein, further including pharmaceutically acceptable derivable prodrugs or prodrugs thereof. A "pharmaceutically acceptable derivable prodrug or prodrug" means any pharmaceutically acceptable salt, ester, salt of an ester, or other derivable prodrug of a compound of this invention which, upon administration to a patient, is capable of providing (directly or indirectly) a compound used in this invention. Preferably, prodrugs are derivatives of the compounds of this invention which are readily convertible into the required compound, in vivo or other environment. Pertaining to methods of treatment or administration of the compounds of the invention, these methods shall encompass the treatment of conditions with a compound that converts to a compound of the invention after administration to the patient. It will be recognized that the efficacy of the compounds of this invention is related to localized reaction sites on the compounds. Accordingly, as illustrated by the examples below, a wide variety of substitutions therefore may be made at various sites on the compounds spatially remote from the localized reaction sites that do not significantly interfere with the efficacy of the compounds. Likewise, substitutions to form pharmaceutically acceptable salts, esters, salts of esters, and other such derivable prodrugs of the compounds of this invention are contemplated herein as well. Thus, compounds with such innocuous substitutions do not depart from the scope of the invention. Examples of these prodrugs are demonstrated herein.

On the other hand, however, certain moieties have been found to be so significant in size or reactivity as to interfere significantly with the efficacy of the compounds. Thus, highly reactive, polar, ionic or large substituents such as those shown in the examples below as having a deleterious effect on the activity of the compound are less preferred.

Pharmaceutically acceptable salts include inorganic and organic salts. Preferably an appropriate salt form is selected based on physical and chemical stability, flowability, hygroscopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic or organic bases. When the compound of the present invention is basic, its corresponding salt can be prepared from inorganic or organic acids.

The pharmaceutically acceptable acid salts of the present invention also comprise solvates that the compositions of the present invention may form, which are included within the scope of the present invention. "Solvate" refers to a complex formed by a compound of the invention or a pharmaceutically acceptable salt thereof and a solvent, of variable stoichiometry. Examples of solvents include, but are not limited to water, ethanol, and acetic acid.

Such pharmacologic compositions may be formulated in various ways known in the art for administration purposes. Pharmaceutical compositions of the present invention can be prepared by combining an effective amount of the particular compound of this invention, as the active ingredient with one or more pharmaceutically acceptable carriers and delivery vehicles. Numerous pharmaceutically acceptable carriers and delivery vehicles exist that are readily accessible and well-known in the art, which may be employed to generate the preparation desired (i.e. that permit administration of the pharmaceutical composition orally, topically, rectally, percutaneously, by parenteral injection, intravenously, intravenous infusion, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like. Other constituents, such as aids for taste, color, tableting, and so forth, may be combined with the active ingredient and carrier for any of the many known purposes of such additives. Examples of such additives are discussed below.

The pharmacologic compositions described herein may further be prepared in unitary dosage form for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivable prodrugs, and disintegrating agents and the like may be used to prepare, for example, powders, pills, capsules and tablets.

For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

For pharmaceutically acceptable carriers that permit intranasal administration, the pharmaceutically acceptable carriers often comprise poly acrylic acids such as Carbopol® 940, polyethylene glycol ethers, nonionic surfactants, a hydrogenated castor oil such as Cremophor® RH40 or Cremophor EL, glycerol, vinylpyrrolidones such as PVP-K90 or PVP-K30, polyethylene glycols such as PEG 1450, benzyl alcohol, edetate sodium, hydroxycellulose, potassium chloride, potassium phosphate, and sodium phosphate. Compositions used for intranasal administration also commonly include benzalkonium chloride as an anti-microbial preservative.

For pharmaceutically acceptable carriers that permit administration by inhalation, the pharmaceutically acceptable carriers often comprise solvent/carrier/water mixtures that are easily dispersed and inhaled via a nebulizer or inhaler. For example, a mixture of ethanol/propylene glycol/water in the ratio of about 85:10:5 (parts ethanol: parts propylene glycol: parts water) can be used to administer the compounds and compositions of the invention via inhalation. Ratios as expressed herein are based on parts by weight.

For pharmaceutically acceptable carriers that permit percutaneous administration, the pharmaceutically acceptable carrier may, optionally, comprise a penetration enhancing agent and/or a wetting agent.

Dosage forms that permit topical or transdermal administration of a compound of this invention include ointments, pastes, creams, lotions, gels, powders, solutions, sprays, inhalants or patches. The active compound or compounds is/are mixed under sterile conditions with a pharmaceutically acceptable carrier and optionally one or more preservatives and/or buffers.

The ointments, pastes, creams and gels may contain, in addition to an active compound or compounds according to the present invention, pharmaceutically acceptable carriers that permit topical or transdermal administration such as animal and vegetable fats, oils, waxes, paraffins, starch, tragacanth, cellulose derivable prodrugs, polyethylene glycols, silicones, bentonites, silicic acid, talc and zinc oxide, or mixtures thereof.

In some cases, the pH of the pharmaceutical formulations contemplated herein may be adjusted with acceptable acids, bases or buffers to enhance the stability of one or more of the active compounds present or their delivery forms.

Still further, in order to prolong the effect of a compound disclosed herein, it may be desirable to slow the absorption of the compound from subcutaneous or intramuscular injection. This may be accomplished using a liquid suspension of crystalline or amorphous material with poor water solubility. The rate of absorption of the compound then depends upon its rate of dissolution, which, in turn, may depend upon crystal size and crystalline form. Alternatively, delayed absorption of a parenterally administered drug form may be accomplished by dissolving or suspending the compound in an oil vehicle.

Injectable depot forms are made, e.g., by forming microencapsule matrices of one or more compounds of the present invention in biodegradable polymers such as polylactide-polyglycolide. Depending upon the ratio of active(s) to polymer and the nature of the particular polymer employed, the rate at which such active(s) is released may be controlled. Examples of other biodegradable polymers include poly(orthoesters) and poly(anhydrides). Depot injectable formulations are also prepared by entrapping the compound in liposomes or microemulsions that are compatible with body tissues.

Compounds of the invention may optionally include heavier isotopes including but not limited to deuterium. For example, hydrogen exchanged for deuterium may include some, most, or all of the hydrogens of the compound of an invention. Enriching for dueterium may afford certain theraputic advantages. Isotopically-enriched compounds can be prepared by techniques well known to those skilled in the art. Examples include, but are not limited to, the following.

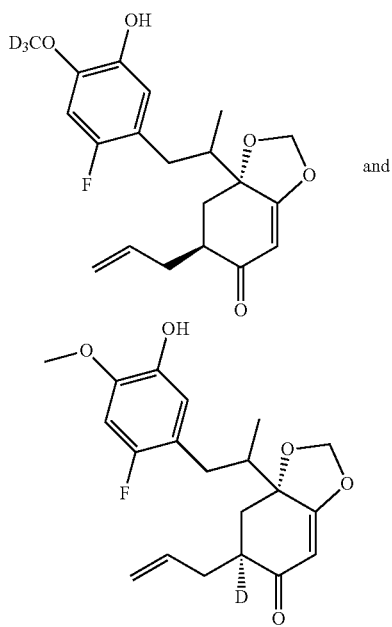

In another embodiment, novel compounds or intermediates produced during the synthesis of the compounds of the invention are provided. As described herein and shown in the examples, novel compounds or intermediates produced during the preparation of compounds selected from the groups of formula (I)-(VII) are provided.

In another embodiment, the present invention provides novel synthetic procedures or processes to produce novel synthetic intermediates for the preparation of the compounds of the invention. Described herein and shown in the examples are procedures and processes for preparing the intermediates of the processes to prepare the compounds selected from the groups of formula (I)-(VII). In addition, the present invention relates to stereospecific processes for preparing intermediates useful in the synthesis of the compounds of this invention, which processes are part of the invention.

In another embodiment, novel synthetic procedures or processes to produce the compounds of the invention are described. These synthetic procedures or processes are described in the examples herein and comprise preparing the compounds selected from the group of formula (I)-(VII). In addition, the present invention relates to stereospecific processes for preparing compounds of this invention having the correct relative and absolute stereochemistry from achiral starting materials, which processes are also part of the invention.

In another embodiment, the present invention provides compositions and methods of administering the compounds of the invention for the treatment of lung cancer. The examples herein demonstrate that the compounds of the invention reduce the growth of NCI-H460 tumors and other lung cancer cell lines in xenograft models. Non-small lung cell xenografts have been demonstrated to be predictive of clinical activity in the same histology (Johnson, J. I., Decker, S., Zaharevitz, D., Rubinstein, L. V., Venditti, J. M., Schepartz, S., Kalyandrug, S., Christian, M., Arbuck, S., Hollingshead, M., Sausville, E. A., 2001.). In particular, those skilled in the art understand that NCI-H460 xenograft models are not responsive to many anticancer compounds, including anticancer compounds that have been approved by regulatory authorities for the treatment of lung cancer. These preclinical data demonstrate that a preferred embodiment of the invention is for the treatment of lung cancer. Preferably, administration of a therapeutically effective amount of a compound of the invention is to a subject in need.

In another embodiment, an effective amount of a compound of this invention is administered, preferably orally or intravenously, with one or more pharmaceutically acceptable carriers to a subject in need every three weeks. Preferably, an effective amount of a compound of this invention is administered orally or intravenously with one or more pharmaceutically acceptable carriers to a subject in need about every two weeks. More preferably, an effective amount of a compound of this invention is administered, preferably orally or intravenously, with one or more pharmaceutically acceptable carriers to a subject in need about every week. Most preferably, an effective amount of a compound of this invention is administered, preferably orally or intravenously, with one or more pharmaceutically acceptable carriers to a subject in need more than once per week. As known to those skilled in the art, certain anticancer treatments may be given approximately every three weeks or more often depending upon tolerability of the treatment by each subject in need, effectiveness of the treatment, and other defined variables. As shown herein, preclinical studies using the compounds of the invention suggest the compounds will be permitted to be given more often than many conventional anticancer treatments. The increased tolerability of the compounds of the invention when administered to a subject in need is a novel aspect of the invention.

In another embodiment, the present invention provides compositions and methods of administration comprising the compounds of the invention covalently attached to a linker compound that is covalently attached to a small molecule, protein, or antibody and a pharmaceutically acceptable carrier or vehicle. The small molecule, protein or antibody may be conjugated directly to the compounds of the invention, but more preferably by the means of a linker. The examples herein teach how to link the compounds of the invention to linkers and/or moieties used as prodrugs. To those skilled in the art, these compositions may be described as drug conjugates, or more specifically antibody drug conjugates or small molecule drug conjugates. The success of these drug conjugates primarily rests on the cytotoxicity of the drugs, and therefore the invention provides novel compounds to be linked or attached to small molecules, protein or antibodies. Examples of said drug conjugates are described in U.S. Pat. Nos. 7,659,241; 7,662,387, 7,989,434; 8,568,728; and 8,609,105. A further review of drug conjugates more specifically related to the mechanism of the compounds of the invention is described by Vergote et al. (Vergote, I., Leamon, C. P., Vintafolide: a novel targeted therapy for the treatment of folate receptor expressing tumors. Therapeutic Advances in Medical Oncology 7, 206-218.). These references are incorporated herein. Antibodies that have been used in drug-antibody conjugates include but are not limited to anti-CD30 and trastuzumab.

In another embodiment, this invention relates to compositions and methods of administering the compounds of the invention for the treatment of inflammatory disorders such as gout and other related disorders including but not limited to inflammatory arthritis, familial Mediterranean fever or Behcet's disease. Not to be bound by theory, colchicine has a mechanism of action broadly related to the compounds of the invention and has been used to treat gout and other inflammatory disorders, including but not limited to, familial Mediterranean fever, pericarditis, Behcet's disease, and constipation.

In another embodiment, methods of seed, seedling, or plant treatment with the compounds of the invention are provided that produce new varieties or advantageous or desirable characteristics or traits. Not to be bound by theory, colchicine has been used historically to treat seeds to produce desired traits. Since the mechanism of the compounds of the invention is broadly related to colchicine's mechanism, the compounds of the invention may be used to treat seeds, seedlings, or plants to produce certain characteristics or traits.

EXAMPLES

Example I

Synthesis Procedures for the Compounds of this Invention

Listed below are general procedures that can be used to synthesize the final compounds of this invention, followed by analytical data for the compounds synthesized. The majority of the analogues described in this invention were prepared by the general procedure A. The analogues with an —OH group on the phenyl were prepared by the general procedure C. The analogues with —NH$_2$, —NHMe, —NMe$_2$, —CO$_2$H, —CONH$_2$, —CONHMe, —CONMe$_2$, -Ph, —CN, morpholine or tetrazole substitutions on the phenyl were prepared from the intermediates in the preparation of the —OH analogues by various synthetic protocols described in this invention. The analogues with variations at R$^4$ were prepared from the advanced intermediates by various synthetic protocols described in this invention. The synthetic procedures described are only examples of syntheses that may be used to prepare the final compounds of the invention. Other synthetic or partially synthetic methods may be used to prepare the final compounds of the invention.

Structures are drawn herein to show relative stereochemistry, and no representation is made to the absolute configuration that corresponds to the (+) or (−) enantiomer. Compound names in this example are provided for illustrative purposes only. To the extent the names are considered inconsistent with the structures, the names do not supersede the drawn structures. Atom numbering applies to this example only and does not necessarily correspond to atom numbering in the rest of the document.

General Synthetic Methods

Unless otherwise noted, reagents and solvents were used as received from commercial suppliers. Proton nuclear magnetic resonance spectra were obtained on a Bruker AVANCE 300 spectrometer at 300 MHz or Bruker AVANCE 500 spectrometer at 500 MHz or Bruker AVANCE 600 spectrometer at 600 MHz. Spectra are given in ppm (□) and coupling constants, J values, are reported in hertz (Hz). Tetramethylsilane was used as an internal standard for $^1$H nuclear magnetic resonance or spectra were referenced to the residual solvent signal. Mass spectra analyses were performed on Agilent 6130A Mass Spectrometer in ESI, APCI, or MultiMode mode when appropriate or Applied Biosystems API-150EX Spectrometer in ESI or APCI mode when appropriate.

Preparative Chiral HPLC

Preparative chiral HPLC was conducted using a CHIRALPAK AD (5 cm×50 cm, 20 μm) or CHIRALCEL OD (5 cm×50 cm, 20 μm) with a flow rate at 100 mL/min.

Preparation of Intermediates

The following describes processes that may be used to synthesize intermedicates that may be used to prepare compounds of the invention. As indicated above, other synthetic methods, either in whole or in part, may be used to prepare the intermediates.

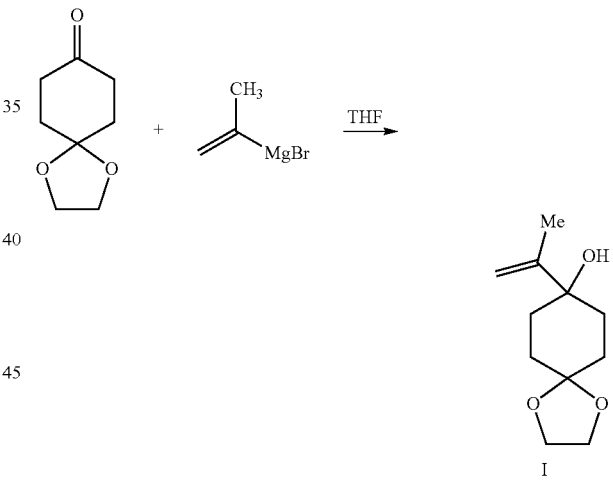

Preparation of intermediate I.

To a three-neck flask equipped with a mechanical stirrer, an addition funnel and a thermometer, was charged a solution of isopropenyl magnesium bromide (0.5M solution in THF, 1.6 L, 0.80 mol) by cannula under a nitrogen atmosphere. The solution was cooled to 0-5° C. A solution of 1,4-dioxaspiro[4.5]decan-8-one (100 g, 0.64 mol) in THF (600 mL) was slowly added by an addition funnel over 2 h while keeping the temperature below 5° C. After the addition, the reaction mixture continued to stir for 2 h. The reaction was quenched by saturated ammonium chloride (200 mL) and extracted with ethyl acetate (2 L). The organic phase was washed with brine, dried (MgSO$_4$), and concentrated in vacuo to provide I as a brown oil (123 g, 100%). The product was used without further purification. $^1$H NMR (300 MHz, CDCl$_3$): δ 5.30 (s, 1H), 5.05 (s, 1H), 4.00-3.91 (m, 4H), 2.04-1.95 (m, 4H), 1.81 (s, 3H), 1.68 (d, J=12.9 Hz, 4H), 1.17 (s, 1H).

Preparation of intermediate II.

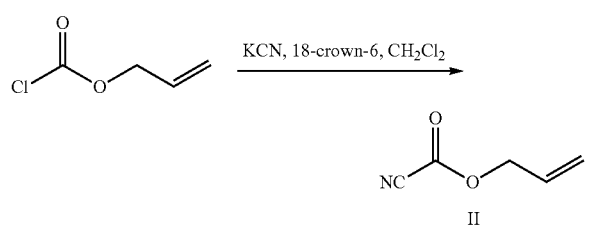

A mixture of allyl chloroformate (48 g, 0.40 mol), KCN (28.8 g, 0.44 mol) and 18-crown-6 (400 mg) in CH$_2$Cl$_2$ (400 mL) was stirred under a nitrogen atmosphere at room temperature for 24 h. The reaction mixture was filtered and washed with CH$_2$Cl$_2$ (50 mL). The filtrate was distilled to remove CH$_2$Cl$_2$ at 60° C. (oil bath temperature). The oil bath temperature was heated to 100° C. The product was distilled under reduced pressure (120 mmHg) to provide II (25 g, 57%) as a colorless oil. $^1$H NMR (500 MHz, CDCl$_3$): δ 6.01-5.93 (m, 1H), 5.44 (dd, J=18.5, 3.0 Hz, 1H), 5.35 (dd, J=10.5, 2.5 Hz, 1H), 4.80 (dd, J=6.5, 5.5 Hz, 2H).

Preparation of intermediate III.

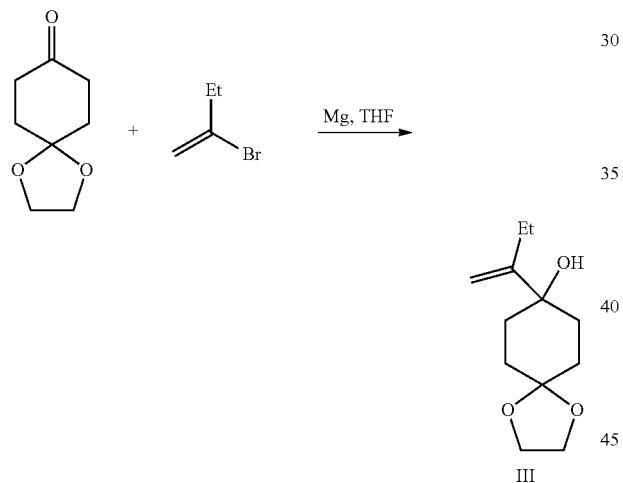

A mixture of magnesium turnings (5.3 g, 220 mmol) and a catalytic amount of I$_2$ in anhydrous THF (400 mL) was heated to 50° C. for 10 min under a nitrogen atmosphere. The dark brown solution became a colorless solution. 2-Bromobut-1-ene (28.5 g, 210 mmol) was added slowly. After the addition, the reaction mixture was heated to 50° C. for 2 h. The reaction mixture was cooled to 5° C. A solution of 1,4-dioxaspiro[4.5]decan-8-one (19.7 g, 120 mmol) in anhydrous THF (40 mL) was added below 5° C. After the addition, the reaction mixture continued to stir for 2 h. The reaction was quenched with saturated ammonium chloride (40 mL) and extracted with ethyl acetate (500 mL). The organic phase was washed with brine, dried (MgSO$_4$), and concentrated in vacuo to provide III as a brown oil (25 g, 91%). The product was used without further purification. $^1$H NMR (300 MHz, CDCl$_3$): δ 5.16 (s, 1H), 4.84 (s, 1H), 3.98 (q, J=5.5 Hz, 4H), 2.15-2.10 (m, 2H), 2.00-1.96 (m, 4H), 1.62-1.53 (d, J=9.5 Hz, 4H), 1.09 (t, J=7.0 Hz, 3H).

Preparation of intermediate IV.

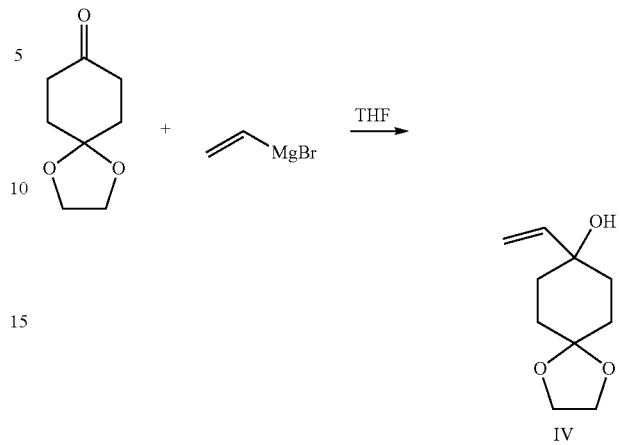

To a solution of vinylmagnesium bromide (1.6M solution in THF, 54 mL, 86.4 mmol) was added a solution of 1,4-dioxaspiro[4.5]decan-8-one (9.0 g, 57.6 mmol) in THF (90 mL) at 0-5° C. under a nitrogen atmosphere. After the addition, the reaction mixture was stirred for 2 h. The reaction was quenched with saturated ammonium chloride (50 mL) and extracted with ethyl acetate (500 mL). The organic phase was washed with brine, dried (MgSO$_4$), and concentrated in vacuo to provide IV (11.1 g, 94%) as a brown oil. The product was used without further purification. $^1$H NMR (500 MHz, CDCl$_3$): δ 6.01 (dd, J=17.0, 10.5 Hz, 1H), 5.30 (d, J=17.0 Hz, 1H), 5.07 (d, J=11.0 Hz, 1H), 3.97-3.92 (m, 4H), 1.97-1.92 (m, 2H), 1.84-1.78 (m, 2H), 1.66-1.61 (m, 4H), 1.27 (s, 1H).

Preparation of intermediate V.

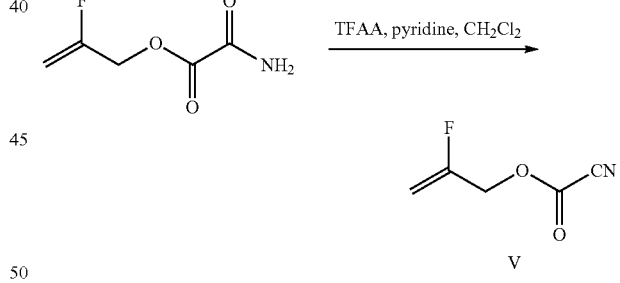

To a solution of 2-fluoroallyl 2-amino-2-oxoacetate (Belokon, Y. N., Clegg, W., Harrington, R. W., Ishibashi, E., Nomura, H., North, M., 2007. Enantioselective and diastereoselective syntheses of cyanohydrin carbonates. Tetrahedron 63, 9724-9740.) (160 mg, 1.08 mmol) and pyridine (0.35 mL, 4.32 mmol) in CH$_2$Cl$_2$ (2 mL) was added trifluoroacetic anhydride (0.27 mL, 1.30 mmol) in an ice bath. The reaction mixture was warmed to room temperature and stirred for 2 h. The reaction mixture was diluted with CH$_2$Cl$_2$ (10 mL) and washed with HCl (2 M), brine, dried (MgSO$_4$). The filtrate was distilled to remove CH$_2$Cl$_2$ at 60° C. (oil bath temperature). The oil bath temperature was then heated to 100° C. The product was distilled under reduced pressure (120 mm Hg) to provide V (50 mg, 30%) as a colorless oil. $^1$H NMR (500 MHz, CDCl$_3$): δ 5.00 (dd, J=8.0, 4.0 Hz, 1H), 4.89 (d, J=24.5 Hz, 2H), 4.88 (d, J=8.0 Hz, 1H).

Preparation of the Final Compounds: General Procedures

The following describes processes that may be used to synthesize the final compounds of the invention. As indicated above, other methods, either in whole or in part, may be used to prepare the compounds of the invention. Reference to compound numbers below refers to the compounds identified in Table 2.

General procedure A: Illustrated with preparation of bifidenone.

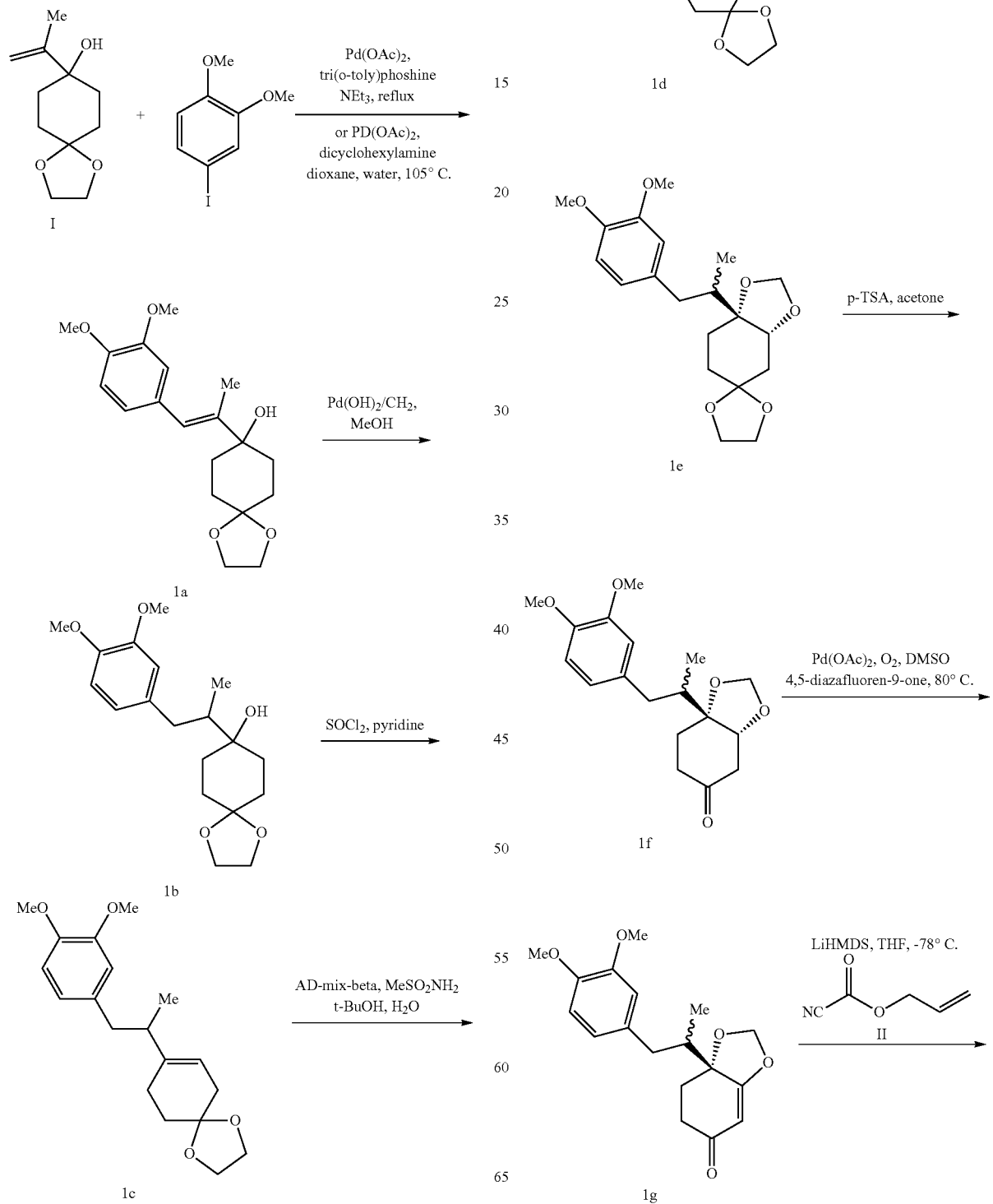

-continued

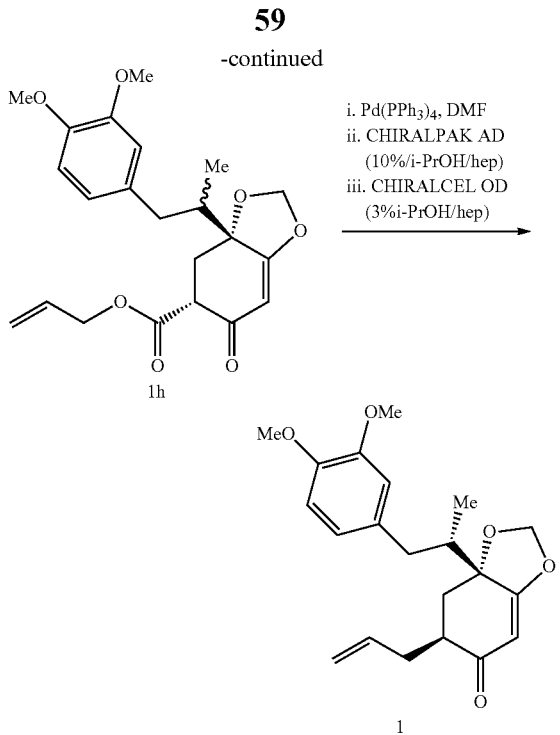

Step 1:

A mixture of I (117.0 g, 590 mmol), 4-iodo-1,2-dimethoxybenzene (85.0 g, 590 mmol), Pd(OAc)$_2$ (13.2 g, 59 mmol) and tri(o-tolyl)phosphine (36.0 g, 118 mmol) in triethylamine (3 L) was heated at 90° C. for 12 h. The mixture was cooled to room temperature and diluted with ethyl acetate (3 L). The organic phase was washed with brine, dried (MgSO$_4$), and concentrated in vacuo to dryness. The crude product was purified by silica gel chromatography (0 to 40% ethyl acetate/hexanes) to provide (la) as a brown oil (87.0 g, 73% based on the recovered starting material). $^1$H NMR (300 MHz, CDCl$_3$): δ 6.85 (s, 2H), 6.79 (s, 1H), 6.64 (s, 1H), 3.98-3.93 (m, 4H), 3.88 (s, 3H), 3.86 (s, 3H), 2.10-2.00 (m, 4H), 1.81 (s, 3H), 1.68 (d, J=12.9 Hz, 4H), 1.17 (s, 1H).

Step 2:

To a solution of la (32.0 g, 100.0 mmol) in 1000 mL of MeOH was added Pd(OH)$_2$/C (20 wt. % Pd on carbon, 6.4 g) under a nitrogen atmosphere. The mixture was stirred under one atmosphere of hydrogen for 1.5 h. The reaction mixture was filtered through a pad of CELITE and the filter cake was washed with ethyl acetate (500 mL). The filtrate was concentrated in vacuo to provide 1b as a colorless oil (28.0 g, 88%). The crude product was used without further purification. $^1$H NMR (500 MHz, CDCl$_3$): δ 6.79 (d, J=8.0 Hz, 1H), 6.70 (dd, J=8.0, 2.0 Hz, 2H), 3.99-3.93 (m, 4H), 3.86 (s, 3H), 3.85 (s, 3H), 3.04 (dd, J=13.0, 3.0 Hz, 1H), 2.15 (t, J=11.0 Hz, 1H), 1.97-1.92 (m, 2H), 1.86-1.77 (m, 2H), 1.75-1.63 (m, 5H), 0.83 (d, J=7.0 Hz, 3H).

Step 3:

To a solution of 1b (28.0 g, 91.5 mmol) in pyridine (180 mL) was added thionyl chloride (13.3 mL, 183.0 mmol) at 0-5° C. The mixture was stirred at 5° C. for 2 h. Most of the pyridine was removed at reduced pressure. The residue was diluted with ethyl acetate (500 mL) and H$_2$O (100 mL). The organic phase was washed with brine, dried (MgSO$_4$), and concentrated in vacuo to dryness. The crude product was purified by silica gel chromatography (0 to 40% ethyl acetate/hexanes) to provide 1c as a brown oil (21.0 g, 80%). $^1$H NMR (500 MHz, CDCl$_3$): δ 6.77 (dd, J=6.5, 2.0 Hz, 1H), 6.66 (dd, J=6.5, 2.0 Hz, 2H), 5.26 (d, J=3.5 Hz, 1H), 3.97 (d, J=3.5 Hz, 4H), 3.86 (s, 3H), 3.85 (s, 3H), 2.74 (dd, J=13.5, 6.5 Hz, 1H), 2.45-2.41 (m, 1H), 2.33-2.29 (m, 1H), 2.23-2.21 (m, 4H), 1.77-1.74 (m, 2H), 0.98 (d, J=6.5 Hz, 3H).

Step 4:

To a mixture of AD-mix-β (132 g) in t-BuOH (480 mL) and H$_2$O (480 mL) was added a solution of 1c (32.0 g, 100.0 mmol) in an ice bath. Methylanesulfonamide (29.0 g, 300.0 mmol) was added. The reaction mixture was stirred at room temperature for 7 d. The reaction mixture was diluted with MTBE (1000 mL). The organic phase was washed with saturated Na$_2$S$_2$O$_5$, brine, dried (MgSO$_4$) and concentrated in vacuo to dryness. The crude product was purified by silica gel chromatography (0 to 40% ethyl acetate/hexanes) to provide the mixture of diastereomers 1d as a brown oil (23.4 g, 67%). $^1$H NMR (500 MHz, CDCl$_3$): δ 6.79 (d, J=8.0 Hz, 1H), 6.71 (m, 2H), 3.99-3.94 (m, 5H), 3.87 (s, 3H), 3.85 (s, 3H), 3.11 (s, 0.6H), 3.05 (dd, J=13.5, 3.5 Hz, 0.4 H), 2.93 (dd, J=13.5, 3.5 Hz, 0.5H), 2.25-2.20 (m, 2H), 2.13-1.95 (m, 3H), 1.89-1.62 (m, 4H), 1.09 (s, 0.4H), 0.87 (t, J=7.0 Hz, 3H).

Step 5:

To a solution of 1d (14.8 g, 44.3 mmol) in 110 mL of DMF was added NaH (60% dispersion in mineral oil, 5.0 g, 124.1 mmol) in an ice bath under a nitrogen atmosphere. After 1 h, dibromomethane (4.0 mL, 57.6 mmol) was added and the reaction mixture was stirred at room temperature for 12 h. The reaction was diluted with ethyl acetate (1000 mL) and washed with H$_2$O (100 mL). The organic phase was washed with brine, dried (MgSO$_4$), and concentrated in vacuo to dryness. The crude product was purified by silica gel chromatography (0 to 40% ethyl acetate/hexanes) to provide 1e as an off-white solid (680 mg, 82% based on the recovered starting material). $^1$H NMR (500 MHz, CDCl$_3$): δ 6.79 (d, J=8.0 Hz, 1H), 6.69-6.65 (m, 2H), 5.19 (0.3H), 5.16 (s, 0.7H), 4.94 (s, 0.3H), 4.89 (s, 0.7H), 4.20-3.94 (m, 4H), 3.87 (s, 3H), 3.86 (s, 3H), 3.09 (d, J=14.0, 3.0 Hz, 0.3H), 2.80 (dd, J=14.0, 3.0 Hz, 0.7H), 2.18-2.02 (m, 2H), 1.98-1.63 (m, 7H), 0.89 (d, J=6.5 Hz, 2.1H), 0.81 (d, J=7.0 Hz, 0.9H).

Step 6:

To a solution of 1e (5.8 g, 16.0 mmol) in 300 mL of acetone wad added p-toluenesulfonic acid monohydrate (304 mg, 1.6 mmol). The reaction mixture was stirred at room temperature for 12 h. The acetone was removed under reduced pressure and the residue was purified by silica gel chromatography (0 to 40% ethyl acetate/hexanes) to provide if as a colorless oil (4.1 g, 80%). $^1$H NMR (500 MHz, CD$_3$OD): δ 6.88 (d, J=21.5 Hz, 1H), 6.81-6.77 (m, 2H), 5.12 (s, 0.3H), 5.08 (s, 0.7H), 4.87 (s, 0.3H), 4.82 (s, 0.7H), 4.43 (t, J=2.5 Hz, 0.7H), 4.25 (t, J=2.5 Hz, 0.3 Hz), 3.84 (s, 3H), 3.83 (s, 3H), 3.21 (dd, J=15.0, 3.0 Hz, 0.3H), 2.85 (dd, J=15.0, 3.0 Hz, 0.7H), 2.72-2.66 (m, 2H), 2.46-2.42 (m, 1H), 2.30-2.24 (m, 1H), 2.18-1.90 (m, 3H), 0.96 (d, J=6.5 Hz, 2.1H), 0.88 (d, J=6.5 Hz, 0.9H).

Step 7:

A mixture of if (1.0 g, 3.12 mmol), Pd(OAc)$_2$ (350 mg, 1.56 mmol) and 4,5-diazafluoren-9-one (278 mg, 1.56 mmol) in 40 mL of DMSO was heated to 80° C. under one atmosphere of oxygen for 6 h. The reaction mixture was cooled to room temperature and diluted with ethyl acetate (400 mL). The organic phase was washed with brine, dried (MgSO$_4$), and concentrated to dryness under reduced pressure. The crude residue was purified by chromatography (0 to 40% ethyl acetate/hexanes) to provide 1g as a white solid (670 mg, 67%). $^1$H NMR (500 MHz, CD$_3$OD): δ 6.87 (d, J=8.0 Hz, 1H), 6.80-6.62 (m, 2H), 5.71 (s, 0.3H), 5.69 (s, 0.7H), 5.65 (s, 0.3H), 5.62 (s, 0.7H), 5.48 (s, 0.3H), 5.44 (s, 0.7H), 3.81 (s, 3H), 3.79 (s, 3H), 3.03 (dd, J=13.5, 4.0 Hz, 0.7H), 2.86 (dd, J=13.0, 4.0 Hz, 0.3H), 2.60-2.56 (m, 1H), 2.50-2.38 (m, 3H), 2.27-2.20 (m, 1H), 2.03-1.96 (m, 1H), 0.99 (d, J=7.0 Hz, 0.9H), 0.94 (d, J=7.0 Hz, 2.1H).

Step 8:

To a solution of 1g (1.8 g, 5.66 mmol) in THF (80 mL) was added LiHMDS (1.0M solution in THF, 8.5 mL, 8.5 mmol) at −78° C. under a nitrogen atmosphere. The reaction mixture was stirred at −78° C. for 30 min. Allyl cyanoformate II (942 mg, 8.49 mmol) was added. The reaction mixture was allowed to warm to 0° C. over 2 h. The reaction was quenched with $H_2O$ and extracted with ethyl acetate (200 mL). The organic phase was washed with brine, dried ($MgSO_4$), and concentrated to dryness under reduced pressure. The residue was purified by silica gel chromatography (0 to 40% ethyl acetate/hexanes) to provide a mixture of isomers 1ii as a brown gum (1.8 g, 82%). $^1$H NMR (500 MHz, $CD_3OD$): δ 6.88-6.85 (m, 2H), 6.78 (d, J=7.5 Hz, 1H), 5.94-5.90 (m, 1H), 5.73 (s, 1H), 5.67 (s, 1H), 5.50 (s, 1H), 5.35 (dd, J=14.0, 3.0 Hz, 1H), 5.24 (d, J=10.5 Hz, 1H), 4.63 (d, J=2.5 Hz, 2H), 3.84 (s, 3H), 3.80 (s, 3H), 3.60 (dd, J=12.5, 5.0 Hz, 1H), 3.03 (dd, J=14.0, 5.0 Hz, 1H), 2.73 (dd, J=12.5, 5.0 Hz, 1H), 2.55 (dd, J=13.5, 9.0 Hz, 1H), 2.30-2.28 (m, 1H), 2.27 (t, J=12.5 Hz, 1H), 0.98 (d, J=7.0 Hz, 3H).

Step 9:

To a solution of 1h (4.9 g, 12.1 mmol) in DMF (120 mL) was added $Pd(PPh_3)_4$ (1.4 g, 1.21 mmol) under a nitrogen atmosphere. The reaction mixture was stirred at room temperature for 1 h, and then diluted with ethyl acetate (200 mL). The organic phase was washed with brine, dried ($MgSO_4$), and concentrated to dryness under reduced pressure. The residue was purified by silica gel chromatography (0 to 30% ethyl acetate/hexanes) to provide a 78:22 mixture of cis-isomer and trans-isomer 1 (3.8 g, 88%). The mixture was separated by CHIRALPAK AD (10% i-PrOH/heptane) to provide the enriched enantiomer 1 (1.5 g) with 63.4% ee. The enriched enantiomer (1.0 g) was further separated by chromatography on CHIRALCEL OD (3% i-PrOH/heptane) to provide 1 as a colorless oil (680 mg).

Compound 1 ((6S,7aR)-6-Allyl-7a-((S)-1-(3,4-dimethoxyphenyl)propan-2-yl)-7,7a-dihydrobenzo[d][1,3]dioxol-5(6H)-one). $^1$H NMR (500 MHz, $CD_3OD$): δ 6.89 (d, J=8.0 Hz, 1H), 6.76 (s, 1H), 6.74 (dd, J=8.0, 2.0 Hz, 1H), 5.94-5.85 (m, 1H), 5.67 (s, 1H), 5.60 (s, 1H), 5.49 (s, 1H), 5.18 (dd, J=17.0, 10.5 Hz, 2H), 3.81 (s, 3H), 3.80 (s, 3H), 3.11 (dd, J=14.0, 4.0 Hz, 1H), 2.91 (dd, J=15.0, 1.5 Hz, 1H), 2.71 (d, J=16.0 Hz, 1H), 2.62 (t, J=3.5 Hz, 1H), 2.46 (t, J=11.0 Hz, 1H), 2.29-2.24 (m, 1H), 2.14 (dd, J=14.0, 9.5 Hz, 1H), 2.00-1.97 (m, 1H), 0.86 (d, J=7.0 Hz, 3H). ESI MS m/z 359 [M+H]$^+$.

General procedure B: Illustrated with preparation of compound 7.

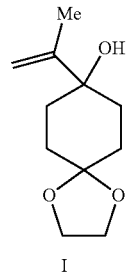
+
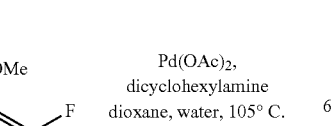

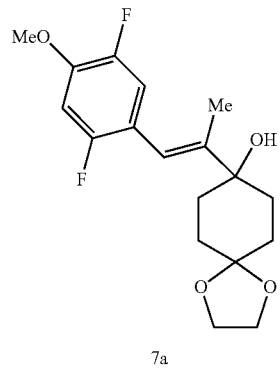

7a

Pd(OH)$_2$/CH$_2$, MeOH

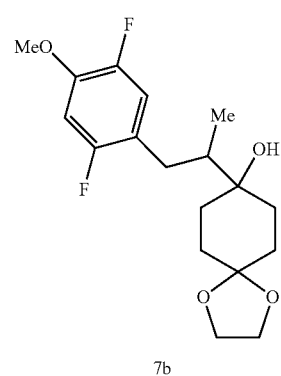

7b

SOCl$_2$, pyridine

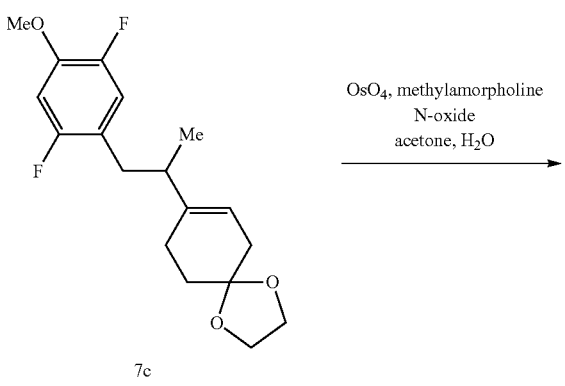

7c

OsO$_4$, methylamorpholine N-oxide
acetone, H$_2$O

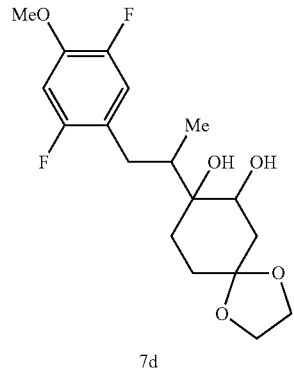

7d

NaH, CH$_2$Br$_2$, DMF

-continued

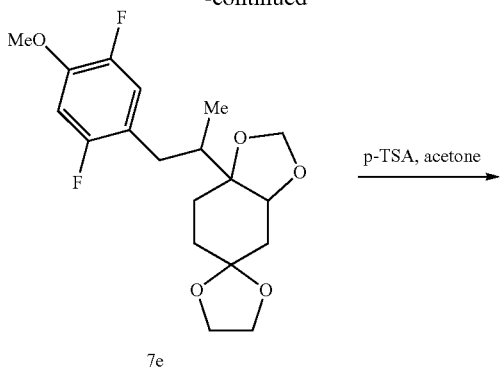

7e

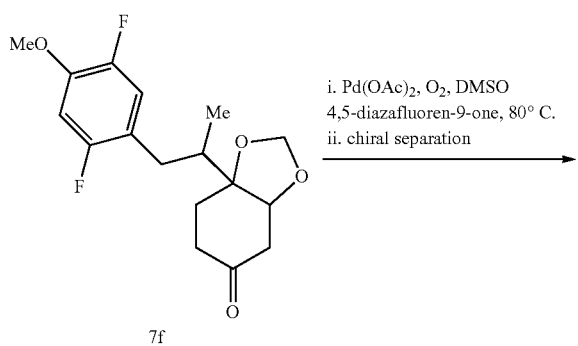

7f

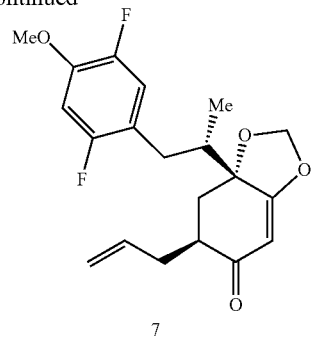

7

Step 1:

A mixture of I (20.0 g, 100 mmol), 1-bromo-2,5-difluoro-4-methoxybenzene (23.2 g, 100 mmol), Pd(OAc)$_2$ (2.3 g, 10 mmol) and dicyclohexylamine (26.0 mL, 130 mmol) in dioxane (200 mL) and H$_2$O (30 mL) was heated at reflux for 24 h. The mixture was cooled to room temperature and diluted with ethyl acetate (200 mL) and brine (60 mL). The organic phase was washed with brine, dried (MgSO$_4$), and concentrated in vacuo to dryness. The crude product was purified by silica gel chromatography (0 to 40% ethyl acetate/hexanes) to provide 7a as a brown oil (13.8 g, 41%). $^1$H NMR (500 MHz, CDCl$_3$): δ 6.95-6.85 (m, 1H), 6.68-6.63 (m, 1H), 6.52 (s, 0.4H), 5.22 (s, 0.6H), 4.58 (s, 0.6H), 3.98-3.93 (m, 4H), 3.87 (s, 3H), 3.38 (s, 1H), 2.10-2.00 (m, 4H), 1.81 (s, 3H), 1.71-1.60 (m, 4H), 1.17 (s, 1H).

Step 2:

To a solution of 7a (13.8 g, 40.8 mmol) in 300 mL of MeOH was added Pd(OH)$_2$/C (20 wt. % Pd on carbon, 2.8 g) under a nitrogen atmosphere. The mixture was stirred under one atmosphere of hydrogen for 1 h. The reaction mixture was filtered through a pad of CELITE and the filter cake was washed with ethyl acetate (100 mL). The filtrate was concentrated in vacuo to provide 7b as a colorless oil (13.8 g, 100%). The crude product was used without further purification. $^1$H NMR (500 MHz, CDCl$_3$): δ 6.85 (dd, J=11.0, 3.5 Hz, 1H), 6.65 (dd, J=11.0, 3.5 Hz, 1H), 3.97-3.92 (m, 4H), 3.85 (s, 3H), 3.48 (s, 1H), 2.98 (d, J=14.0 Hz, 1H), 2.65-2.62 (m, 1H), 2.21 (t, J=11.0 Hz, 1H), 1.97-1.92 (m, 2H), 1.86-1.77 (m, 2H), 1.75-1.63 (m, 4H), 0.83 (d, J=7.0 Hz, 3H).

Step 3:

To a solution of 7b (13.8 g, 40.8 mmol) in pyridine (60 mL) was added thionyl chloride (9.6 mL, 134.0 mmol) at 0-5° C. The mixture was stirred at 5° C. for 2 h, and then most of the pyridine was removed under reduced pressure. The residue was diluted with ethyl acetate (300 mL). The organic phase was washed with brine, dried (MgSO$_4$), and concentrated in vacuo to dryness. The crude product was purified by silica gel chromatography (0 to 30% ethyl acetate/hexanes) to provide 7c as a brown oil (8.2 g, 60%). $^1$H NMR (500 MHz, CDCl$_3$): δ 6.85 (dd, J=11.5, 7.5 Hz, 1H), 6.64 (dd, J=10.5, 7.0 Hz, 1H), 5.21 (s, 1H), 3.98-3.96 (m, 4H), 3.85 (s, 3H), 2.66-2.62 (m, 1H), 2.50-2.46 (m, 1H), 2.38-2.31 (m, 2H), 2.20 (s, 2H), 1.78-1.63 (m, 2H), 1.00 (d, J=6.5 Hz, 3H).

Step 4:

A solution of 7c (8.2 g, 25.3 mmol) and methylmorpholine N-oxide (4.5 g, 37.9 mmol) in acetone (240 mL) and H$_2$O (24 mL) was stirred at room temperature for 10 min. Osmium tetroxide (4 wt. % solution in H$_2$O, 16 mL, 2.53 mmol) was added. The reaction mixture was stirred at room temperature for 24 h, and then diluted with ethyl acetate (400 mL). The organic phase was washed with saturated Na$_2$S$_2$O$_5$ and brine, dried (MgSO$_4$), and concentrated in vacuo to dryness. The crude product was purified by silica gel chromatography (0 to 60% ethyl acetate/hexanes) to provide 7d as a brown oil (8.0 g, 88%). $^1$H NMR (500 MHz, CDCl$_3$): δ 6.89-6.84 (m, 1H), 6.75-6.72 (m, 1H), 3.99-3.94 (m, 5H), 3.86 (s, 3H), 2.99 (d, J=14.0 Hz, 0.5H), 2.88 (d, J=14.0 Hz, 0.5H), 2.23-2.18 (m, 1H), 2.13-1.92 (m, 5H), 1.85-1.60 (m, 3H), 0.87 (t, J=7.5 Hz, 3H).

Step 5:

To a solution of 7d (8.0 g, 22.3 mmol) in 150 mL of DMF was added NaH (60% dispersion in mineral oil, 2.7 g, 67.0 mmol) in an ice bath under a nitrogen atmosphere. After 1 h, dibromomethane (2.1 mL, 31.2 mmol) was added and the reaction mixture was stirred at room temperature for 24 h. The reaction was diluted with ethyl acetate (400 mL) and washed with H$_2$O (100 mL). The organic phase was washed with brine, dried (MgSO$_4$), and concentrated in vacuo to dryness. The crude product was purified by silica gel chromatography (0 to 30% ethyl acetate/hexanes) to provide 7e as an off-white solid (4.2 g, 51%). $^1$H NMR (500 MHz, CDCl$_3$): δ 6.85-6.82 (m, 1H), 6.69-6.63 (m, 1H), 5.17 (d, J=9.5 Hz, 1H), 4.93 (s, 0.5H), 4.87 (s, 0.5H), 4.18-3.94 (m, 4H), 3.85 (s, 3H), 2.99 (d, J=14.0 Hz, 0.5H), 2.72 (d, J=14.0 Hz, 0.5H), 2.20 (t, J=9.0 Hz, 1H), 2.15-2.08 (m, 1H), 1.95-1.62 (m, 6H), 0.89 (d, J=6.5 Hz, 1.5H), 0.82 (d, J=6.5 Hz, 1.5H).

Step 6:

To a solution of 7e (4.2 g, 11.3 mmol) in 200 mL of acetone wad added p-toluenesulfonic acid monohydrate (216 mg, 1.13 mmol). The reaction mixture was stirred at room temperature for 12 h. The acetone was removed under reduced pressure and the residue was purified by silica gel chromatography (0 to 30% ethyl acetate/hexanes) to provide 7f as a colorless oil (3.1 g, 84%). $^1$H NMR (500 MHz, CD$_3$OD): δ 6.88-6.85 (m, 1H), 6.68-6.63 (m, 1H), 5.14 (d, J=11.0 Hz, 1H), 4.81 (d, J=11.0 Hz, 1H), 4.33 (t, J=2.5 Hz, 0.5H), 4.15 (t, J=2.5 Hz, 0.5H), 3.86 (s, 3H), 3.09 (d, J=14.0 Hz, 0.5H), 2.85 (t, J=15.0 Hz, 1H), 2.75 (d, J=14.0 Hz, 0.5H), 2.56-2.52 (m, 1H), 2.45 (t, J=14.0 Hz, 1H), 2.33-2.24 (m, 2H), 2.08-1.85 (m, 3H), 0.97 (d, J=7.0 Hz, 1.5H), 0.86 (d, J=7.0 Hz, 1.5H).

Step 7:

A mixture of 7f (3.1 g, 9.50 mmol), Pd(OAc)$_2$ (1.1 g, 4.80 mmol) and 4,5-diazafluoren-9-one (845 mg, 4.80 mmol) in 90 mL of DMSO was heated to 80° C. under one atmosphere of oxygen for 6 h. The reaction mixture was cooled to room temperature and diluted with ethyl acetate (300 mL). The organic phase was washed with brine, dried (MgSO$_4$), and concentrated to dryness under reduced pressure. The crude residue was purified by silica gel chromatography (0 to 30% ethyl acetate/hexanes) to provide 7g as a white solid (1.8 g, 60%). The mixture of diastereomers was further separated by chromatography on CHIRALCEL OD (6% i-PrOH/heptane) to provide the enantiomer 7g (230 mg). $^1$H NMR (500 MHz, CD$_3$OD): δ 7.04 (dd, J=11.5, 7.5 Hz, 1H), 6.90 (dd, J=11.5, 7.5 Hz, 1H), 5.69 (s, 1H), 5.63 (s, 1H), 5.45 (s, 1H), 3.84 (s, 3H), 3.04 (dd, J=13.5, 2.0 Hz, 1H), 2.67-2.63 (m, 1H), 2.52-2.46 (m, 3H), 2.26-2.24 (m, 1H), 2.07-2.03 (m, 1H), 0.96 (d, J=7.0 Hz, 3H).

Step 8:

To a solution of 7g (230 mg, 0.70 mmol) in THF (7 mL) was added LiHMDS (1.0M solution in THF, 1.1 mL, 1.1 mmol) at −78° C. under a nitrogen atmosphere. The reaction mixture was stirred for 30 min. Allyl cyanoformate II (110 mg, 0.98 mmol) was added. The reaction mixture was allowed to warm to 0° C. over 2 h. The reaction was quenched with H$_2$O and extracted with ethyl acetate (100 mL). The organic phase was washed with brine, dried (MgSO$_4$), and concentrated to dryness under reduced pressure. The residue was purified by silica gel chromatography (0 to 30% ethyl acetate/hexanes) to provide a mixture of diastereomers 7h as a brown gum-like material (250 mg, 88%). $^1$H NMR (500 MHz, CD$_3$OD): δ 7.05-7.02 (m, 1H), 6.90-6.86 (m, 1H), 5.99-5.87 (m, 1H), 5.70 (s, 1H), 5.66 (s, 1H), 5.55 (s, 1H), 5.36-5.21 (m, 2H), 3.82 (s, 3H), 3.56 (dd, J=13.0, 5.0 Hz, 1H), 3.02 (d, J=8.0 Hz, 1H), 2.87-2.84 (m, 1H), 2.51-2.46 (m, 1H), 2.34-2.29 (m, 1H), 2.21-2.19 (m, 1H), 0.94 (d, J=7.0 Hz, 1.8H), 0.86 (d, J=6.5 Hz, 1.2H).

Step 9:

To a solution of 7h (250 mg, 0.61 mmol) in DMF (10 mL) was added Pd(PPh$_3$)$_4$ (70 mg, 0.06 mmol) under a nitrogen atmosphere. The reaction mixture was stirred at room temperature for 1.5 h, and then diluted with ethyl acetate (100 mL). The organic phase was washed with brine, dried (MgSO$_4$), and concentrated to dryness under reduced pressure. The residue was purified by silica gel chromatography (0 to 30% ethyl acetate/hexanes) to provide 7 (100 mg, 45%) as a colorless oil.

Compound 7 ((6S,7aR)-6-allyl-7a-((S)-1-(2,5-difluoro-4-methoxyphenyl)propan-2-yl)-7,7a-dihydrobenzo[d][1,3]dioxol-5(6H)-one). $^1$H NMR (500 MHz, CD$_3$OD): δ 6.99 (dd, J=11.5, 7.0 Hz, 1H), 6.89 (dd, J=9.0, 4.0 Hz, 1H), 5.92-5.85 (m, 1H), 5.65 (s, 1H), 5.60 (s, 1H), 5.50 (s, 1H), 5.19-5.10 (m, 2H), 3.84 (s, 3H), 3.06 (dd, J=14.5, 4.0 Hz, 1H), 2.82-2.79 (m, 1H), 2.66 (d, J=14.0 Hz, 1H), 2.63-2.51 (m, 2H), 2.26-2.21 (m, 1H), 2.15 (dd, J=14.0, 10.0 Hz, 1H), 2.03-1.99 (m, 1H), 0.84 (d, J=7.0 Hz, 3H). ESI MS m/z 365 [C$_{20}$H$_{22}$F$_2$O$_4$+H]$^+$.

General procedure C: Illustrated with preparation of compound 5.

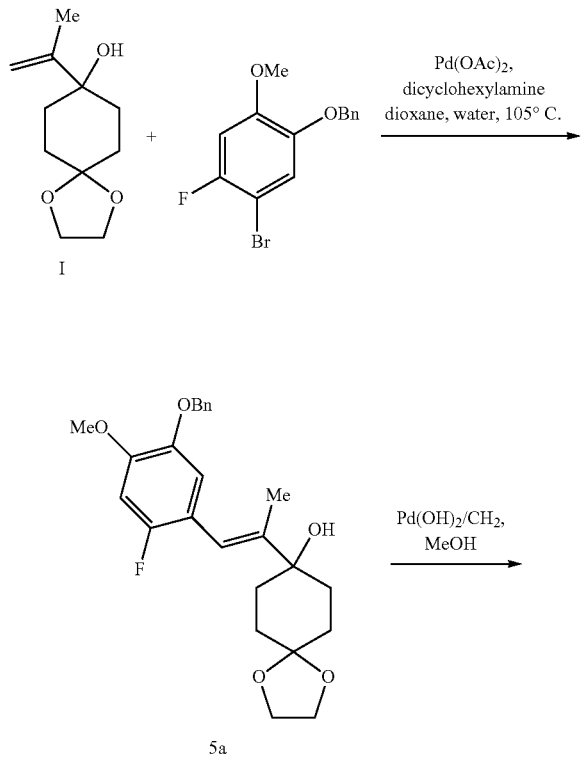

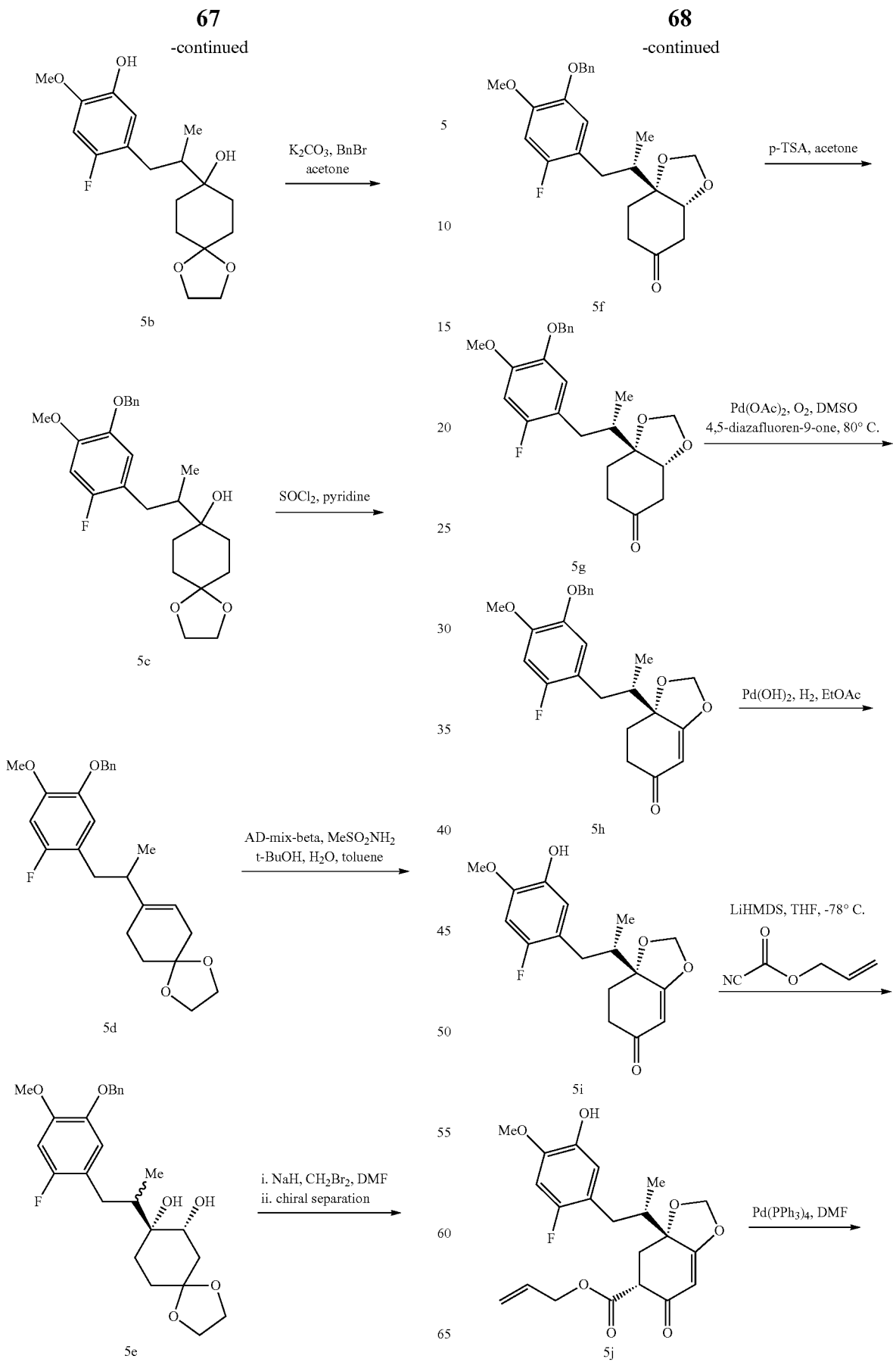

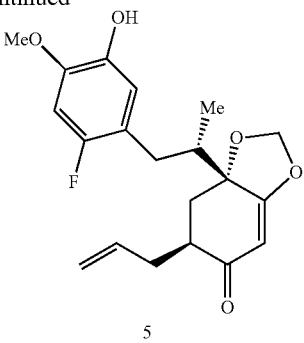

5

Step 1:

A mixture of I (62.0 g, 300 mmol), 1-(benzyloxy)-5-bromo-4-fluoro-2-methoxybenzene (84.0 g, 380 mmol), Pd(OAc)$_2$ (6.6 g, 30 mmol) and dicyclohexylamine (80.0 mL, 400 mmol) in dioxane (600 mL) and H$_2$O (112 mL) was heated at reflux for 12 h. The mixture was cooled to room temperature and diluted with ethyl acetate (600 mL) and brine (300 mL). The reaction mixture was filtered and the filter cake was washed with ethyl acetate (600 mL). The filtrate was washed with brine, dried (MgSO$_4$), and concentrated in vacuo to dryness. The crude product was purified by silica gel chromatography (0 to 60% ethyl acetate/hexanes) to provide 5a as a brown oil (50.0 g, 50%). $^1$H NMR (500 MHz, CDCl$_3$): δ 6.77 (dd, J=26.5, 7.5 Hz, 1H), 6.61 (dd, J=10.5, 3.0 Hz, 1H), 6.55 (s, 0.5H), 5.27 (s, 0.5H), 4.60 (s, 0.5H), 3.99-3.93 (m, 4H), 3.87 (s, 3H), 3.37 (s, 1H), 2.07-1.98 (m, 4H), 1.82 (s, 2H), 1.72-1.62 (m, 4H), 1.22 (d, J=13.0 Hz, 1H).

Step 2:

To a solution of 5a (12.0 g, 35.5 mmol) in 400 mL of MeOH was added Pd(OH)$_2$/C (20 wt. % Pd on carbon, 2.4 g) under a nitrogen atmosphere. The mixture was stirred under one atmosphere of hydrogen for 1 h. The reaction mixture was filtered through a pad of CELITE and the filter cake was washed with ethyl acetate (300 mL). The filtrate was concentrated in vacuo to provide 5b as a colorless oil (12.0 g, 100%). The crude product was used without further purification. $^1$H NMR (500 MHz, CDCl$_3$): δ 6.69 (d, J=7.0 Hz, 1H), 6.58 (d, J=11.0 Hz, 1H), 3.98-3.93 (m, 4H), 3.85 (s, 3H), 2.95 (d, J=12.5 Hz, 1H), 2.71-2.61 (m, 1H), 2.19 (t, J=11.5 Hz, 1H), 1.96-1.87 (m, 4H), 1.85-1.65 (m, 5H), 0.82 (d, J=7.0 Hz, 3H).

Step 3:

To a mixture of 5b (66.0 g, 190 mmol) and potassium carbonate (32.0 g, 220 mmol) in 800 mL of acetone was added benzyl bromide (22.6 mL, 190 mmol) at room temperature. The reaction mixture was stirred at room temperature for 12 h, and then the acetone was removed under reduced pressure. The residue was diluted with ethyl acetate (1000 mL) and H$_2$O (100 mL). The organic phase was washed with brine, dried (MgSO$_4$), and concentrated in vacuo to dryness. The crude product was purified by silica gel chromatography (0 to 40% ethyl acetate/hexanes) to provide 5c as a brown oil (65.0 g, 78%). $^1$H NMR (500 MHz, CDCl$_3$): δ 7.46-7.29 (m, 5H), 6.62 (d, J=6.0 Hz, 1H), 6.61 (d, J=11.0 Hz, 1H), 5.08 (s, 2H), 3.98-3.92 (m, 4H), 3.84 (s, 3H), 2.93 (d, J=13.0 Hz, 1H), 2.16 (t, J=11.5 Hz, 1H), 1.95-1.90 (m, 2H), 1.81-1.75 (m, 2H), 1.65-1.63 (m, 5H), 0.74 (d, J=6.5 Hz, 3H).

Step 4:

To a solution of 5c (64.4 g, 150 mmol) in pyridine (175 mL) was added thionyl chloride (21.2 mL, 300 mmol) at 0-5° C. The mixture was stirred at 5° C. for 2 h. Most of the pyridine was removed under reduced pressure. The residue was diluted with ethyl acetate (1000 mL) and H$_2$O (100 mL). The organic phase was washed with brine, dried (MgSO$_4$), and concentrated in vacuo to dryness. The crude product was purified by silica gel chromatography (0 to 30% ethyl acetate/hexanes) to provide 5d as a brown oil (60.0 g, 97%). $^1$H NMR (500 MHz, CDCl$_3$): δ 7.42-7.29 (m, 5H), 6.62 (d, J=7.5 Hz, 1H), 6.62 (d, J=11.0 Hz, 1H), 5.16 (s, 1H), 5.07 (s, 2H), 2.64-2.58 (m, 1H), 2.42-2.38 (m, 1H), 2.28-2.22 (m, 1H), 2.19-2.18 (m, 4H), 1.73-1.65 (m, 2H), 0.93 (d, J=7.0 Hz, 3H).

Step 5:

A three-necked flask equipped with a mechanical stirrer was charged with a mixture of AD-mix-β (83 g) in t-BuOH (470 mL) and H$_2$O (470 mL). The mixture was cooled in an ice bath and stirred for 1 h. A solution of 5d (21.0 g, 50.9 mmol) in toluene (94 mL), and methylanesulfonamide (4.8 g, 50.9 mmol), were then added. The reaction mixture was stirred at room temperature for 25 d, and then diluted with MTBE (1000 mL). The organic phase was washed with saturated Na$_2$S$_2$O$_5$ and brine, dried (MgSO$_4$), and concentrated in vacuo to dryness. The crude product was purified by silica gel chromatography (0 to 60% ethyl acetate/hexanes) to provide the mixture of diastereomers 5e as a brown oil (16.6 g, 73%). $^1$H NMR (500 MHz, CDCl$_3$): δ 7.41-7.28 (m, 5H), 6.64 (s, 1H), 6.62 (d, J=11.5 Hz, 1H), 5.10 (s, 2H), 3.98-3.93 (m, 4H), 3.84 (s, 3H), 2.87 (dd, J=14.0, 3.0 Hz, 1H), 2.23-2.05 (m, 2H), 1.98-1.60 (m, 7H), 0.78 (t, J=7.0 Hz, 3H).

Step 6:

To a solution of 5e (16.6 g, 37.2 mmol) in 300 mL of DMF was added NaH (60% dispersion in mineral oil, 4.4 g, 111.6 mmol) in an ice bath under a nitrogen atmosphere. After 1 h, dibromomethane (3.6 mL, 52.1 mmol) was added and the reaction mixture was stirred at room temperature for 24 h. The reaction was diluted with ethyl acetate (400 mL) and washed with H$_2$O (100 mL). The organic phase was washed with brine, dried (MgSO$_4$), and concentrated in vacuo to dryness. The crude product was purified by silica gel chromatography (0 to 40% ethyl acetate/hexanes) to provide a mixture of diastereomers of 5f as an off-white solid (12.4 g, 74%). The mixture of diastereomers was further separated by chromatography on CHIRALCEL OD (15% i-PrOH/heptane) to provide 5f. $^1$H NMR (500 MHz, CDCl$_3$): δ 7.41-7.28 (m, 5H), 6.63 (s, 1H), 6.61 (d, J=11.5 Hz, 1H), 5.14 (s, 2H), 5.08 (s, 1H), 4.84 (s, 1H), 4.18 (t, J=6.5 Hz, 1H), 3.98-3.93 (m, 3H), 3.84 (s, 3H), 2.68 (d, J=12.5 Hz, 1H), 2.15-2.05 (m, 2H), 1.93-1.80 (m, 4H), 1.62-1.56 (m, 2H), 0.80 (d, J=7.0 Hz, 3H).

Step 7:

To a solution of 5f (14.0 g, 30.5 mmol) in 600 mL of acetone wad added p-toluenesulfonic acid monohydrate (580 mg, 3.05 mmol). The reaction mixture was stirred at room temperature for 12 h. The acetone was removed under reduced pressure and the residue was purified by silica gel chromatography (0 to 40% ethyl acetate/hexanes) to provide 5g as a colorless oil (11.9 g, 94%). $^1$H NMR (500 MHz, CDCl$_3$): δ 7.41-7.29 (m, 5H), 6.64 (t, J=7.0 Hz, 1H), 5.09 (s, 3H), 4.75 (s, 1H), 4.29 (s, 1H), 3.86 (s, 3H), 2.82 (d, J=14.0, 2.5 Hz, 1H), 2.70 (d, J=14.0 Hz, 1H), 2.56-2.48 (m, 1H), 2.45 (dd, J=17.0, 3.0 Hz, 1H), 2.31-2.27 (m, 1H), 2.20-2.15 (m, 1H), 2.04-1.96 (m, 2H), 1.86-1.83 (m, 1H), 0.87 (d, J=7.0 Hz, 3H).

Step 8:

A mixture of 5g (11.6 g, 28.0 mmol), Pd(OAc)$_2$ (3.1 g, 14.0 mmol) and 4,5-diazafluoren-9-one (2.5 g, 14.0 mmol) in 240 mL of DMSO was heated to 80° C. under one atmosphere of oxygen for 6 h. The reaction mixture was cooled to room temperature and diluted with ethyl acetate (300 mL). The organic phase was washed with brine, dried (MgSO$_4$), and concentrated to dryness under reduced pressure. The crude residue was purified by silica gel chromatography (0 to 40% ethyl acetate/hexanes) to provide 5h as a white solid (5.7 g, 49%). $^1$H NMR (500 MHz, CD$_3$OD): δ 7.46-7.27 (m, 5H), 6.63 (d, J=12.0 Hz, 1H), 6.57 (d, J=7.5 Hz, 1H), 5.58 (s, 1H), 5.56 (s, 1H), 5.09 (s, 1H), 5.09 (s, 2H), 3.85 (s, 3H), 2.96 (d, J=11.0 Hz, 1H), 2.58 (dd, J=9.0, 7.5 Hz, 1H), 2.50-2.46 (m, 1H), 2.40-2.24 (m, 2H), 2.10-2.09 (m, 1H), 2.01-1.96 (m, 1H), 0.81 (d, J=7.0 Hz, 3H).

Step 9:

To a solution of 5h (1.2 g, 2.91 mmol) in 50 mL of ethyl acetate was added Pd(OH)$_2$/C (20 wt. % Pd on carbon, 250 mg) under a nitrogen atmosphere. The mixture was stirred under one atmosphere of hydrogen for 1 h. The reaction mixture was filtered through a pad of CELITE and the filter cake was washed with ethyl acetate (300 mL). The filtrate was concentrated in vacuo to provide 5i as a colorless oil (930 mg, 100%). The crude product was used without further purification. $^1$H NMR (500 MHz, CDCl$_3$): δ 6.72 (d, J=11.5 Hz, 1H), 6.58 (d, J=8.0 Hz, 1H), 5.69 (s, 1H), 5.63 (s, 1H), 5.44 (s, 1H), 3.82 (s, 3H), 3.00 (dd, J=14.0, 3.0 Hz, 1H), 2.68-2.64 (m, 1H), 2.48-2.40 (m, 3H), 2.22-2.20 (m, 1H), 2.06-1.99 (m, 1H), 0.94 (d, J=7.0 Hz, 3H).

Step 10:

To a solution of 5i (510 mg, 1.58 mmol) in THF (24 mL) was added LiHMDS (1.0M solution in THF, 4.0 mL, 4.0 mmol) at −78° C. under a nitrogen atmosphere. The reaction mixture was stirred for 30 min. Allyl cyanoformate II (440 mg, 3.95 mmol) was added. The reaction mixture was allowed to warm to 0° C. over 2 h. The reaction was quenched with H$_2$O and extracted with ethyl acetate (100 mL). The organic phase was washed with brine, dried (MgSO$_4$) and concentrated to dryness under reduced pressure. The residue was purified by silica gel chromatography (0 to 30% ethyl acetate/hexanes) to provide a mixture of 5j (320 mg, 41%) as a brown gum-like material. $^1$H NMR (500 MHz, CD$_3$OD): δ 7.09 (d, J=8.0 Hz, 0.5H), 6.92 (d, J=11.5 Hz, 0.5H), 6.73 (d, J=11.5 Hz, 0.5H), 6.66 (d, J=7.5 Hz, 0.5H), 6.02-5.85 (m, 2H), 5.72 (s, 1H), 5.67 (s, 1H), 5.50 (s, 1H), 5.37-5.22 (m, 4H), 4.70 (dd, J=27.5, 6.0 Hz, 4H), 3.81 (s, 3H), 3.58-3.47 (m, 1H), 3.06-2.95 (m, 1H), 2.87-2.82 (m, 1H), 2.54-2.40 (m, 1H), 2.33-2.28 (m, 1H), 2.25-2.15 (m, 1H), 0.96 (d, J=7.0 Hz, 3H).

Step 11:

To a solution of 5j (300 mg, 0.73 mmol) in DMF (12 mL) was added Pd(PPh$_3$)$_4$ (85 mg, 0.073 mmol) under a nitrogen atmosphere. The reaction mixture was stirred at room temperature for 1.5 h. The reaction mixture was diluted with ethyl acetate (200 mL). The organic phase was washed with brine, dried (MgSO$_4$) and concentrated to dryness under reduced pressure. The residue was purified by silica gel chromatography (0 to 40% ethyl acetate/hexanes) to provide 5 (140 mg, 53%) as a colorless oil.

Compound 5 ((6S,7aR)-6-allyl-7a-((S)-1-(2-fluoro-5-hydroxy-4-methoxyphenyl)propan-2-yl)-7,7a-dihydrobenzo[d][1,3]dioxol-5(6H)-one). $^1$H NMR (500 MHz, CD$_3$OD): δ 6.72 (t, J=11.5 Hz, 1H), 6.63 (d, J=7.5 Hz, 1H), 5.92-5.85 (m, 1H), 5.65 (s, 1H), 5.60 (s, 1H), 5.49 (s, 1H), 5.18-5.11 (m, 2H), 3.81 (s, 3H), 3.02 (d, J=14.0 Hz, 1H), 2.85-2.82 (m, 1H), 2.68 (d, J=14.0 Hz, 1H), 2.62-2.58 (m, 1H), 2.48 (t, J=11.5 Hz, 1H), 2.25-2.20 (m, 1H), 2.13 (dd, J=14.0, 10.0 Hz, 1H), 2.03-1.95 (m, 1H), 0.83 (d, J=7.0 Hz, 3H). ESI MS m/z 363 [C$_{20}$H$_{23}$FO$_5$+H]$^+$.

General procedure D: Illustrated with preparation of compound 48.

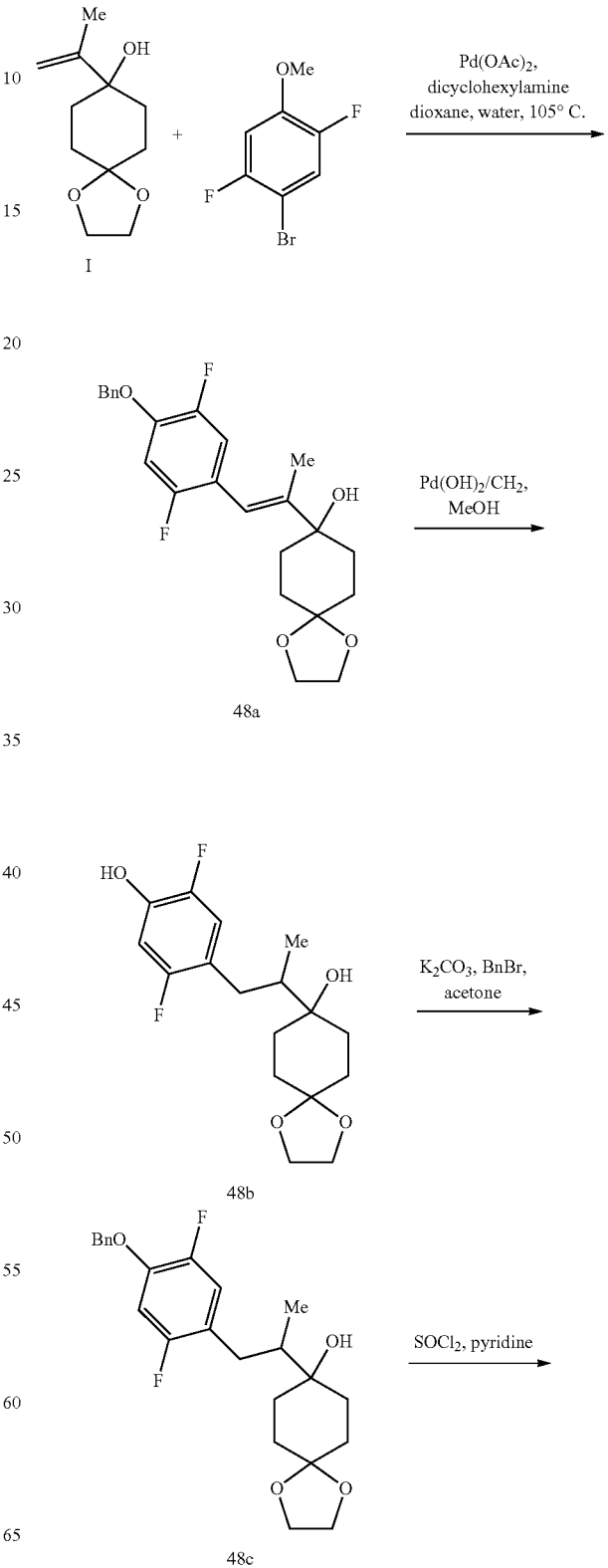

73
-continued
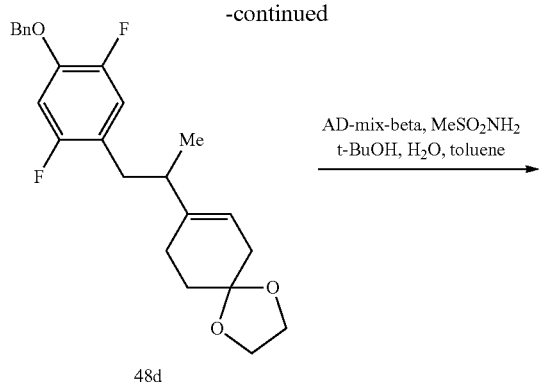
48d
AD-mix-beta, MeSO₂NH₂
t-BuOH, H₂O, toluene →
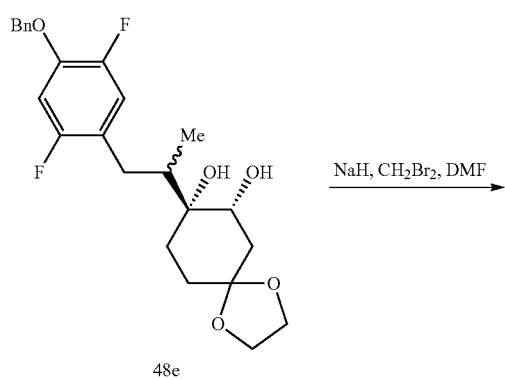
48e
NaH, CH₂Br₂, DMF →
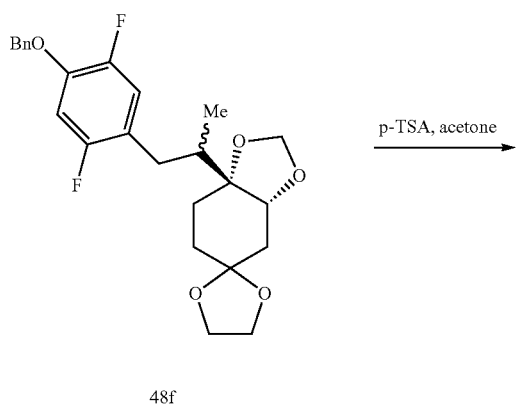
48f
p-TSA, acetone →
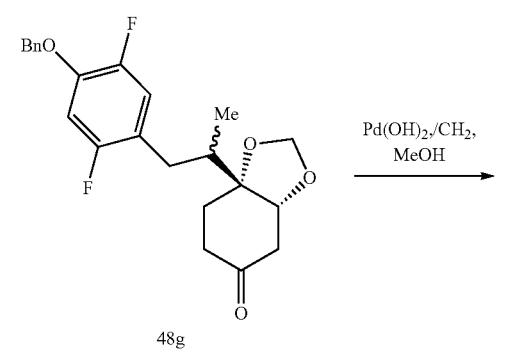
48g
Pd(OH)₂/CH₂,
MeOH →
74
-continued
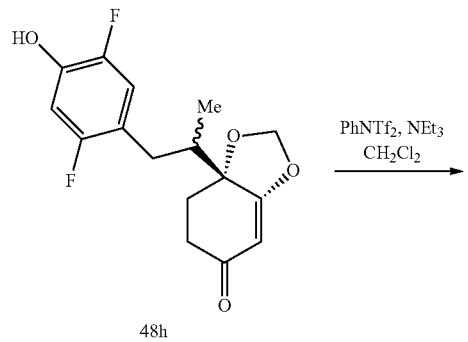
48h
PhNTf₂, NEt₃
CH₂Cl₂ →
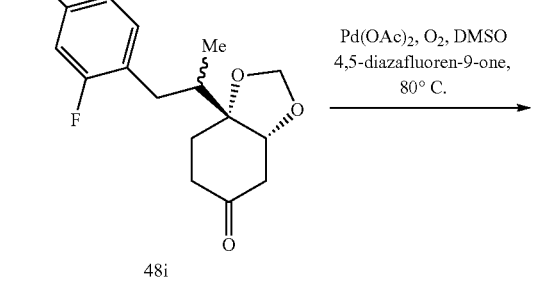
48i
Pd(OAc)₂, O₂, DMSO
4,5-diazafluoren-9-one,
80° C. →
48j
FmocNH₂, Pd₂(dba)₃
ligand, K₃PO₄, dioxane
100° C. →
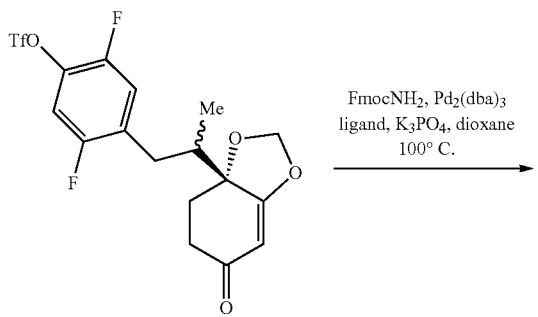
48k
HCHO,
NaBH₃(CN)
ZnCl₂, MeOH →
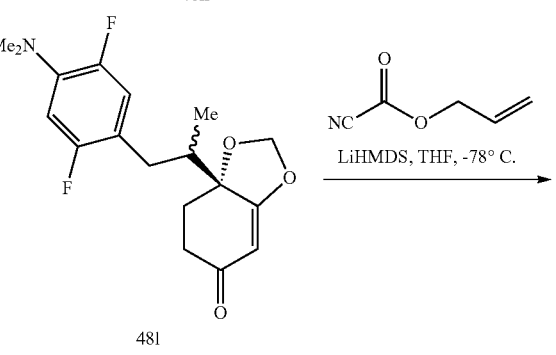
48l
LiHMDS, THF, -78° C. →

-continued

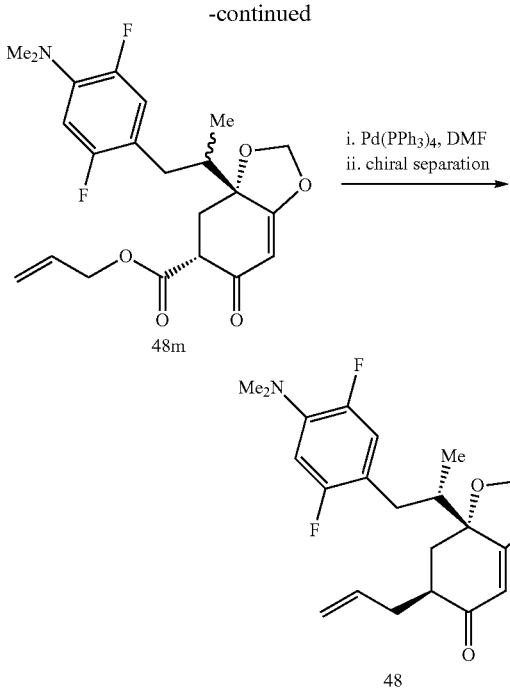

i. Pd(PPh₃)₄, DMF
ii. chiral separation

Step 1:

A mixture of I (7.5 g, 37.6 mmol), 1-(benzyloxy)-4-bromo-2,5-difluorobenzene (13.5 g, 45.1 mmol), Pd(OAc)₂ (844 mg, 3.7 mmol) and dicyclohexylamine (9.8 mL, 48.9 mmol) in dioxane (75 mL) and H₂O (15 mL) was heated at reflux for 12 h. The mixture was cooled to room temperature and diluted with ethyl acetate (300 mL) and brine (100 mL). The organic phase was washed with brine, dried (MgSO₄), and concentrated in vacuo to dryness. The crude product was purified by silica gel chromatography (0 to 40% ethyl acetate/hexanes) to provide 48a as a brown oil (12.6 g, 80%). ¹H NMR (500 MHz, CDCl₃): δ 7.44-7.37 (m, 5H), 6.97-6.85 (m, 1H), 6.72 (dd, J=14.0, 3.0 Hz, 1H), 6.51 (s, 0.5H), 5.22 (s, 0.5H), 5.11 (d, J=7.5 Hz, 2H), 4.56 (s, 0.5H), 5.27 (s, 0.5H), 4.60 (s, 0.5H), 3.99-3.93 (m, 4H), 3.38 (s, 3H), 2.08-1.95 (m, 6H), 1.81 (s, 3H), 1.72-1.62 (m, 2H), 1.25 (s, 1H).

Step 2:

To a solution of 48a (11.0 g, 33.9 mmol) in 200 mL of MeOH was added Pd(OH)₂/C (20 wt. % Pd on carbon, 2.2 g) under a nitrogen atmosphere. The mixture was stirred under one atmosphere of hydrogen for 2 h. The reaction mixture was filtered through a pad of CELITE and the filter cake was washed with ethyl acetate (300 mL). The filtrate was concentrated in vacuo to provide 48b as a colorless oil (11.0 g, 100%). The crude product was used without further purification. ¹H NMR (500 MHz, CDCl₃): δ 6.87-6.85 (m, 1H), 6.69-6.65 (m, 1H), 3.97-3.93 (m, 4H), 3.74 (s, 3H), 3.02-2.95 (m, 1H), 2.80-2.65 (m, 1H), 2.30-2.12 (m, 2H), 2.01-1.87 (m, 2H), 1.82-1.75 (m, 2H), 1.65-1.55 (m, 2H), 0.80 (d, J=6.5 Hz, 3H).

Step 3:

To a mixture of 48b (11.0 g, 33.7 mmol) and potassium carbonate (5.6 g, 40.5 mmol) in 140 mL of acetone was added benzyl bromide (4.0 mL, 33.7 mmol) at room temperature. The reaction mixture was stirred at room temperature for 12 h. The acetone was removed under reduced pressure, and the residue was diluted with ethyl acetate (300 mL). The organic phase was washed with brine, dried (MgSO₄), and concentrated in vacuo to dryness. The crude product was purified by silica gel chromatography (0 to 40% ethyl acetate/hexanes) to provide 48c as a brown oil (6.8 g, 49%). ¹H NMR (500 MHz, CDCl₃): δ 7.43-7.33 (m, 5H), 6.89 (d, J=7.0 Hz, 1H), 6.71 (d, J=7.0 Hz, 1H), 5.09 (s, 2H), 3.98-3.93 (m, 4H), 2.95 (d, J=14.0 Hz, 1H), 2.21 (t, J=11.5 Hz, 1H), 1.95-1.91 (m, 2H), 1.83-1.62 (m, 6H), 1.07 (s, 1H), 0.83 (d, J=7.0 Hz, 3H).

Step 4:

To a solution of 48c (8.0 g, 19.1 mmol) in pyridine (40 mL) was added thionyl chloride (3.5 mL, 49.0 mmol) at 0-5° C. The mixture was stirred at 5° C. for 2 h. Most of the pyridine was removed under reduced pressure. The residue was diluted with ethyl acetate (300 mL) and H₂O (60 mL). The organic phase was washed with brine, dried (MgSO₄), and concentrated in vacuo to dryness. The crude product was purified by silica gel chromatography (0 to 40% ethyl acetate/hexanes) to provide 48d as a brown oil (5.8 g, 76%). ¹H NMR (500 MHz, CDCl₃): δ 7.43-7.31 (m, 5H), 6.86 (dd, J=11.5, 7.0 Hz, 1H), 6.68 (dd, J=11.0, 7.0 Hz, 1H), 5.20 (s, 1H), 5.09 (s, 2H), 3.97 (s, 4H), 2.66-2.61 (m, 1H), 2.49-2.32 (m, 2H), 2.20 (s, 3H), 1.76-1.65 (m, 1H), 0.99 (d, J=7.0 Hz, 3H).

Step 5:

A three-necked flask equipped with a mechanical stirrer was charged with a mixture of AD-mix-β (22.0 g) in t-BuOH (60 mL) and H₂O (60 mL). The mixture was cooled in an ice bath and stirred for 1 h. A solution of 48d (5.8 g, 14.5 mmol) in toluene (12 mL) and methylanesulfonamide (1.8 g, 14.5 mmol) was added. The reaction mixture was stirred at room temperature for 12 d, and then diluted with MTBE (500 mL). The organic phase was washed with saturated Na₂S₂O₃ and brine, dried (MgSO₄), and concentrated in vacuo to dryness. The crude product was purified by silica gel chromatography (0 to 60% ethyl acetate/hexanes) to provide a mixture of diastereomers 48e as a brown oil (3.6 g, 58%). ¹H NMR (500 MHz, CDCl₃): δ 7.43-7.33 (m, 5H), 6.91-6.88 (m, 1H), 6.71-6.68 (m, 1H), 5.09 (s, 2H), 4.00-3.93 (m, 4H), 2.87 (dd, J=14.0, 3.0 Hz, 1H), 2.21-2.05 (m, 1H), 1.98-1.60 (m, 7H), 0.87 (t, J=7.0 Hz, 3H).

Step 6:

To a solution of 48e (3.6 g, 8.2 mmol) in 77 mL of anhydrous DMF was added NaH (60% dispersion in mineral oil, 995 mg, 24.8 mmol) in an ice bath under a nitrogen atmosphere. After 1 h, dibromomethane (0.8 mL, 11.6 mmol) was added and the reaction mixture was stirred at room temperature for 24 h. The reaction was diluted with ethyl acetate (400 mL). The organic phase was then washed with brine, dried (MgSO₄), and concentrated in vacuo to dryness. The crude product was purified by silica gel chromatography (0 to 30% ethyl acetate/hexanes) to provide 48f as an off-white solid (2.3 g, 62%). ¹H NMR (500 MHz, CDCl₃): δ 7.43-7.33 (m, 5H), 6.88-6.85 (m, 1H), 6.71-6.68 (m, 1H), 5.16 (s, 0.35H), 5.14 (s, 0.65H), 5.09 (s, 2H), 4.92 (s, 0.35H), 4.86 (s, 0.65H), 4.18-3.86 (m, 4H), 3.02 (d, J=14.0 Hz, 0.35H), 2.72 (d, J=14.0 Hz, 0.65H), 2.23 (t, J=13.5 Hz, 1H), 2.10 (t, J=5.5 Hz, 1H), 1.97-1.65 (m, 6H), 0.89 (d, J=6.5 Hz, 1.95H), 0.82 (d, J=7.0 Hz, 1.05H).

Step 7:

To a solution of 48f (2.3 g, 5.1 mmol) in 102 mL of acetone was added p-toluenesulfonic acid monohydrate (98 mg, 0.51 mmol). The reaction mixture was stirred at room temperature for 12 h. The acetone was then removed under reduced pressure and the residue was purified by silica gel chromatography (0 to 30% ethyl acetate/hexanes) to provide 48g as a colorless oil (1.8 g, 86%). ¹H NMR (500 MHz, CDCl₃): δ 7.43-7.34 (m, 5H), 6.91-6.89 (m, 1H), 6.74-6.70

(m, 1H), 5.13 (s, 0.35H), 5.11 (s, 0.65H), 5.10 (s, 2H), 4.80 (s, 0.35H), 4.78 (s, 0.65H), 4.34 (s, 0.65H), 4.14 (s, 0.35H), 3.08 (d, J=13.5 Hz, 0.35H), 2.87 (t, J=14.5 Hz, 1H), 2.73 (d, J=14.0 Hz, 1H), 2.55-2.46 (m, 1H), 2.44-2.38 (m, 1H), 2.29-2.24 (m, 2H), 2.08-1.85 (m, 2H), 0.97 (d, J=7.0 Hz, 0.6H), 0.86 (d, J=7.0 Hz, 2.4H).

Step 8:

To a solution of 48g (1.8 g, 4.4 mmol) in 30 mL of MeOH was added Pd(OH)$_2$/C (20 wt. % Pd on carbon, 360 mg) under a nitrogen atmosphere. The mixture was stirred under one atmosphere of hydrogen for 30 min. The reaction mixture was filtered through a pad of CELITE and the filter cake was washed with ethyl acetate (200 mL). The filtrate was concentrated in vacuo to provide 48h as a colorless oil (1.4 g, 100%). The crude product was used without further purification. $^1$H NMR (500 MHz, CDCl$_3$): δ 6.88-6.86 (m, 1H), 6.74-6.71 (m, 1H), 5.14 (s, 0.35H), 5.11 (s, 0.65H), 4.81 (s, 0.35H), 4.79 (s, 0.65H), 4.34 (s, 0.65H), 4.13 (s, 0.35H), 3.09 (d, J=14.0 Hz, 0.35H), 2.85 (t, J=14.0 Hz, 1H), 2.78 (d, J=14.0 Hz, 0.65H), 2.55-2.48 (m, 1H), 2.45-2.37 (m, 1H), 2.30-2.21 (m, 2H), 2.05-1.85 (m, 2H), 0.97 (d, J=6.5 Hz, 1.95H), 0.86 (d, J=7.0 Hz, 1.05H).

Step 9:

N-phenyl bis-trifluoromethane sulfonimide (599 mg, 1.67 mmol) was added to a solution of 48h (350 mg, 1.11 mmol), triethylamine (0.30 mL, 2.22 mmol) and a catalytic amount of DMAP in CH$_2$Cl$_2$ (10 mL). The reaction mixture was stirred at room temperature for 12 h, and then concentrated to dryness. The crude residue was then purified by silica gel chromatography (0 to 30% ethyl acetate/hexanes) to provide 48i as a colorless oil (350 mg, 71%). $^1$H NMR (500 MHz, CD$_3$OD): δ 7.13-7.07 (m, 2H), 5.13 (s, 1H), 4.80 (s, 1H), 4.36 (t, J=3.0 Hz, 0.6H), 4.14 (t, J=2.5 Hz, 0.4H), 3.20 (d, J=14.0 Hz, 0.4H), 2.90 (dd, J=18.5, 3.0 Hz, 1H), 2.82 (d, J=14.0 Hz, 0.6H), 2.57-2.53 (m, 1H), 2.47-2.30 (m, 3H), 2.09-1.87 (m, 3H), 0.99 (d, J=7.0 Hz, 1.8H), 0.89 (d, J=7.0 Hz, 1.2H).

Step 10:

A mixture of 48i (350 mg, 0.78 mmol), Pd(OAc)$_2$ (88 mg, 0.39 mmol) and 4,5-diazafluoren-9-one (70 mg, 0.39 mmol) in 10 mL of DMSO was heated to 80° C. under one atmosphere of oxygen for 4.5 h. The reaction mixture was cooled to room temperature and diluted with ethyl acetate (300 mL). The organic phase was washed with brine, dried (MgSO$_4$), and concentrated to dryness under reduced pressure. The crude residue was then purified by silica gel chromatography (0 to 30% ethyl acetate/hexanes) to provide 48j as a colorless gum-like material (155 mg, 44%). $^1$H NMR (500 MHz, CD$_3$OD): δ 7.13-7.07 (m, 2H), 5.29 (s, 1H), 4.80 (s, 1H), 4.36 (s, 0.6H), 4.14 (s, 0.4H), 3.22 (dd, J=14.0, 3.0 Hz, 0.4H), 2.90 (dd, J=17.5, 3.0 Hz, 1H), 2.85 (dd, J=14.5, 3.0 Hz, 1H), 2.62-2.58 (m, 1H), 2.57-2.30 (m, 2.6H), 2.15-1.87 (m, 3H), 0.99 (d, J=7.0 Hz, 1.8H), 0.89 (d, J=7.0 Hz, 1.2H).

Step 11:

A mixture of 48j (155 mg, 0.35 mmol), 9-fluorenylmethyl carbamate (167 mg, 0.70 mmol), Pd$_2$(dba)$_3$ (32 mg, 0.035 mmol), 2-di-tert-butylphosphino-3,4,5,6-tetramethyl-2',4', 6'-triisopropyl-1,1'-biphenyl (84 mg, 0.18 mmol) and K$_3$PO$_4$ (223 mg, 1.05 mmol) in 6 mL of dioxane was heated to 105° C. under a nitrogen atmosphere for 4 h. The reaction mixture was diluted with ethyl acetate (100 mL) and washed with brine, dried (MgSO$_4$), and concentrated to dryness. The crude residue was purified by silica gel chromatography (0 to 30% ethyl acetate/hexanes) to provide 48k as a colorless gum-like material (60 mg, 56%). $^1$H NMR (500 MHz, CD$_3$OD): δ 6.85-6.81 (m, 1H), 6.54-6.50 (m, 1H), 5.69 (s, 0.6H), 5.67 (s, 0.4H), 5.64 (s, 0.4H), 5.62 (s, 0.6H), 5.48 (s, 0.4H), 5.44 (s, 0.6H), 2.95 (d, J=12.5 Hz, 0.6H), 2.82 (d, J=12.5 Hz, 0.4H), 2.63-2.54 (m, 1H), 2.42-2.32 (m, 3H), 2.25-2.18 (m, 1H), 2.06-1.98 (m, 1H), 1.00 (d, J=6.5 Hz, 1.2H), 0.94 (d, J=7.0 Hz, 1.8H).

Step 12:

To a solution of 48k (30 mg, 0.09 mmol) in MeOH (4 mL) was added HCHO (37 wt. % solution in H$_2$O, 0.071 mL, 0.87 mmol). The solution was stirred for 10 min, and then a solution of NaBH$_3$(CN) (19 mg, 0.29 mmol) and ZnCl$_2$ (0.5M solution in THF, 0.30 mL, 0.15 mmol) in MeOH (4 mL) was added. The reaction mixture was stirred at room temperature for 4 h; the reaction was not complete. A solution of NaBH$_3$(CN) (19 mg, 0.29 mmol) and ZnCl$_2$ (0.5M solution in THF, 0.30 mL, 0.15 mmol) in MeOH (4 mL) was then added, and the reaction mixture continued to stir for 4 h. The reaction mixture was diluted with ethyl acetate (100 mL), washed with brine, dried (MgSO$_4$), and concentrated to dryness. The crude residue was purified by silica gel chromatography (0 to 40% ethyl acetate/hexanes) to provide 48l as a colorless gum-like material (20 mg, 65%). $^1$H NMR (500 MHz, CD$_3$OD): δ 6.84-6.80 (m, 1H), 6.41-6.37 (m, 1H), 5.69 (s, 0.65H), 5.67 (s, 0.35H), 5.64 (s, 0.65H), 5.63 (s, 0.35H), 5.48 (s, 0.35H), 5.44 (s, 0.65H), 3.02 (d, J=12.5 Hz, 1H), 2.76 (s, 6H), 2.65-2.55 (m, 1H), 2.45-2.35 (m, 3H), 2.25-2.18 (m, 1H), 2.05-2.01 (m, 1H), 0.99 (d, J=6.5 Hz, 1.05H), 0.94 (d, J=6.5 Hz, 1.95H).

Step 13:

To a solution of 48l (12 mg, 0.036 mmol) in THF (3 mL) was added LiHMDS (1.0M solution in THF, 0.19 mL, 0.19 mmol) at −78° C. under a nitrogen atmosphere. The reaction mixture was stirred for 30 min. Allyl cyanoformate II (20 mg, 0.187 mmol) was added. The reaction mixture was allowed to warm to 0° C. over 2 h. The reaction was quenched with H$_2$O and extracted with ethyl acetate (50 mL). The organic phase was washed with brine, dried (MgSO$_4$) and concentrated to dryness under reduced pressure. The residue was purified by silica gel chromatography (0 to 40% ethyl acetate/hexanes) to provide 48m as a brown gum-like material (14 mg, 93%). $^1$H NMR (500 MHz, CD$_3$OD): δ 7.15-7.10 (m, 1H), 6.68-6.62 (m, 1H), 5.99-5.87 (m, 1H), 5.73 (s, 1H), 5.68 (s, 1H), 5.55 (s, 1H), 5.36-5.21 (m, 2H), 3.65 (dd, J=13.0, 5.0 Hz, 1H), 2.85-2.82 (m, 1H), 2.80 (s, 6H), 2.62-2.58 (m, 1H), 2.52-2.48 (m, 1H), 2.38-2.25 (m, 2H), 0.94 (d, J=7.0 Hz, 1.8H), 0.86 (d, J=6.5 Hz, 1.2H).

Step 14:

To a solution of 48m (14 mg, 0.033 mmol) in DMF (2 mL) was added Pd(PPh$_3$)$_4$ (4 mg, 0.004 mmol) under a nitrogen atmosphere. The reaction mixture was stirred at room temperature for 1.5 h, and then diluted with ethyl acetate (50 mL). The organic phase was washed with brine, dried (MgSO$_4$), and concentrated to dryness under reduced pressure. The residue was purified by silica gel chromatography (0 to 40% ethyl acetate/hexanes) to provide a mixture of diastereomers as a colorless oil. The mixture of diastereomers were separated by CHIRALCEL OD (3% i-PrOH/heptane) to provide 48 (2 mg) as a brown gum-like material.

Compound 48 ((6S,7aR)-6-allyl-7a-((S)-1-(4-(dimethylamino)-2,5-difluorophenyl)propan-2-yl)-7,7a-dihydrobenzo [d][1,3]dioxol-5(6H)-one). $^1$H NMR (500 MHz, CD$_3$OD): δ 6.88-6.85 (m, 1H), 6.70 (dd, J=10.0, 8.0 Hz, 1H), 5.92-5.85 (m, 1H), 5.66 (s, 1H), 5.62 (s, 1H), 5.49 (s, 1H), 5.18-5.01 (m, 2H), 3.02-2.98 (m, 1H), 2.80-2.78 (m, 1H), 2.79 (s, 6H), 2.65-2.58 (m, 2H), 2.54-2.42 (m, 1H), 2.27-2.15 (m, 1H), 2.14 (dd, J=14.0, 9.5 Hz, 1H), 2.03-1.99 (m, 1H), 0.84 (d, J=7.0 Hz, 3H). ESI MS m/z 378 [C$_{21}$H$_{25}$F$_2$NO$_3$+H]$^+$.

General procedure E: Illustrated with preparation of compound 14.

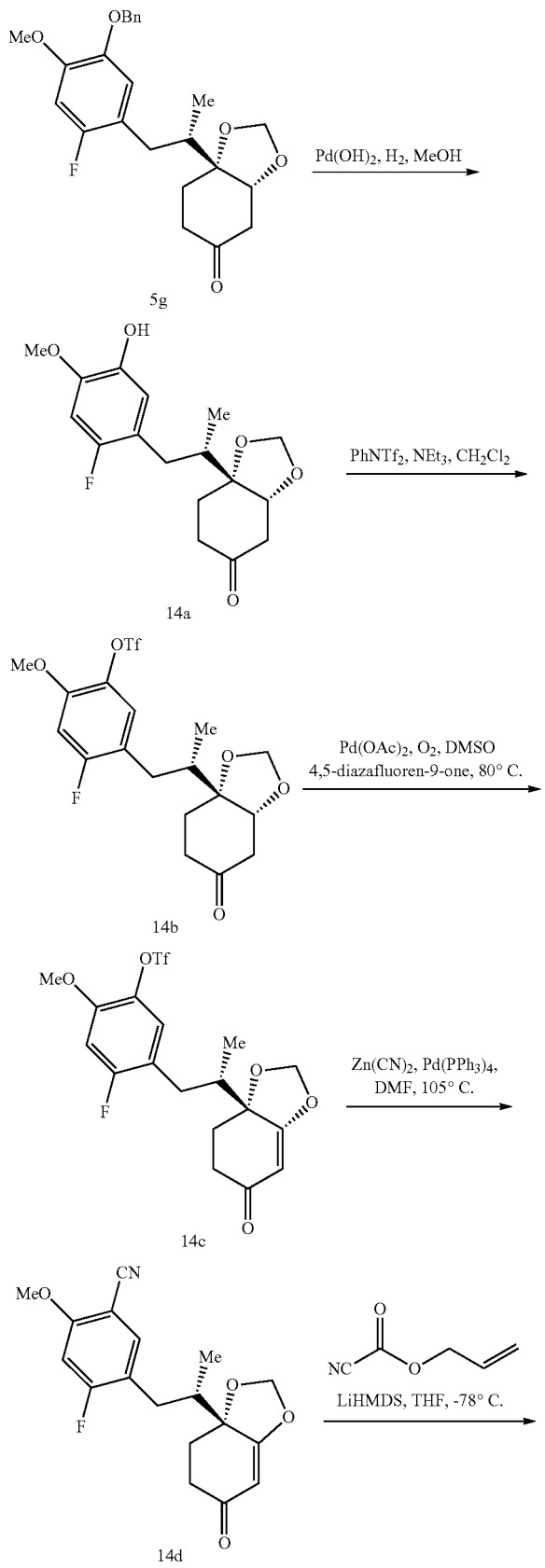

Step 1:

To a solution of 5g (3.4 g, 8.2 mmol) in 65 mL of ethyl acetate was added Pd(OH)$_2$/C (20 wt. % Pd on carbon, 680 mg) under a nitrogen atmosphere. The mixture was stirred under one atmosphere of hydrogen for 1 h. The reaction mixture was filtered through a pad of CELITE and the filter cake was washed with ethyl acetate (300 mL). The filtrate was concentrated in vacuo to provide 14a as a colorless oil (2.6 g, 100%). The crude product was used without further purification. $^1$H NMR (500 MHz, CDCl$_3$): δ 6.70 (d, J=7.0 Hz, 1H), 6.58 (d, J=10.5 Hz, 1H), 5.31 (s, 1H), 5.10 (s, 1H), 4.78 (s, 1H), 4.35 (t, J=3.0 Hz, 1H), 3.87 (s, 3H), 2.87 (dd, J=17.0, 4.5 Hz, 1H), 3.75 (d, J=14.0 Hz, 1H), 2.57-2.45 (m, 2H), 2.33-2.22 (m, 2H), 2.07-2.01 (m, 2H), 1.90-1.83 (m, 1H), 0.97 (d, J=7.0 Hz, 3H).

Step 2:

To a solution of 14a (2.6 g, 8.21 mmol), triethylamine (2.3 mL, 16.42 mmol) and 4-(dimethylamnio)pyridine (20 mg) in CH$_2$Cl$_2$ (80 mL) was added N-phenyl bis-trifluoromethane sulfonimide (4.4 g, 12.31 mmol). The reaction mixture was stirred at room temperature for 12 h, and then concentrated to dryness. The crude residue was purified by silica gel chromatography (0 to 30% ethyl acetate/hexanes) to provide 14b as a colorless oil (3.2 g, 86%). $^1$H NMR (500 MHz, CD$_3$OD): δ 7.04 (d, J=7.5 Hz, 1H), 6.77 (d, J=11.0 Hz, 1H), 5.12 (s, 1H), 4.79 (s, 1H), 4.36 (t, J=3.0 Hz, 0.6H), 3.89 (s, 3H), 2.89 (dd, J=17.5, 3.0 Hz, 1H), 2.83 (d, J=13.0 Hz, 1H), 2.56-2.51 (m, 1H), 2.48 (dd, J=17.0, 3.0 Hz, 1H), 2.34-2.25 (m, 2H), 2.06-2.03 (m, 1H), 1.89 (t, J=4.0 Hz, 1H), 0.99 (d, J=7.0 Hz, 3H).

Step 3:

A mixture of 14b (3.2 g, 7.04 mmol), Pd(OAc)$_2$ (791 mg, 3.52 mmol) and 4,5-diazafluoren-9-one (626 mg, 3.52 mmol) in 75 mL of DMSO was heated to 80° C. under one atmosphere of oxygen for 4 h. The reaction mixture was cooled to room temperature and diluted with ethyl acetate (300 mL). The organic phase was washed with brine, dried (MgSO₄), and concentrated to dryness under reduced pressure. The crude residue was purified by silica gel chromatography (0 to 30% ethyl acetate/hexanes) to provide 14c as a colorless gum-like material (1.6 g, 49%). $^1$H NMR (500 MHz, CD₃OD): δ 7.28 (d, J=7.0 Hz, 1H), 7.06 (d, J=11.0 Hz, 1H), 5.69 (s, 1H), 5.63 (s, 1H), 5.45 (s, 1H), 3.90 (s, 3H), 3.06 (dd, J=13.5, 2.0 Hz, 1H), 2.65 (d, J=12.0 Hz, 1H), 2.57 (t, J=10.5 Hz, 1H), 2.53-2.46 (m, 2H), 2.26-2.24 (m, 1H), 2.07-2.03 (m, 1H), 0.95 (d, J=7.0 Hz, 3H).

Step 4:

A mixture of 14c (50 mg, 0.11 mmol), Zn(CN)₂ (52 mg, 0.44 mmol), and Pd(PPh₃)₄ (19 mg, 0.02 mmol) in 3 mL of DMF in amicrowave tube was sealed and heated to 105° C. for 4 h. The reaction mixture was diluted with ethyl acetate (100 mL), washed with brine, dried (MgSO₄), and concentrated to dryness. The crude residue was purified by silica gel chromatography (0 to 40% ethyl acetate/hexanes) to provide 14d as a colorless gum-like material (30 mg, 83%). $^1$H NMR (500 MHz, CD₃OD): δ 7.61 (d, J=8.5 Hz, 1H), 7.01 (d, J=12.0 Hz, 1H), 5.69 (s, 1H), 5.63 (s, 1H), 5.45 (s, 1H), 3.93 (s, 3H), 3.08 (d, J=14.0 Hz, 1H), 2.63 (d, J=14.0 Hz, 1H), 2.54 (t, J=10.0 Hz, 1H), 2.51-2.48 (m, 2H), 2.25-2.20 (m, 1H), 2.06-2.01 (m, 1H), 0.93 (d, J=7.0 Hz, 3H).

Step 5:

To a solution of 14d (38 mg, 0.11 mmol) in THF (3 mL) was added LiHMDS (1.0M solution in THF, 0.18 mL, 0.18 mmol) at −78° C. under a nitrogen atmosphere. The reaction mixture was stirred for 30 min. Allyl cyanoformate II (18 mg, 0.16 mmol) was then added, and the reaction mixture was allowed to warm to 0° C. over 2 h. The reaction was quenched with H₂O and extracted with ethyl acetate (50 mL). The organic phase was washed with brine, dried (MgSO₄), and concentrated to dryness under reduced pressure. The residue was purified by silica gel chromatography (0 to 40% ethyl acetate/hexanes) to provide 14e as a brown gum-like material (42 mg, 89%). $^1$H NMR (500 MHz, CD₃OD): δ 7.64 (d, J=8.5 Hz, 1H), 7.02 (d, J=12.0 Hz, 1H), 5.99-5.87 (m, 1H), 5.72 (s, 1H), 5.67 (s, 1H), 5.51 (s, 1H), 5.38-5.22 (m, 2H), 3.93 (s, 3H), 3.61 (dd, J=13.0, 5.0 Hz, 1H), 3.08 (d, J=14.0, 3.0 Hz, 1H), 2.90 (dd, J=13.0, 5.5 Hz, 1H), 2.59 (t, J=10.5 Hz, 1H), 2.37 (t, J=12.5 Hz, 1H), 2.28-2.21 (m, 1H), 0.94 (d, J=7.0 Hz, 3H).

Step 6:

To a solution of 14e (41 mg, 0.10 mmol) in DMF (2 mL) was added Pd(PPh₃)₄ (12 mg, 0.01 mmol) under a nitrogen atmosphere. The reaction mixture was stirred at room temperature for 1.5 h, and then diluted with ethyl acetate (50 mL). The organic phase was washed with brine, dried (MgSO₄) and concentrated to dryness under reduced pressure. The residue was purified by silica gel chromatography (0 to 30% ethyl acetate/hexanes) to provide 14 as a colorless gum-like material (8 mg, 22%).

Compound 14 (5-((S)-2-((3aR,5S)-5-allyl-6-oxo-3a,4,5,6-tetrahydrobenzo[d][1,3]dioxol-3a-yl)propyl)-4-fluoro-2-methoxybenzonitrile). $^1$H NMR (500 MHz, CD₃OD): δ 7.56 (t, J=8.0 Hz, 1H), 7.02 (d, J=12.0 Hz, 1H), 5.92-5.85 (m, 1H), 5.65 (s, 1H), 5.60 (s, 1H), 5.50 (s, 1H), 5.18-5.11 (m, 2H), 3.93 (s, 3H), 3.10 (d, J=14.0, 8.0 Hz, 1H), 2.85-2.79 (m, 1H), 2.68-2.58 (m, 3H), 2.25-2.20 (m, 1H), 2.17 (t, J=10.0 Hz, 1H), 2.05-2.01 (m, 1H), 0.86 (d, J=7.0 Hz, 3H). ESI MS m/z 372 [C₂₁H₂₂FNO₄+H]⁺.

General procedure F: Illustrated with preparatin of compound 17.

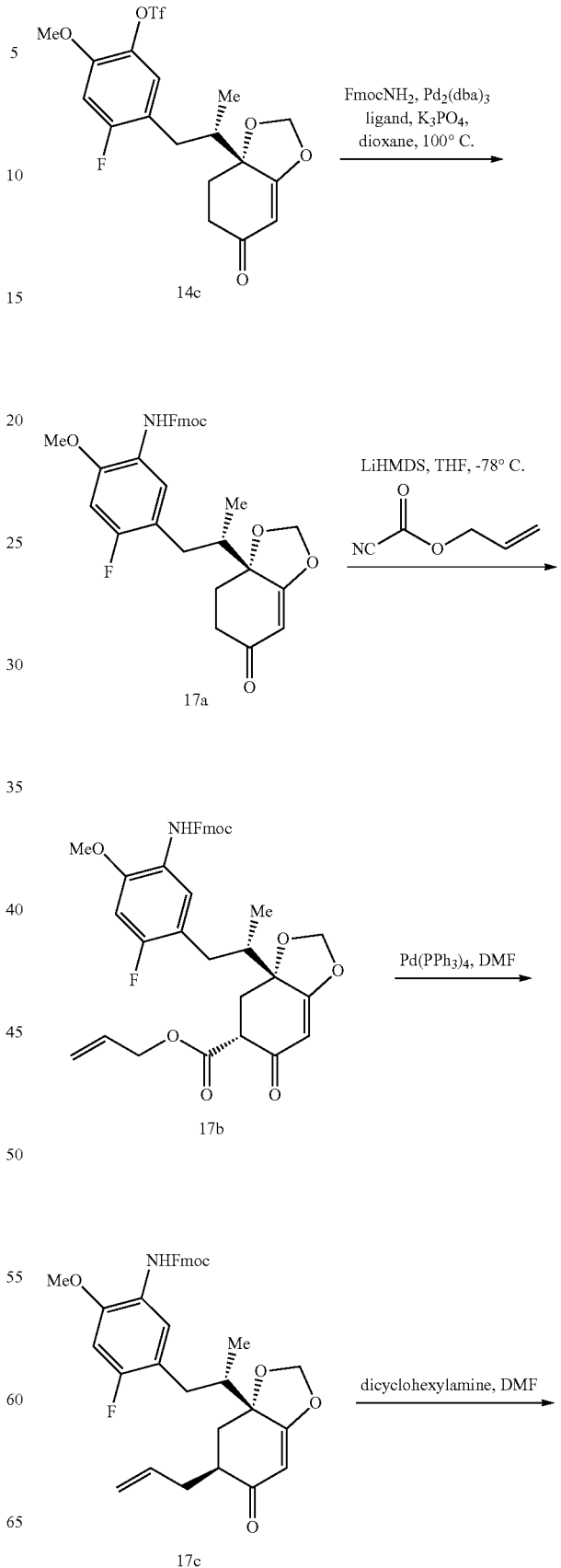

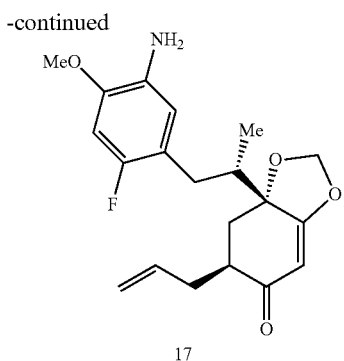

17

Step 1:

A mixture of 14c (100 mg, 0.22 mmol), 9-fluorenylmethyl carbamate (105 mg, 0.44 mmol), Pd$_2$(dba)$_3$ (20 mg, 0.02 mmol), 2-di-tert-butylphosphino-3,4,5,6-tetramethyl-2',4',6'-triisopropyl-1,1'-biphenyl (42 mg, 0.09 mmol), and K$_3$PO$_4$ (140 mg, 0.66 mmol) in 4 mL of dioxane was heated to 105° C. under a nitrogen atmosphere for 4 h. The reaction mixture was diluted with ethyl acetate (100 mL), washed with brine, dried (MgSO$_4$), and concentrated to dryness. The crude residue was purified by silica gel chromatography (0 to 40% ethyl acetate/hexanes) to provide 17a as a colorless gum-like material (32 mg, 26%). $^1$H NMR (500 MHz, CD$_3$OD): δ 7.81-7.78 (m, 2H), 7.66-7.65 (m, 1H), 7.41-7.38 (m, 3H), 7.32-7.29 (m, 2H), 6.80 (d, J=11.5 Hz, 1H), 5.69 (s, 1H), 5.63 (s, 1H), 5.44 (s, 1H), 4.47 (d, J=7.0 Hz, 2H), 4.32-4.30 (m, 1H), 3.83 (s, 3H), 3.02 (dd, J=14.0, 3.0 Hz, 1H), 2.68-2.66 (m, 1H), 2.48-2.46 (m, 3H), 2.25-2.18 (m, 1H), 2.06-1.98 (m, 1H), 0.97 (d, J=7.0 Hz, 3H).

Step 2:

To a solution of 17a (31 mg, 0.06 mmol) in THF (3 mL) was added LiHMDS (1.0M solution in THF, 0.09 mL, 0.09 mmol) at −78° C. under a nitrogen atmosphere. The reaction mixture was stirred for 30 min, and then TMS-Cl (1.0M solution in THF, 0.06 mL, 0.06 mmol) was added. The reaction mixture was stirred for 1 h and cooled to −78° C. LiHMDS (1.0M solution in THF, 0.11 mL, 0.11 mmol) was added, and the reaction mixture was stirred for 30 min. Allyl cyanoformate II (13 mg, 0.11 mmol) was added, and the reaction mixture was allowed to warm to 0° C. over 2 h. The reaction was quenched with H$_2$O and extracted with ethyl acetate (50 mL). The organic phase was washed with brine, dried (MgSO$_4$), and concentrated to dryness under reduced pressure. The residue was purified by silica gel chromatography (0 to 30% ethyl acetate/hexanes) to provide 17b as a brown gum-like material (30 mg, 90%). $^1$H NMR (500 MHz, CD$_3$OD): δ 7.81 (d, J=7.5 Hz, 2H), 7.68 (d, J=7.5 Hz, 2H), 7.39-7.35 (m, 2H), 7.33-7.31 (m, 3H), 7.02 (d, J=11.5 Hz, 1H), 5.99-5.87 (m, 1H), 5.72 (s, 1H), 5.67 (s, 1H), 5.51 (s, 1H), 5.36-5.21 (m, 2H), 4.47 (d, J=7.0 Hz, 2H), 4.32-4.30 (m, 1H), 3.90 (s, 3H), 3.56-3.52 (m, 1H), 3.07 (d, J=14.0 Hz, 1H), 2.88 (d, J=8.0 Hz, 1H), 2.57 (t, J=12.0 Hz, 1H), 2.32 (t, J=14.0 Hz, 1H), 2.28-2.22 (m, 1H), 0.96 (d, J=7.0 Hz, 3H).

Step 3:

To a solution of 17b (23 mg, 0.056 mmol) in DMF (3 mL) was added Pd(PPh$_3$)$_4$ (7 mg, 0.006 mmol) under a nitrogen atmosphere. The reaction mixture was stirred for 1.5 h, and then diluted with ethyl acetate (50 mL). The organic phase was washed with brine, dried (MgSO$_4$) and concentrated to dryness under reduced pressure. The residue was purified by silica gel chromatography (0 to 40% ethyl acetate/hexanes) to provide 17c (10 mg, 35%) as a colorless gum-like material. ESI MS m/z 584 [C$_{35}$H$_{34}$FNO$_6$+H]$^+$.

Step 4:

A solution of 17c (10 mg, 0.016 mmol) and dicyclohexylamine (0.5 mL, 2.5 mmol) in 0.5 mL of DMF was stirred at room temperature for 2 h. The reaction mixture was diluted with ethyl acetate (50 mL). The organic phase was washed with brine, dried (MgSO$_4$) and concentrated to dryness under reduced pressure. The residue was chromatographed by SiO$_2$ (0 to 40% ethyl acetate/hexanes) to provide 17 (2 mg, 33%) as a colorless gum-like material.

Compound 17 ((6S,7aR)-6-allyl-7a-((S)-1-(5-amino-2-fluoro-4-methoxyphenyl)propan-2-yl)-7,7a-dihydrobenzo[d][1,3]dioxol-5(6H)-one). $^1$H NMR (500 MHz, CD$_3$OD): δ 6.65 (d, J=11.5 Hz, 1H), 6.59 (d, J=8.0 Hz, 1H), 5.92-5.85 (m, 1H), 5.64 (s, 1H), 5.60 (s, 1H), 5.49 (s, 1H), 5.18-5.11 (m, 2H), 3.82 (s, 3H), 3.01 (dd, J=14.0, 10.0 Hz, 1H), 2.85-2.82 (m, 1H), 2.68 (d, J=13.5 Hz, 1H), 2.63-2.60 (m, 1H), 2.47 (t, J=10.5 Hz, 1H), 2.25-2.22 (m, 1H), 2.13 (dd, J=14.0, 9.5 Hz, 1H), 2.03-1.98 (m, 1H), 0.83 (d, J=7.0 Hz, 3H). ESI MS m/z 362 [C$_{20}$H$_{24}$FNO$_4$+H]$^+$.

General procedure G: Illustrated with preparatin of compound 92.

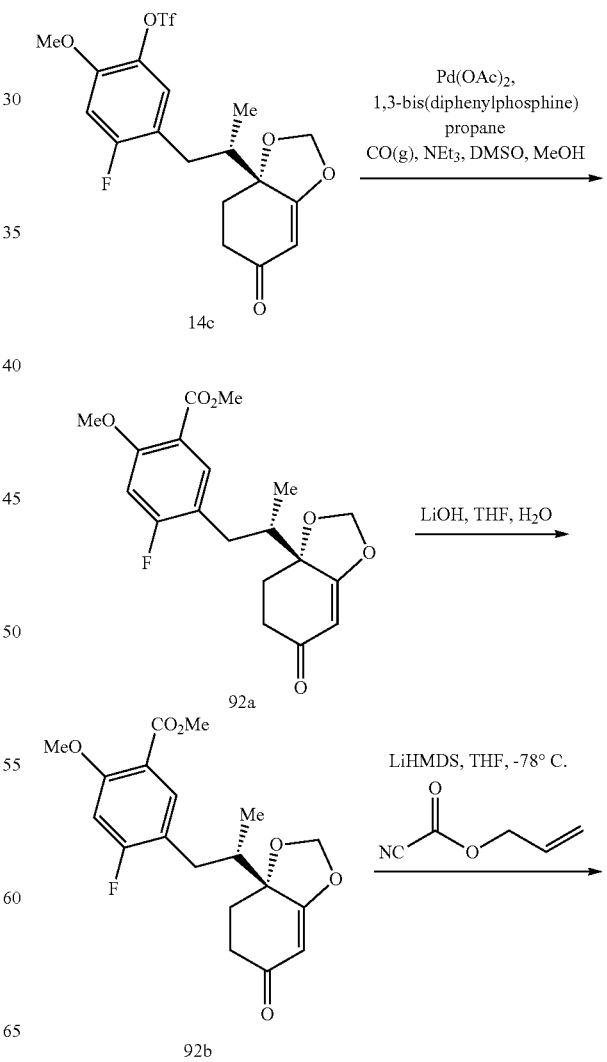

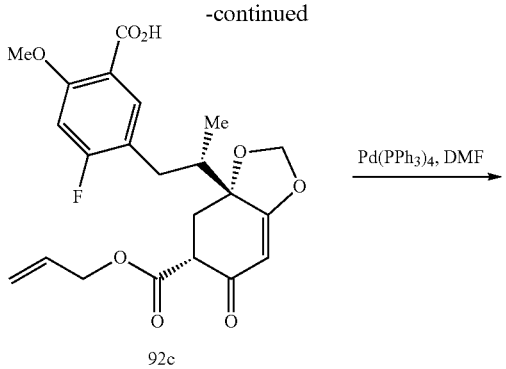

92c

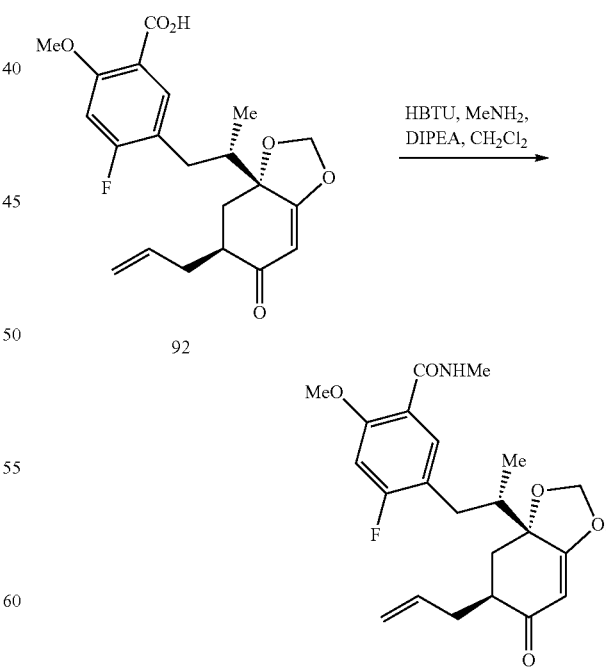

92

Step 1:

A mixture of Pd(OAc)$_2$ (52 mg, 0.24 mmol), 1,3-bis(diphenylphosphine)propane (100 mg, 0.24 mmol), and triethylamine (0.67 mL, 4.8 mmol) in 10 mL of DMSO was stirred at room temperature for 10 min. A solution of 14c (440 mg, 0.96 mmol) in MeOH (10 mL) was then added, and the reaction mixture was transferred to a pressure reactor. The reactor was charged with 50 psi of CO and sealed. The reaction mixture was heated to 45° C. for 12 h. The reaction mixture then was diluted with ethyl acetate (100 mL), washed with brine, dried (MgSO$_4$), and concentrated to dryness. The crude residue was purified by silica gel chromatography (0 to 40% ethyl acetate/hexanes) to provide 92a as a colorless solid (150 mg, 88%). $^1$H NMR (500 MHz, CD$_3$OD): δ 7.72 (d, J=10.5 Hz, 1H), 6.93 (d, J=12.5 Hz, 1H), 5.70 (s, 1H), 5.64 (s, 1H), 5.46 (s, 1H), 3.86 (s, 3H), 3.84 (s, 3H), 3.10 (dd, J=13.0, 3.0 Hz, 1H), 2.69-2.66 (m, 1H), 2.57-2.45 (m, 3H), 2.27-2.24 (m, 1H), 2.07-2.01 (m, 1H), 0.94 (d, J=7.0 Hz, 3H).

Step 2:

A mixture of 92a (310 mg, 0.78 mmol) and LiOH (78 mg, 3.91 mmol) in THF (20 mL) and H$_2$O (10 mL) was stirred at room temperature for 4 h. The reaction mixture was neutralized by HCl (2 M) and extracted with ethyl acetate (100 mL). The organic phase was washed with brine, dried (MgSO$_4$) and concentrated to dryness. The crude residue was purified by silica gel chromatography (0 to 10% MeOH/CH$_2$Cl$_2$) to provide 92b as an off-white solid (250 mg, 84%). $^1$H NMR (500 MHz, CD$_3$OD): δ 7.72-7.68 (m, 1H), 6.93 (d, J=7.0 Hz, 1H), 5.71 (s, 1H), 5.65 (s, 1H), 5.45 (s, 1H), 3.87 (s, 3H), 3.10 (dd, J=13.0, 3.0 Hz, 1H), 2.66-2.50 (m, 4H), 2.28-2.22 (m, 1H), 2.08-2.01 (m, 1H), 0.95 (d, J=12.0 Hz, 3H).

Step 3:

To a solution of 92b (250 mg, 0.65 mmol) in THF (20 mL) was added LiHMDS (1.0M solution in THF, 1.7 mL, 1.70 mmol) at −78° C. under a nitrogen atmosphere. The reaction mixture was stirred for 30 min. Allyl cyanoformate II (150 mg, 1.30 mmol) was then added, and the reaction mixture was allowed to warm to 0° C. over 2 h. The reaction was then quenched with H$_2$O and extracted with ethyl acetate (50 mL). The organic phase was washed with brine, dried (MgSO$_4$), and concentrated to dryness under reduced pressure. The residue was purified by silica gel chromatography (0 to 10% MeOH/CH$_2$Cl$_2$) to provide 92c as a brown solid (200 mg, 66%). $^1$H NMR (500 MHz, CD$_3$OD): δ 7.73 (d, J=7.0 Hz, 1H), 6.91 (d, J=12.5 Hz, 1H), 5.95-5.90 (m, 1H), 5.73 (s, 1H), 5.69 (s, 1H), 5.48 (s, 1H), 5.38-5.22 (m, 2H), 3.86 (s, 3H), 3.08 (d, J=14.0 Hz, 1H), 2.91 (d, J=13.0 Hz, 1H), 2.82-2.80 (d, J=14.0 Hz, 1H), 2.55-2.52 (m, 1H), 2.35 (d, J=12.5 Hz, 1H), 2.25-2.18 (m, 1H), 0.96 (d, J=7.0 Hz, 3H).

Step 4:

To a solution of 92c (200 mg, 0.42 mmol) in DMF (8 mL) was added Pd(PPh$_3$)$_4$ (50 mg, 0.04 mmol) under a nitrogen atmosphere. The reaction mixture was stirred at room temperature for 1.5 h, and then diluted with ethyl acetate (100 mL). The organic phase was washed with brine, dried (MgSO$_4$), and concentrated to dryness under reduced pressure. The residue was purified by silica gel chromatography (0 to 80% ethyl acetate/hexanes) to provide 92 (92 mg, 51%) as a colorless solid.

Compound 92 (5-(2-((3aR,5S)-5-allyl-6-oxo-3a,4,5,6-tetrahydrobenzo[d][1,3]dioxol-3a-yl)propyl)-4-fluoro-2-methoxybenzoic acid). $^1$H NMR (500 MHz, CD$_3$OD): δ 7.68 (d, J=9.5 Hz, 1H), 6.90 (d, J=8.0 Hz, 1H), 5.92-5.78 (m, 1H), 5.69 (s, 1H), 5.61 (s, 1H), 5.54 (s, 1H), 5.18-5.01 (m, 2H), 3.88 (s, 3H), 2.82-2.78 (m, 2H), 2.64-2.58 (m, 1H), 2.55 (d, J=14.0 Hz, 1H), 2.41 (t, J=11.5 Hz, 1H), 2.10-1.99 (m, 3H), 0.97 (d, J=7.0 Hz, 3H). ESI MS m/z 391 [C$_{21}$H$_{23}$FO$_6$+H]$^+$.

General Procedure H: Illustrated with preparation of compound 12

Methylamine (2.0M solution in THF, 0.06 mL, 0.12 mmol) was added to a solution of 92 (22 mg, 0.06 mmol), HBTU (46 mg, 0.12 mmol) and DIPEA (0.03 mL, 0.18 mmol), in CH$_2$Cl$_2$ (3 mL). The mixture was stirred at room temperature for 24 h, and was then diluted with ethyl acetate (50 mL), washed with brine, dried (MgSO$_4$), filtered, and concentrated to dryness. The residue was purified by silica gel chromatography (0 to 70% ethyl acetate/hexanes) to provide a mixture of diastereomers (15 mg). The mixture was further purified by CHIRALCEL OD (20% i-PrOH/heptane) to provide 12 (6 mg, 25%) as a colorless gum-like material.

Compound 12 (5-((S)-2-((3aR,5S)-5-allyl-6-oxo-3a,4,5,6-tetrahydrobenzo[d][1,3]dioxol-3a-yl)propyl)-4-fluoro-2-methoxy-N-methylbenzamide). $^1$H NMR (500 MHz, CD$_3$OD): δ 7.85 (t, J=9.0 Hz, 1H), 6.95 (d, J=12.0 Hz, 1H), 5.95-5.85 (m, 1H), 5.66 (s, 1H), 5.61 (s, 1H), 5.50 (s, 1H), 5.18-5.11 (m, 2H), 3.95 (s, 3H), 3.09 (d, J=14.0 Hz, 1H), 2.92 (s, 3H), 2.82-2.79 (m, 1H), 2.70 (d, J=14.0 Hz, 1H), 2.64-2.58 (m, 2H), 2.25-2.21 (m, 1H), 2.16 (dd, J=14.0, 9.5 Hz, 1H), 2.03-1.95 (m, 1H), 0.83 (d, J=8.0 Hz, 3H). ESI MS m/z 404 [C$_{22}$H$_{26}$FO$_5$+H]$^+$.

(m, 1H), 5.69 (s, 1H), 5.62 (s, 1H), 5.53 (s, 1H), 5.09-5.02 (m, 2H), 3.85 (s, 3H), 3.83 (s, 3H), 2.86-2.78 (m, 2H), 2.62-2.61 (m, 1H), 2.55 (d, J=14.0 Hz, 1H), 2.45 (t, J=8.5 Hz, 1H), 2.11-2.03 (m, 3H), 0.97 (d, J=7.0 Hz, 3H). ESI MS m/z 405 [C$_{20}$H$_{25}$FO$_6$+H]$^+$.

General procedure J: Illustrated with preparation of compound 95

General Procedure I: Illustrated with preparation of compound 10

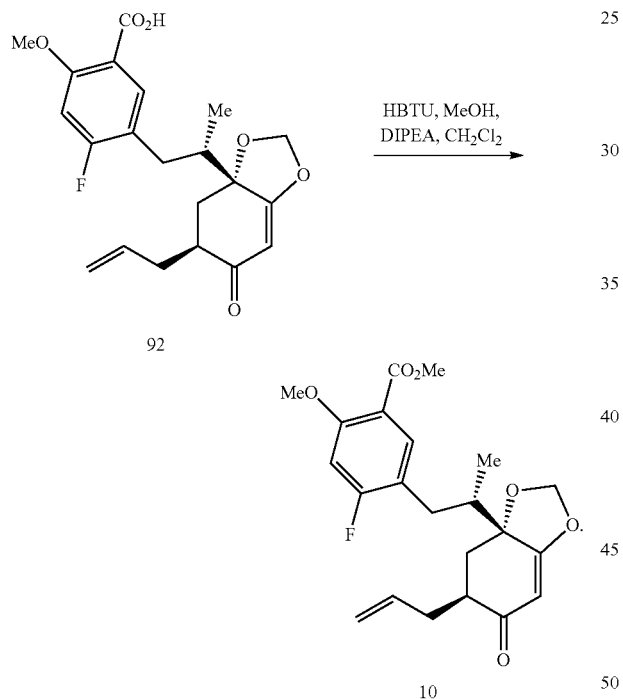

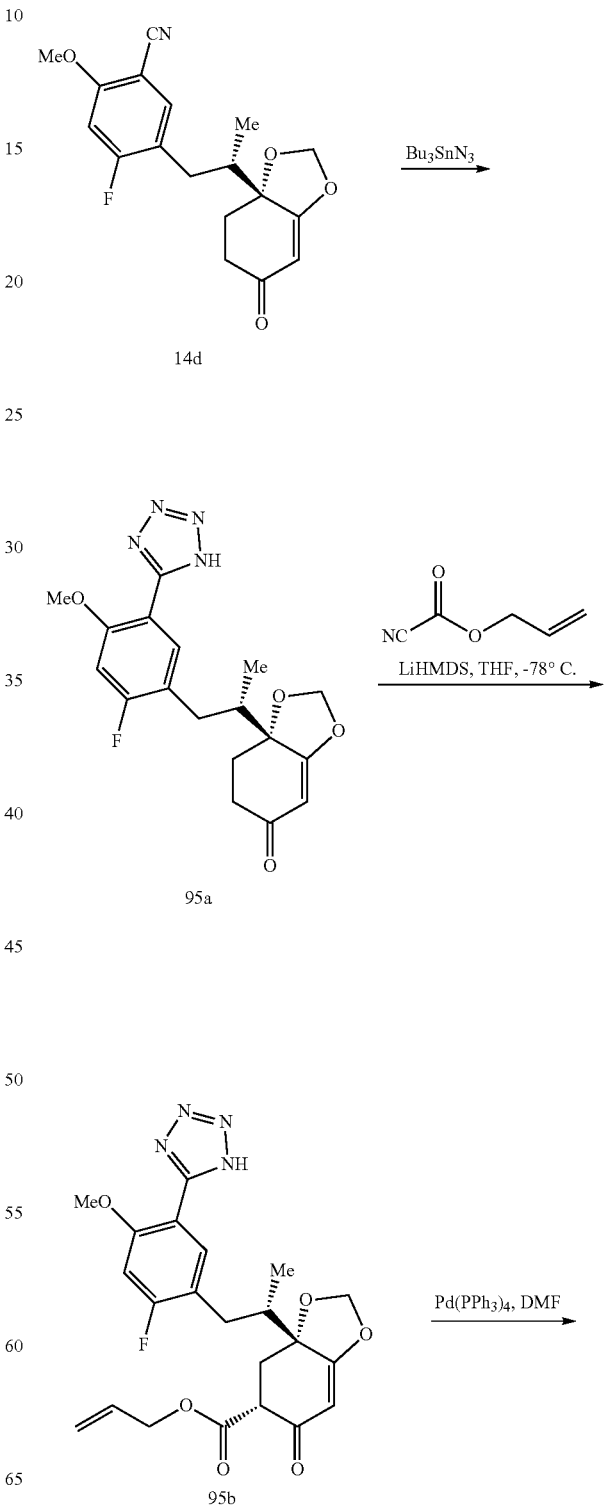

Methanol (0.005 mL, 0.15 mmol) was added to a solution of 92 (30 mg, 0.08 mmol), HBTU, (60 mg, 0.15 mmol) and DIPEA (0.10 mL, 0.61 mmol) in CH$_2$Cl$_2$ (3 mL). The mixture was stirred at room temperature for 24 h. The reaction mixture was then diluted with ethyl acetate (50 mL), washed with brine, dried (MgSO$_4$), filtered, and concentrated to dryness. The residue was purified by silica gel chromatography (0 to 70% ethyl acetate/hexanes) to provide a mixture of diastereomers (15 mg). The product was further purified by CHIRALCEL OD (20% i-PrOH/hep) to provide 10 (3 mg, 10%) as a colorless gum-like material.

Compound 10 (methyl 5-((S)-2-((3aR,5S)-5-allyl-6-oxo-3a,4,5,6-tetrahydrobenzo[d][1,3]dioxol-3a-yl)propyl)-4-fluoro-2-methoxybenzoate). $^1$H NMR (500 MHz, CD$_3$OD): δ 7.63 (d, J=9.0 Hz, 1H), 6.90 (d, J=12.5 Hz, 1H), 5.85-5.75

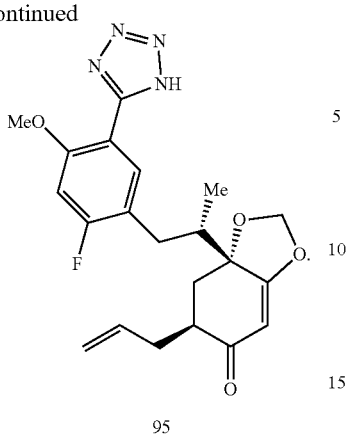

95

Step 1:
A mixture of 14d (50 mg, 0.15 mmol) and Bu₃SnN₃ (0.5 mL) was heated to 90° C. for 12 h. The reaction mixture was then purified by silica gel chromatography (0 to 30% ethyl acetate/hexanes) to provide 95a as a colorless oil (34 mg, 61%). ¹H NMR (500 MHz, CDCl₃): δ 7.99 (d, J=7.0 Hz, 1H), 7.05 (d, J=11.5 Hz, 1H), 5.73 (s, 1H), 5.65 (s, 1H), 5.46 (s, 1H), 3.99 (s, 3H), 3.15 (d, J=14.0 Hz, 1H), 2.75 (dd, J=12.0, 4.5 Hz, 1H), 2.65 (d, J=14.0 Hz, 1H), 2.54-2.51 (m, 2H), 2.35-2.31 (m, 1H), 2.07-2.01 (m, 1H), 0.98 (d, J=7.0 Hz, 3H). ESI MS 375 [C$_{18}$H$_{19}$FN$_4$O$_4$+H]$^+$.

Step 2:
To a solution of 95a (33 mg, 0.09 mmol) in THF (3 mL) was added LiHMDS (1.0M solution in THF, 0.22 mL, 0.22 mmol) at −78° C. under a nitrogen atmosphere. The reaction mixture was stirred for 30 min, and then a llyl cyanoformate II (20 mg, 0.18 mmol) was added. The reaction mixture was allowed to warm to 0° C. over 2 h; it was then quenched with H₂O and extracted with ethyl acetate (50 mL). The organic phase was washed with brine, dried (MgSO₄), and concentrated to dryness under reduced pressure. The residue was purified by silica gel chromatography (0 to 40% ethyl acetate/hexanes) to provide 95b as a brown gum-like material (10 mg, 25%). ¹H NMR (500 MHz, CD₃OD): δ 8.10 (d, J=14.0 Hz, 1H), 7.10 (t, J=20.0 Hz, 1H), 5.92-5.85 (m, 1H), 5.75 (s, 1H), 5.68 (s, 1H), 5.51 (s, 1H), 5.35-5.18 (m, 2H), 4.01 (s, 3H), 2.98-2.89 (m, 2H), 2.65-2.55 (m, 1H), 2.52-2.48 (m, 1H), 2.38-2.25 (m, 2H), 0.98 (d, J=11.5 Hz, 3H).

Step 3:
To a solution of 95b (10 mg, 0.02 mmol) in DMF (2 mL) was added Pd(PPh₃)₄ (3 mg, 0.003 mmol) under a nitrogen atmosphere. The reaction mixture was stirred at room temperature for 2 h, and then diluted with ethyl acetate (50 mL). The organic phase was washed with brine, dried (MgSO₄) and concentrated to dryness under reduced pressure. The residue was purified by silica gel chromatography (0 to 70% ethyl acetate/hexanes) to provide 95 (2.0 mg, 22%) as a colorless gum-like material.

Compound 95 ((6S,7aR)-6-allyl-7a-((S)-1-(2-fluoro-4-methoxy-5-(1H-tetrazol-5-yl)phenyl)propan-2-yl)-7,7a-dihydrobenzo[d][1,3]dioxol-5(6H)-one). ¹H NMR (500 MHz, CD₃OD): δ 7.39 (d, J=8.0 Hz, 1H), 7.06 (d, J=12.0 Hz, 1H), 5.92-5.85 (m, 1H), 5.69 (s, 1H), 5.63 (s, 1H), 5.45 (s, 1H), 5.22 (d, J=10.5 Hz, 1H), 5.10 (d, J=17.0 Hz, 1H), 3.86 (s, 3H), 3.12 (d, J=14.0 Hz, 1H), 2.67 (d, J=10.0 Hz, 1H), 2.63 (t, J=10.5 Hz, 1H), 2.51-2.48 (m, 2H), 2.33-2.15 (m, 1H), 2.08-2.02 (m, 2H), 0.96 (d, J=7.0 Hz, 3H). ESI MS m/z 415 [C$_{21}$H$_{23}$FN$_4$O$_4$+H]$^+$.

General procedure K: Illustrated with preparation of compound 96

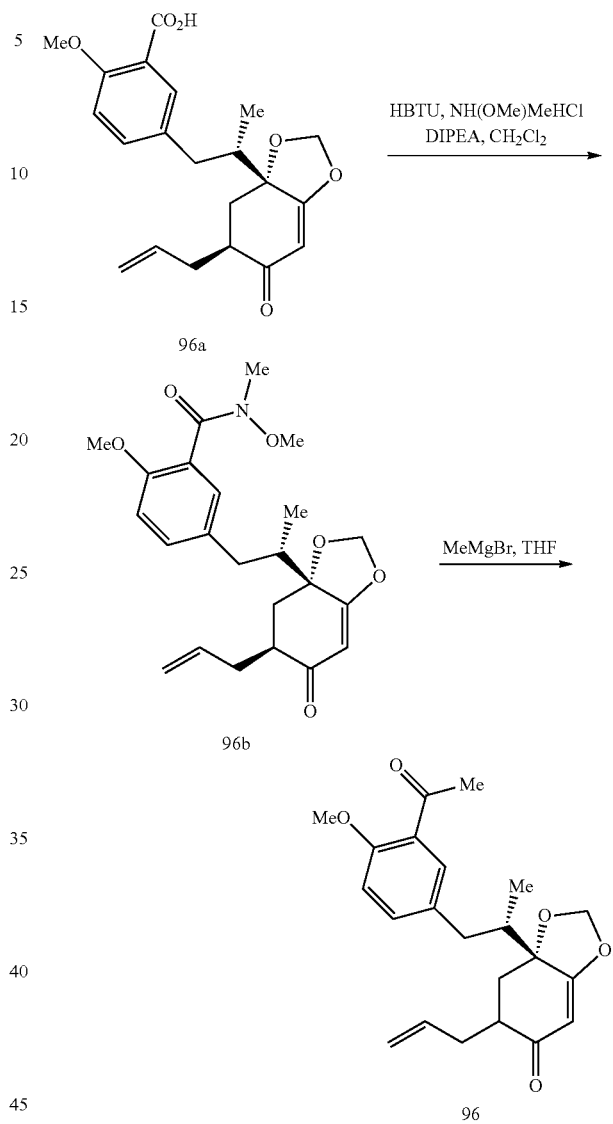

Step 1:
Compound 96a was prepared according to general procedure G. To a mixture of 96a (16 mg, 0.04 mmol), HBTU (46 mg, 0.12 mmol) and DIPEA (0.03 mL, 0.18 mmol), in CH₂Cl₂ (3 mL) was added N,O-dimethylhydroxylamine hydrochloride (9 mg, 0.09 mmol). The mixture was stirred at room temperature for 24 h. The reaction mixture was then diluted with ethyl acetate (50 mL), washed with brine, dried (MgSO₄), filtered and concentrated to dryness. The residue was purified by silica gel chromatography (0 to 70% ethyl acetate/hexanes) to provide 96b (17 mg, 100%) as a colorless gum-like material. ¹H NMR (500 MHz, CDCl₃): δ 7.07 (dd, J=11.5, 7.0 Hz, 1H), 6.89-5.82 (m, 1H), 5.72 (s, 1H), 5.67 (s, 1H), 5.57 (s, 1H), 5.51 (s, 1H), 5.34 (s, 1H), 4.69 (d, J=8.0 Hz, 2H), 3.84 (s, 3H), 3.62 (dd, J=12.5, 5.0 Hz, 1H), 3.02 (dd, J=14.0, 3.0 Hz, 1H), 2.90-2.86 (m, 1H), 2.52-2.49 (s, 2H), 2.36-2.30 (m, 1H), 2.25-2.18 (m, 1H), 0.86 (d, J=7.0 Hz, 3H).

Step 2:
To a solution of 96b (17 mg, 0.04 mmol) in THF (2 mL) was added methylmagnesium bromide (3.0M solution in Et$_2$O, 0.10 mL, 0.30 mmol) in an ice bath under a nitrogen atmosphere. The reaction mixture was stirred at room temperature for 12 h, and then diluted with ethyl acetate (50 mL), washed with brine, dried (MgSO$_4$), and concentrated to dryness under reduced pressure. The residue was purified by silica gel chromatography (0 to 40% ethyl acetate/hexanes) to provide a mixture of diastereomers 96 as a brown gum-like material (1.0 mg, 8%).

Compound 96 ((7aR)-7a-((S)-1-(3-acetyl-4-methoxyphenyl)propan-2-yl)-6-allyl-7,7a-dihydrobenzo[d][1,3]dioxol-5 (6H)-one. $^1$H NMR (500 MHz, CD$_3$OD): δ 7.51 (d, J=13.0 Hz, 1H), 7.36 (t, J=8.0 Hz, 1H), 7.09 (dd, J=8.0, 6.0 Hz, 1H), 5.92-5.85 (m, 0.5H), 5.66 (s, 1H), 5.66-5.61 (m, 0.5H), 5.60 (s, 1H), 5.50 (s, 0.5H), 5.43 (s, 0.5H), 5.18-5.01 (m, 2H), 3.92 (s, 3H), 3.08 (d, J=14.0 Hz, 0.5H), 2.98 (d, J=14.0 Hz, 0.5H), 2.82-2.79 (m, 0.5H), 2.67 (d, J=14.0 Hz, 1H), 2.60-2.58 (m, 0.5H), 2.55 (s, 3H), 2.53-2.45 (m, 1H), 2.25-2.12 (m, 3H), 1.95-1.85 (m, 0.5H), 1.70 (t, J=7.0 Hz, 0.5H), 0.94 (d, J=9.5 Hz, 1.5H), 0.84 (d, J=6.5 Hz, 1.5H). ESI MS m/z 371 [C$_{22}$H$_{26}$O$_5$+H]$^+$.

phenyl dimethylcarbamate). $^1$H NMR (500 MHz, CD$_3$OD): δ 7.03-6.98 (m, 2H), 6.88 (s, 1H), 5.92-5.85 (m, 1H), 5.65 (s, 1H), 5.60 (s, 1H), 5.49 (s, 1H), 5.18-5.12 (m, 2H), 3.79 (s, 3H), 3.11 (s, 3H), 3.09 (m, 1H), 2.97 (s, 3H), 2.89-2.84 (m, 1H), 2.69 (d, J=14.5 Hz, 1H), 2.65-2.60 (m, 1H), 2.47 (t, J=11.5 Hz, 1H), 2.24-2.21 (m, 1H), 2.14 (dd, J=14.0, 9.5 Hz, 1H), 1.98-1.90 (m, 1H), 0.87 (d, J=7.0 Hz, 3H). ESI MS m/z 416 [C$_{23}$H$_{29}$O$_6$+H]$^+$.

General procedure M: Illustrated with preparation of compound 28

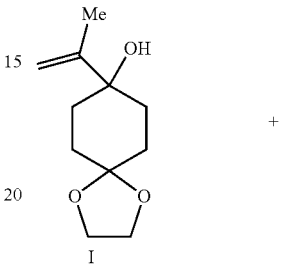

I

General procedure L: Illustrated with preparation of compound 73

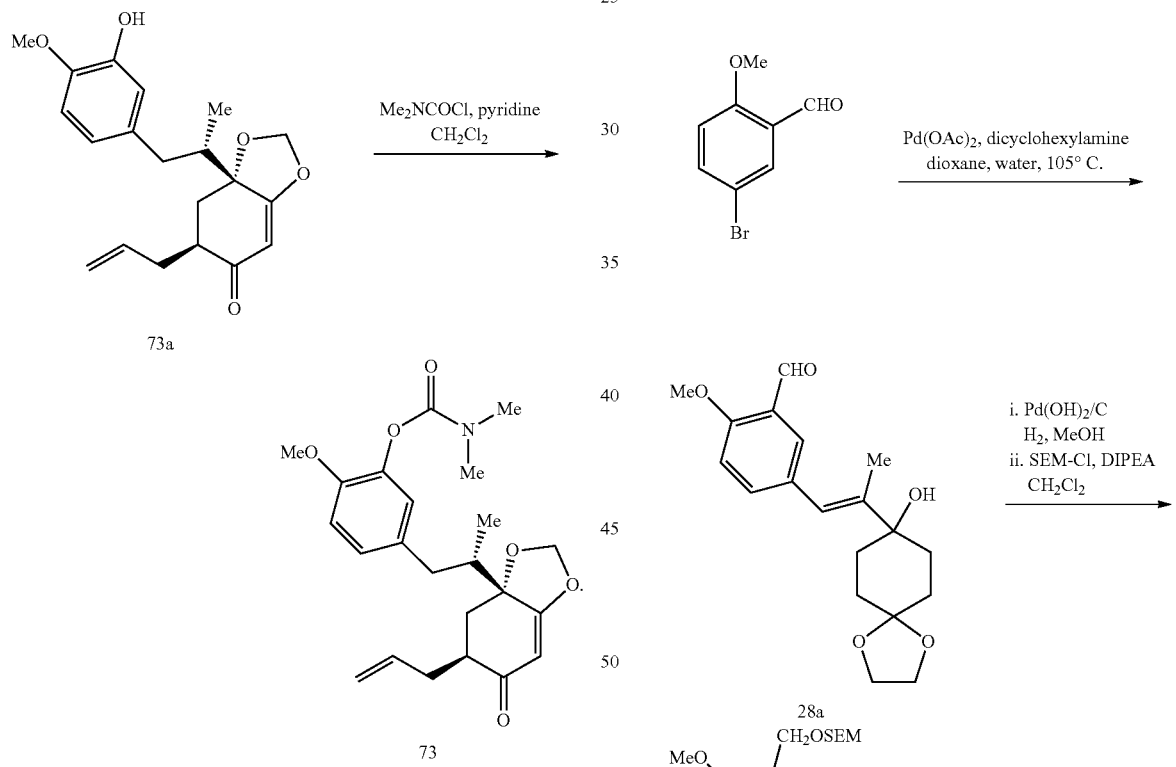

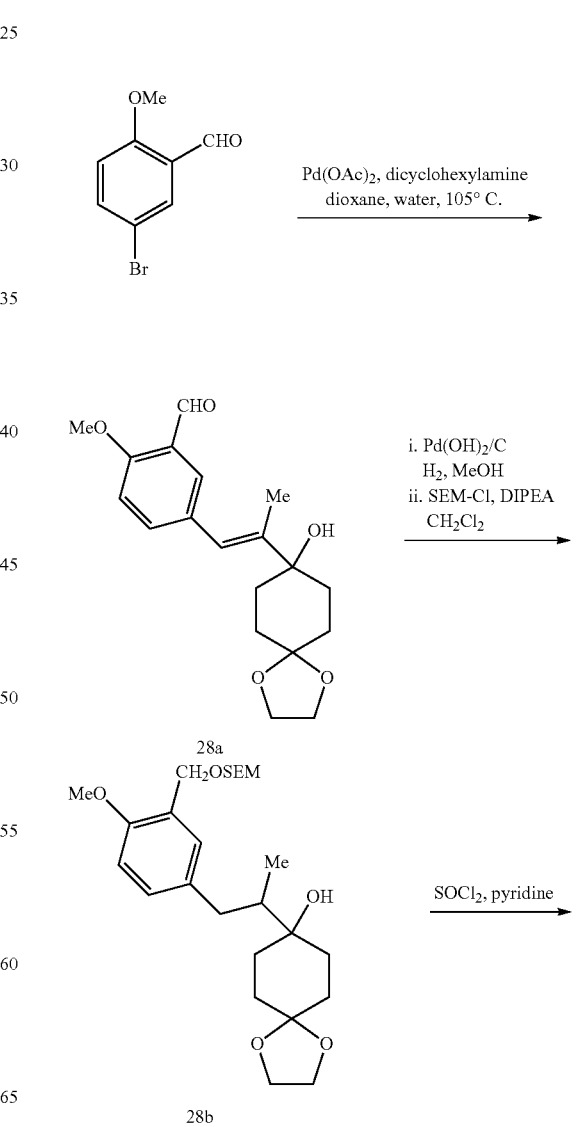

Compound 73a was prepared according to general procedure C. To a mixture of 73a (10 mg, 0.029 mmol) and pyridine (0.005 mL, 0.058 mmol) in CH$_2$Cl$_2$ (2 mL) was added dimethylcarbamyl chloride (0.04 ml, 0.035 mmol). The mixture was stirred at room temperature for 12 h. The reaction mixture was diluted with ethyl acetate (50 mL), washed with brine, dried (MgSO$_4$), filtered, and concentrated to dryness. The residue was purified by silica gel chromatography (0 to 30% ethyl acetate/hexanes) to provide 73 (2 mg, 17%) as a colorless oil.

Compound 73 (5-((S)-2-((3aR,5S)-5-allyl-6-oxo-3a,4,5,6-tetrahydrobenzo[d][1,3]dioxol-3a-yl)propyl)-2-methoxy- 93
-continued
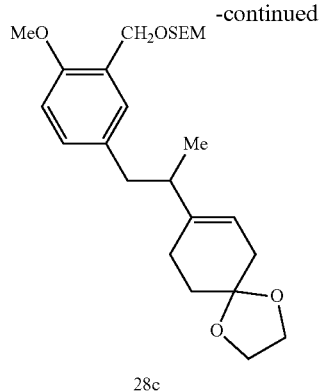
28c
TBAF, HMPA →
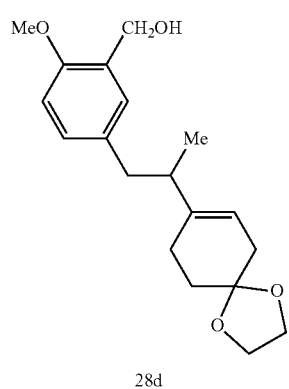
28d
Dess-Martin reagent
CH₂Cl₂ →
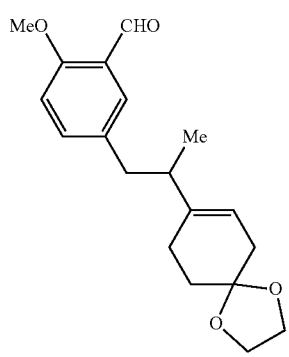
28e
AD-mix-beta, MeSO₂NH₂
t-BuOH, H₂O, toluene →
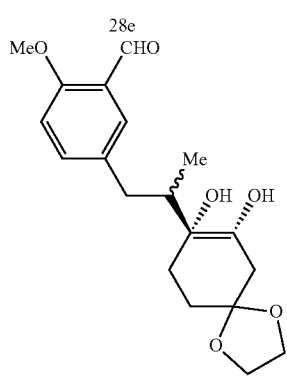
28f
(CH₂O)ₙ, p-TSA
CH₂Cl₂ →
94
-continued
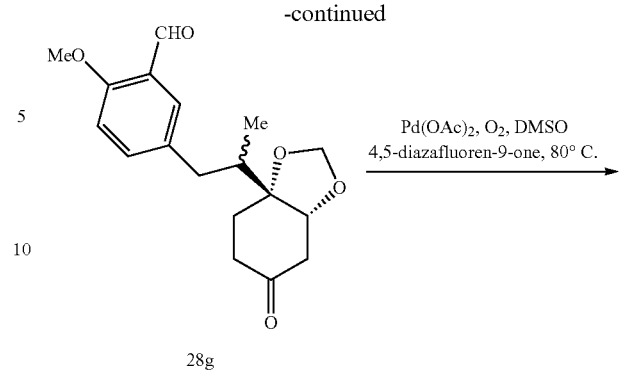
28g
Pd(OAc)₂, O₂, DMSO
4,5-diazafluoren-9-one, 80° C. →
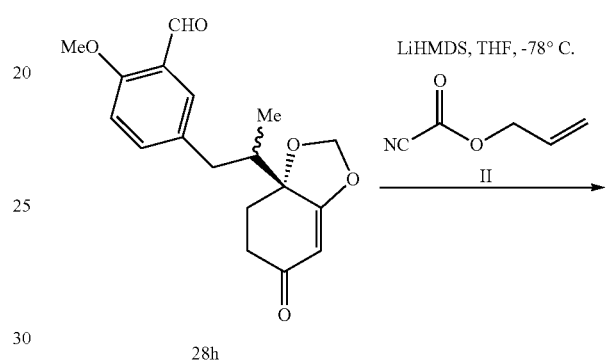
28h
LiHMDS, THF, -78° C.
II →
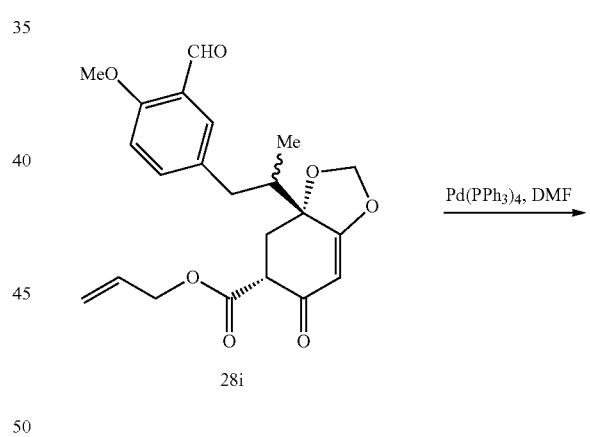
28i
Pd(PPh₃)₄, DMF →
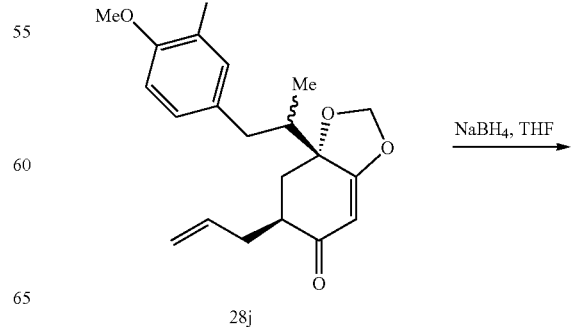
28j
NaBH₄, THF →

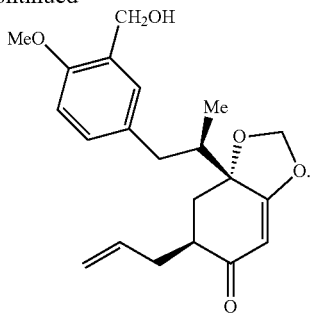

28

Step 1:

A mixture of I (5.0 g, 25.5 mmol), 5-bromo-2-methoxybenzaldehyde (6.6 g, 30.6 mmol), Pd(OAc)$_2$ (573 mg, 2.55 mmol), and dicyclohexylamine (6.6 mL, 33.2 mmol) in dioxane (50 mL) and H$_2$O (10 mL) was heated at reflux for 12 h. The mixture was cooled to room temperature and diluted with ethyl acetate (200 mL) and brine (50 mL). The mixture was filtered and the filter cake was washed with ethyl acetate (100 mL). The organic phase was then washed with brine, dried (MgSO$_4$), and concentrated in vacuo to dryness. The crude product was purified by silica gel chromatography (0 to 40% ethyl acetate/hexanes) to provide 28a as a brown oil (4.5 g, 54%). $^1$H NMR (500 MHz, CDCl$_3$): δ 10.46 (s, 1H), 7.71 (s, 1H), 7.42 (d, J=9.0 Hz, 1H), 6.91 (d, J=9.0 Hz, 1H), 6.64 (s, 0.84H), 5.27 (s, 0.16H), 4.62 (s, 0.16H), 3.98-3.93 (m, 4H), 3.91 (s, 3H), 2.05-1.95 (m, 4H), 1.88 (s, 3H), 1.68 (d, J=9.0 Hz, 4H), 1.22 (s, 1H).

Step 2:

To a solution of 28a (4.5 g, 13.6 mmol) in 100 mL of MeOH was added Pd(OH)$_2$/C (20 wt. % Pd on carbon, 900 mg) under a nitrogen atmosphere. The mixture was stirred under one atmosphere of hydrogen for 1.5 h. The reaction mixture was filtered through a pad of CELITE and the filter cake was washed with ethyl acetate (100 mL). The filtrate was concentrated in vacuo to provide the reduced product (4.5 g).

A solution of the reduced product (3.6 g, 10.7 mmol), SEM-Cl (2.1 mL, 11.8 mmol) and DIPEA (2.4 mL, 16.1 mmol) in CH$_2$Cl$_2$ (70 mL) was stirred at room temperature for 12 h. The crude product was concentrated under reduced pressure and purified by silica gel chromatography (0 to 40% ethyl acetate/hexanes) to provide 28b as a brown oil (3.5 g, 71%). $^1$H NMR (500 MHz, CDCl$_3$): δ 7.14 (s, 1H), 7.06 (d, J=8.5 Hz, 1H), 6.79 (d, J=8.5 Hz, 1H), 4.74 (s, 2H), 4.61 (s, 2H), 4.12-4.11 (m, 4H), 3.81 (s, 3H), 3.69-3.66 (m, 2H), 3.02 (dd, J=13.0, 3.0 Hz, 1H), 2.04 (t, J=11.0 Hz, 1H), 1.97-1.92 (m, 2H), 1.86-1.75 (m, 2H), 1.65-1.61 (m, 3H), 1.08 (s, 1H), 0.98-0.95 (m, 2H), 0.82 (d, J=6.5 Hz, 3H), 0.03 (s, 9H).

Step 3:

To a solution of 28b (3.5 g, 7.54 mmol) in pyridine (18 mL) was added thionyl chloride (1.1 mL, 15.08 mmol) at 0-5° C. The mixture was stirred at 5° C. for 2 h. Most of the pyridine was removed under reduced pressure. The residue was diluted with ethyl acetate (200 mL) and H$_2$O (20 mL). The organic phase was washed with brine, dried (MgSO$_4$), and concentrated in vacuo to dryness. The crude product was purified by silica gel chromatography (0 to 40% ethyl acetate/hexanes) to provide 28c as a brown oil (2.7 g, 82%). $^1$H NMR (500 MHz, CDCl$_3$): δ 7.11 (s, 1H), 7.02 (d, J=8.5 Hz, 1H), 6.77 (d, J=8.0 Hz, 1H), 5.25 (s, 1H), 4.77 (s, 2H), 4.61 (s, 2H), 3.97 (d, J=4.0 Hz, 4H), 3.80 (s, 3H), 3.69-3.66 (m, 2H), 2.75 (dd, J=13.5, 6.5 Hz, 1H), 2.42-2.37 (m, 1H), 2.33-2.29 (m, 1H), 2.23-2.21 (m, 4H), 1.77-1.74 (m, 2H), 0.96 (d, J=7.0 Hz, 3H), 0.03 (s, 9H).

Step 4:

TBAF (1.0M solution in THF solution, 12.6 mL, 12.6 mmol) was added to a solution of 28c (1.4 g, 3.13 mmol) in HMPA (12 mL)) and heated to 45° C. for 12 h. The reaction mixture was washed with brine, dried (MgSO$_4$), and concentrated in vacuo to dryness. The crude product was purified by silica gel chromatography (0 to 40% ethyl acetate/hexanes) to provide 28d as a brown oil (720 mg, 68%). $^1$H NMR (500 MHz, CDCl$_3$): δ 7.04 (dd, J=9.0, 7.0 Hz, 1H), 6.78 (d, J=8.5 Hz, 1H), 5.29 (s, 1H), 4.68-4.64 (m, 2H), 4.00 (s, 4H), 3.84 (s, 3H), 2.71 (d, J=13.0 Hz, 1H), 2.46-2.38 (m, 2H), 2.29-2.17 (m, 5H), 1.77 (t, J=6.5 Hz, 2H), 0.97 (d, J=6.5 Hz, 3H).

Step 5:

A mixture of 28d (720 mg, 2.26 mmol) and Dess-Martin reagent (1.1 g, 2.71 mmol) in CH$_2$Cl$_2$ (20 mL) was stirred at room temperature for 3 h. The reaction mixture was washed with brine, dried (MgSO$_4$), and concentrated in vacuo to dryness. The crude product was purified by silica gel chromatography (0 to 40% ethyl acetate/hexanes) to provide 28e as a brown oil (610 mg, 85%). $^1$H NMR (500 MHz, CDCl$_3$): δ 10.43 (s, 1H), 7.58 (s, 1H), 7.30 (d, J=8.5, 2.5 Hz, 1H), 6.89 (d, J=8.5 Hz, 1H), 5.22 (s, 1H), 3.98 (s, 4H), 3.87 (s, 3H), 2.74 (dd, J=13.5, 6.0 Hz, 1H), 2.49-2.45 (m, 1H), 2.34-2.29 (m, 1H), 2.21 (s, 4H), 1.78-1.61 (m, 2H), 0.96 (d, J=7.0 Hz, 3H).

Step 6:

To a mixture of AD-mix-β (2.5 g) in t-BuOH (15 mL) and H$_2$O (15 mL) was added a solution of 28e (610 mg, 1.93 mmol) in toluene (3 mL) in an ice bath. Methylanesulfonamide (184 mg, 1.93 mmol) was added. The reaction mixture was stirred at room temperature for 7 d, and then diluted with MTBE (200 mL). The organic phase was washed with saturated Na$_2$S$_2$O$_3$ and brine, dried (MgSO$_4$), and concentrated in vacuo to dryness. The crude product was purified by silica gel chromatography (0 to 40% ethyl acetate/hexanes) to provide a mixture of diastereomers 28f as a brown oil (380 mg, 56%). $^1$H NMR (500 MHz, CDCl$_3$): δ 10.46 (s, 1H), 7.63 (d, J=8.5 Hz, 1H), 7.37-7.35 (m, 1H), 6.92 (d, J=8.5 Hz, 1H), 3.98-3.90 (m, 4H), 3.91 (s, 3H), 2.93 (dd, J=13.5, 6.0 Hz, 1H), 2.25-2.15 (m, 1H), 2.09-1.65 (m, 8H), 0.83 (t, J=6.5 Hz, 3H).

Step 7:

To a solution of 28f (150 mg, 0.42 mmol) and paraformaldehyde (386 mg, 12.85 mmol) in 15 mL of CH$_2$Cl$_2$ wad added p-toluenesulfonic acid monohydrate (8 mg, 0.04 mmol). The reaction mixture was stirred at room temperature for 12 h. The acetone was then removed under reduced pressure, and the residue was purified by silica gel chromatography (0 to 40% ethyl acetate/hexanes) to provide 28g as a colorless oil (80 mg, 60%). $^1$H NMR (500 MHz, CDCl$_3$): δ 10.47 (s, 1H), 7.65 (s, 1H), 7.37 (d, J=8.5 Hz, 1H), 6.95 (d, J=8.5 Hz, 1H), 5.15 (s, 0.8H), 5.12 (s, 0.2H), 4.83 (s, 0.8H), 4.80 (s, 0.2H), 4.13 (s, 1H), 3.93 (s, 4H), 3.21 (dd, J=14.0, 3.0 Hz, 1H), 2.85 (dd, J=17.0, 3.0 Hz, 1H), 2.55-2.52 (m, 1H), 2.44-2.38 (m, 1H), 2.33-2.22 (m, 2H), 2.08-1.83 (m, 3H), 0.93 (d, J=7.0 Hz, 0.6H), 0.82 (d, J=7.0 Hz, 2.4H).

Step 8:

A mixture of 28g (80 mg, 0.24 mmol), Pd(OAc)$_2$ (28 mg, 0.12 mmol) and 4,5-diazofluoren-9-one (22 mg, 0.12 mmol) in 2 mL of DMSO was heated to 80° C. under one atmosphere of oxygen for 6 h. The reaction mixture was then cooled to room temperature and diluted with ethyl acetate (50 mL). The organic phase was washed with brine, dried (MgSO$_4$), and concentrated to dryness under reduced pressure. The crude residue was purified by silica gel chromatography (0 to 40% ethyl acetate/hexanes) to provide 28h as a white solid (40 mg, 50%). $^1$H NMR (500 MHz, CD$_3$OD): δ 10.38 (s, 1H), 7.54 (s, 1.2H), 7.42 (d, J=8.5 Hz, 0.8H), 7.11 (d, J=8.5 Hz, 1H), 5.73 (s, 0.8H), 5.69 (s, 0.2H), 5.65 (s, 0.8H), 5.63 (s, 0.2H), 5.48 (s, 0.8H), 5.45 (s, 0.2H), 3.93 (s, 3H), 3.09 (dd, J=14.0, 3.0 Hz, 0.2H), 2.90 (dd, J=17.0, 3.0 Hz, 0.8H), 2.65-2.45 (m, 4H), 2.25-2.15 (m, 1H), 2.08-1.83 (m, 1H), 0.98 (d, J=6.5 Hz, 2.4H), 0.92 (d, J=7.0 Hz, 0.6H).

Step 9:

To a solution of 28h (50 mg, 0.16 mmol) in THF (3 mL) was added LiHMDS (1.0M solution in THF, 0.30 mL, 0.30 mmol) at −78° C. under a nitrogen atmosphere. The reaction mixture was stirred for 30 min, and then allyl cyanoformate II (33 mg, 0.30 mmol) was added. The reaction mixture was allowed to warm to 0° C. over 2 h. The reaction was quenched with H$_2$O and extracted with ethyl acetate (50 mL). The organic phase was then washed with brine, dried (MgSO$_4$), and concentrated to dryness under reduced pressure. The residue was purified by silica gel chromatography (0 to 40% ethyl acetate/hexanes) to provide a mixture of isomers 28i as a brown gum-like material (20 mg, 32%). $^1$H NMR (500 MHz, CD$_3$OD): δ 10.38 (s, 1H), 7.54 (s, 1H), 7.42 (d, J=8.5 Hz, 1H), 7.11 (d, J=8.5 Hz, 1H), 5.99-5.88 (m, 1H), 5.76 (s, 1H), 5.69 (s, 1H), 5.48 (s, 1H), 5.35-5.21 (m, 2H), 3.93 (s, 3H), 3.62-3.58 (m, 1H), 2.89-2.80 (m, 2H), 2.52 (t, J=12.0 Hz, 1H), 2.32 (d, J=7.5 Hz, 1H), 2.25-2.15 (m, 1H), 0.98 (d, J=6.5 Hz, 2.4H), 0.92 (d, J=7.0 Hz, 0.6H).

Step 10:

To a solution of 28i (20 mg, 0.05 mmol) in DMF (2 mL) was added Pd(PPh$_3$)$_4$ (7 mg, 0.005 mmol) under a nitrogen atmosphere. The reaction mixture was stirred at room temperature for 1 h, and then diluted with ethyl acetate (50 mL). The organic phase was washed with brine, dried (MgSO$_4$), and concentrated to dryness under reduced pressure. The residue was purified by silica gel chromatography (0 to 40% ethyl acetate/hexanes) to provide 28j (6 mg, 35%). $^1$H NMR (500 MHz, CD$_3$OD): δ 10.38 (s, 1H), 7.50 (s, 1H), 7.42 (d, J=8.5 Hz, 1H), 7.10 (d, J=8.5 Hz, 1H), 5.89-5.78 (m, 1H), 5.71 (s, 1H), 5.66 (s, 0.8H), 5.63 (s, 0.2H), 5.50 (s, 0.8H), 5.48 (s, 0.2H), 5.35-5.21 (m, 2H), 3.93 (s, 3H), 3.0 (dd, J=14.0, 3.0 Hz, 0.2H), 2.85-2.80 (m, 1H), 2.65-2.40 (m, 3.8H), 2.30-2.02 (m, 2H), 1.95-1.85 (m, 1H), 0.95 (d, J=6.5 Hz, 2.4H), 0.92 (d, J=7.0 Hz, 0.6H).

Step 11:

To a solution of 28j (6 mg, 0.016 mmol) in THF (1 mL) was added NaBH$_4$ (1 mg, 0.028 mmol) at room temperature. The reaction mixture was stirred for 1 h, and then diluted with ethyl acetate (50 mL). The organic phase was washed with brine, dried (MgSO$_4$), and concentrated to dryness under reduced pressure. The residue was purified by silica gel chromatography (0 to 50% ethyl acetate/hexanes) to provide 28 (1.4 mg, 23%) as a brown gum-like material.

Compound 28 ((6S,7aR)-6-allyl-7a-((R)-1-(3-(hydroxymethyl)-4-methoxyphenyl)propan-2-yl)-7,7a-dihydrobenzo[d][1,3]dioxol-5(6H)-one). $^1$H NMR (300 MHz, CD$_3$OD): δ 7.07 (s, 1H), 6.95 (d, J=14.0 Hz, 1H), 6.86 (d, J=14.0 Hz, 1H), 5.85-5.78 (m, 1H), 5.69 (s, 1H), 5.63 (s, 1H), 5.55 (s, 1H), 5.08-5.01 (m, 2H), 4.57 (s, 2H), 3.79 (s, 3H), 2.82-2.79 (m, 2H), 2.64-2.58 (m, 1H), 2.57 (d, J=14.0 Hz, 1H), 2.35 (t, J=11.5 Hz, 1H), 2.14-1.95 (m, 3H), 0.96 (d, J=11.5 Hz, 3H). ESI MS m/z 341 [C$_{21}$H$_{26}$O$_5$+H−H$_2$O]$^+$.

General procedure N: Illustrated with preparation of compound 40

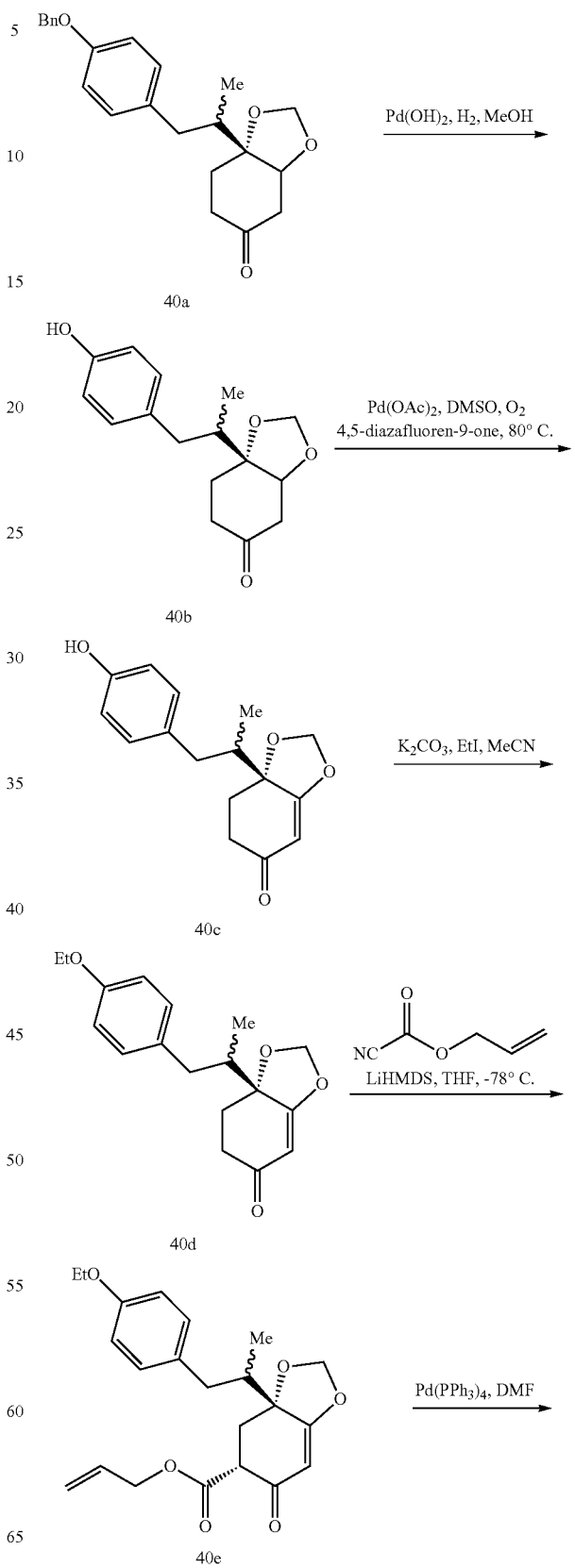

-continued

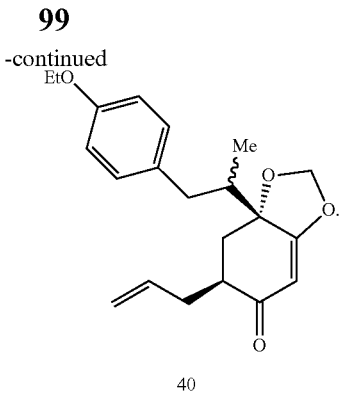

40

Step 1:

Compound 40a was prepared according to the general procedure A. To a mixture of 40a (100 mg, 0.27 mmol) in 10 mL of MeOH was added Pd(OH)$_2$/C (20 wt. % Pd on carbon, 20 mg) under a nitrogen atmosphere. The mixture was stirred under one atmosphere of hydrogen for 1.5 h. The reaction mixture was then filtered through a pad of CELITE and the filter cake was washed with ethyl acetate (40 mL). The filtrate was concentrated in vacuo to provide 40b as a colorless oil (75 mg, 61%). $^1$H NMR (500 MHz, CD$_3$OD): δ 7.01 (d, J=8.5 Hz, 2H), 6.71 (d, J=6.0 Hz, 2H), 5.10 (s, 0.2H), 5.08 (s, 0.8H), 4.55 (s, 1H), 4.38 (s, 0.8H), 4.22 (s, 1H), 3.12 (dd, J=14.0, 3.0 Hz, 0.2H), 2.82 (dd, J=14.0, 3.0 Hz, 0.8H), 2.68-2.63 (m, 2H), 2.45-2.41 (m, 1H), 2.28-2.15 (m, 2H), 2.02-1.85 (m, 3H), 0.97 (d, J=6.5 Hz, 2.4H), 0.93 (d, J=7.0 Hz, 0.6H).

Step 2:

A mixture of 40b (75 mg, 0.27 mmol), Pd(OAc)$_2$ (31 mg, 0.14 mmol) and 4,5-diazafluoren-9-one (25 mg, 0.14 mmol) in 4 mL of DMSO was heated to 80° C. under one atmosphere of oxygen for 6 h. The reaction mixture was then cooled to room temperature and diluted with ethyl acetate (50 mL). The organic phase was washed with brine, dried (MgSO$_4$), and concentrated to dryness under reduced pressure. The crude residue was purified by silica gel chromatography (0 to 40% ethyl acetate/hexanes) to provide 40c as a white solid (30 mg, 40%). $^1$H NMR (500 MHz, CD$_3$OD): δ 7.01 (d, J=8.5 Hz, 2H), 6.71 (d, J=6.0 Hz, 2H), 5.70 (s, 0.2H), 5.68 (s, 0.8H), 5.65 (s, 0.2H), 5.62 (s, 0.8H), 5.44 (s, 1H), 2.98 (dd, J=14.0, 3.0 Hz, 0.8H), 2.82 (dd, J=14.0, 3.0 Hz, 0.2H), 2.58-2.53 (m, 1H), 2.45-2.32 (m, 3H), 2.23-2.13 (m, 1H), 2.02-1.98 (m, 1H), 0.97 (d, J=6.5 Hz, 0.6H), 0.93 (d, J=7.0 Hz, 2.4H).

Step 3:

To a mixture of 40c (18 mg, 0.065 mmol) and K$_2$CO$_3$ (14 mg, 0.099 mmol) in MeCN (2 mL) was added EtI (7 mg, 0.078 mmol). The reaction mixture was stirred at room temperature for 12 h. It was then diluted with ethyl acetate (50 mL), washed with brine, dried (MgSO$_4$), and concentrated to dryness under reduced pressure. The crude residue was purified by silica gel chromatography (0 to 30% ethyl acetate/hexanes) to provide 40d as a white solid (12 mg, 65%). $^1$H NMR (500 MHz, CD$_3$OD): δ 7.09 (d, J=8.5 Hz, 2H), 6.81 (d, J=6.0 Hz, 2H), 5.70 (s, 0.2H), 5.68 (s, 0.8H), 5.65 (s, 0.2H), 5.62 (s, 0.8H), 5.44 (s, 1H), 3.95 (q, J=7.0 Hz, 2H), 3.02 (dd, J=14.0, 3.0 Hz, 1H), 2.62-2.58 (m, 1H), 2.43-2.40 (m, 3H), 2.18-2.15 (m, 1H), 2.06-2.01 (m, 1H), 1.31 (t, J=7.0 Hz, 3H), 0.97 (d, J=6.5 Hz, 0.6H), 0.93 (d, J=7.0 Hz, 2.4H).

Step 4:

To a solution of 40d (12 mg, 0.039 mmol) in THF (2 mL) was added LiHMDS (1.0M solution in THF, 0.079 mL, 0.079 mmol) at −78° C. under a nitrogen atmosphere. The reaction mixture was stirred for 30 min, and then allyl cyanoformate II (9 mg, 0.079 mmol) was added. The reaction mixture was allowed to warm to 0° C. over 2 h. The reaction was then quenched with H$_2$O and extracted with ethyl acetate (50 mL). The organic phase was washed with brine, dried (MgSO$_4$), and concentrated to dryness under reduced pressure. The residue was purified by silica gel chromatography (0 to 30% ethyl acetate/hexanes) to provide 40e as a brown gum-like material (10 mg, 67%). $^1$H NMR (500 MHz, CD$_3$OD): δ 7.01 (d, J=8.5 Hz, 1H), 7.02 (d, J=12.0 Hz, 1H), 5.99-5.87 (m, 1H), 5.72 (s, 1H), 5.67 (s, 1H), 5.51 (s, 1H), 5.38-5.22 (m, 2H), 3.93 (s, 3H), 3.61 (dd, J=13.0, 5.0 Hz, 1H), 3.08 (d, J=14.0, 3.0 Hz, 1H), 2.90 (dd, J=13.0, 5.5 Hz, 1H), 2.59 (t, J=10.5 Hz, 1H), 2.37 (t, J=12.5 Hz, 1H), 2.28-2.21 (m, 1H), 0.94 (d, J=7.0 Hz, 3H).

Step 5:

To a solution of 40e (10 mg, 0.026 mmol) in DMF (2 mL) was added Pd(PPh$_3$)$_4$ (3 mg, 0.003 mmol) under a nitrogen atmosphere. The reaction mixture was stirred at room temperature for 1 h and then diluted with ethyl acetate (50 mL). The organic phase was washed with brine, dried (MgSO$_4$), and concentrated to dryness under reduced pressure. The residue was purified by silica gel chromatography (0 to 70% ethyl acetate/hexanes) to provide a mixture of diastereomers 40 (5.0 mg, 60%) as a colorless gum-like material.

Compound 40 ((6S,7aR)-6-allyl-7a-(1-(4-ethoxyphenyl) propan-2-yl)-7,7a-dihydrobenzo[d][1,3]dioxol-5(6H)-one). $^1$H NMR (500 MHz, CD$_3$OD): δ 7.08 (d, J=9.0 Hz, 1.4H), 6.97 (d, J=8.0 Hz, 0.6H), 6.83-6.80 (m, 2H), 5.92-5.85 (m, 0.7H), 5.85-5.81 (m, 0.3H), 5.68 (s, 0.3H), 5.65 (s, 0.7H), 5.63 (s, 0.3H), 5.60 (s, 0.7H), 5.54 (s, 0.3H), 5.50 (s, 0.7H), 5.18-5.13 (m, 2H), 4.01 (q, J=7.0 Hz, 2H), 3.09 (dd, J=14.0, 4.0 Hz, 0.7H), 2.90-2.75 (m, 1.3H), 2.70 (d, J=14.0 Hz, 0.7H), 2.65-2.58 (m, 1H), 2.53 (d, J=14.0 Hz, 0.3H), 2.44 (t, J=11.5 Hz, 0.7H), 2.28-2.22 (m, 1H), 2.14 (dd, J=14.0, 10.0 Hz, 1H), 1.99-1.93 (m, 1.3H), 1.37 (t, J=7.0 Hz, 3H), 0.95 (d, J=6.0 Hz, 0.9H), 0.83 (d, J=6.0 Hz, 2.1H). ESI MS m/z 343 [C$_{21}$H$_{26}$O$_4$+H]$^+$.

General procedure O: Illustrated with preparation of compound 99

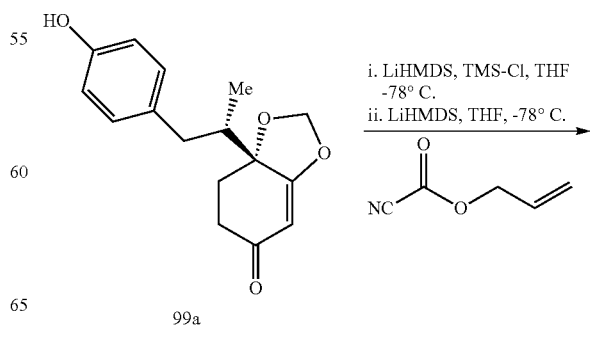

99a

-continued

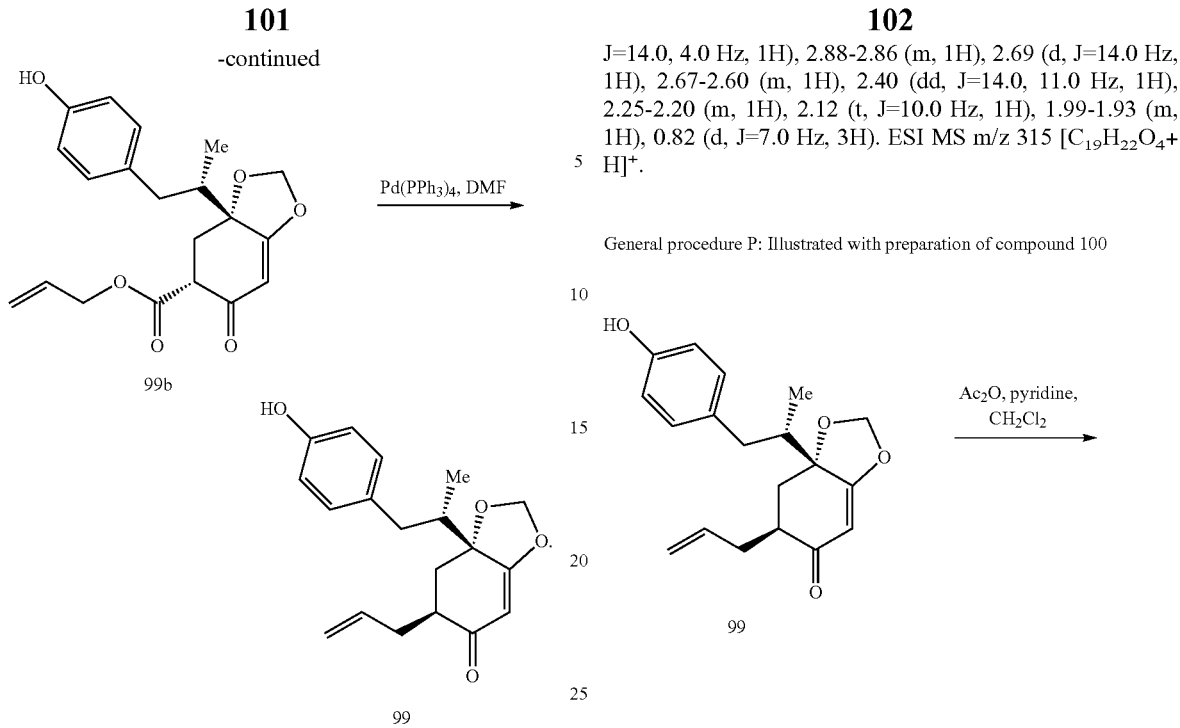

Step 1:
Compound 99a was prepared according to general procedure A. To a mixture of 99a (40 mg, 0.14 mmol) in THF (2 mL) was added LiHMDS (1.0M solution in THF, 0.21 mL, 0.21 mmol) at −78° C. under a nitrogen atmosphere. The reaction mixture was stirred for 30 min, and then TMS-Cl (1.0M solution in THF, 0.16 mL, 0.16 mmol) was added. The reaction mixture continued to stir for 1 h, and then LiHMDS (1.0M solution in THF, 0.28 mL, 0.28 mmol) was added at −78° C. The reaction mixture continued to stir for 30 min before allyl cyanoformate II (24 mg, 0.21 mmol) was added. The reaction mixture was allowed to warm to 0° C. over 2 h; it was then quenched with H₂O and extracted with ethyl acetate (50 mL). The organic phase was washed with brine, dried (MgSO₄), and concentrated to dryness under reduced pressure. The residue was purified by silica gel chromatography (0 to 30% ethyl acetate/hexanes) to provide 99b as a brown gum-like material (52 mg, 100%). $^1$H NMR (500 MHz, CD₃OD): δ 7.01 (d, J=8.5 Hz, 2H), 6.70 (d, J=12.0 Hz, 2H), 5.99-5.87 (m, 1H), 5.71 (s, 1H), 5.67 (s, 1H), 5.45 (s, 1H), 5.38-5.22 (m, 2H), 3.55-3.52 (m, 1H), 2.95 (dd, J=13.0, 5.0 Hz, 1H), 2.75 (dd, J=14.0, 3.0 Hz, 1H), 2.43-2.41 (m, 1H), 2.25 (t, J=9.0 Hz, 1H), 2.17-2.12 (m, 1H), 0.94 (d, J=7.0 Hz, 3H).

Step 2:
To a solution of 99b (52 mg, 0.14 mmol) in DMF (3 mL) was added Pd(PPh₃)₄ (16 mg, 0.02 mmol) under a nitrogen atmosphere. The reaction mixture was stirred at room temperature for 1 h, and then diluted with ethyl acetate (50 mL). The organic phase was washed with brine, dried (MgSO₄), and concentrated to dryness under reduced pressure. The residue was purified by silica gel chromatography (0 to 40% ethyl acetate/hexanes) to provide 99 (16 mg, 37%) as a white solid.

Compound 99 ((6S,7aR)-6-allyl-7a-((S)-1-(4-hydroxyphenyl)propan-2-yl)-7,7a-dihydrobenzo[d][1,3]dioxol-5(6H)-one). $^1$H NMR (500 MHz, CD₃OD): δ 6.98 (d, J=7.5 Hz, 2H), 6.71 (d, J=7.5 Hz, 2H), 5.92-5.85 (m, 1H), 5.64 (s, 1H), 5.59 (s, 1H), 5.48 (s, 1H), 5.17-5.11 (m, 2H), 3.05 (dd, J=14.0, 4.0 Hz, 1H), 2.88-2.86 (m, 1H), 2.69 (d, J=14.0 Hz, 1H), 2.67-2.60 (m, 1H), 2.40 (dd, J=14.0, 11.0 Hz, 1H), 2.25-2.20 (m, 1H), 2.12 (t, J=10.0 Hz, 1H), 1.99-1.93 (m, 1H), 0.82 (d, J=7.0 Hz, 3H). ESI MS m/z 315 [C₁₉H₂₂O₄+H]⁺.

General procedure P: Illustrated with preparation of compound 100

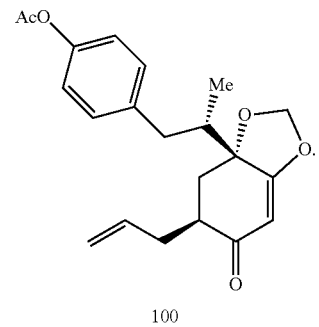

Acetic anhydride (7 mg, 0.049 mmol) was added to a solution of 99 (12 mg, 0.038 mmol) and pyridine (10 mg, 0.057 mmol) in CH₂Cl₂ (1 mL) at room temperature under a nitrogen atmosphere. The reaction mixture was stirred for 12 h, and then diluted with ethyl acetate (50 mL). The organic phase was washed with brine, dried (MgSO₄), and concentrated to dryness under reduced pressure. The residue was purified by silica gel chromatography (0 to 30% ethyl acetate/hexanes) to provide 100 as a brown gum-like material (10 mg, 74%).

Compound 100 (4-((S)-2-((3aR,5S)-5-allyl-6-oxo-3a,4,5,6-tetrahydrobenzo[d]dioxol-3a-yl)propyl)phenyl acetate). $^1$H NMR (500 MHz, CD₃OD): δ 7.22 (d, J=7.5 Hz, 2H), 7.03 (d, J=7.5 Hz, 2H), 5.92-5.85 (m, 1H), 5.67 (s, 1H), 5.61 (s, 1H), 5.50 (s, 1H), 5.14-5.11 (m, 2H), 3.16 (dd, J=14.5, 4.0 Hz, 1H), 2.90-2.87 (m, 1H), 2.68 (d, J=14.0 Hz, 1H), 2.67-2.60 (m, 1H), 2.53 (t, J=11.0 Hz, 1H), 2.25 (s, 3H), 2.25-2.20 (m, 1H), 2.16 (t, J=9.5 Hz, 1H), 2.02-1.95 (m, 1H), 0.86 (d, J=7.0 Hz, 3H). ESI MS m/z 356 [C₂₁H₂₄O₅+H]⁺.

General procedure Q: Illustrated with preparation of compound 70

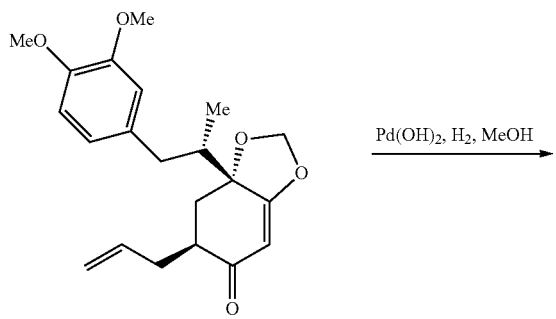

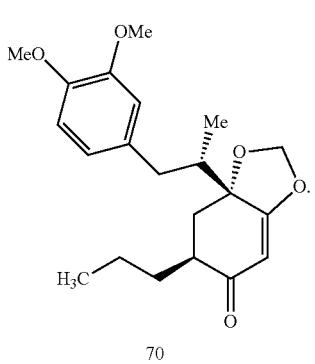

To a solution of 1 (12 mg, 0.033 mmol) in 10 mL of MeOH was added Pd(OH)$_2$/C (20 wt. % Pd on carbon, 4 mg) under a nitrogen atmosphere. The mixture was stirred under one atmosphere of hydrogen for 30 min. The reaction mixture was then filtered on an inorganic membrane filter and washed with ethyl acetate (10 mL). The filtrate was concentrated in vacuo to provide 70 (10 mg, 83%) as a colorless oil.

Compound 70 ((6S,7aR)-7a-((S)-1-(3,4-dimethoxyphenyl)propan-2-yl)-6-propyl-7,7a-dihydrobenzo[d][1,3]dioxol-5(6H)-one). $^1$H NMR (500 MHz, CD$_3$OD): δ 6.88 (d, J=8.0 Hz, 1H), 6.75 (s, 1H), 6.73 (dd, J=8.0, 1.5 Hz, 1H), 5.67 (s, 1H), 5.60 (s, 1H), 5.45 (s, 1H), 3.80 (s, 3H), 3.79 (s, 3H), 3.12 (dd, J=10.0, 3.5 Hz, 1H), 2.67 (d, J=14.0 Hz, 1H), 2.48-2.43 (m, 2H), 2.16 (dd, J=14.0, 9.0 Hz, 1H), 2.01-1.98 (m, 2H), 1.52-1.49 (m, 3H), 1.00 (t, J=7.0 Hz, 3H), 0.88 (d, J=7.0 Hz, 3H). ESI MS m/z 361 [C$_{21}$H$_{28}$O$_5$+H]$^+$.

General procedure R: Illustrated with preparation of compound 71

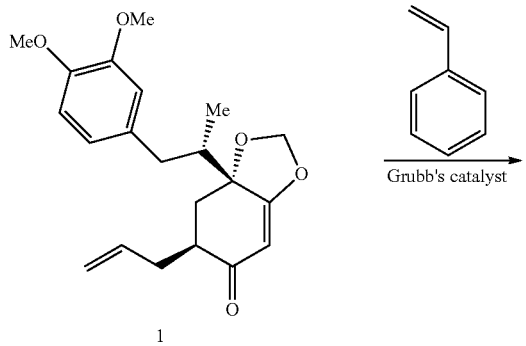

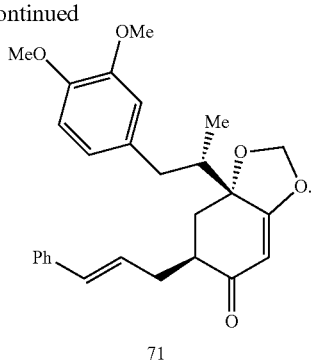

A vial was charged with 1 (10 mg, 0.028 mmol), styrene (15 mg, 0.14 mmol), and Grubb's catalyst (3 mg, 0.028 mmol) in 2 mL of CH$_2$Cl$_2$. The vial was sealed and heated to 40° C. for 12 h. The mixture was then washed with brine, dried (MgSO$_4$), and concentrated to dryness under reduced pressure. The residue was purified by silica gel chromatography (0 to 30% ethyl acetate/hexanes) to provide 71 (4.9 mg, 41%) as a brown gum-like material.

Compound 71 ((6S,7aR)-6-cinnamyl-7a-((S)-1-(3,4-dimethoxyphenyl)propan-2-yl)-7,7a-dihydrobenzo[d][1,3]dioxol-5(6H)-one). $^1$H NMR (500 MHz, CD$_3$OD): δ 7.31-7.26 (m, 4H), 7.19-7.17 (m, 1H), 6.87 (d, J=8.0 Hz, 1H), 6.80 (d, J=8.0 Hz, 2H), 6.48 (d, J=8.0 Hz, 1H), 6.28-6.24 (m, 1H), 5.67 (s, 1H), 5.61 (s, 1H), 5.52 (s, 1H), 3.80 (s, 3H), 3.78 (s, 3H), 3.16 (d, J=3.5 Hz, 1H), 3.03-3.00 (m, 1H), 2.71-2.69 (m, 2H), 2.48-2.35 (m, 2H), 2.17-2.09 (m, 2H), 0.92 (d, J=8.4 Hz, 3H). ESI MS m/z 435 [C$_{27}$H$_{30}$O$_5$+H]$^+$.

General procedure S: Illustrated with preparation of compound 106

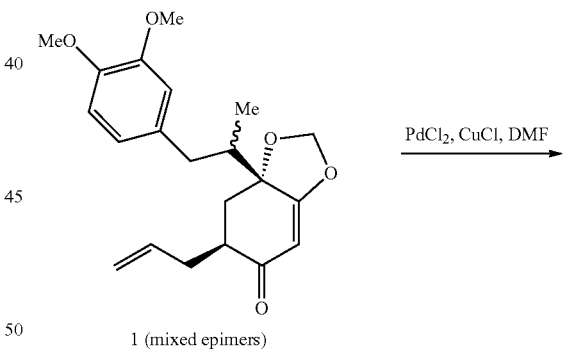

A mixture of 1 and its methyl epimer (25 mg, 0.07 mmol), Cu(I)C$_1$ (16 mg, 0.16 mmol), and PdCl$_2$ (4 mg, 0.02 mmol)

in DMF (2 mL) and H₂O (0.8 mL) was stirred under one atmosphere of oxygen for 2 h. The mixture was washed with brine, dried (MgSO₄), and concentrated to dryness under reduced pressure. The residue was purified by silica gel chromatography (0 to 50% ethyl acetate/hexanes) to provide a mixture of diastereomers 106 (19 mg, 73%) as a brown gum-like material.

Compound 106 (1-(3,4-dimethoxyphenyl)propan-2-yl)-6-(2-oxopropyl)-7,7a-dihydrobenzo[d][1,3]dioxol-5(6H)-one). $^1$H NMR (500 MHz, CD₃OD): δ 6.89 (d, J=7.5 Hz, 1H), 6.82 (s, 1H), 6.75 (dd, J=8.0, 2.0 Hz, 1H), 5.66 (s, 1H), 5.61 (s, 1H), 5.49 (s, 1H), 3.82 (s, 3H), 3.80 (s, 3H), 3.16-3.13 (m, 2H), 3.01-3.00 (m, 1H), 2.62 (dd, J=17.5, 8.0 Hz, 1H), 2.47 (t, J=13.5 Hz, 2H), 2.28 (t, J=10.0 Hz, 1H), 2.18 (s, 3H), 1.95-1.87 (m, 1H), 0.91 (d, J=7.0 Hz, 3H). ESI MS m/z 375 [C₂₁H₂₆O₆+H]⁺.

General procedure T: Illustrated with preparation of compound 64

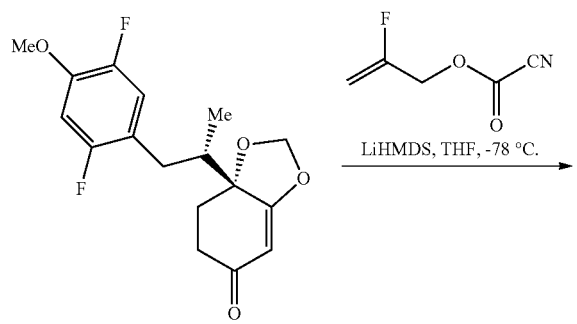

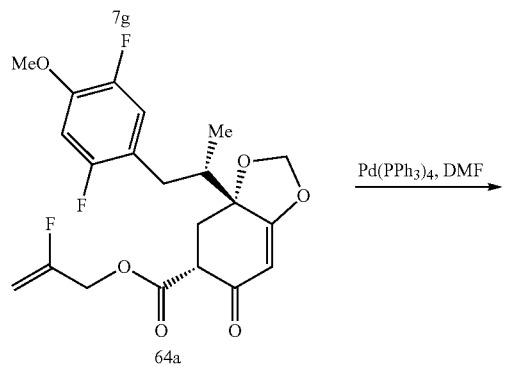

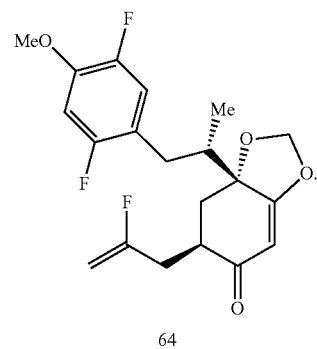

Step 1:
To a mixture of 7g (40 mg, 0.12 mmol) in THF (3 mL) was added LiHMDS (1.0M solution in THF, 0.24 mL, 0.24 mmol) at −78° C. under a nitrogen atmosphere. The reaction mixture was stirred for 30 min, and then 2-Fluoroallyl carbonocyanidate (21 mg, 0.24 mmol) was added. The reaction mixture was allowed to warm to 0° C. over 2 h. The reaction was quenched with H₂O and extracted with ethyl acetate (50 mL). The organic phase was washed with brine, dried (MgSO₄), and concentrated to dryness under reduced pressure. The residue was purified by silica gel chromatography (0 to 30% ethyl acetate/hexanes) to provide 64a as a brown gum-like material (40 mg, 78%). $^1$H NMR (500 MHz, CD₃OD): δ 7.01 (d, J=8.5 Hz, 2H), 6.70 (d, J=12.0 Hz, 2H), 5.99-5.87 (m, 1H), 5.71 (s, 1H), 5.67 (s, 1H), 5.45 (s, 1H), 5.38-5.22 (m, 2H), 3.55-3.52 (m, 1H), 2.95 (dd, J=13.0, 5.0 Hz, 1H), 2.75 (dd, J=14.0, 3.0 Hz, 1H), 2.43-2.41 (m, 1H), 2.25 (t, J=9.0 Hz, 1H), 2.17-2.12 (m, 1H), 0.94 (d, J=7.0 Hz, 3H).

Step 2:
To a solution of 64a (40 mg, 0.09 mmol) in DMF (3 mL) was added Pd(PPh₃)₄ (11 mg, 0.009 mmol) under a nitrogen atmosphere. The reaction mixture was stirred at room temperature for 5 h, and then diluted with ethyl acetate (50 mL). The organic phase was washed with brine, dried (MgSO₄), and concentrated to dryness under reduced pressure. The residue was purified by silica gel chromatography (0 to 40% ethyl acetate/hexanes) to provide the product (12 mg). The product was further purified by CHIRALPAK AD (8% i-PrOH/heptane) to provide 64 (2 mg, 5%) as a colorless gum.

Compound 64 ((6R,7aR)-7a-((S)-1-(2,5-difluoro-4-methoxyphenyl)propan-2-yl)-6-(2-fluoroallyl)-7,7a-dihydrobenzo[d][1,3]dioxol-5(6H)-one). $^1$H NMR (500 MHz, CD₃OD): δ 7.00 (dd, J=19.0, 12.0 Hz, 1H), 6.88 (d, J=19.0, 7.0 Hz, 1H), 5.64 (s, 1H), 5.60 (s, 1H), 5.50 (s, 1H), 4.85-4.36 (m, 2H), 3.81 (s, 3H), 3.09-2.95 (m, 2H), 2.82-2.79 (m, 1H), 2.53 (d, J=14.0 Hz, 1H), 2.49-2.29 (m, 2H), 2.19 (dd, J=14.0, 7.0 Hz, 1H), 1.98-1.89 (m, 1H), 0.82 (d, J=11.5 Hz, 3H). ESI MS m/z 383 [C₂₀H₂₁F₃O₄+H]⁺.

General procedure U: Illustrated with preparation of compound 107

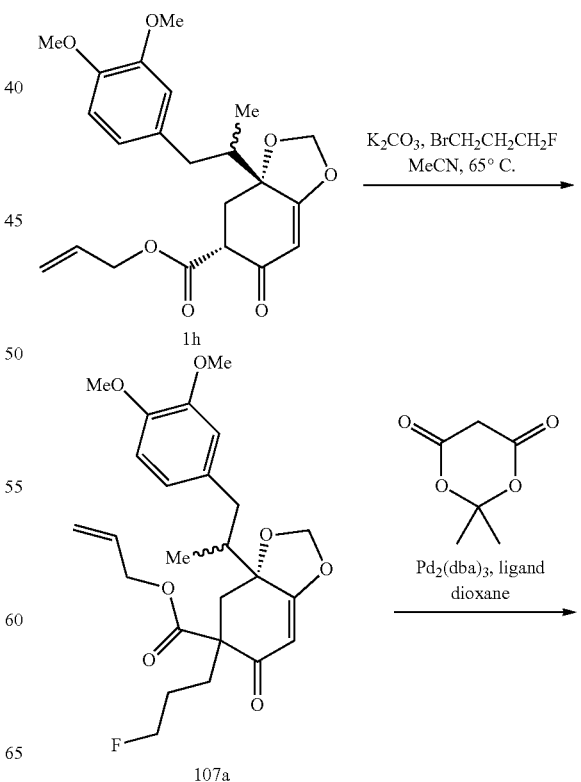

-continued

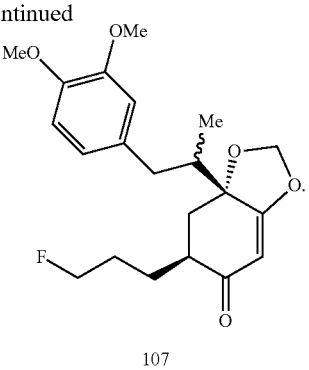

107

Step 1:

A mixture of 1h (20 mg, 0.056 mmol), K₂CO₃ (14 mg, 0.10 mmol), and 3-fluoro-1-bromopropane (10 mg, 0.075 mmol) in MeCN (3 mL) was heated to 65° C. for 48 h. The reaction mixture was diluted with ethyl acetate (50 mL). The organic phase was then washed with brine, dried (MgSO₄), and concentrated to dryness under reduced pressure. The residue was purified by silica gel chromatography (0 to 30% ethyl acetate/hexanes) to provide 107a (15 mg, 65%) as a colorless gum-like material. ¹H NMR (500 MHz, CD₃OD): δ 6.86-6.62 (m, 3H), 5.99-5.89 (m, 1H), 5.75-5.50 (m, 3H), 5.35-5.20 (m, 2H), 4.87-4.83 (m, 2H), 3.84 (s, 3H), 3.83 (s, 3H), 3.65-3.55 (m, 1H), 3.05-2.72 (m, 3H), 2.53-2.10 (m, 4H), 2.08-1.90 (m, 1H), 0.99-0.82 (m, 3H).

Step 2:

A mixture of Pd₂(dba)₃ (3 mg, 0.003 mmol) and (S)-4-tert-butyl-2-[2-(diphenylphosphinoyl)]-2-oxazoline (3 mg, 0.008 mmol) in dioxane (2 mL) was stirred at room temperature for 40 min. A solution of 107a (15 mg, 0.032 mmol) and Meldrum's acid (14 mg, 0.096 mmol) in dioxane (1 mL) was then added. The reaction mixture was stirred for 12 h, and then diluted with ethyl acetate (50 mL). The organic phase was washed with brine, dried (MgSO₄), and concentrated to dryness under reduced pressure. The residue was purified by silica gel chromatography (0 to 30% ethyl acetate/hexanes) to provide 107 as a colorless gum-like material (2 mg, 20%).

Compound 107 ((6S,7aR)-7a-(1-(3,4-dimethoxyphenyl)propan-2-yl)-6-(3-fluoropropyl)-7,7a-dihydrobenzo[d][1,3]dioxol-5(6H)-one). ¹H NMR (500 MHz, CD₃OD): δ 6.87 (t, J=8.0 Hz, 1H), 6.76-6.72 (m, 1.3H), 6.63 (s, 0.7H), 5.69 (s, 1H), 5.63 (s, 0.35H), 5.61 (s, 0.65H), 5.52 (s, 0.35H), 5.46 (s, 0.65H), 4.87-4.83 (m, 2H), 3.79 (s, 3H), 3.77 (s, 3H), 3.12 (dd, J=14.0, 3.0 Hz, 0.65H), 2.79-2.78 (m, 0.35H), 2.67 (d, J=14.0 Hz, 0.65H), 2.51-2.43 (m, 2.35H), 2.32-2.28 (m, 0.35H), 2.16-2.10 (m, 2.65H), 1.98-1.82 (m, 2.35H), 1.68-1.62 (m, 0.65H), 0.97 (d, J=7.0 Hz, 1.05H), 0.85 (d, J=11.5 Hz, 1.95H). ESI MS m/z 379 [C₂₁H₂₇FO₅+H]

General procedure V: Illustrated with preparation of compound 62

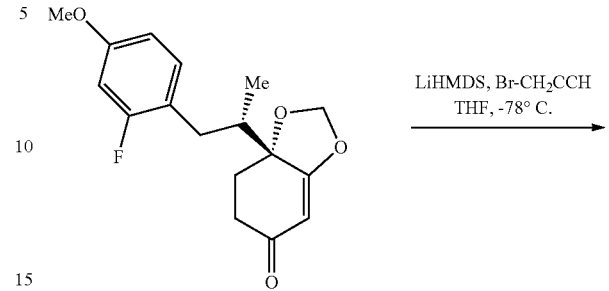

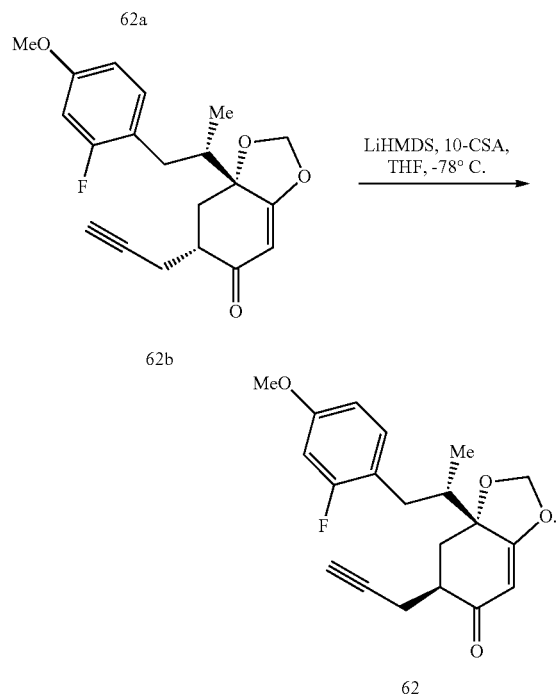

Step 1:

Compound 62a was prepared according to general procedure A. To a solution of 62a (112 mg, 0.36 mmol) in THF (3 mL) was added LiHMDS (1.0M solution in THF, 0.55 mL, 0.55 mmol) at −78° C. under a nitrogen atmosphere. The reaction mixture was stirred for 30 min, and then 3-Bromoprop-1-yne (82 mg, 0.55 mmol) was added. The reaction mixture was allowed to warm to 0° C. over 3 h. It was then quenched with H₂O and extracted with ethyl acetate (50 mL). The organic phase was washed with brine, dried (MgSO₄), and concentrated to dryness under reduced pressure. The residue was purified by silica gel chromatography (0 to 20% ethyl acetate/hexanes) to provide 62b as a colorless gum-like material (63 mg, 51%). ¹H NMR (500 MHz, CD₃OD): δ 7.15 (t, J=8.0 Hz, 1H), 6.69-6.64 (m, 2H), 5.69 (s, 1H), 5.63 (s, 1H), 5.45 (s, 1H), 3.76 (s, 3H), 3.07 (dd, J=14.0, 3.5 Hz, 1H), 2.89 (dd, J=12.5, 4.5 Hz, 1H), 2.65-2.48 (m, 4H), 2.29 (s, 1H), 2.22-2.18 (m, 1H), 2.05 (t, J=12.0 Hz, 1H), 0.94 (d, J=7.0 Hz, 3H).

Step 2:

To a mixture of 62b (63 mg, 0.18 mmol) in THF (3 mL) was added LiHMDS (1.0M solution in THF, 0.40 mL, 0.40 mmol) at −78° C. under a nitrogen atmosphere. The reaction mixture was stirred for 30 min, and then 10-Camphorsulfonic acid (85 mg, 0.40 mmol) in THF (1 mL) was added. The reaction mixture continued to stir at −78° C. over 3 h. The reaction was quenched with H₂O and extracted with ethyl acetate (50 mL). The organic phase was washed with brine, dried (MgSO₄), and concentrated to dryness under reduced pressure. The residue was purified by silica gel chromatography (0 to 20% ethyl acetate/hexanes) to provide 62 as a brown gum (10 mg, 16%).

Compound 62 ((6S,7aR)-7a-((S)-1-(2-fluoro-4-methoxyphenyl)propan-2-yl)-6-(prop-2-yn-1-yl)-7,7a-dihydrobenzo[d][1,3]dioxol-5(6H)-one). ¹H NMR (500 MHz, CD₃OD): δ 7.18 (t, J=8.5 Hz, 1H), 6.70-6.63 (m, 2H), 5.67 (s, 1H), 5.62 (s, 1H), 5.48 (s, 1H), 3.76 (s, 3H), 3.12-3.10 (m, 1H), 3.08 (d, J=14.5 Hz, 1H), 2.92 (d, J=10.0 Hz, 1H), 2.75-2.72 (m, 1H), 2.62 (t, J=10.5 Hz, 1H), 2.45 (s, 1H), 2.44-2.37 (m, 1H), 2.25 (dd, J=14.0, 9.5 Hz, 1H), 1.99-1.95 (m, 1H), 0.83 (d, J=6.5 Hz, 3H). ESI MS m/z 345 [C₂₀H₂₁FO₄+H]⁺.

to afford a 2:1 mixture of cis and trans isomers 63 (4.5 mg, 12%) as a colorless oil. The mixture was then further separated by a Thermo HYPERSIL GOLD C18 column (10×250 mm, 5 nm, 3 mL/min, isocratic 50% acetonitrile/50% H₂O with 0.05% TFA) to afford the cis isomer.

Compound 63 ((7aR)-6-(cyclopropylmethyl)-7a-((S)-1-(2-fluoro-4-methoxyphenyl)propan-2-yl)-7,7a-dihydrobenzo[d][1,3]dioxol-5(6H)-one). ¹H NMR (600 MHz, CD₃OD): δ 7.12 (t, J=8.4 Hz, 1H), 6.70-6.65 (m, 2H), 5.68 (s, 1H), 5.62 (s, 1H), 5.47 (s, 1H), 3.77 (s, 3H), 3.11-3.09 (m, 1H), 2.83 (d, J=13.8 Hz, 1H), 2.61-2.55 (m, 2H), 2.22 (dd, J=14.4, 9.6 Hz, 1H), 2.08-2.01 (m, 1H), 1.73-1.68 (m, 1H), 1.61-1.57 (m, 1H), 1.05-0.89 (m, 2H), 0.85 (d, J=7.2 Hz, 3H), 0.60-0.55 (m, 1H), 0.49-0.45 (m, 1H), 0.25-0.20 (m, 1H), 0.12-0.08 (m, 1H). ESI MS m/z 361 [C₂₁H₂₅FO₄+H]⁺.

General procedure W: Illustrated with preparation of compound 63.

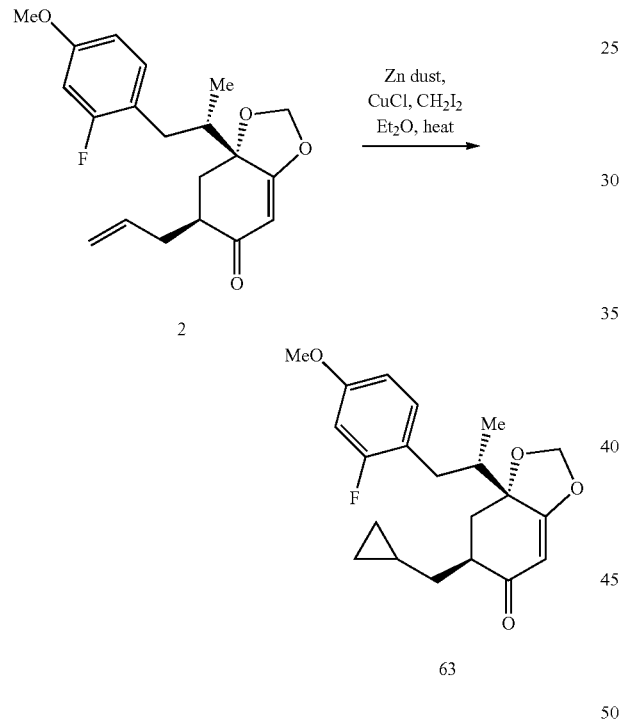

General procedure X: Illustrated with preparation of compound 66.

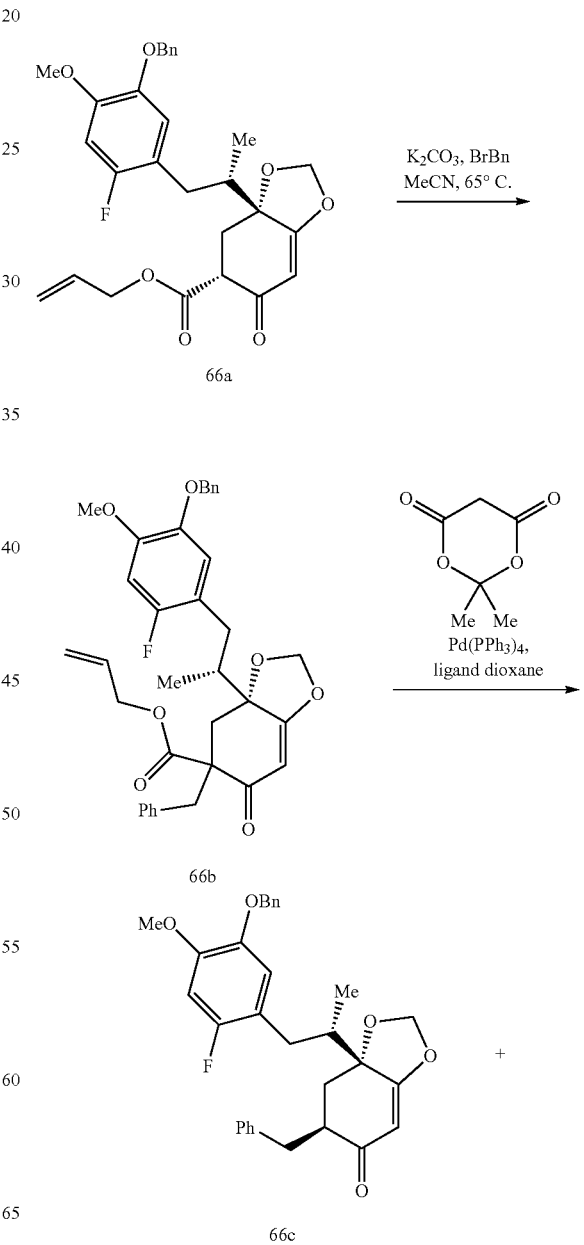

Compound 2 was prepared according to the general procedure A. A mixture of zinc dust (45 mg, 0.70 mmol) and copper(I) chloride (7.0 mg, 0.07 mmol) in diethyl ether (1 mL) was heated to reflux under a nitrogen atmosphere. After 30 min, the mixture was removed from the heating bath and a solution of 2 (40 mg, 0.12 mmol) and diiodomethane (40 mg, 0.15 mmol) in diethyl ether (1 mL) was added. The resulting mixture continued to reflux under a nitrogen atmosphere for 18 h. The reaction was cooled to room temperature, diluted in diethyl ether (2 mL) and filtered through CELITE, rinsing with diethyl ether (50 mL). The organic layer was washed with H₂O (10 mL), dried (Na₂SO₄), filtered, and concentrated under reduced pressure. The crude residue was purified by reverse-phase column chromatography (Varian POLARIS C18-A 10 μm, 30×250 mm, 43 mL/min, 10% CH₃CN/90% H₂O for 5 min, 10% CH₃CN to 90% CH₃CN for 45 min, 90% CH₃CN/10% H₂O for 5 min)

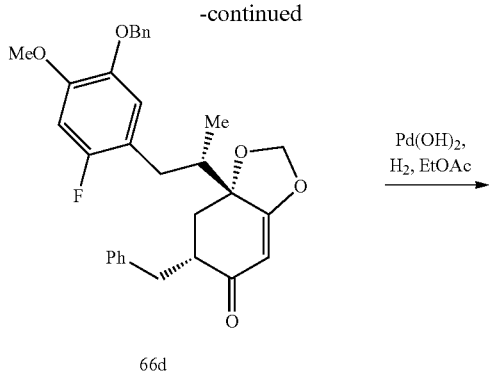

66d

66

Step 1:

Compound 66a was prepared according to the general procedure C. A mixture of 66a (100 mg, 0.20 mmol), $K_2CO_3$ (56 mg, 0.40 mmol), and benzyl bromide (0.036 mL, 0.30 mmol) in MeCN (5 mL) was heated to 65° C. for 12 h. The reaction mixture was then diluted with ethyl acetate (50 mL). The organic phase was washed with brine, dried ($MgSO_4$), and concentrated to dryness under reduced pressure. The residue was purified by silica gel chromatography (0 to 40% ethyl acetate/hexanes) to provide a mixture of diastereomers 66b (85 mg, 73%). $^1$H NMR (500 MHz, $CD_3OD$): δ 7.42 (d, J=7.0 Hz, 2H), 7.34-7.23 (m, 6H), 7.12 (d, J=6.5 Hz, 2H), 6.86 (d, J=7.0 Hz, 1H), 6.75 (d, J=11.5 Hz, 1H), 5.85-5.77 (m, 1H), 5.54 (s, 1H), 5.43 (s, 1H), 5.42 (s, 1H), 5.22-5.12 (m, 2H), 5.09 (d, J=4.5 Hz, 2H), 3.82 (s, 3H), 3.58 (d, J=13.5 Hz, 1H), 3.05 (dd, J=14.0, 9.0 Hz, 2H), 2.82-2.80 (m, 1H), 2.58 (t, J=9.0 Hz, 1H), 2.16 (t, J=9.0 Hz, 1H), 1.98-1.92 (m, 1H), 0.74 (d, J=3.0 Hz, 3H).

Step 2:

To a solution of 66b (85 mg, 0.14 mmol) and Meldrum's acid (61 mg, 0.42 mmol) in dioxane (6 mL) was added $Pd(PPh_3)_4$ (17 mg, 0.014 mmol) under a nitrogen atmosphere. The reaction mixture was stirred at room temperature for 12 h, and then diluted with ethyl acetate (50 mL). The organic phase was washed with brine, dried ($MgSO_4$), and concentrated to dryness under reduced pressure. The residue was purified by silica gel chromatography (0 to 30% ethyl acetate/hexanes) to provide 66c (10 mg, 14%). $^1$H NMR (500 MHz, $CD_3OD$): δ 7.36-7.20 (m, 10H), 6.80 (d, J=11.5 Hz, 1H), 6.73 (d, J=7.5 Hz, 1H), 5.60 (s, 1H), 5.57 (s, 1H), 5.53 (s, 1H), 5.06 (s, 2H), 3.84 (s, 3H), 3.44 (d, J=3.5 Hz, 1H), 2.95-2.85 (m, 2H), 2.61 (t, J=11.5 Hz, 1H), 2.48 (dd, J=14.0, 2.5 Hz, 2H), 2.00-1.95 (m, 2H), 0.74 (d, J=7.0 Hz, 3H).

Step 3:

To a solution of 66c (14 mg, 0.075 mmol) in 5 mL of ethyl acetate was added $Pd(OH)_2/C$ (20 wt. % Pd on carbon, 4 mg) under a nitrogen atmosphere. The mixture was stirred under one atmosphere of hydrogen for 1 h. The reaction mixture was then filtered on an inorganic membrane filter and washed with ethyl acetate (10 mL). The filtrate was concentrated to dryness under reduced pressure, and then purified by silica gel chromatography (0 to 40% ethyl acetate/hexanes) to provide 66 as an off-white semisolid (10 mg, 92%).

Compound 66 ((6S,7aR)-6-benzyl-7a-((S)-1-(2-fluoro-5-hydroxy-4-methoxyphenyl)propan-2-yl)-7,7a-dihydrobenzo[d][1,3]dioxol-5(6H)-one). $^1$H NMR (500 MHz, $CD_3OD$): δ 7.30 (s, 4H), 7.22-7.19 (m, 1H), 6.74 (d, J=13.5 Hz, 1H), 6.67 (d, J=17.5 Hz, 1H), 5.64 (s, 1H), 5.58 (s, 1H), 5.54 (s, 1H), 3.83 (s, 3H), 3.50 (dd, J=14.5, 4.0 Hz, 1H), 3.02 (dd, J=13.0, 3.5 Hz, 1H), 2.92-2.88 (m, 1H), 2.72-2.66 (m, 1H), 2.53-2.45 (m, 2H), 2.11-2.09 (m, 1H), 2.04 (dd, J=14.5, 10.5 Hz, 1H), 0.86 (d, J=7.0 Hz, 3H). ESI MS (Positive Mode) m/z 413 $[C_{24}H_{25}FO_5+H]^+$.

General procedure Y: Illustrated with preparation of compound 75.

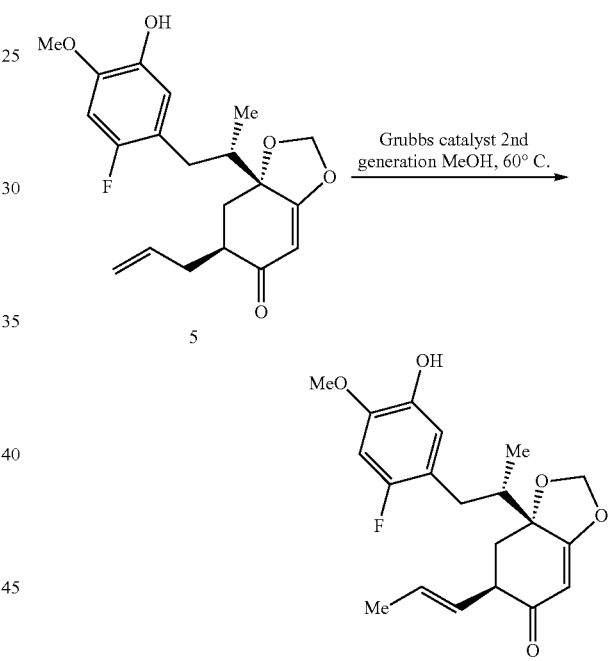

75

To a solution of 5 (36 mg, 0.10 mmol) in MeOH (9 mL) was added Grubbs catalyst 2$^{1}$ generation (9 mg, 0.01 mmol). The reaction mixture was heated to 60° C. for 3 h and then concentrated to dryness under reduced pressure. The residue was purified by silica gel chromatography (0 to 40% ethyl acetate/hexanes) to provide the product (20 mg). The product was repurified by reverse preparative HPLC to provide 75 as a colorless gum-like material (3.6 mg, 10%).

Compound 75 ((6R,7aR)-7a-((S)-1-(2-fluoro-5-hydroxy-4-methoxyphenyl)propan-2-yl)-6-((E)-prop-1-en-1-yl)-7,7a-dihydrobenzo[d][1,3]dioxol-5 (6H)-one). $^1$H NMR (500 MHz, $CD_3OD$): δ 6.68 (d, J=11.5 Hz, 1H), 6.61 (d, J=7.0 Hz, 1H), 5.75-5.72 (m, 1H), 5.67 (s, 1H), 5.62 (s, 1H), 5.54-5.52 (m, 1H), 5.49 (s, 1H), 3.81 (s, 3H), 3.57-3.55 (m, 1H), 3.20 (d, J=14.5 Hz, 1H), 2.84-2.82 (m, 1H), 2.64 (d, J=13.0 Hz, 1H), 2.52-2.50 (m, 1H), 2.34-2.30 (m, 1H), 2.12-1.10 (m, 1H), 1.71 (d, J=6.0 Hz, 3H), 0.86 (d, J=7.0 Hz, 3H). ESI MS (Positive Mode) m/z 363 [C$_{20}$H$_{23}$FO$_5$+H]$^+$.

General procedure Z: Illustrated with preparation of compound 68.

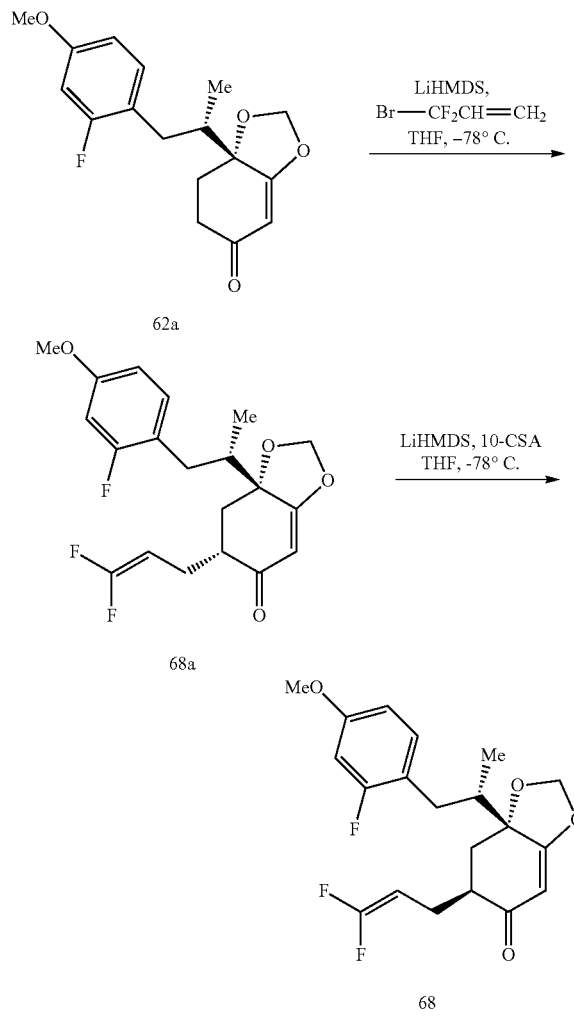

Step 1:

To a solution of 62a (100 mg, 0.32 mmol) in THF (3 mL) was added LiHMDS (1.0M solution in THF, 0.49 mL, 0.49 mmol) at −78° C. under a nitrogen atmosphere. The reaction mixture was stirred for 30 min, and then 3-Bromo-3,3-difluoroprop-1-ene (66 mg, 0.42 mmol) was added. The reaction mixture was allowed to warm to 0° C. over 3 h. The reaction was quenched with H$_2$O and extracted with ethyl acetate (50 mL). The organic phase was washed with brine, dried (MgSO$_4$), and concentrated to dryness under reduced pressure. The residue was purified by silica gel chromatography (0 to 30% ethyl acetate/hexanes) to provide 68a (84 mg, 69%). $^1$H NMR (500 MHz, CD$_3$OD): δ 7.19 (t, J=15.0 Hz, 1H), 6.72-6.65 (m, 2H), 5.70 (s, 1H), 5.63 (s, 1H), 5.45 (s, 1H), 4.24-4.12 (m, 1H), 3.77 (s, 3H), 3.10-3.04 (m, 1H), 2.69 (dd, J=20.5, 7.5 Hz, 1H), 2.55-2.46 (m, 3H), 2.26-2.18 (m, 2H), 1.79 (t, J=20.5 Hz, 1H), 0.97 (d, J=12.0 Hz, 3H).

Step 2:

To a mixture of 68a (84 mg, 0.22 mmol) in THF (3 mL) was added LiHMDS (1.0M solution in THF, 0.44 mL, 0.44 mmol) at −78° C. under a nitrogen atmosphere. The reaction mixture was stirred for 30 min, and then a solution of 10-camphorsulfonic acid (102 mg, 0.44 mmol) in THF (1 mL) was added. The reaction mixture continued to stir at −78° C. over 3 h. The reaction was quenched with H$_2$O and extracted with ethyl acetate (50 mL). The organic phase was washed with brine, dried (MgSO$_4$), and concentrated to dryness under reduced pressure. The residue was purified by silica gel chromatography (0 to 30% ethyl acetate/hexanes) to provide 68 as a colorless oil (47 mg, 56%).

Compound 68 ((6S,7aR)-6-(3,3-difluoroallyl)-7a-((S)-1-(2-fluoro-4-methoxyphenyl)propan-2-yl)-7,7a-dihydrobenzo[d][1,3]dioxol-5(6H)-one). $^1$H NMR (500 MHz, CD$_3$OD): δ 7.12 (t, J=8.5 Hz, 1H), 6.69-6.64 (m, 2H), 5.65 (s, 1H), 5.61 (s, 1H), 5.49 (s, 1H), 4.48-4.42 (m, 1H), 3.76 (s, 3H), 3.06 (dd, J=14.0, 4.0 Hz, 1H), 2.73-2.69 (m, 1H), 2.62-2.52 (m, 3H), 2.22-2.17 (m, 2H), 1.99-1.97 (m, 1H), 0.85 (d, J=7.0 Hz, 3H). ESI MS (Positive Mode) m/z 383 [C$_{20}$H$_{21}$F$_3$O$_4$+H]$^+$.

General procedure AA: Illustrated with preparation of compound 88.

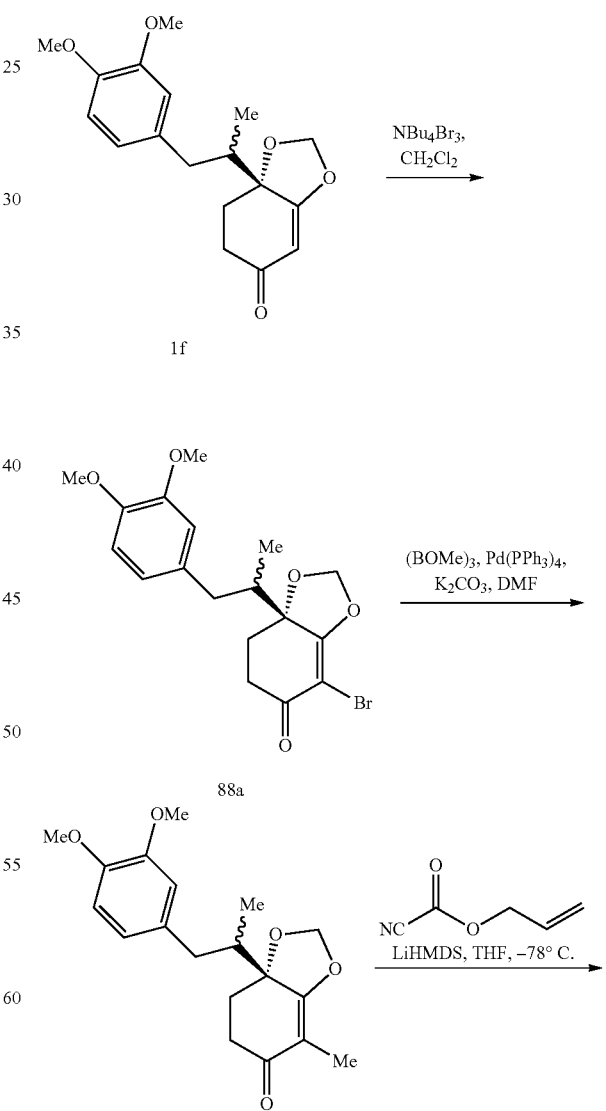

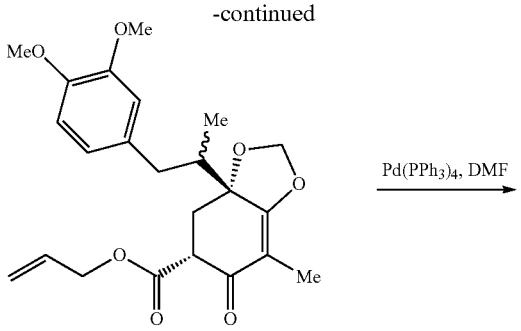

88c

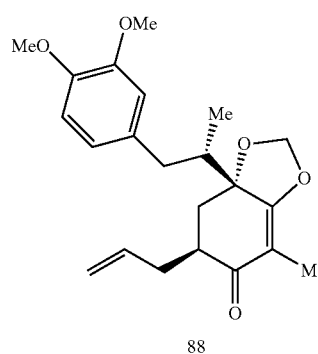

88

Step 1:

To a solution of 1f (100 mg, 0.31 mmol) in CH$_2$Cl$_2$ (20 mL) was added tetrabutylammonium tribromide (152 mg, 0.31 mmol). The reaction mixture was stirred at room temperature for 2 h. It was then diluted with ethyl acetate (50 mL), washed with brine, dried (MgSO$_4$), and concentrated to dryness under reduced pressure. The residue was purified by silica gel chromatography (0 to 30% ethyl acetate/hexanes) to provide 88a (105 mg, 85%). $^1$H NMR (500 MHz, CD$_3$OD): δ 6.90-6.73 (m, 3H), 5.89 (s, 0.4H), 5.85 (s, 0.6H), 5.79 (s, 0.4H), 5.77 (s, 0.6H), 3.84 (s, 2.4H), 3.82 (s, 3.6H), 3.05-3.01 (m, 0.6H), 2.81-2.45 (m, 4.4H), 2.35-2.32 (m, 1H), 2.09-2.05 (m, 1H), 0.98 (d, J=7.0 Hz, 1.2H), 0.90 (d, J=7.0 Hz, 1.8H).

Step 2:

A microwave tube was charged with 88a (50 mg, 0.125 mmol), trimethylboroxine (32 mg, 0.25 mmol), Pd(PPh$_3$)$_4$ (14 mg, 0.012 mmol) and K$_2$CO$_3$ (52 mg, 0.375 mmol) in toluene (3 mL) under a nitrogen atmosphere. The tube was then sealed and heated to 110° C. for 1 h. The resulting mixture was diluted with ethyl acetate (50 mL), washed with brine, dried (MgSO$_4$), and concentrated to dryness under reduced pressure. The crude residue was purified by silica gel chromatography (0 to 40% ethyl acetate/hexanes) to provide 88b (30 mg, 73%). $^1$H NMR (500 MHz, CD$_3$OD): δ 6.88-6.70 (m, 3H), 5.74 (s, 0.4H), 5.72 (s, 0.6H), 5.65 (s, 0.4H), 5.63 (s, 0.6H), 3.83 (s, 3H), 3.81 (s, 3H), 3.05-3.02 (m, 0.6H), 2.84-2.82 (m, 0.4H), 2.57-2.43 (m, 4H), 2.25-2.23 (m, 1H), 2.02-1.98 (m, 1H), 1.92 (s, 1.8H), 1.90 (s, 1.2H), 0.99 (d, J=6.5 Hz, 1.2H), 0.92 (d, J=7.0 Hz, 1.8H).

Step 3:

To a solution of 88b (30 mg, 0.09 mmol) in THF (2 mL) was added LiHMDS (1.0M solution in THF, 0.14 mL, 0.14 mmol) at −78° C. under a nitrogen atmosphere. The reaction mixture was stirred for 30 min, and then allyl cyanoformate II (15 mg, 0.14 mmol) was added. The reaction mixture was allowed to warm to 0° C. over 2 h. It was then quenched with H$_2$O and extracted with ethyl acetate (50 mL). The organic phase was washed with brine, dried (MgSO$_4$), and concentrated to dryness under reduced pressure. The residue was purified by silica gel chromatography (0 to 40% ethyl acetate/hexanes) to provide 88c (27 mg, 73%). $^1$H NMR (500 MHz, CD$_3$OD): δ 6.89-6.64 (m, 3H), 5.99-5.92 (m, 1H), 5.78 (s, 0.4H), 5.74 (s, 0.6H), 5.69 (s, 0.4H), 5.67 (s, 0.6H), 5.38-5.22 (m, 2H), 3.86 (s, 3H), 3.84 (s, 3H), 3.64-3.61 (m, 1H), 3.02-2.98 (m, 1H), 2.82-2.80 (m, 1H), 2.68-2.66 (m, 1H), 2.53-2.42 (m, 1H), 2.28 (m, 1H), 1.76 (s, 1.8H), 1.71 (s, 1.2H), 0.97 (d, J=7.0 Hz, 1.2H), 0.87 (d, J=7.0 Hz, 1.8H).

Step 4:

To a solution of 88c (27 mg, 0.064 mmol) in DMF (2 mL) was added Pd(PPh$_3$)$_4$ (9 mg, 0.006 mmol) under a nitrogen atmosphere. The reaction mixture was stirred at room temperature for 3 h. The reaction mixture was diluted with ethyl acetate (50 mL). The organic phase was washed with brine, dried (MgSO$_4$) and concentrated to dryness under reduced pressure. The residue was purified by silica gel chromatography (0 to 30% ethyl acetate/hexanes) to provide a mixture of diastereomers 88 (3.0 mg, 13%) as a colorless oil.

Compound 88 ((6S,7aR)-6-allyl-7a-(1-(3,4-dimethoxyphenyl)propan-2-yl)-4-methyl-7,7a-dihydrobenzo[d][1,3]dioxol-5(6H)-one). $^1$H NMR (500 MHz, CD$_3$OD): δ 6.88-6.83 (m, 1H), 6.75-6.73 (m, 1H), 6.61 (s, 1H), 5.95-5.78 (m, 1H), 5.69 (d, J=7.5 Hz, 1H), 5.60 (d, J=9.0 Hz, 1H), 5.15-5.05 (m, 2H), 3.81 (s, 3H), 3.79 (s, 3H), 3.09-2.83 (m, 1H), 2.72-2.15 (m, 4H), 2.08-1.90 (m, 3H), 1.70 (s, 3H), 0.93 (d, J=7.0 Hz, 1.8H), 0.82 (d, J=6.5 Hz, 1.2H). ESI MS (Positive Mode) m/z 373 [C$_{22}$H$_{28}$O$_5$+H]$^+$.

General procedure AB: Illustrated with preparation of compound 89.

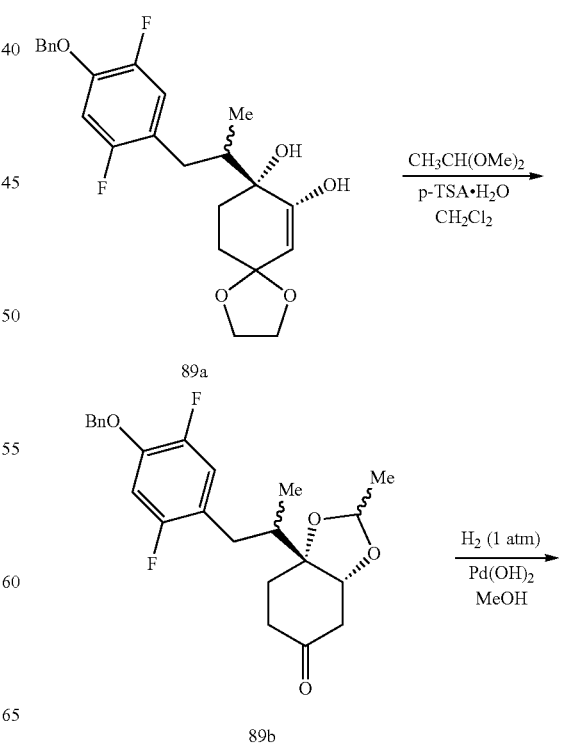

89a

89b

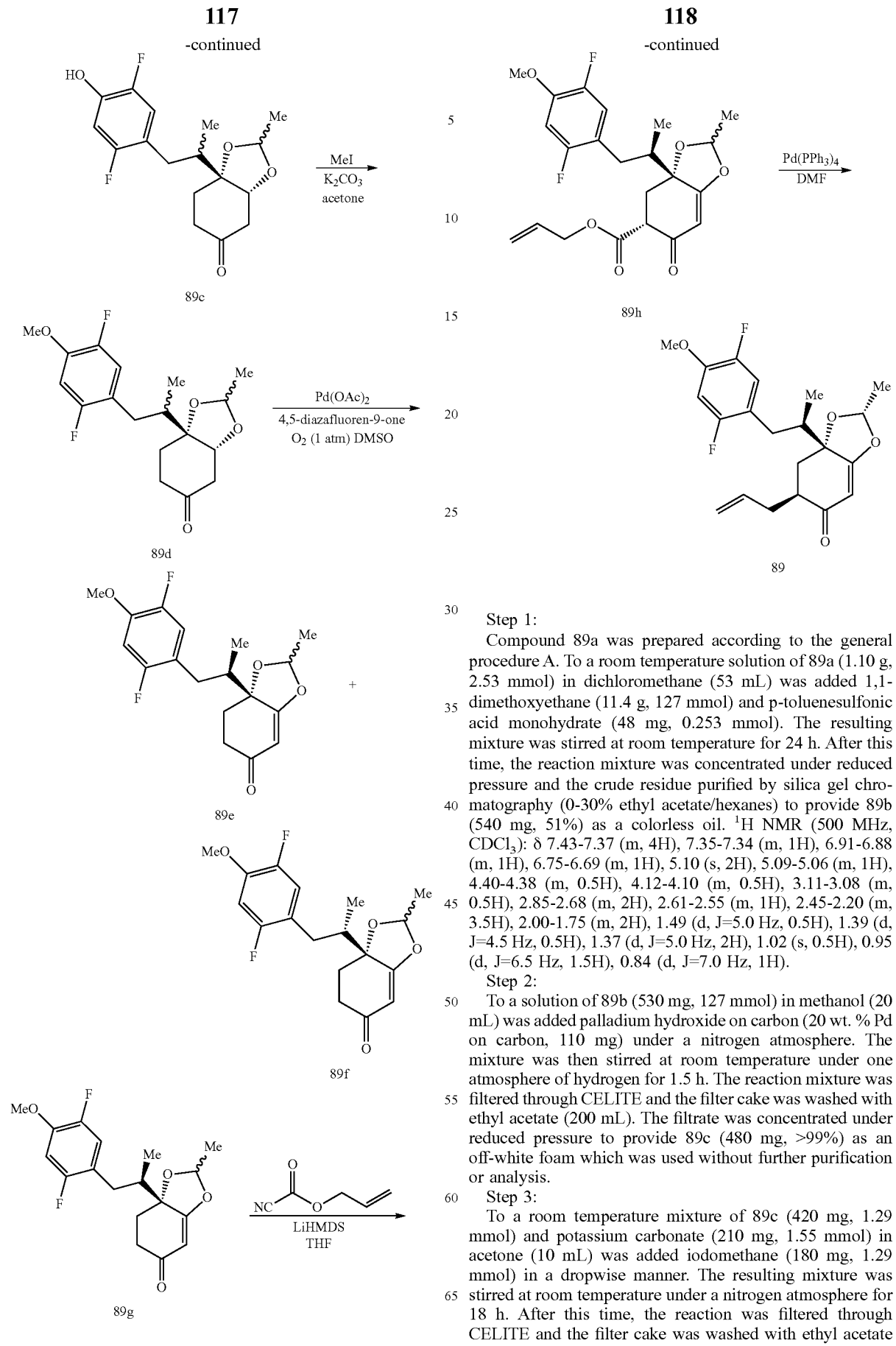

Step 1:
Compound 89a was prepared according to the general procedure A. To a room temperature solution of 89a (1.10 g, 2.53 mmol) in dichloromethane (53 mL) was added 1,1-dimethoxyethane (11.4 g, 127 mmol) and p-toluenesulfonic acid monohydrate (48 mg, 0.253 mmol). The resulting mixture was stirred at room temperature for 24 h. After this time, the reaction mixture was concentrated under reduced pressure and the crude residue purified by silica gel chromatography (0-30% ethyl acetate/hexanes) to provide 89b (540 mg, 51%) as a colorless oil. $^1$H NMR (500 MHz, CDCl$_3$): δ 7.43-7.37 (m, 4H), 7.35-7.34 (m, 1H), 6.91-6.88 (m, 1H), 6.75-6.69 (m, 1H), 5.10 (s, 2H), 5.09-5.06 (m, 1H), 4.40-4.38 (m, 0.5H), 4.12-4.10 (m, 0.5H), 3.11-3.08 (m, 0.5H), 2.85-2.68 (m, 2H), 2.61-2.55 (m, 1H), 2.45-2.20 (m, 3.5H), 2.00-1.75 (m, 2H), 1.49 (d, J=5.0 Hz, 0.5H), 1.39 (d, J=4.5 Hz, 0.5H), 1.37 (d, J=5.0 Hz, 2H), 1.02 (s, 0.5H), 0.95 (d, J=6.5 Hz, 1.5H), 0.84 (d, J=7.0 Hz, 1H).

Step 2:
To a solution of 89b (530 mg, 127 mmol) in methanol (20 mL) was added palladium hydroxide on carbon (20 wt. % Pd on carbon, 110 mg) under a nitrogen atmosphere. The mixture was then stirred at room temperature under one atmosphere of hydrogen for 1.5 h. The reaction mixture was filtered through CELITE and the filter cake was washed with ethyl acetate (200 mL). The filtrate was concentrated under reduced pressure to provide 89c (480 mg, >99%) as an off-white foam which was used without further purification or analysis.

Step 3:
To a room temperature mixture of 89c (420 mg, 1.29 mmol) and potassium carbonate (210 mg, 1.55 mmol) in acetone (10 mL) was added iodomethane (180 mg, 1.29 mmol) in a dropwise manner. The resulting mixture was stirred at room temperature under a nitrogen atmosphere for 18 h. After this time, the reaction was filtered through CELITE and the filter cake was washed with ethyl acetate (100 mL). The filtrate was concentrated under reduced pressure and the crude residue purified by silica gel chromatography (0-30% ethyl acetate/hexanes) to afford 89d (270 mg, 61%) as a colorless oil. ¹H NMR (300 MHz, CDCl₃): δ 6.93-6.85 (m, 1H), 6.72-6.65 (m, 1H), 5.12-5.05 (m, 1H), 4.40 (t, J=2.7 Hz, 0.6H), 4.19 (t, J=2.7 Hz, 0.4H), 3.86 (s, 3H), 3.14-3.07 (m, 0.4H), 2.87-2.72 (m, 1.6H), 2.65-2.20 (m, 4H), 2.61-1.79 (m, 3H), 1.40-1.36 (m, 3H), 0.96 (d, J=6.9 Hz, 1.8H), 0.84 (d, J=6.9 Hz, 1.2H).

Step 4:

A solution of 89d (270 mg, 0.790 mmol), palladium acetate (89.0 mg, 0.395 mmol), and 4,5-diazofluoren-9-one (72.0 mg, 0.395 mmol) in dimethyl sulfoxide (7 mL) was heated to 80° C. under one atmosphere of oxygen for 4 h. After this time, the reaction mixture was cooled to room temperature and diluted with ethyl acetate (400 mL). The organic phase was washed with brine, dried (Na₂SO₄) and concentrated to dryness under reduced pressure. The crude residue was purified by silica gel chromatography (0-30% ethyl acetate/hexanes) to provide a mixture of diastereomers. The mixture was separated by chromatography on CHIRALPAK OD (5% i-PrOH/hepane) to provide 89e (38 mg) as a colorless oil. ¹H NMR (500 MHz, CDCl₃): δ 6.82-6.79 (m, 1H), 6.67-6.63 (m, 1H), 5.91 (q, J=10.0, 5.0 Hz, 1H), 5.50 (s, 1H), 3.85 (s, 3H), 2.89-2.87 (m, 1H), 2.53-2.48 (m, 2H), 2.42-2.37 (m, 2H), 2.18-2.13 (m, 1H), 2.06-2.00 (m, 1H), 1.55 (d, J=5.0 Hz, 3H), 0.98 (d, J=7.0 Hz, 3H).

Step 5:

To a solution of 89e (38 mg, 0.112 mmol) in anhydrous THF (2.0 mL) at –78° C. under a nitrogen atmosphere, was added LiHMDS (1.0M solution in THF, 0.17 mL, 0.17 mmol). The reaction mixture was stirred at room temperature for 30 min before a solution of allyl cyanoformate II (17.0 mg, 0.157 mmol) in tetrahydrofuran (0.2 mL) was added. The reaction mixture was allowed to warm to –40° C. over 1.5 h. The reaction was diluted with ethyl acetate (15 mL) and the organic phase was washed with brine, dried (Na₂SO₄), and concentrated to dryness under reduced pressure. The residue was purified by silica gel chromatography (0-15% ethyl acetate/hexanes) to provide 89g (30 mg, 64%) as a colorless oil. ¹H NMR (500 MHz, CDCl₃): δ 6.81-6.77 (m, 1H), 6.67-6.63 (m, 1H), 5.91 (q, J=10.0, 5.0 Hz, 1H), 5.56 (s, 1H), 5.39-5.25 (m, 2H), 4.70-4.65 (m, 2H), 3.85 (s, 3H), 3.47-3.44 (m, 1H), 2.89-2.87 (m, 1H), 2.73-2.69 (m, 1H), 2.45-2.27 (m, 2H), 2.11-2.07 (m, 1H), 1.57 (d, J=5.0 Hz, 3H), 1.55-1.52 (m, 1H), 0.98 (d, J=7.0 Hz, 3H).

Step 6:

A room temperature solution of 89g (30.0 mg, 0.071 mmol) in dimethylformamide (1 mL) was briefly sparged with nitrogen before Pd(PPh₃)₄ (8 mg, 0.007 mmol) was added. The reaction was stirred at room temperature under a nitrogen atmosphere for 1.5 h. After this time, the mixture was diluted in ethyl acetate (25 mL) and washed with brine (15 mL). The organic layer was dried (Na₂SO₄), filtered, and concentrated under reduced pressure, and the crude residue was purified by silica gel chromatography (0-20% ethyl acetate/hexanes) to provide 89 (13 mg, 48%) as a colorless oil.

Compound 89 ((2R,6S,7aR)-6-allyl-7a-((R)-1-(2,5-difluoro-4-methoxyphenyl)propan-2-yl)-2-methyl-7,7a-dihydrobenzo[d][1,3]dioxol-5(6H)-one). ¹H NMR (500 MHz, CD₃OD): δ 6.92-6.84 (m, 2H), 6.02 (q, J=10.0, 5.0 Hz, 1H), 5.85-5.77 (m, 1H), 5.47 (s, 1H), 5.08-5.01 (m, 2H), 3.83 (s, 3H), 2.80-2.77 (m, 2H), 2.63-2.59 (m, 1H), 2.52 (d, J=14.5 Hz, 1H), 2.40 (t, J=11.5 Hz, 1H), 2.08-1.97 (m, 3H), 1.50 (d, J=4.5 Hz, 3H), 0.95 (d, J=7.0 Hz, 3H). ESI MS (Positive Mode) m/z 379 [C₂₁H₂₄F₂O₄+H]⁺.

General procedure AC: Illustrated with preparation of compound 108.

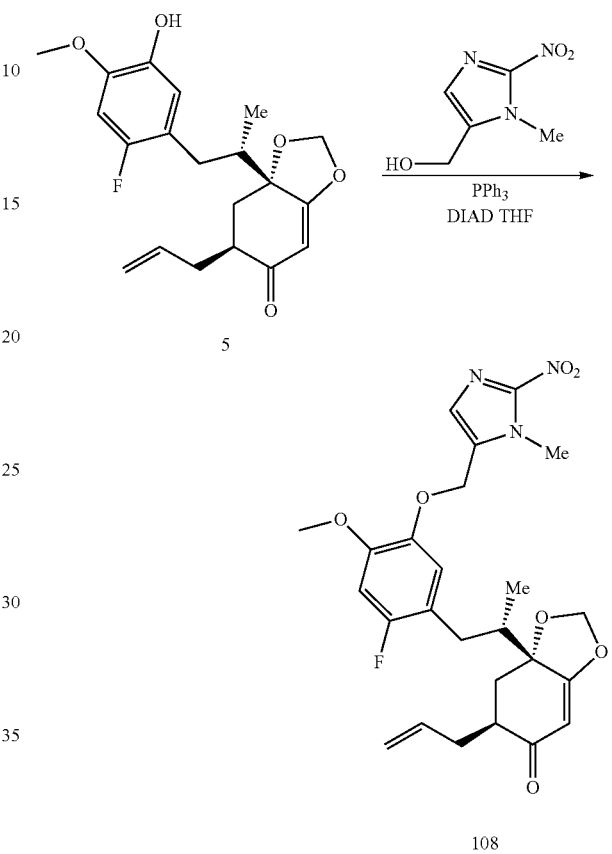

Step 1:

A mixture of 5 (200 mg, 0.552 mmol), (1-methyl-2-nitro-1H-imidazol-5-yl)methanol prepared by the procedure described in the patent (Matteucci, M.; Duan, J.-X.; Jiao, H.; Kaizerman, J.; Ammons, S. Phosphoramidate alkylator prodrugs and their preparation, pharmacokinetics and use in the treatment of cancer and hyperproliferative diseases. WO2007002931A2, 2007) (170 mg, 1.10 mmol), and triphenylphosphine (290 mg, 1.10 mmol) in anhydrous THF (15 mL) was cooled to ~0° C. in an ice-H₂O bath. Diisopropyl azodicarboxylate (220 mg, 1.10 mmol) was then added in a dropwise manner, the ice-bath removed, and the reaction mixture allowed to stir at room temperature for 2.5 h. After this time, the reaction was concentrated under reduced pressure and the crude residue purified by silica gel chromatography (0-15% ethyl acetate/dichloromethane) to afford 108 (250 mg, 89%) as a yellow solid.

Compound 108 ((6S,7aR)-6-allyl-7a-((S)-1-(2-fluoro-4-methoxy-5-((l-methyl-2-nitro-1H-imidazol-5-yl)methoxy)phenyl)propan-2-yl)-7,7a-dihydrobenzo[d][1,3]dioxol-5(6H)-one). ¹H NMR (500 MHz, CD₃OD): δ 7.10 (s, 1H), 6.87 (d, J=7.5 Hz, 1H), 6.81 (d, J=11.5 Hz, 1H), 5.92-5.84 (m, 1H), 5.64 (s, 1H), 5.60 (s, 1H), 5.50 (s, 1H), 5.17-5.09 (m, 4H), 4.11 (s, 3H), 3.81 (s, 3H), 3.03 (dd, J=14.0, 4.0 Hz, 1H), 2.85-2.81 (m, 1H), 2.62 (d, J=14.0 Hz, 1H), 2.58 (dd, J=10.0, 3.5 Hz, 1H), 2.54-2.49 (m, 1H), 2.25-2.18 (m, 1H), 2.11 (dd, J=14.0, 4.0 Hz, 1H), 2.04-2.00 (m, 1H), 0.80 (d, J=7.0 Hz, 3H). ESI MS (Positive Mode) m/z 502 [C$_{25}$H$_{28}$FO$_7$+H]$^+$.

General procedure AD: Illustrated with preparation of compound 65.

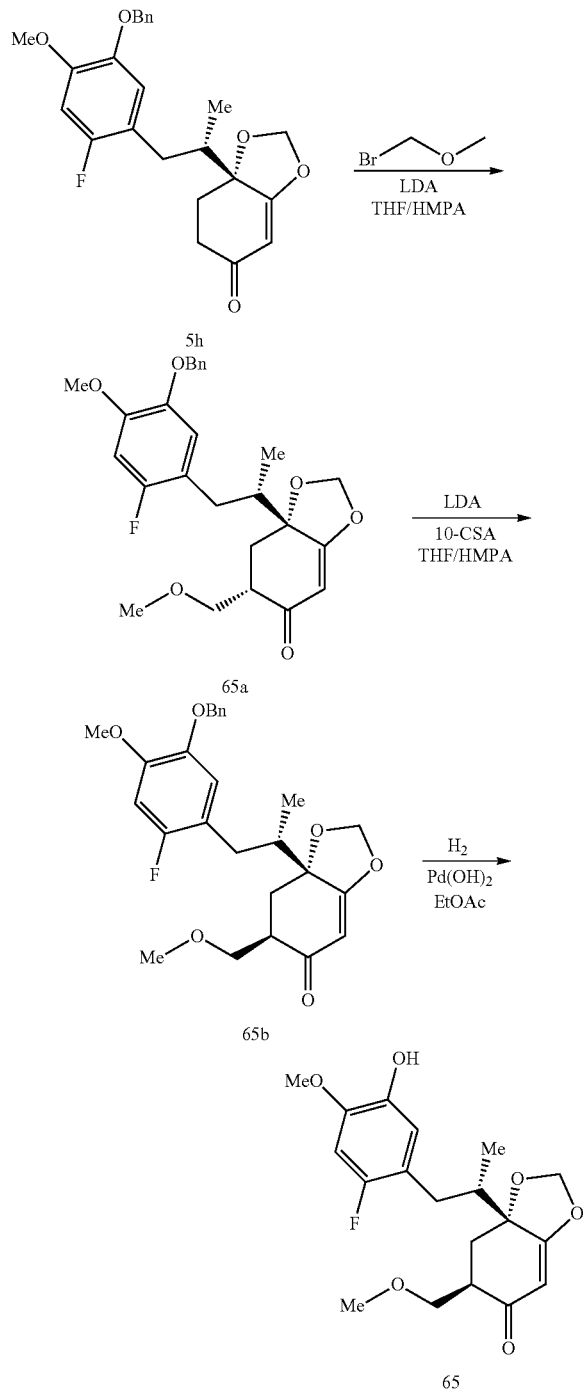

Step 1:

To a −78° C. solution of lithium diisopropylamide (1.0 M in THF/hexanes, 1.6 mL, 1.6 mmol) in anhydrous THF (2 mL) was added a solution of 5h (500 mg, 1.21 mmol) in HMPA/THF (0.8 mL/3.9 mL). The resulting mixture was stirred at −40° C. for 2 h. After this time, the reaction was cooled to −78° C. and slowly quenched with a saturated solution of ammonium chloride (1 mL). The reaction was removed from the cooling bath and diluted in ethyl acetate (30 mL) and washed with saturated ammonium chloride solution (5 mL). The organic layer was dried (Na$_2$SO$_4$), filtered, and concentrated under reduced pressure. The crude residue was purified by silica chromatography (0-20% ethyl acetate/hexanes) to afford 65a (90 mg, 16%) as a colorless oil. $^1$H NMR (500 MHz, CDCl$_3$): δ 7.40-7.38 (m, 2H), 7.36-7.32 (m, 2H), 7.30-7.27 (m, 1H), 6.61 (d, J=11.0 Hz, 1H), 6.56 (d, J=7.5 Hz, 1H), 5.57 (s, 1H), 5.54 (s, 1H), 5.50 (s, 1H), 5.09-5.08 (m, 2H), 3.84 (s, 3H), 3.75-3.72 (m, 1H), 3.65 (dd, J=9.5, 4.0 Hz, 1H), 3.33 (s, 3H), 2.98-2.96 (m, 1H), 2.71 (dd, J=13.0, 5.5 Hz, 1H), 2.55-2.49 (m, 1H), 2.36-2.31 (m, 1H), 2.07-2.02 (m, 2H), 0.80 (d, J=7.0 Hz, 3H).

Step 2:

To a solution of 65a (45.0 mg, 0.099 mmol) in THF/HMPA (0.5 mL/0.5 mL) at −78° C. was added lithium diisopropylamide (1.0 M solution THF/hexanes, 0.20 mL, 0.2 mmol) under a nitrogen atmosphere. The resulting mixture was stirred at −78° C. for 15 min before adding a solution of 10-camphorsulfonic acid (46 mg, 0.197 mmol) in THF (0.3 mL). After stirring at −78° C. for 2 h, the reaction mixture was slowly quenched with brine (1 mL), removed from the cooling bath, and diluted in ethyl acetate (10 mL). The organic layer was washed with brine (5 mL), dried (Na$_2$SO$_4$), filtered, and concentrated under reduced pressure. The crude residue was purified by silica gel chromatography (0-20% ethyl acetate/hexanes) to afford 65b (12 mg, 27%) as a colorless oil that was a mixture of isomers. $^1$H NMR (500 MHz, CDCl$_3$): δ 7.40-7.38 (m, 2H), 7.35-7.32 (m, 2H), 7.30-7.27 (m, 1H), 6.64-6.55 (m, 2H), 5.57-5.52 (m, 3H), 5.09-5.07 (m, 2H), 3.84 (s, 3H), 3.77-3.72 (m, 1H), 3.66-3.61 (m, 1H), 3.50-3.33 (m, 3H), 3.04-2.97 (m, 1H), 2.90-2.49 (m, 2H), 2.48-2.43 (m, 0.3H), 2.36-2.31 (m, 0.7H), 2.09-2.01 (m, 2H), 0.80 (d, J=7.0 Hz, 1.8H), 0.71 (d, J=7.0 Hz, 1.2H).

Step 3:

A mixture of 65b (22.0 mg, 0.048 mmol) and palladium hydroxide on carbon (20 wt. % Pd on carbon, 5 mg) in ethyl acetate (6 mL) was stirred at room temperature under one atmosphere of hydrogen for 30 min. After this time, the reaction was filtered through CELITE and the filter cake washed with ethyl acetate (50 mL). The filtrate was concentrated to dryness under reduced pressure. The crude residue was purified by silica gel chromatography (0-25% ethyl acetate/hexanes) followed by CHIRALPAK AD (20% isopropanol/heptane) to afford 65 (4.2 mg) as a colorless oil.

Compound 65 ((6R,7aR)-7a-((S)-1-(2-fluoro-5-hydroxy-4-methoxyphenyl)propan-2-yl)-6-(methoxymethyl)-7,7a-dihydrobenzo[d][1,3]dioxol-5(6H)-one). $^1$H NMR (500 MHz, CD$_3$OD): δ 6.69 (d, J=11.0 Hz, 1H), 6.65 (d, J=7.5 Hz, 1H), 5.65 (s, 1H), 5.60 (s, 1H), 5.49 (s, 1H), 3.81 (s, 3H), 3.74-3.71 (m, 1H), 3.68-3.65 (m, 1H), 3.36 (s, 3H), 2.97 (dd, J=13.5, 3.0 Hz, 1H), 2.88-2.83 (m, 2H), 2.54-2.49 (m, 1H), 2.21-2.12 (m, 2H), 0.84 (d, J=7.0 Hz, 3H). ESI MS (Positive Mode) m/z 367 [C$_{19}$H$_{23}$FO$_6$+H]$^+$.

General procedure AE: Illustrated with preparation of compound 77.

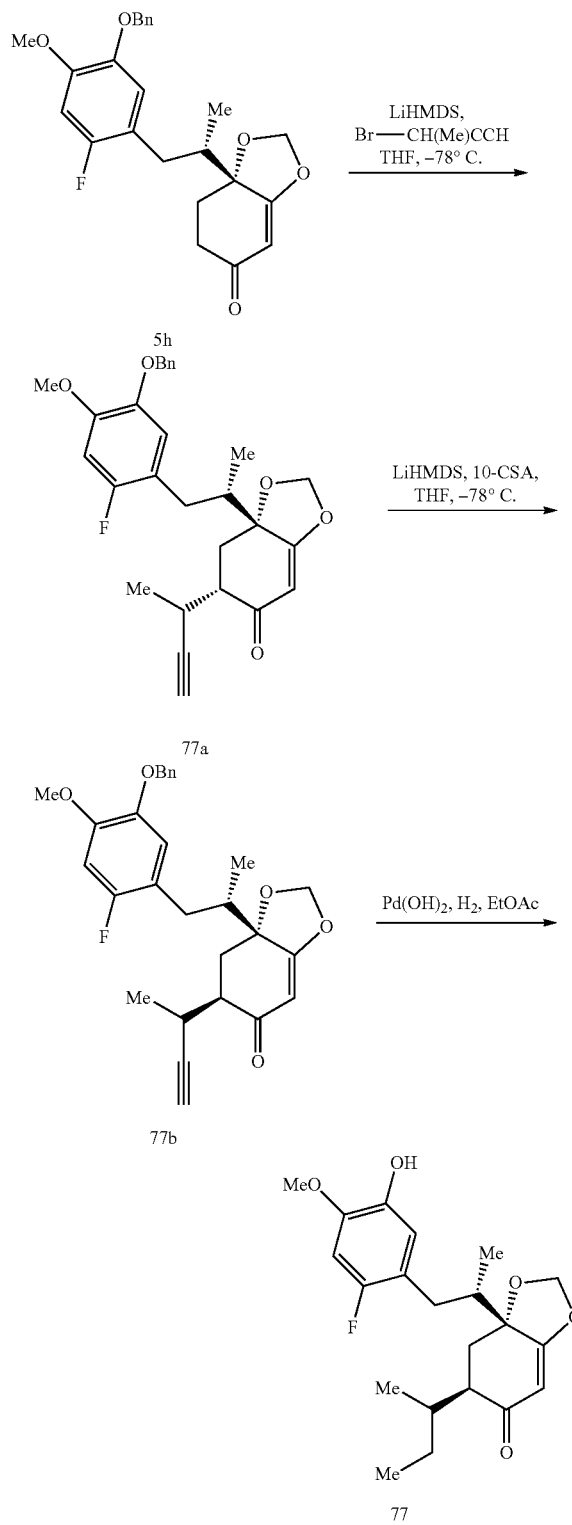

Step 1:
To a solution of 5h (120 mg, 0.29 mmol) in THF (3 mL) was added LiHMDS (1.0 M solution in THF, 0.44 mL, 0.44 mmol) at −78° C. under a nitrogen atmosphere. The reaction mixture was stirred for 30 min, and then 3-bromobut-1-yne (0.035 mL, 0.38 mmol) was added. The reaction mixture was allowed to warm to 0° C. over 3 h. The reaction was quenched with $H_2O$ and extracted with ethyl acetate (50 mL). The organic phase was washed with brine, dried ($MgSO_4$) and concentrated to dryness under reduced pressure. The residue was purified by silica gel chromatography (0 to 30% ethyl acetate/hexanes) to provide 77a as a colorless gum-like material (50 mg, 37%). $^1$H NMR (500 MHz, $CD_3OD$): δ 7.38-7.30 (m, 5H), 6.76 (d, J=11.5 Hz, 1H), 6.71 (d, J=7.5 Hz, 1H), 5.66 (s, 1H), 5.62 (s, 1H), 5.44 (s, 1H), 5.06 (s, 2H), 3.81 (s, 3H), 3.35-3.32 (m, 1H), 2.92-2.89 (m, 1H), 2.82-2.79 (m, 1H), 2.60-2.57 (m, 1H), 2.48-2.45 (m, 1H), 2.44 (s, 1H), 2.07-2.04 (m, 1H), 1.91 (t, J=7.0 Hz, 1H), 1.02 (d, J=7.0 Hz, 3H), 0.84 (d, J=7.0 Hz, 3H).

Step 2:
To a mixture of 77a (50 mg, 0.11 mmol) in THF (3 mL) and HMPA (1 mL) was added LiHMDS (1.0M solution in THF, 0.27 mL, 0.27 mmol) at −78° C. under a nitrogen atmosphere. The reaction mixture was stirred for 30 min, and then a solution of 10-camphorsulfonic acid (63 mg, 0.27 mmol) in THF (1 mL) was added. The reaction mixture continued to stir at −78° C. over 3 h; it was then quenched with $H_2O$ and extracted with ethyl acetate (50 mL). The organic phase was washed with brine, dried ($MgSO_4$), and concentrated to dryness under reduced pressure. The residue was purified by silica gel chromatography (0 to 30% ethyl acetate/hexanes) to provide 77b as a brown gum (10 mg, 20%). ESI MS (Positive Mode) m/z 465 $[C_{28}H_{29}FO_5+H]^+$.

Step 3:
To a solution of 77b (10 mg, 0.021 mmol) in 8 mL of ethyl acetate was added $Pd(OH)_2$/C (20 wt. % Pd on carbon, 3 mg) under a nitrogen atmosphere. The mixture was stirred under one atmosphere of hydrogen for 30 min. The reaction mixture was filtered by an inorganic membrane filter and washed with ethyl acetate (10 mL). The filtrate was concentrated to dryness under reduced pressure. The residue was then purified by silica gel chromatography (0 to 30% ethyl acetate/hexanes) to provide the product (7 mg). The product was further purified by reverse preparative HPLC to provide a mixture of diastereomers 77 as a colorless gum-like material (1 mg).

Compound 77 ((6R,7aR)-6-((S)-sec-butyl)-7a-((S)-1-(2-fluoro-5-hydroxy-4-methoxyphenyl)propan-2-yl)-7,7a-dihydrobenzo[d][1,3]dioxol-5(6H)-one). $^1$H NMR (500 MHz, $CD_3OD$): δ 6.71 (d, J=11.5 Hz, 1H), 6.61 (d, J=7.5 Hz, 1H), 5.68 (s, 0.44H), 5.62 (s, 0.56H), 5.61 (s, 0.56H), 5.56 (s, 1H), 5.48 (s, 0.44H), 3.81 (s, 3H), 3.05-2.89 (m, 1H), 2.52-2.25 (m, 3H), 2.18-2.05 (m, 3H), 1.75-1.72 (m, 1H), 1.42-1.38 (m, 1H), 0.96-0.71 (m, 9H). ESI MS (Positive Mode) m/z 379 $[C_{21}H_{27}FO_5+H]^+$.

General procedure AF: Illustrated with preparation of compound 115.

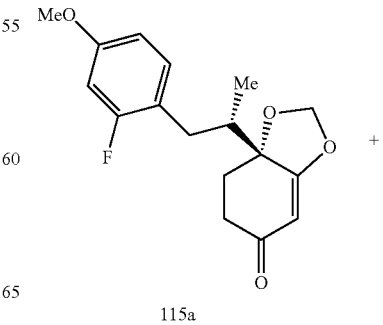

115a

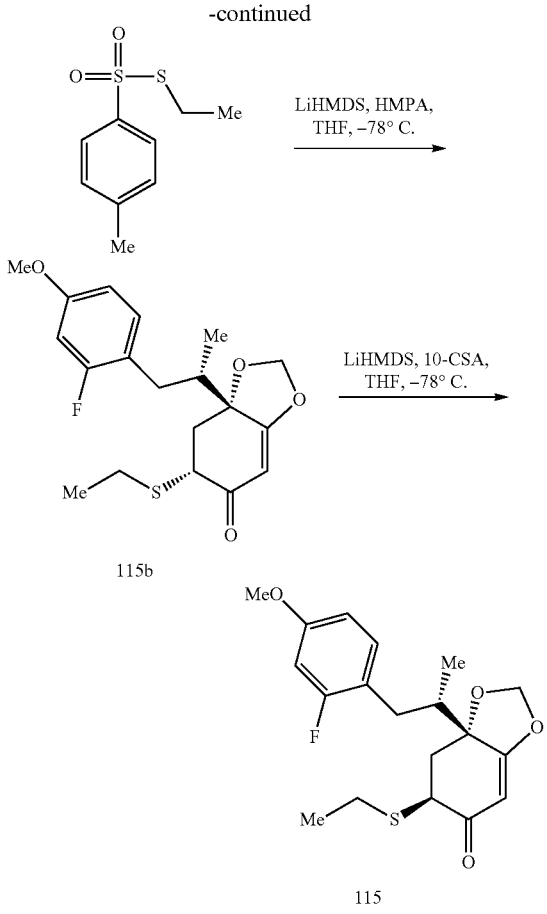

115b

115

Step 1:

Compound 115a was prepared according to the general procedure A. To a solution of 115a (130 mg, 0.42 mmol) in THF (1.5 mL) and HMPA (0.5 mL) was added LiHMDS (1.0M solution in THF, 0.55 mL, 0.55 mmol) at −78° C. under a nitrogen atmosphere. Stirring was continued for 30 min, and then S-Ethyl 4-methylbenzenesulfonothioate (100 mg, 0.46 mmol) in THF (0.5 mL) was added. The reaction mixture was stirred at −78° C. for 4 h and allowed to warm to 0° C. over 1 h. The reaction was quenched with H$_2$O and extracted with EtOAc (50 mL). The organic phase was washed with brine, dried (MgSO$_4$), and concentrated to dryness under reduced pressure. The residue was purified by silica gel chromatography (0 to 30% EtOAc/hexanes) to provide 115b as a colorless gum (150 mg, 96%). $^1$H NMR (500 MHz, CDCl$_3$): δ 7.03 (t, J=10.5 Hz, 1H), 6.64-6.58 (m, 2H), 5.62 (s, 1H), 5.59 (s, 1H), 5.53 (s, 1H), 3.78 (s, 3H), 3.45 (dd, J=13.5, 6.0 Hz, 1H), 3.09 (dd, J=13.5, 2.5 Hz, 1H), 3.02 (dd, J=13.5, 6.0 Hz, 1H), 2.84-2.71 (m, 2H), 2.42 (t, J=12.0 Hz, 1H), 2.13-2.10 (m, 1H), 2.03 (t, J=14.0 Hz, 1H), 1.30 (t, J=7.5 Hz, 3H), 0.91 (d, J=7.0 Hz, 3H).

Step 2:

To a mixture of 115b (150 mg, 0.41 mmol) in THF (4 mL) and HMPA (1 mL) was added LiHMDS (1.0M solution in THF, 0.82 mL, 0.82 mmol) at −78° C. under a nitrogen atmosphere, and the reaction mixture was stirred at −78° C. for 15 min. A solution of 10-camphorsulfonic acid (190 mg, 0.82 mmol) in THF (0.75 mL) was added. Stirring was continued −78° C. for 2 h. The reaction was then quenched with H$_2$O and extracted with EtOAc (50 mL). The organic phase was washed with brine, dried (MgSO$_4$), and concentrated to dryness under reduced pressure. The residue was purified by silica gel chromatography (0 to 25% EtOAc/hexanes) to provide 115 as a pale yellow oil (16 mg, 11%).

Compound 115 (6S,7aR)-6-(ethylthio)-7a-((S)-1-(2-fluoro-4-methoxyphenyl)propan-2-yl)-7,7a-dihydrobenzo[d][1,3]dioxol-5(6H)-one. $^1$H NMR (500 MHz, CD$_3$OD): δ 7.30 (t, J=10.5 Hz, 1H), 6.70 (dd, J=14.0, 2.5 Hz, 1H), 6.52 (dd, J=12.0, 2.5 Hz, 1H), 5.68 (s, 1H), 5.60 (s, 1H), 5.46 (s, 1H), 3.76 (s, 3H), 3.63 (d, J=8.0 Hz, 1H), 2.99-2.81 (m, 4H), 2.72 (t, J=11.5 Hz, 1H), 2.63-2.59 (m, 1H), 2.53 (d, J=8.0 Hz, 1H), 1.33 (t, J=7.5 Hz, 3H), 0.86 (d, J=7.0 Hz, 3H). ESI MS m/z 367 [C$_{19}$H$_{23}$FO$_4$S+H]$^+$.

General procedure AG: Illustrated with preparation of compound 111.

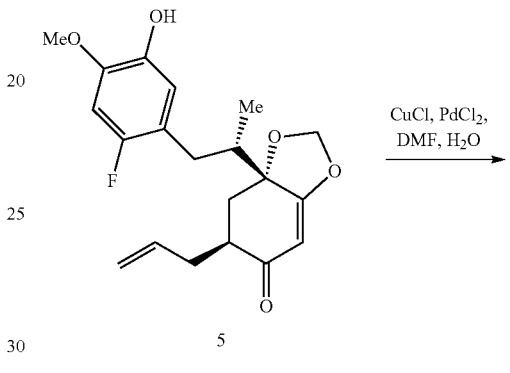

5

111

A mixture of 5 (16 mg, 0.04 mmol), Cu(I)Cl (10 mg, 0.10 mmol), PdCl$_2$ (3 mg, 0.01 mmol) in DMF (2 mL), and H$_2$O (0.8 mL) was stirred under one atmosphere of oxygen for 2 h. The mixture was washed with brine, dried (MgSO$_4$), and concentrated to dryness under reduced pressure. The residue was purified by silica gel chromatography (0 to 50% EtOAc/hexanes) to provide 111 (9 mg, 52%) as a brown gum.

Compound 111 ((6R,7aR)-7a-((S)-1-(2-fluoro-5-hydroxy-4-methoxyphenyl)propan-2-yl)-6-(2-oxopropyl)-7,7a-dihydrobenzo[d][1,3]dioxol-5(6H)-one. $^1$H NMR (500 MHz, CD$_3$OD): δ 6.73 (d, J=11.5 Hz, 1H), 6.64 (d, J=8.0 Hz, 1H), 5.66 (s, 1H), 5.61 (s, 1H), 5.49 (s, 1H), 3.82 (s, 3H), 3.16 (dd, J=9.0, 1.5 Hz, 1H), 3.11 (d, J=14.0 Hz, 1H), 3.0 (dd, J=13.5, 3.5 Hz, 1H), 2.73-2.68 (m, 1H), 2.48 (d, J=14.0 Hz, 1H), 2.41 (t, J=11.5 Hz, 1H), 2.29-2.20 (m, 1H), 2.17 (s, 3H), 1.87-1.84 (m, 1H), 0.88 (d, J=7.0 Hz, 3H). ESI MS m/z 379 [C$_{20}$H$_{23}$FO$_6$+H]$^+$.

General procedure AH: Illustrated with preparation of compound 109.

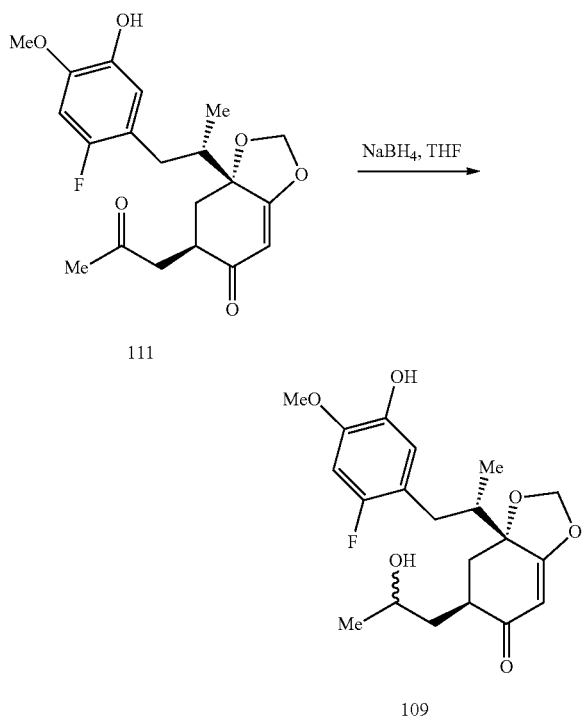

111

109

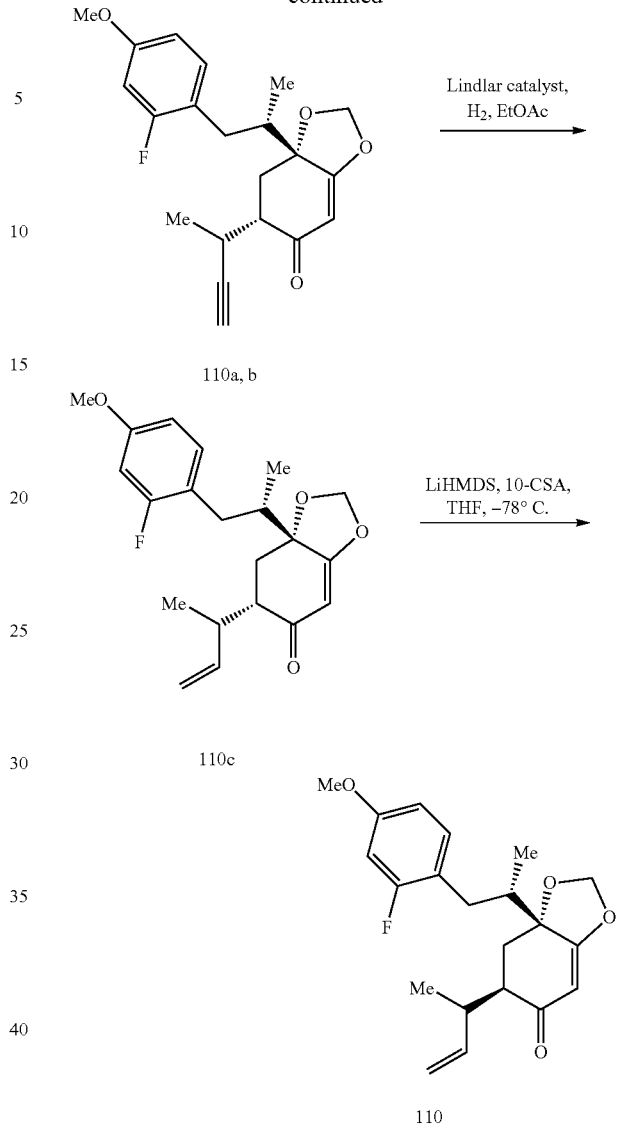

110a, b

110c

110

To a solution of 1h (6 mg, 0.016 mmol) in THF (2 mL) was added NaBH$_4$ (2 mg, 0.032 mmol) at room temperature. Stirring was continued at room temperature for 1 h. The mixture was diluted with ethyl acetate (50 mL), washed with brine, dried (MgSO$_4$), and concentrated to dryness under reduced pressure. The residue was purified by silica gel chromatography (0 to 70% EtOAc/hexanes) to provide a mixture of diastereomers 109 (2 mg, 33%) as a brown gum.

Compound 109 ((6S,7aR)-7a-((S)-1-(2-fluoro-5-hydroxy-4-methoxyphenyl)propan-2-yl)-6-(2-hydroxypropyl)-7,7a-dihydrobenzo[d][1,3]dioxol-5(6H)-one). $^1$H NMR (500 MHz, CD$_3$OD): δ 6.71 (d, J=11.0 Hz, 1H), 6.62-6.58 (m, 1H), 5.66 (s, 1H), 5.61 (s, 1H), 5.48 (s, 0.7H), 5.44 (s, 0.3H), 3.90-3.85 (m, 1H), 3.81 (s, 3H), 3.04 (dd, J=9.0, 1.5 Hz, 1H), 2.82-2.78 (m, 1H), 2.65 (d, J=14.0 Hz, 1H), 2.49-2.45 (m, 1H), 2.19-2.14 (m, 1H), 2.00-1.96 (m, 2H), 1.65-1.60 (m, 1H), 1.28 (d, J=8.0 Hz, 3H), 0.87 (d, J=8.0 Hz, 3H). ESI MS m/z 381 [C$_{20}$H$_{25}$FO$_6$+H]$^+$.

General procedure AI: Illustrated with preparation of compound 110.

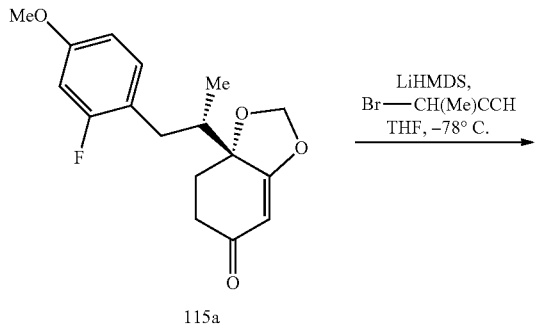

115a

Step 1:

To a solution of 115a (130 mg, 0.42 mmol) in THF (3 mL) was added LiHMDS (1.0M solution in THF, 0.64 mL, 0.64 mmol) at −78° C. under a nitrogen atmosphere. The reaction mixture was stirred for 30 min, and then 3-bromobut-1-yne (0.046 mL, 0.50 mmol) was added. The reaction mixture was allowed to warm to 0° C. over 3 h. It was then quenched with H$_2$O and extracted with EtOAc (50 mL). The organic phase was washed with brine, dried (MgSO$_4$), and concentrated to dryness under reduced pressure. The residue was purified by silica gel chromatography (0 to 30% EtOAc/hexanes) to provide two diastereomers 110a (23 mg, 15%) and 110b (12 mg, 8%). 110a: $^1$H NMR (500 MHz, CD$_3$OD): δ 7.12 (t, J=9.0 Hz, 1H), 6.67 (t, J=12.0 Hz, 2H), 5.70 (s, 1H), 5.64 (s, 1H), 5.45 (s, 1H), 3.76 (s, 3H), 3.06-3.02 (m, 1H), 2.89 (dd, J=14.0, 3.5 Hz, 2H), 2.67-2.63 (m, 1H), 2.51 (t, J=11.0 Hz, 1H), 2.44 (s, 1H), 2.22-2.17 (m, 1H), 1.95 (t, J=14.0 Hz, 1H), 1.03 (d, J=7.0 Hz, 3H), 0.93 (d, J=7.0 Hz, 3H). 110b: $^1$H NMR (500 MHz, CD$_3$OD): δ 7.16 (t, J=9.0 Hz, 1H), 6.69-6.64 (m, 2H), 5.70 (s, 1H), 5.64 (s, 1H), 5.48 (s, 1H), 3.76 (s, 3H), 3.45-3.44 (m, 1H), 3.07-3.06 (m, 1H), 2.70 (dd, J=12.5, 4.5 Hz, 1H), 2.49 (dd, J=10.0, 13.5 Hz, 1H), 2.35-2.34 (m, 1H), 2.31 (s, 1H), 2.18-2.13 (m, 1H), 2.08 (t, J=12.5 Hz, 1H), 1.17 (d, J=7.5 Hz, 3H), 0.96 (d, J=7.0 Hz, 3H).

Step 2:

To a solution of 110a (20 mg, 0.055 mmol) in 6 mL of EtOAc was added Pd(OH)$_2$/C (20 wt. % Pd on carbon, 3 mg) under a nitrogen atmosphere. The mixture was stirred under one atmosphere of hydrogen for 30 min. The reaction mixture was then filtered through a filter and the syringe filter was washed with ethyl acetate (10 mL). The filtrate was concentrated to dryness under reduced pressure. The residue was chromatographed by silica gel chromatography (0 to 30% EtOAc/hexanes) to provide the product (7 mg). The product was further purified by reverse phase-preparative HPLC to provide 110c as a colorless gum (19 mg, 95%). $^1$H NMR (500 MHz, CD$_3$OD): δ 7.11 (t, J=9.0 Hz, 1H), 6.68-6.65 (m, 2H), 5.82-5.78 (m, 1H), 5.68 (s, 1H), 5.61 (s, 1H), 5.45 (s, 1H), 5.08-5.04 (m, 2H), 3.76 (s, 3H), 3.12 (t, J=8.0 Hz, 1H), 3.02 (dd, J=12.0, 4.0 Hz, 1H), 2.47-2.42 (m, 3H), 2.21-2.17 (m, 1H), 1.76 (t, J=14.0 Hz, 1H), 0.93 (d, J=7.0 Hz, 3H), 0.87 (d, J=7.0 Hz, 3H).

Step 3:

To a mixture of 110c (19 mg, 0.053 mmol) in THF (2 mL) and HMPA (0.5 mL) was added LiHMDS (1.0M solution in THF, 0.14 mL, 0.14 mmol) at −78° C. under a nitrogen atmosphere. The reaction mixture was stirred for 30 min, and then a solution of 10-camphorsulfonic acid (31 mg, 0.14 mmol) in THF (0.5 mL) was added. Stirring was continued at −78° C. for 2 h. The reaction was quenched with H$_2$O and extracted with EtOAc (50 mL). The organic phase was washed with brine, dried (MgSO$_4$), and concentrated to dryness under reduced pressure. The residue was purified by silica gel chromatography (0 to 30% EtOAc/hexanes) to provide crude 110 as a brown gum (18 mg). The product was further purified by chromatography on a CHIRALPAK AD column (3% IPA/heptane) to provide pure 110 (4 mg, 21%).

Compound 110 ((6R,7aR)-6-((S)-but-3-en-2-yl)-7a-((S)-1-(2-fluoro-4-methoxyphenyl)propan-2-yl)-7,7a-dihydrobenzo[d][1,3]dioxol-5(6H)-one). $^1$H NMR (500 MHz, CD$_3$OD): δ 7.10 (t, J=9.0 Hz, 1H), 6.69 (dd, J=11.0, 2.0 Hz, 1H), 6.63 (dd, J=12.0, 3.0 Hz, 1H), 5.85-5.75 (m, 1H), 5.57 (s, 1H), 5.56 (s, 1H), 5.53 (s, 1H), 5.13-5.06 (m, 2H), 3.76 (s, 3H), 3.06-3.02 (m, 1H), 2.85 (dd, J=3.5, 14.0 Hz, 1H), 2.63-2.61 (m, 1H), 2.51-2.47 (m, 2H), 2.17 (d, J=11.5 Hz, 1H), 2.11-2.05 (m, 1H), 1.13 (d, J=7.0 Hz, 3H), 0.82 (d, J=7.0 Hz, 3H). ESI MS m/z 361 [C$_{21}$H$_{25}$FO$_4$+H]$^+$.

General procedure AJ: Illustrated with preparation of the HCl salt of compound 66.

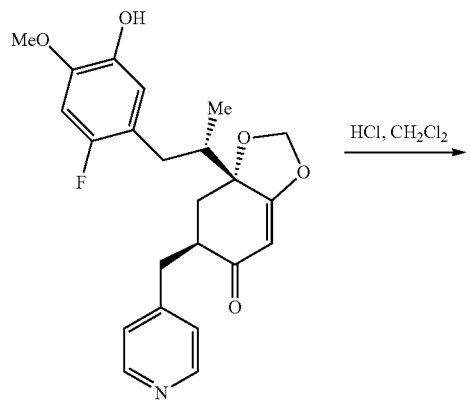

66

HCl, CH$_2$Cl$_2$ →

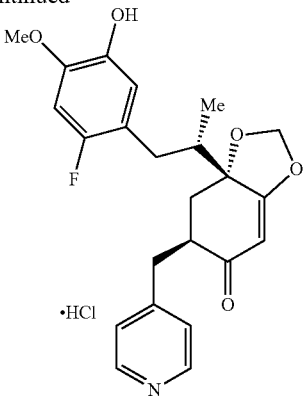

·HCl

Compound 66 was prepared according to general procedures C and X. To a solution of 66 (5 mg, 0.012 mmol) in THF (1 mL) was added HCl (2 M in Et$_2$O, 0.06 mL, 0.012 mmol) at room temperature. Stirring was continued for 30 min, and then the mixture was concentrated to dryness under reduced pressure to provide a mixture of diastereomers 66.HCl (5 mg, 100%) as a brown gum.

66.HCl ((6S,7aR)-7a-((S)-1-(2-fluoro-5-hydroxy-4-methoxyphenyl)propan-2-yl)-6-(pyridin-4-ylmethyl)-7,7a-dihydrobenzo[d][1,3]dioxol-5(6H)-one hydrochloride)$^1$H NMR (500 MHz, CD$_3$OD): δ 8.73 (d, J=6.5 Hz, 2H), 8.01 (d, J=6.5 Hz, 1.6H), 7.92 (d, J=6.5 Hz, 0.4H), 6.72 (d, J=11.5 Hz, 1H), 6.66 (d, J=8.0 Hz, 1H), 6.62 (d, J=8.0 Hz, 0.2H), 5.69 (s, 1H), 5.63 (s, 0.8H), 5.60 (s, 0.2H), 5.53 (s, 1H), 3.82 (s, 3H), 3.62-3.58 (m, 1H), 3.16-3.05 (m, 2.6H), 2.92-2.88 (m, 0.4H), 2.61 (d, J=14.0 Hz, 0.8H), 2.45 (t, J=11.0 Hz, 1H), 2.36 (dd, J=14.5, 10.0 Hz, 1.2H), 2.09-2.03 (m, 0.8H), 1.87 (t, J=12.0 Hz, 0.2H), 0.98 (d, J=7.0 Hz, 0.6H), 0.93 (d, J=7.0 Hz, 2.4H). ESI MS m/z 414 [C$_{23}$H$_{25}$ClFNO$_5$−HCl+H]$^+$.

General procedure AK: Illustrated with preparation of compound 116.

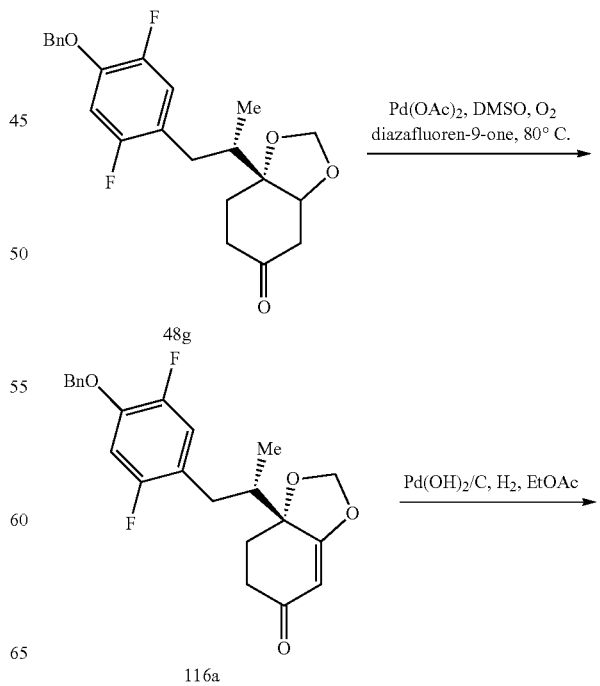

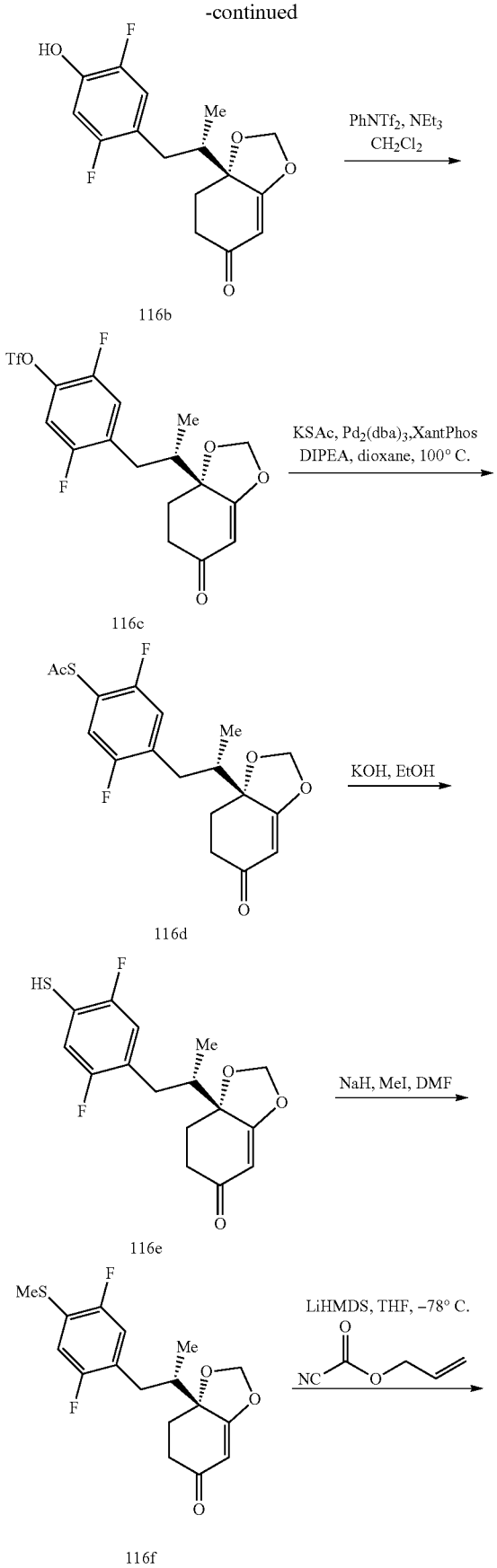

Step 1:

A mixture of 48g (8 g, 19.9 mmol), Pd(OAc)$_2$ (2.2 g, 9.95 mmol) and 4,5-diazafluoren-9-one (1.77 g, 9.95 mmol) in 60 mL of DMSO was heated at 80° C. under one atmosphere of oxygen for 8 h. The reaction mixture was cooled to room temperature and diluted with ethyl acetate (250 mL). The organic phase was washed with brine, dried (MgSO$_4$), and concentrated to dryness under reduced pressure. The crude residue was purified by silica gel chromatography (0 to 40% EtOAc/hexanes) to provide 116a (4.8 g, 60%). $^1$H NMR (500 MHz, CD$_3$OD): δ 7.44-7.31 (m, 5H), 7.07 (dd, J=11.5, 7.0 Hz, 1H), 6.95 (dd, J=7.0, 11.5 Hz, 1H), 5.69 (s, 1H), 5.63 (s, 1H), 5.44 (s, 1H), 5.11 (s, 2H), 3.01 (dd, J=14.0, 3.0 Hz, 1H), 2.65-2.62 (m, 1H), 2.52-2.45 (m, 3H), 2.24-2.21 (m, 1H), 2.06-2.04 (m, 1H), 0.94 (d, J=7.0 Hz, 3H).

Step 2:

To a solution of 116a (4.8 g, 12.0 mmol) in 100 mL of EtOAc was added Pd(OH)$_2$/C (20 wt. % Pd on carbon, 720 mg) under a nitrogen atmosphere. The mixture was stirred under one atmosphere of hydrogen for 1 h. The reaction mixture was filtered through a pad of diatomaceous earth and the filter cake was washed with ethyl acetate (140 mL). The filtrate was concentrated in vacuo to provide 116b (3.7 g, 100%). $^1$H NMR (500 MHz, CD$_3$OD): δ 6.98 (dd, J=11.0, 7.0 Hz, 1H), 6.65 (dd, J=11.0, 7.0 Hz, 1H), 5.69 (s, 1H), 5.63 (s, 1H), 5.44 (s, 1H), 3.02 (dd, J=14.0, 3.0 Hz, 1H), 2.66-2.62 (m, 1H), 2.48-2.43 (m, 3H), 2.24-2.21 (m, 1H), 2.06-2.04 (m, 1H), 0.94 (d, J=7.0 Hz, 3H).

Step 3:

N-phenyl-bis(trifluoromethanesulfonimide) (1.73 g, 4.83 mmol) was added to a solution of 116b (1.25 g, 4.03 mmol), triethylamine (1.1 mL, 8.06 mmol), and a catalytic amount of DMAP in CH$_2$Cl$_2$ (36 mL); the reaction mixture was stirred at room temperature for 12 h. After this time, ethyl acetate (150 mL) was added, and the reaction mixture was washed with brine, dried (MgSO$_4$), and concentrated to dryness under reduced pressure. The crude residue was purified by silica gel chromatography (0 to 30% EtOAc/hexanes) to provide 116c as a white solid (1.8 g, 100%). $^1$H NMR (500 MHz, CD$_3$OD): δ 7.10-7.07 (m, 2H), 5.62 (s, 1H), 5.60 (s, 1H), 5.52 (s, 1H), 3.12 (d, J=13.5 Hz, 1H), 2.62-2.50 (m, 3H), 2.45-2.37 (m, 1H), 2.27-2.24 (m, 1H), 2.11-2.05 (m, 1H), 0.95 (d, J=6.5 Hz, 3H).

Step 4:

A mixture of 116c (50 mg, 0.11 mmol), KSAc (14 mg, 0.12 mmol), Pd$_2$(dba)$_3$ (6 mg, 0.006 mmol), 4,5-bis(diphenylphosphino)-9,9-dimethylxanthene (Xantphos) (7 mg, 0.011 mmol) and DIPEA (0.034 mL, 0.22 mmol) in 2 mL of dioxane was heated at 100° C. under a nitrogen atmosphere for 12 h. The reaction mixture was diluted with EtOAc (100 mL), washed with brine, dried (MgSO$_4$), and concentrated to dryness. The crude residue was purified by silica gel chromatography (0 to 30% EtOAc/hexanes) to provide 116d (16 mg, 42%). $^1$H NMR (500 MHz, CD$_3$OD): δ 7.47-7.37 (m, 0.7H), 7.23-7.19 (m, 1.3H), 5.70 (s, 1H), 5.64 (s, 1H), 5.46 (s, 1H), 3.15 (d, J=13.5 Hz, 1H), 2.69-2.62 (m, 2H), 2.55-2.48 (m, 2H), 2.42 (s, 3H), 2.37-2.29 (m, 1H), 2.09-2.03 (m, 1H), 0.97 (t, J=7.5 Hz, 3H).

Step 5:

To a solution of 116d (16 mg, 0.043 mmol) in EtOH (1 mL) was added KOH (5 mg, 0.086 mmol), and the reaction mixture was stirred at room temperature for 12 h. After this time, ethyl acetate (50 mL) was added, and the reaction mixture was washed with brine, dried (MgSO$_4$), and concentrated to dryness under reduced pressure. The crude residue was purified by silica gel chromatography (0 to 40% EtOAc/hexanes) to provide 116e (8 mg, 57%). ESI MS m/z 327 [C$_{16}$H$_{16}$F$_2$O$_3$S+H]$^+$.

Step 6:

To a mixture of 116e (31 mg, 0.065 mmol) in DMF (3 mL) was added NaH (60% in mineral oil, 8 mg, 0.099 mmol). After stirring for 20 min, MeI (0.012 ml, 0.078 mmol) was added, and the reaction mixture was stirred at room temperature for another 4 h. After this time, ethyl acetate (50 mL) was added, and the reaction mixture was washed with brine, dried (MgSO$_4$), and concentrated to dryness under reduced pressure. The crude residue was purified by silica gel chromatography (0 to 30% EtOAc/hexanes) to provide 116f (10 mg, 31%). ESI MS m/z 341 [C$_{17}$H$_{18}$F$_2$O$_3$S+H]$^+$.

Step 7:

To a solution of 116f (10 mg, 0.029 mmol) in THF (2 mL) was added LiHMDS (1.0M solution in THF, 0.06 mL, 0.06 mmol) at −78° C. under a nitrogen atmosphere; the reaction mixture was stirred for 30 min. Allyl cyanoformate II (7 mg, 0.058 mmol) was then added, and the reaction mixture was allowed to warm to 0° C. over 2 h. The reaction was quenched with H$_2$O and extracted with EtOAc (50 mL). The organic phase was washed with brine, dried (MgSO$_4$), and concentrated to dryness under reduced pressure. The residue was purified by silica gel chromatography (0 to 30% EtOAc/hexanes) to provide 116g (6 mg, 50%).

Step 8:

To a solution of 116g (6 mg, 0.014 mmol) in DMF (1 mL) was added Pd(PPh$_3$)$_4$ (2 mg, 0.0014 mmol) under a nitrogen atmosphere, and the reaction mixture was stirred at room temperature for 1.5 h. After this time, ethyl acetate (50 mL) was added. The reaction mixture was washed with brine, dried (MgSO$_4$), and concentrated to dryness under reduced pressure. The residue was purified by silica gel chromatography (0 to 30% EtOAc/hexanes) to provide 116 (1 mg, 20%) as a colorless gum.

Compound 116 ((6S,7aR)-6-allyl-7a-((S)-1-(2,5-difluoro-4-(methylthio)phenyl)propan-2-yl)-7,7a-dihydrobenzo[d][1,3]dioxol-5(6H)-one). $^1$H NMR (500 MHz, CD$_3$OD): δ 7.07 (dd, J=10.5, 7.0 Hz, 1H), 6.99 (dd, J=10.0, 1.5 Hz, 1H), 5.92-5.88 (m, 1H), 5.66 (s, 1H), 5.60 (s, 1H), 5.50 (s, 1H), 5.19-5.10 (m, 2H), 3.11 (dd, J=10.0, 2.0 Hz, 1H), 2.86-2.81 (m, 1H), 2.66-2.58 (m, 3H), 2.45 (s, 3H), 2.16-2.05 (m, 3H), 0.86 (d, J=7.0 Hz, 3H). ESI MS m/z 381 [C$_{20}$H$_{22}$F$_2$O$_3$S+H]$^+$.

Preparation of the Final Compounds: Individual Final Compounds

The following describes processes that may be used to synthesize the final compounds of the invention. As indicated above, other methods, either in whole or in part, may be used to prepare the compounds of the invention. Reference to compound numbers below refers to the compounds identified in Table 2.

Compound 2 ((6S,7aR)-6-allyl-7a-((S)-1-(2-fluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.13 (t, J=7.5 Hz, 1H), 6.70 (t, J=7.5 Hz, 2H), 5.92-5.85 (m, 1H), 5.65 (s, 1H), 5.60 (s, 1H), 5.49 (s, 1H), 5.20-5.10 (m, 2H), 3.77 (s, 3H), 3.06 (dd, J=14.5, 4.0 Hz, 1H), 2.90-2.87 (m, 1H), 2.69 (d, J=14.0 Hz, 1H), 2.67-2.60 (m, 1H), 2.57 (t, J=11.0 Hz, 1H), 2.25-2.20 (m, 1H), 2.15 (dd, J=14.0, 10.0 Hz, 1H), 2.03-1.95 (m, 1H), 0.82 (d, J=7.0 Hz, 3H). ESI MS m/z 347 [C$_{20}$H$_{23}$FO$_4$+H]$^+$.

Compound 3 ((6S,7aR)-6-allyl-7a-((R)-1-(2-fluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.04 (t, J=7.5 Hz, 1H), 6.68-6.62 (m, 2H), 5.85-5.78 (m, 1H), 5.68 (s, 1H), 5.62 (s, 1H), 5.53 (s, 1H), 5.08-5.01 (m, 2H), 3.76 (s, 3H), 2.82-2.79 (m, 2H), 2.64-2.58 (m, 1H), 2.54 (d, J=14.0 Hz, 1H), 2.40 (t, J=11.5 Hz, 1H), 2.10 (dd, J=14.0, 9.5 Hz, 1H), 2.03-1.95 (m, 2H), 0.95 (d, J=6.5 Hz, 3H). ESI MS m/z 347 [C$_{20}$H$_{23}$FO$_4$+H]$^+$.

Compound 4 ((6S,7aR)-6-allyl-7a-((R)-1-(2-fluoro-5-hydroxy-4-methoxyphenyl)propan-2-yl)-7,7a-dihydrobenzo[d][1,3]dioxol-5(6H)-one) was prepared by general procedure C. $^1$H NMR (500 MHz, CD$_3$OD): δ 6.69 (d, J=9.0 Hz, 1H), 6.53 (d, J=7.5 Hz, 1H), 5.85-5.78 (m, 1H), 5.66 (s, 1H), 5.62 (s, 1H), 5.54 (s, 1H), 5.08-5.01 (m, 2H), 3.80 (s, 3H), 2.82-2.79 (m, 2H), 2.64-2.58 (m, 1H), 2.55 (d, J=14.0 Hz, 1H), 2.33 (t, J=11.5 Hz, 1H), 2.10 (dd, J=13.5, 9.5 Hz, 1H), 2.03-1.95 (m, 2H), 0.96 (d, J=7.0 Hz, 3H). ESI MS m/z 363 [C$_{20}$H$_{23}$FO$_5$+H]$^+$.

Compound 6 ((6S,7aR)-6-allyl-7a-((R)-1-(2,5-difluoro-4-methoxyphenyl)propan-2-yl)-7,7a-dihydrobenzo[d][1,3]dioxol-5(6H)-one) was prepared by general procedure B. $^1$H NMR (500 MHz, CD$_3$OD): δ 6.89 (dd, J=11.5, 7.0 Hz, 1H), 6.83 (dd, J=11.5, 7.0 Hz, 1H), 5.83-5.74 (m, 1H), 5.64 (s, 1H), 5.58 (s, 1H), 5.50 (s, 1H), 5.06-4.99 (m, 2H), 3.80 (s, 3H), 2.79-2.76 (m, 2H), 2.64-2.58 (m, 1H), 2.54 (d, J=14.0 Hz, 1H), 2.36 (t, J=11.5 Hz, 1H), 2.07-1.94 (m, 2H), 0.93 (d, J=7.0 Hz, 3H). ESI MS m/z 365 [C$_{20}$H$_{22}$F$_2$O$_4$+H]$^+$.

Compound 8 ((6S,7aR)-6-allyl-7a-((S)-1-(2-fluoro-4-methoxy-5-methylphenyl)propan-2-yl)-7,7a-dihydrobenzo[d][1,3]dioxol-5(6H)-one) was prepared by general procedure A. $^1$H NMR (500 MHz, CD$_3$OD): δ 6.92 (d, J=7.0 Hz, 1H), 6.67 (d, J=12.5 Hz, 1H), 5.92-5.85 (m, 1H), 5.65 (s, 1H), 5.60 (s, 1H), 5.49 (s, 1H), 5.18-5.11 (m, 2H), 3.79 (s, 3H), 3.09 (d, J=14.0 Hz, 1H), 2.82-2.79 (m, 1H), 2.67 (d, J=14.0 Hz, 1H), 2.62-2.58 (m, 1H), 2.51 (t, J=11.5 Hz, 1H), 2.28-2.25 (m, 1H), 2.12-2.09 (m, 1H), 2.11 (s, 3H), 2.03-1.95 (m, 1H), 0.82 (d, J=7.0 Hz, 3H). ESI MS m/z 361 [C$_{21}$H$_{25}$FO$_4$+H]$^+$.

Compound 9 (methyl 5-((R)-2-((3aR,5S)-5-allyl-6-oxo-3a,4,5,6-tetrahydrobenzo[d][1,3]dioxol-3a-yl)propyl)-4-fluoro-2-methoxybenzoate) was prepared by general procedures C, G, and I. $^1$H NMR (500 MHz, CD$_3$OD): δ 7.63 (d, J=9.0 Hz, 1H), 6.90 (d, J=12.5 Hz, 1H), 5.85-5.75 (m, 1H), 5.69 (s, 1H), 5.62 (s, 1H), 5.53 (s, 1H), 5.09-5.02 (m, 2H), 3.85 (s, 3H), 3.83 (s, 3H), 2.86-2.78 (m, 2H), 2.62-2.61 (m, 1H), 2.55 (d, J=14.0 Hz, 1H), 2.45 (t, J=8.5 Hz, 1H), 2.11-2.03 (m, 3H), 0.97 (d, J=7.0 Hz, 3H). ESI MS m/z 405 $[C_{20}H_{25}FO_6+H]^+$.

Compound 11 (5-(2-((3aR,5S)-5-allyl-6-oxo-3a,4,5,6-tetrahydrobenzo[d][1,3]dioxol-3a-yl)propyl)-4-fluoro-2-methoxybenzamide) was prepared by general procedures C, G, and H. $^1$H NMR (500 MHz, CD$_3$OD): δ 7.92 (d, J=16.5 Hz, 0.5H), 7.83 (d, J=15.0 Hz, 0.5H), 6.99 (dd, J=20.0, 14.5 Hz, 1H), 5.95-5.85 (m, 1H), 5.70 (s, 0.5H), 5.69 (s, 0.5H), 5.70 (s, 0.5H), 5.69 (s, 0.5H), 5.54 (s, 0.5H), 5.50 (s, 0.5H), 5.18-5.01 (m, 2H), 3.96 (s, 3H), 3.06 (s, 0.5H), 2.89-2.79 (m, 1.5H), 2.68-2.45 (m, 3H), 2.30-1.95 (m, 3H), 0.97 (d, J=11.0 Hz, 1.5H), 0.84 (d, J=11.5 Hz, 1.5H). ESI MS m/z 390 $[C_{21}H_{24}FNO_5+H]^+$.

Compound 13 (5-((R)-2-((3aR,5S)-5-allyl-6-oxo-3a,4,5,6-tetrahydrobenzo[d][1,3]dioxol-3a-yl)propyl)-4-fluoro-2-methoxy-N-methylbenzamide) was prepared by general procedures C, G, and H. $^1$H NMR (500 MHz, CD$_3$OD): δ 7.76 (d, J=8.0 Hz, 1H), 6.92 (d, J=12.0 Hz, 1H), 5.85-5.78 (m, 1H), 5.70 (s, 1H), 5.62 (s, 1H), 5.53 (s, 1H), 5.08-5.01 (m, 2H), 3.93 (s, 3H), 2.92 (s, 3H), 2.82-2.79 (m, 2H), 2.64-2.58 (m, 1H), 2.55 (d, J=14.0 Hz, 1H), 2.47 (t, J=8.5 Hz, 1H), 2.10-1.97 (m, 3H), 0.97 (d, J=6.5 Hz, 3H). ESI MS m/z 404 $[C_{22}H_{26}FO_5+H]^+$.

Compound 14 (5-((S)-2-((3aR,5S)-5-allyl-6-oxo-3a,4,5,6-tetrahydrobenzo[d][1,3]dioxol-3a-yl)propyl)-4-fluoro-2-methoxybenzonitrile) was prepared by general procedures C and E. $^1$H NMR (500 MHz, CD$_3$OD): δ 7.56 (t, J=8.0 Hz, 1H), 7.02 (d, J=12.0 Hz, 1H), 5.92-5.85 (m, 1H), 5.65 (s, 1H), 5.60 (s, 1H), 5.50 (s, 1H), 5.18-5.11 (m, 2H), 3.93 (s, 3H), 3.10 (dd, J=14.0, 8.0 Hz, 1H), 2.85-2.79 (m, 1H), 2.68-2.58 (m, 3H), 2.25-2.20 (m, 1H), 2.17 (t, J=10.0 Hz, 1H), 2.05-2.01 (m, 1H), 0.86 (d, J=7.0 Hz, 3H). ESI MS m/z 372 $[C_{21}H_{22}FNO_4+H]^+$.

Compound 15 ((6S,7aR)-6-allyl-7a-((S)-1-(2-fluoro-4,5-dimethoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.77 (d, J=3.5 Hz, 1H), 6.74 (s, 1H), 5.92-5.85 (m, 1H), 5.67 (s, 1H), 5.61 (s, 1H), 5.49 (s, 1H), 5.21-5.10 (m, 2H), 3.80 (s, 3H), 3.78 (s, 3H), 3.07 (dd, J=14.0, 3.0 Hz, 1H), 2.86-2.83 (m, 1H), 2.69 (d, J=14.5 Hz, 1H), 2.62-2.52 (m, 2H), 2.29-2.22 (m, 1H), 2.15 (t, J=9.0 Hz, 1H), 2.03-1.99 (m, 1H), 0.86 (d, J=6.5 Hz, 3H). ESI MS m/z 377 $[C_{21}H_{25}FO_5+H]^+$.

Compound 16 ((6S,7aR)-6-allyl-7a-((R)-1-(5-(allyloxy)-2-fluoro-4-methoxyphenyl)propan-2-yl)-7,7a-dihydrobenzo[d][1,3]dioxol-5(6H)-one) was prepared by general procedure C. $^1$H NMR (500 MHz, CD$_3$OD): δ 6.74 (t, J=11.5 Hz, 1H), 6.68 (d, J=7.5 Hz, 1H), 6.01-5.99 (m, 1H), 5.85-5.78 (m, 1H), 5.68 (s, 1H), 5.62 (s, 1H), 5.53 (s, 1H), 5.36 (dd, J=17.5, 2.0 Hz, 1H), 5.22 (d, J=10.5, 1.5 Hz, 1H), 5.08-5.01 (m, 2H), 4.50 (d, J=5.5 Hz, 2H), 3.80 (s, 3H), 2.82-2.79 (m, 2H), 2.64-2.58 (m, 1H), 2.54 (d, J=14.0 Hz, 1H), 2.38 (t, J=11.5 Hz, 1H), 2.10-1.95 (m, 3H), 0.96 (d, J=6.5 Hz, 3H). ESI MS m/z 403 $[C_{23}H_{27}FO_5+H]^+$.

Compound 18 (N-(5-((S)-2-((3aR,5S)-5-allyl-6-oxo-3a,4,5,6-tetrahydrobenzo[d][1,3]dioxol-3a-yl)propyl)-4-fluoro-2-methoxyphenyl)acetamide) was prepared by general procedures C and F. $^1$H NMR (500 MHz, CD$_3$OD): δ 7.79 (d, J=7.5 Hz, 1H), 6.81 (d, J=11.5 Hz, 1H), 5.95-5.85 (m, 1H), 5.65 (s, 1H), 5.59 (s, 1H), 5.48 (s, 1H), 5.22-5.09 (m, 2H), 3.84 (s, 3H), 3.02 (s, 3H), 2.85-2.79 (m, 1H), 2.69 (d, J=14.0 Hz, 1H), 2.58-2.50 (m, 2H), 2.25-2.21 (m, 1H), 2.14 (s, 3H), 2.14-2.11 (m, 1H), 2.03-1.99 (m, 1H), 0.83 (d, J=7.0 Hz, 3H). ESI MS m/z 404 $[C_{20}H_{26}FNO_5+H]^+$.

Compound 19 (N-(5-((S)-2-((3aR,5S)-5-allyl-6-oxo-3a,4,5,6-tetrahydrobenzo[d][1,3]dioxol-3a-yl)propyl)-4-fluoro-2-methoxyphenyl)acetamide) was prepared by general procedures C and F. $^1$H NMR (500 MHz, CD$_3$OD): δ 7.66 (d, J=8.5 Hz, 1H), 6.79 (d, J=8.5 Hz, 1H), 5.85-5.78 (m, 1H), 5.67 (s, 1H), 5.61 (s, 1H), 5.53 (s, 1H), 5.08-5.01 (m, 2H), 3.85 (s, 3H), 2.82-2.79 (m, 2H), 2.64-2.58 (m, 1H), 2.54 (d, J=14.0 Hz, 1H), 2.39 (t, J=12.0 Hz, 1H), 2.12 (s, 3H), 2.12-2.05 (m, 3H), 0.97 (d, J=7.0 Hz, 3H). ESI MS m/z 404 $[C_{22}H_{26}FNO_5+H]^+$.

Compound 20 ((6S,7aR)-6-allyl-7a-((S)-1-(2-fluoro-3,4-dimethoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.89 (t, J=3.5 Hz, 1H), 6.77 (t, J=8.5 Hz, 1H), 5.92-5.85 (m, 1H), 5.65 (s, 1H), 5.60 (s, 1H), 5.49 (s, 1H), 5.18-5.08 (m, 2H), 3.83 (s, 3H), 3.82 (s, 3H), 3.07 (dd, J=13.5, 3.5 Hz, 1H), 2.85-2.82 (m, 1H), 2.69 (d, J=14.0 Hz, 1H), 2.58-2.52 (m, 2H), 2.27 (m, 1H), 2.15 (dd, J=14.0, 10.0 Hz, 1H), 2.08-2.02 (m, 1H), 0.83 (d, J=6.5 Hz, 3H). ESI MS m/z 377 $[C_{21}H_{25}FO_5+H]^+$.

Compound 21 ((6S,7aR)-6-allyl-7a-((R)-1-(2-fluoro-3,4-dimethoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.81 (d, J=7.5 Hz, 1H), 6.75 (d, J=7.0 Hz, 1H), 5.85-5.78 (m, 1H), 5.68 (s, 1H), 5.62 (s, 1H), 5.53 (s, 1H), 5.08-5.01 (m, 2H), 3.84 (s, 3H), 3.80 (s, 3H), 2.82-2.79 (m, 2H), 2.61-2.58 (m, 1H), 2.55 (d, J=14.0 Hz, 1H), 2.42 (t, J=12.0 Hz, 1H), 2.10 (dd, J=14.0, 10.0 Hz, 1H), 2.03-1.95 (m, 2H), 0.96 (d, J=7.0 Hz, 3H). ESI MS m/z 377 $[C_{21}H_{25}FO_5+H]^+$.

Compound 22 ((6S,7aR)-6-allyl-7a-((R)-1-(2,3-difluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.86-6.83 (m, 2H), 5.81-5.78 (m, 1H), 5.68 (s, 1H), 5.62 (s, 1H), 5.54 (s, 1H), 5.08-5.01 (m, 2H), 3.86 (s, 3H), 2.85-2.80 (m, 2H), 2.64-2.58 (m, 1H), 2.54 (d, J=14.0 Hz, 1H), 2.46 (t, J=11.5 Hz, 1H), 2.12 (dd, J=14.0, 9.5 Hz, 1H), 2.03-1.95 (m, 2H), 0.96 (d, J=7.0 Hz, 3H). ESI MS m/z 365 $[C_{20}H_{22}F_2O_4+H]^+$.

Compound 23 ((6S,7aR)-6-allyl-7a-((R)-1-(2,6-difluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.56 (s, 1H), 6.52 (s, 1H), 5.85-5.78 (m, 1H), 5.67 (s, 1H), 5.63 (s, 1H), 5.54 (s, 1H), 5.09-5.00 (m, 2H), 3.77 (s, 3H), 2.85-2.50 (m, 5H), 2.10-1.95 (m, 3H), 0.97 (d, J=11.5 Hz, 3H). ESI MS m/z 365 $[C_{20}H_{22}F_2O_4+H]^+$.

Compound 24 ((6S,7aR)-6-allyl-7a-((R)-1-(3,4-dimethoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.86 (d, J=7.5 Hz, 1H), 6.63 (s, 1H), 6.62 (d, J=2.0 Hz, 1H), 5.85-5.79 (m, 1H), 5.68 (s, 1H), 5.63 (s, 1H), 5.55 (s, 1H), 5.09-5.02 (m, 2H), 3.79 (s, 3H), 3.77 (s, 3H), 2.81-2.78 (m, 2H), 2.65-2.60 (m, 1H), 2.56 (d, J=14.0 Hz, 1H), 2.34 (dd, J=12.5 Hz, 1H), 2.11-2.02 (m, 2H), 1.94-1.86 (m, 1H), 0.97 (d, J=6.5 Hz, 3H). ESI MS m/z 359 $[C_{21}H_{26}O_5+H]^+$.

Compound 25 ((6S,7aR)-6-allyl-7a-((S)-1-(4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.09 (d, J=8.5 Hz, 2H), 6.86 (dd, J=7.0, 2.5 Hz, 2H), 5.92-5.85 (m, 1H), 5.66 (s, 1H), 5.60 (s, 1H), 5.49 (s, 1H), 5.18-5.12 (m, 2H), 3.76 (s, 3H), 3.10 (dd, J=13.5, 3.5 Hz, 1H), 2.90-2.87 (m, 1H), 2.70 (d, J=14.0 Hz, 1H), 2.62-2.60 (m, 1H), 2.45 (t, J=11.0 Hz, 1H), 2.25-2.20

(m, 1H), 2.14 (dd, J=13.5, 9.5 Hz, 1H), 1.96-1.93 (m, 1H), 0.83 (d, J=6.0 Hz, 3H). ESI MS m/z 329 [$C_{20}H_{24}O_4$+H]$^+$.

Compound 26 ((6S,7aR)-6-allyl-7a-((R)-1-(4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.98 (d, J=8.5 Hz, 2H), 6.83 (dd, J=6.5, 2.0 Hz, 2H), 5.83-5.78 (m, 1H), 5.68 (s, 1H), 5.63 (s, 1H), 5.54 (s, 1H), 5.08-5.02 (m, 2H), 3.75 (s, 3H), 2.80-2.78 (m, 2H), 2.64-2.58 (m, 1H), 2.55 (d, J=14.0 Hz, 1H), 2.33 (t, J=11.5 Hz, 1H), 2.11 (dd, J=14.0, 10.0 Hz, 1H), 2.05-2.02 (m, 1H), 1.89-1.85 (m, 1H), 0.95 (d, J=6.5 Hz, 3H). ESI MS m/z 329 [$C_{20}H_{24}O_4$+H]$^+$.

Compound 27 ((6S,7aR)-6-allyl-7a-((S)-1-(4-methoxy-3-methylphenyl)propan-2-yl)-7,7a-dihydrobenzo[d][1,3]dioxol-5(6H)-one) was prepared by general procedure A. $^1$H NMR (500 MHz, CD$_3$OD): δ 6.96-6.92 (m, 2H), 6.82 (d, J=7.0 Hz, 1H), 5.92-5.85 (m, 1H), 5.65 (s, 1H), 5.60 (s, 1H), 5.49 (s, 1H), 5.15-5.12 (m, 2H), 3.78 (s, 3H), 3.07 (dd, J=13.5, 3.5 Hz, 1H), 2.90-2.87 (m, 1H), 2.70 (d, J=14.0 Hz, 1H), 2.62-2.60 (m, 1H), 2.37 (t, J=11.0 Hz, 1H), 2.25-2.20 (m, 1H), 2.15 (s, 3H), 2.14-2.11 (m, 1H), 1.96-1.93 (m, 1H), 0.84 (d, J=7.0 Hz, 3H). ESI MS m/z 343 [$C_{21}H_{26}O_4$+H]$^+$.

Compound 29 (5-((S)-2-((3aR,5S)-5-allyl-6-oxo-3a,4,5,6-tetrahydrobenzo[d][1,3]dioxol-3a-yl)propyl)-2-methoxybenzamide) was prepared by general procedures C, G, and H. $^1$H NMR (500 MHz, CD$_3$OD): δ 7.84 (d, J=3.0 Hz, 1H), 7.36 (d, J=6.0 Hz, 1H), 7.11 (d, J=8.5 Hz, 1H), 5.92-5.85 (m, 1H), 5.66 (s, 1H), 5.61 (s, 1H), 5.50 (s, 1H), 5.22-5.13 (m, 2H), 3.96 (s, 3H), 3.13 (dd, J=11.0, 3.0 Hz, 1H), 2.90-2.85 (m, 1H), 2.70 (d, J=10.5 Hz, 1H), 2.65-2.64 (m, 1H), 2.53 (t, J=11.5 Hz, 1H), 2.18-2.11 (m, 1H), 2.15 (dd, J=13.5, 9.5 Hz, 1H), 2.03-1.95 (m, 1H), 0.85 (d, J=7.0 Hz, 3H). ESI MS m/z 372 [$C_{21}H_{25}NO_5$+H]$^+$.

Compound 30 (5-((S)-2-((3aR,5S)-5-allyl-6-oxo-3a,4,5,6-tetrahydrobenzo[d][1,3]dioxol-3a-yl)propyl)-2-methoxy-N-methylbenzamide) was prepared by general procedures C, G, and H. $^1$H NMR (500 MHz, CD$_3$OD): δ 7.78 (s, 1H), 7.32 (d, J=8.5 Hz, 1H), 7.09 (d, J=8.5 Hz, 1H), 5.95-5.85 (m, 1H), 5.66 (s, 1H), 5.60 (s, 1H), 5.50 (s, 1H), 5.18-5.11 (m, 2H), 3.94 (s, 3H), 3.10 (dd, J=14.0, 3.5 Hz, 1H), 2.94 (s, 3H), 2.92-2.89 (m, 1H), 2.70 (d, J=14.0 Hz, 1H), 2.68-2.65 (m, 1H), 2.52 (dd, J=14.0, 10.0 Hz, 1H), 2.27-2.22 (m, 1H), 2.15 (dd, J=14.0, 9.5 Hz, 1H), 2.03-1.95 (m, 1H), 0.84 (d, J=7.0 Hz, 3H). ESI MS m/z 386 [$C_{22}H_{27}NO_5$+H]$^+$.

Compound 31 (5-((S)-2-((3aR,5S)-5-allyl-6-oxo-3a,4,5,6-tetrahydrobenzo[d][1,3]dioxol-3a-yl)propyl)-2-methoxybenzonitrile) was prepared by general procedures C and E. $^1$H NMR (500 MHz, CD$_3$OD): δ 7.48-7.43 (m, 2H), 7.14 (d, J=14.5 Hz, 1H), 5.92-5.85 (m, 1H), 5.65 (s, 1H), 5.60 (s, 1H), 5.50 (s, 1H), 5.18-5.11 (m, 2H), 3.92 (s, 3H), 3.11 (dd, J=14.0, 10.0 Hz, 1H), 2.92-2.85 (m, 1H), 2.66-2.58 (m, 2H), 2.53 (t, J=14.0 Hz, 1H), 2.25-2.21 (m, 1H), 2.13 (dd, J=14.0, 9.5 Hz, 1H), 2.03-1.95 (m, 1H), 0.86 (d, J=7.0 Hz, 3H). ESI MS m/z 354 [$C_{21}H_{23}NO_4$+H]$^+$.

Compound 32 ((6S,7aR)-6-allyl-7a-((S)-1-(3-hydroxy-4-methoxyphenyl)propan-2-yl)-7,7a-dihydrobenzo[d][1,3]dioxol-5(6H)-one) was prepared by general procedures C, G, and H. $^1$H NMR (500 MHz, CD$_3$OD): δ 6.84 (d, J=8.0 Hz, 1H), 6.64-6.60 (m, 2H), 5.92-5.85 (m, 1H), 5.65 (s, 1H), 5.60 (s, 1H), 5.49 (s, 1H), 5.15-5.12 (m, 2H), 3.81 (s, 3H), 3.08-3.02 (m, 1H), 2.90-2.87 (m, 1H), 2.69 (d, J=14.0 Hz, 1H), 2.58-2.53 (m, 1H), 2.38 (t, J=11.5 Hz, 1H), 2.20-2.15 (m, 1H), 2.13 (dd, J=14.0, 9.5 Hz, 1H), 1.95-1.92 (m, 1H), 0.84 (d, J=7.0 Hz, 3H). ESI MS m/z 345 [$C_{20}H_{24}O_5$+H]$^+$.

Compound 33 (5-(2-((3aR,5S)-5-allyl-6-oxo-3a,4,5,6-tetrahydrobenzo[d][1,3]dioxol-3a-yl)propyl)-2-methoxyphenyl acetate) was prepared by general procedures A and P. $^1$H NMR (500 MHz, CD$_3$OD): δ 7.04-7.00 (m, 2H), 6.68 (s, 1H), 5.92-5.85 (m, 1H), 5.65 (s, 1H), 5.59 (s, 1H), 5.49 (s, 1H), 5.13-5.11 (m, 2H), 3.79 (s, 3H), 3.08 (dd, J=13.5, 3.5 Hz, 1H), 2.92-2.87 (m, 1H), 2.68 (d, J=14.5 Hz, 1H), 2.65-2.60 (m, 1H), 2.47 (t, J=11.5 Hz, 1H), 2.24 (s, 3H), 2.23-2.17 (m, 1H), 2.14 (dd, J=14.0, 9.5 Hz, 1H), 1.95-1.90 (m, 1H), 0.86 (d, J=7.0 Hz, 3H). ESI MS m/z 387 [$C_{22}H_{26}O_6$+H]$^+$.

Compound 34 ((6S,7aR)-6-allyl-7a-(1-(3-amino-4-methoxyphenyl)propan-2-yl)-7,7a-dihydrobenzo[d][1,3]dioxol-5(6H)-one) was prepared by general procedures C and F. $^1$H NMR (500 MHz, CD$_3$OD): δ 6.76 (dd, J=13.0, 8.0 Hz, 1H), 6.60 (s, 0.5H), 6.51 (d, J=14.5 Hz, 1H), 6.42 (d, J=8.0 Hz, 0.5H), 5.92-5.75 (m, 1H), 5.66 (s, 1H), 5.62 (s, 1H), 5.60 (s, 1H), 5.55 (s, 0.5H), 5.48 (s, 0.5H), 5.19-5.03 (m, 2H), 3.81 (s, 3H), 3.01 (m, 0.5H), 2.89-2.79 (m, 1H), 2.74-2.53 (m, 2.5H), 2.34-1.85 (m, 3H), 0.95 (d, J=6.5 Hz, 1.5H), 0.83 (d, J=6.5 Hz, 1.5H). ESI MS m/z 344 [$C_{20}H_{25}NO_4$+H]$^+$.

Compound 35 (N-(5-((S)-2-((3aR,5S)-5-allyl-6-oxo-3a,4,5,6-tetrahydrobenzo[d][1,3]dioxol-3a-yl)propyl)-2-methoxyphenyl)acetamide) was prepared by general procedures D and F. $^1$H NMR (500 MHz, CD$_3$OD): δ 7.88 (s, 1H), 6.95-6.92 (m, 2H), 5.95-5.85 (m, 1H), 5.66 (s, 1H), 5.60 (s, 1H), 5.49 (s, 1H), 5.19-5.11 (m, 2H), 3.85 (s, 3H), 3.11 (dd, J=23.0, 5.5 Hz, 1H), 2.92-2.85 (m, 1H), 2.72 (d, J=24.7 Hz, 1H), 2.66-2.59 (m, 1H), 2.42 (t, J=11.5 Hz, 1H), 2.28-1.98 (m, 1H), 2.11 (s, 3H), 2.10-1.95 (m, 2H), 0.84 (d, J=11.5 Hz, 3H). ESI MS m/z 386

Compound 36 ((6S,7aR)-6-allyl-7a-(1-(3-(allylamino)-4-methoxyphenyl)propan-2-yl)-7,7a-dihydrobenzo[d][1,3]dioxol-5(6H)-one) (mixture of diastereomers) was prepared by general procedures C and F. $^1$H NMR (500 MHz, CD$_3$OD): δ 6.73 (d, J=8.0 Hz, 1H), 6.42-6.40 (s, 2H), 5.92-5.85 (m, 2H), 5.66 (s, 1H), 5.60 (s, 1H), 5.55 (s, 0.2H), 5.48 (s, 0.8H), 5.19-5.03 (m, 4H), 3.81 (s, 3H), 3.75-3.74 (m, 2H), 3.01 (d, J=14.0 Hz, 1H), 2.85-2.82 (m, 1H), 2.72 (d, J=14.5 Hz, 1H), 2.65-2.52 (m, 1H), 2.32-2.28 (m, 1H), 2.27-2.22 (m, 1H), 2.12-2.10 (m, 1H), 1.95-1.90 (m, 1H), 0.95 (d, J=6.5 Hz, 0.6H), 0.83 (d, J=6.5 Hz, 2.4H). ESI MS m/z 384 [$C_{23}H_{29}NO_4$+H]$^+$.

Compound 37 ((6S,7aR)-6-allyl-7a-((S)-1-(3-fluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.01 (d, J=7.5 Hz, 1H), 6.93 (s, 1H), 6.91 (d, J=4.5 Hz, 1H), 5.92-5.85 (m, 1H), 5.65 (s, 1H), 5.60 (s, 1H), 5.50 (s, 1H), 5.17-5.12 (m, 2H), 3.84 (s, 3H), 3.08 (d, J=13.5 Hz, 1H), 2.90-2.87 (m, 1H), 2.67 (d, J=14.0 Hz, 1H), 2.62-2.60 (m, 1H), 2.47 (t, J=11.5 Hz, 1H), 2.25-2.20 (m, 1H), 2.14 (d, J=9.5 Hz, 1H), 2.03-1.97 (m, 1H), 0.85 (d, J=6.5 Hz, 3H). ESI MS m/z 347 [$C_{20}H_{23}FO_4$+H]$^+$.

Compound 38 ((6S,7aR)-6-allyl-7a-((S)-1-(3-chloro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.18 (d, J=2.5 Hz, 1H), 7.10 (dd, J=7.5, 2.0 Hz, 1H), 7.01 (d, J=7.0 Hz, 1H), 5.92-5.85 (m, 1H), 5.65 (s, 1H), 5.60 (s, 1H), 5.50 (s, 1H), 5.15-5.13 (m, 2H), 3.85 (s, 3H), 3.08 (dd, J=14.0, 4.0 Hz, 1H), 2.92-2.87 (m, 1H), 2.67 (d, J=14.0 Hz, 1H), 2.64-2.62 (m, 1H), 2.47 (dd, J=14.0, 11.0 Hz, 1H), 2.25-2.20 (m, 1H), 2.15 (dd, J=14.0, 10.0 Hz, 1H), 1.97-1.95 (m, 1H), 0.86 (d, J=7.0 Hz, 3H). ESI MS m/z 363 [$C_{20}H_{23}ClO_4$+H]$^+$.

Compound 39 ((6S,7aR)-6-allyl-7a-((R)-1-(3-chloro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.08 (s, 1H), 6.97 (s, 2H), 5.85-5.82 (m, 1H), 5.68 (s, 1H), 5.62 (s, 1H), 5.55 (s, 1H), 5.07-5.02 (m, 2H), 3.84 (s, 3H), 2.83-2.79 (m, 2H), 2.63-2.58 (m, 1H), 2.56 (d, J=14.0 Hz, 1H), 2.45-2.42 (m, 1H), 2.15-2.02 (m, 2H), 1.85-1.82 (m, 1H), 0.96 (d, J=7.0 Hz, 3H). ESI MS m/z 363 $[C_{20}H_{23}ClO_4+H]^+$.

Compound 41 ((6S,7aR)-6-allyl-7a-((S)-1-(4-(trifluoromethoxy)phenyl)propan-2-yl)-7,7a-dihydrobenzo[d][1,3]dioxol-5(6H)-one) was prepared by general procedure A. $^1$H NMR (500 MHz, CD$_3$OD): δ 7.29 (d, J=6.5 Hz, 2H), 7.21 (d, J=8.0 Hz, 2H), 5.92-5.85 (m, 1H), 5.66 (s, 1H), 5.61 (s, 1H), 5.51 (s, 1H), 5.16-5.12 (m, 2H), 3.15 (d, J=13.5 Hz, 1H), 2.90-2.87 (m, 1H), 2.68 (d, J=14.5 Hz, 1H), 2.67-2.60 (m, 1H), 2.59 (dd, J=14.0, 9.0 Hz, 1H), 2.25-2.20 (m, 1H), 2.16 (t, J=10.0 Hz, 1H), 2.04-2.01 (m, 1H), 0.86 (d, J=7.0 Hz, 3H). ESI MS m/z 383 $[C_{20}H_{21}F_3O_4+H]^+$.

Compound 42 ((6S,7aR)-6-allyl-7a-((S)-1-(4-amino-3-fluorophenyl)propan-2-yl)-7,7a-dihydrobenzo[d][1,3]dioxol-5(6H)-one) was prepared by general procedures D and F. $^1$H NMR (500 MHz, CD$_3$OD): δ 6.80-6.73 (m, 3H), 5.90-5.89 (m, 1H), 5.65 (s, 1H), 5.60 (s, 1H), 5.50 (s, 1H), 5.18-5.13 (m, 2H), 3.05 (dd, J=14.0, 3.5 Hz, 1H), 2.90 (d, J=10.5 Hz, 1H), 2.68 (d, J=9.5 Hz, 1H), 2.64-2.60 (m, 1H), 2.40 (t, J=11.5 Hz, 1H), 2.25-2.21 (m, 1H), 2.14 (dd, J=14.0, 9.5 Hz, 1H), 1.95-1.92 (m, 1H), 0.86 (d, J=8.0 Hz, 3H). ESI MS m/z 332 $[C_{19}H_{22}FNO_3+H]^+$.

Compound 43 ((6S,7aR)-6-allyl-7a-((R)-1-(3-fluoro-4-(methylamino)phenyl)propan-2-yl)-7,7a-dihydrobenzo[d][1,3]dioxol-5(6H)-one) was prepared by general procedure D. $^1$H NMR (500 MHz, CD$_3$OD): δ 6.71-6.61 (m, 3H), 5.85-5.78 (m, 1H), 5.66 (s, 1H), 5.62 (s, 1H), 5.49 (s, 1H), 5.08-5.01 (m, 2H), 2.81-2.73 (m, 2H), 2.79 (s, 3H), 2.64-2.58 (m, 1H), 2.55 (d, J=14.0 Hz, 1H), 2.27 (t, J=11.5 Hz, 1H), 2.10 (dd, J=14.0, 10.0 Hz, 1H), 2.05-2.01 (m, 1H), 1.85-1.81 (m, 1H), 0.95 (d, J=6.5 Hz, 3H). ESI MS m/z 346 $[C_{20}H_{24}FNO_3+H]^+$.

Compound 44 ((6S,7aR)-6-allyl-7a-((R)-1-(2,5-difluoro-4-(methylamino)phenyl)propan-2-yl)-7,7a-dihydrobenzo[d][1,3]dioxol-5(6H)-one) was prepared by general procedure D. $^1$H NMR (500 MHz, CD$_3$OD): δ 6.72 (dd, J=11.0, 4.0 Hz, 1H), 6.36 (dd, J=11.0, 4.0 Hz, 1H), 5.85-5.78 (m, 1H), 5.66 (s, 1H), 5.61 (s, 1H), 5.52 (s, 1H), 5.09-5.01 (m, 2H), 2.82-2.76 (m, 2H), 2.77 (s, 3H), 2.64-2.58 (m, 1H), 2.54 (d, J=14.0 Hz, 1H), 2.31 (t, J=11.5 Hz, 1H), 2.10-2.03 (m, 2H), 2.03-1.95 (m, 1H), 0.96 (d, J=7.0 Hz, 3H). ESI MS m/z 364 $[C_{20}H_{23}F_2NO_3+H]^+$.

Compound 45 (7aR)-6-allyl-7a-((S)-1-(2,5-difluoro-4-(methylamino)phenyl)propan-2-yl)-7,7a-dihydrobenzo[d][1,3]dioxol-5(6H)-one) (mixture of diastereomers) was prepared by general procedure D. $^1$H NMR (500 MHz, CD$_3$OD): δ 6.79 (dd, J=12.0, 6.5 Hz, 1H), 6.41 (dd, J=12.0, 6.0 Hz, 1H), 5.85-5.78 (m, 0.7H), 5.67 (s, 0.3H), 5.66 (s, 0.7H), 5.61 (s, 0.3H), 5.60 (s, 0.7H), 5.49 (s, 0.7H), 5.42 (s, 0.3H), 5.18-5.01 (m, 2H), 2.99 (d, J=14.0 Hz, 0.7H), 2.85-2.79 (m, 0.7H), 2.78 (s, 3H), 2.64 (d, J=14.0 Hz, 0.7H), 2.65-2.61 (m, 0.7H), 2.47 (t, J=11.5 Hz, 0.7H), 2.44 (d, J=11.5 Hz, 0.3H), 2.25-2.15 (m, 2.2H), 2.13 (dd, J=14.0, 9.5 Hz, 0.7H), 2.03-1.95 (m, 1H), 1.72 (t, J=7.0 Hz, 0.3H), 0.97 (d, J=7.0 Hz, 1.2H), 0.84 (d, J=6.5 Hz, 1.8H). ESI MS m/z 364 $[C_{20}H_{23}F_2NO_3+H]^+$.

Compound 46 ((6S,7aR)-6-allyl-7a-((R)-1-(4-(dimethylamino)-3-fluorophenyl)propan-2-yl)-7,7a-dihydrobenzo[d][1,3]dioxol-5(6H)-one) was prepared by general procedure D. $^1$H NMR (500 MHz, CD$_3$OD): δ 6.92-6.91 (m, 1H), 6.85-6.74 (m, 1H), 5.85-5.78 (m, 1H), 5.67 (s, 1H), 5.62 (s, 1H), 5.54 (s, 1H), 5.09-5.01 (m, 2H), 2.82-2.79 (m, 2H), 2.77 (s, 6H), 2.65-2.62 (m, 1H), 2.55 (d, J=14.0 Hz, 1H), 2.34-2.30 (m, 1H), 2.11 (dd, J=14.0, 10.0 Hz, 1H), 2.05-2.01 (m, 1H), 1.95-1.91 (m, 1H), 0.96 (d, J=7.0 Hz, 3H). ESI MS m/z 360 $[C_{21}H_{26}FNO_3+H]^+$.

Compound 47 ((6S,7aR)-6-allyl-7a-((R)-1-(4-(dimethylamino)-2,5-difluorophenyl)propan-2-yl)-7,7a-dihydrobenzo[d][1,3]dioxol-5(6H)-one) was prepared by general procedure D. $^1$H NMR (500 MHz, CD$_3$OD): δ 6.82 (dd, J=11.0, 4.0 Hz, 1H), 6.65 (dd, J=11.0, 4.0 Hz, 1H), 5.85-5.78 (m, 1H), 5.67 (s, 1H), 5.61 (s, 1H), 5.53 (s, 1H), 5.08-5.01 (m, 2H), 2.82 (s, 6H), 2.82-2.79 (m, 2H), 2.65-2.61 (m, 1H), 2.63 (d, J=14.0 Hz, 1H), 2.37 (t, J=11.5 Hz, 1H), 2.10-1.95 (m, 3H), 0.96 (d, J=7.0 Hz, 3H). ESI MS m/z 378 $[C_{21}H_{25}F_2NO_3+H]^+$.

Compound 50 ((6S,7aR)-6-allyl-7a-((S)-1-(3-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.21 (t, J=8.0 Hz, 1H), 6.77-6.73 (m, 3H), 5.92-5.87 (m, 1H), 5.67 (s, 1H), 5.61 (s, 1H), 5.50 (s, 1H), 5.18-5.12 (m, 2H), 3.77 (s, 3H), 3.15-3.13 (m, 1H), 2.95-2.88 (m, 1H), 2.70 (d, J=9.5 Hz, 1H), 2.65-2.62 (m, 1H), 2.48 (dd, J=14.5, 11.0 Hz, 1H), 2.25-2.22 (m, 1H), 2.15 (dd, J=14.0, 9.5 Hz, 1H), 2.02-1.98 (m, 1H), 0.97 (d, J=7.0 Hz, 3H). ESI MS m/z 329 $[C_{20}H_{24}O_4+H]^+$.

Compound 51 ((6S,7aR)-6-allyl-7a-((R)-1-(4-methoxy-2-methylphenyl)propan-2-yl)-7,7a-dihydrobenzo[d][1,3]dioxol-5(6H)-one) was prepared by general procedure A. $^1$H NMR (500 MHz, CD$_3$OD): δ 6.93 (d, J=8.0 Hz, 1H), 6.69-6.62 (m, 2H), 5.85-5.78 (m, 1H), 5.71 (s, 1H), 5.65 (s, 1H), 5.57 (s, 1H), 5.08-5.01 (m, 2H), 3.73 (s, 3H), 2.82-2.79 (m, 2H), 2.64-2.58 (m, 1H), 2.57 (d, J=13.5 Hz, 1H), 2.32 (t, J=11.5 Hz, 1H), 2.14 (s, 3H), 2.08 (dd, J=14.0, 9.5 Hz, 1H), 2.03-1.95 (m, 1H), 1.85-1.81 (m, 1H), 0.97 (d, J=7.0 Hz, 3H). ESI MS m/z 343 $[C_{21}H_{26}O_4+H]^+$.

Compound 52 ((6S,7aR)-6-allyl-7a-(1-(2,4-dimethoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.99 (d, J=8.0 Hz, 0.7H), 6.92 (d, J=8.0 Hz, 0.3H), 6.50 (d, J=0.3 Hz, 1H), 6.44-6.42 (m, 2H), 5.92-5.85 (m, 0.7H), 5.85-5.80 (m, 0.3H), 5.65 (s, 1H), 5.61 (s, 0.7H), 5.54 (s, 0.3H), 5.46 (s, 1H), 5.22-5.02 (m, 2H), 3.76 (s, 4.2H), 3.68 (s, 1.8H), 3.12 (dd, J=14.0, 4.0 Hz, 1H), 2.85-2.82 (m, 1H), 2.71 (d, J=14.0 Hz, 1H), 2.54-2.50 (m, 1H), 2.43-2.38 (m, 1H), 2.15-2.03 (m, 3H), 0.92 (d, J=6.5 Hz, 0.9H), 0.73 (d, J=7.0 Hz, 2.1H). ESI MS m/z 359 $[C_{21}H_{26}O_5+H]^+$.

Compound 53 (2-((S)-2-((3aR,5S)-5-allyl-6-oxo-3a,4,5,6-tetrahydrobenzo[d][1,3]dioxol-3a-yl)propyl)-5-methoxyphenyl acetate) was prepared by general procedures A and P. $^1$H NMR (500 MHz, CD$_3$OD): δ 7.15 (d, J=7.5 Hz, 1H), 6.80 (d, J=7.5 Hz, 1H), 6.64 (s, H), 5.85-5.78 (m, 1H), 5.61 (s, 1H), 5.60 (s, 1H), 5.52 (s, 1H), 5.08-5.01 (m, 2H), 3.76 (s, 3H), 2.82-2.79 (m, 2H), 2.64-2.58 (m, 1H), 2.57 (d, J=14.5 Hz, 1H), 2.43 (t, J=11.5 Hz, 1H), 2.28 (s, 3H), 2.18-2.02 (m, 3H), 0.84 (d, J=7.0 Hz, 3H). ESI MS m/z 387 $[C_{22}H_{26}O_6+H]^+$.

Compound 54 ((6S,7aR)-6-allyl-7a-((R)-1-(2-chloro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 7.10 (d, J=14.0 Hz, 1H), 6.90 (d, J=4.5 Hz, 1H), 6.79 (d, J=10.0 Hz, 1H), 5.85-5.78 (m, 1H), 5.67 (s, 1H), 5.60 (s, 1H), 5.53 (s, 1H), 5.05-5.01 (m, 2H), 3.73 (s, 3H), 2.95 (d, J=10.5 Hz, 1H), 2.82-2.79 (m, 1H), 2.64-2.58 (m, 1H), 2.54 (d, J=14.0 Hz, 1H), 2.40 (t, J=11.5 Hz, 1H), 2.08-1.98 (m, 3H), 0.93 (d, J=11.0 Hz, 3H). ESI MS m/z 363 $[C_{20}H_{23}ClO_4+H]^+$.

Compound 55 ((6S,7aR)-6-allyl-7a-(1-(3,5-difluoro-4-methoxyphenyl)propan-2-yl)-7,7a-dihydrobenzo[d][1,3]dioxol-5(6H)-one) was prepared by general procedure A. $^1$H NMR (500 MHz, CD$_3$OD): δ 6.83 (d, J=9.0 Hz, 1.6H), 6.72 (d, J=9.0 Hz, 0.4H), 5.92-5.80 (m, 1H), 5.67 (s, 0.2H), 5.65 (s, 0.8H), 5.61 (s, 0.2H), 5.60 (s, 0.8H), 5.50 (s, 0.8H), 5.48 (s, 0.2H), 5.15-5.05 (m, 2H), 3.91 (s, 3H), 3.07 (dd, J=14.5, 4.0 Hz, 0.8H), 2.90-2.78 (m, 1H), 2.67-2.63 (m, 1H), 2.62 (d, J=14.0 Hz, 1H), 2.52 (t, J=10.0 Hz, 1H), 2.38 (t, J=10.0 Hz, 0.2H), 2.21-2.18 (m, 1H), 2.15 (dd, J=14.5, 10.0 Hz, 1H), 2.03-1.95 (m, 0.8H), 1.92-1.85 (m, 0.2H), 0.96 (d, J=7.0 Hz, 0.6H), 0.88 (d, J=7.0 Hz, 2.4H). ESI MS m/z 365 [C$_{20}$H$_{22}$F$_2$O$_4$+H]$^+$.

Compound 56 ((6S,7aR)-7a-(1-(2,5-difluoro-4-methoxyphenyl)propan-2-yl)-6-methyl-7,7a-dihydrobenzo[d][1,3]dioxol-5(6H)-one) was prepared by general procedures B and V. $^1$H NMR (500 MHz, CD$_3$OD): δ 7.00-6.85 (m, 2H), 5.68 (s, 1H), 5.62 (s, 0.4H), 5.60 (s, 0.6H), 5.51 (s, 0.4H), 5.47 (s, 0.6H), 3.83 (s, 3H), 3.07 (d, J=5.5 Hz, 0.6H), 2.82-2.79 (m, 0.4H), 2.75-2.62 (m, 1H), 2.57 (d, J=14.0 Hz, 1H), 2.40-2.21 (m, 3H), 1.36 (d, J=13.0 Hz, 1.8H), 1.26 (d, J=13.0 Hz, 1.2H), 1.00 (d, J=7.0 Hz, 1.2H), 0.88 (d, J=7.0 Hz, 1.8H). ESI MS m/z 339 [C$_{18}$H$_{20}$F$_2$O$_4$+H]$^+$.

Compound 57 ((6S,7aR)-7a-((S)-1-(2,5-difluoro-4-methoxyphenyl)propan-2-yl)-6-ethyl-7,7a-dihydrobenzo[d][1,3]dioxol-5(6M-one) was prepared by general procedures B and V. $^1$H NMR (500 MHz, CD$_3$OD): δ 6.99-6.85 (m, 2H), 5.66 (s, 1H), 5.60 (s, 1H), 5.46 (s, 1H), 3.83 (s, 3H), 2.69 (d, J=23.0 Hz, 1H), 2.57 (t, J=18.5 Hz, 1H), 2.36-2.32 (m, 1H), 2.23-2.02 (m, 2H), 1.54-1.51 (m, 2H), 1.28 (t, J=12.5 Hz, 3H), 0.87 (d, J=7.0 Hz, 3H). ESI MS m/z 353 [C$_{19}$H$_{22}$F$_2$O$_4$+H]$^+$.

Compound 58 ((6S,7aR)-7a-((R)-1-(2,5-difluoro-4-methoxyphenyl)propan-2-yl)-6-ethyl-7,7a-dihydrobenzo[d][1,3]dioxol-5(6M-one) was prepared by general procedures B and V. $^1$H NMR (500 MHz, CD$_3$OD): δ 6.89-6.83 (m, 2H), 5.67 (s, 1H), 5.61 (s, 1H), 5.50 (s, 1H), 3.82 (s, 3H), 2.82 (d, J=14.0 Hz, 0.5H), 2.55 (m, 1H), 2.37-2.35 (m, 1.5H), 2.16-2.13 (m, 1H), 2.03-1.95 (m, 2H), 1.35-1.31 (m, 2H), 1.06 (t, J=7.5 Hz, 3H), 0.97 (d, J=7.0 Hz, 3H). ESI MS m/z 353 [C$_{19}$H$_{22}$F$_2$O$_4$+H]$^+$.

Compound 59 ((6S,7aR)-7a-((S)-1-(2-fluoro-5-hydroxy-4-methoxyphenyl)propan-2-yl)-6-propyl-7,7a-dihydrobenzo[d][1,3]dioxol-5(6M-one) was prepared by general procedures C and Q. $^1$H NMR (500 MHz, CD$_3$OD): δ 6.71 (d, J=11.5 Hz, 1H), 6.62 (d, J=7.5 Hz, 1H), 5.65 (s, 1H), 5.59 (s, 1H), 5.45 (s, 1H), 3.81 (s, 3H), 3.02 (dd, J=13.5, 3.5 Hz, 1H), 2.65 (d, J=14.0 Hz, 1H), 2.51-2.42 (m, 2H), 2.15-2.08 (m, 1H), 2.05-2.02 (m, 1H), 1.94-1.92 (m, 1H), 1.60-1.55 (m, 1H), 1.53-1.49 (m, 1H), 1.48-1.41 (m, 1H), 0.99 (t, J=7.5 Hz, 3H), 0.87 (d, J=7.0 Hz, 3H). ESI MS m/z 365 [C$_{20}$H$_{25}$FO$_5$+H]$^+$.

Compound 60 ((6S,7aR)-7a-((R)-1-(2-fluoro-5-hydroxy-4-methoxyphenyl)propan-2-yl)-6-propyl-7,7a-dihydrobenzo[d][1,3]dioxol-5(6M-one) was prepared by general procedures C and Q. $^1$H NMR (500 MHz, CD$_3$OD): δ 6.68 (d, J=7.5 Hz, 1H), 6.52 (d, J=7.0 Hz, 1H), 5.67 (s, 1H), 5.61 (s, 1H), 5.50 (s, 1H), 3.80 (s, 3H), 2.75 (d, J=13.0 Hz, 1H), 2.53 (d, J=13.5 Hz, 1H), 2.46-2.44 (m, 1H), 2.35 (t, J=12.0 Hz, 1H), 2.15 (dd, J=13.5, 7.5 Hz, 1H), 2.03-1.95 (m, 2H), 1.55-1.30 (m, 3H), 0.97 (d, J=7.0 Hz, 3H), 0.93 (d, J=7.0 Hz, 3H). ESI MS m/z 365 [C$_{20}$H$_{25}$FO$_5$+H]$^+$.

Compound 61 ((6S,7aR)-7a-((R)-1-(2,5-difluoro-4-methoxyphenyl)propan-2-yl)-6-propyl-7,7a-dihydrobenzo[d][1,3]dioxol-5(6H)-one) was prepared by general procedures B and Q. $^1$H NMR (500 MHz, CD$_3$OD): δ 6.91-6.83 (m, 2H), 5.67 (s, 1H), 5.61 (s, 1H), 5.50 (s, 1H), 3.83 (s, 3H), 2.82-2.79 (m, 1H), 2.52 (t, J=11.0 Hz, 1H), 2.48-2.42 (m, 1H), 2.54 (t, J=11.0 Hz, 1H), 2.11 (dd, J=14.0, 9.5 Hz, 1H), 2.03-1.95 (m, 2H), 1.55-1.27 (m, 3H), 0.97 (t, J=6.5 Hz, 3H), 0.93 (d, J=7.5 Hz, 3H). ESI MS m/z 367 [C$_{20}$H$_{24}$F$_2$O$_4$+H]$^+$.

Compound 67 ((6S,7aR)-6-((E)-but-2-en-1-yl)-7a-((S)-1-(2-fluoro-4-methoxyphenyl)propan-2-yl)-7,7a-dihydrobenzo[d][1,3]dioxol-5(6H)-one) was prepared by general procedure V. $^1$H NMR (500 MHz, CD$_3$OD): δ 7.13 (t, J=10.5 Hz, 1H), 6.70-6.65 (m, 1H), 5.65 (s, 1H), 5.64 (s, 1H), 5.64-5.60 (m, 1H), 5.49-5.48 (m, 1H), 5.48 (s, 1H), 3.77 (s, 3H), 3.05-3.01 (m, 1H), 2.73-2.70 (m, 1H), 2.68 (d, J=14.5 Hz, 1H), 2.58-2.52 (m, 2H), 2.21-2.02 (m, 3H), 1.68 (d, J=5.0 Hz, 3H), 0.82 (d, J=7.0 Hz, 3H). ESI MS (Positive Mode) m/z 361 [C$_{21}$H$_{25}$FO$_4$+H]$^+$.

Compound 69 ((6S,7aR)-7a-((S)-1-(2-fluoro-5-hydroxy-4-methoxyphenyl)propan-2-yl)-6-(3-fluoropropyl)-7,7a-dihydrobenzo[d][1,3]dioxol-5(6H)-one) was prepared by general procedure X. $^1$H NMR (300 MHz, CD$_3$OD): δ 6.72 (d, J=19.0 Hz, 1H), 6.63 (d, J=12.5 Hz, 1H), 5.66 (s, 1H), 5.60 (s, 1H), 5.46 (s, 1H), 4.57-4.38 (m, 2H), 3.81 (s, 3H), 3.07-2.99 (m, 1H), 2.65 (d, J=23.5 Hz, 1H), 2.51-2.43 (m, 2H), 2.20-2.09 (m, 2H), 2.03-1.82 (m, 3H), 1.59-1.54 (m, 1H), 0.87 (d, J=11.5 Hz, 3H). ESI MS (Positive Mode) m/z 383 [C$_{20}$H$_{24}$F$_2$O$_5$+H]$^+$.

Compound 72 ((6S,7aS)-6-allyl-7a-(3,4-dimethoxyphenethyl)-7,7a-dihydrobenzo[d][1,3]dioxol-5(6H)-one) was prepared by general procedure A. $^1$H NMR (500 MHz, CD$_3$OD): δ 6.90 (d, J=8.0 Hz, 1H), 6.83 (s, 1H), 6.79 (d, J=8.0 Hz, 1H), 5.96-5.92 (m, 1H), 5.67 (s, 1H), 5.60 (s, 1H), 5.40 (s, 1H), 5.22-5.18 (m, 2H), 3.83 (s, 3H), 3.81 (s, 3H), 2.80-2.75 (m, 3H), 2.69 (d, J=13.5 Hz, 1H), 2.64-2.60 (m, 1H), 2.29-2.24 (m, 2H), 2.15-2.12 (m, 1H), 1.82-1.78 (m, 1H). ESI MS m/z 345 [C$_{20}$H$_{24}$O$_5$+H]$^+$.

Compound 74 (6R,7aR)-7a-((R)-1-(2-fluoro-5-hydroxy-4-methoxyphenyl)propan-2-yl)-6-((E)-prop-1-en-1-yl)-7,7a-dihydrobenzo[d][1,3]dioxol-5(6H)-one was prepared by general procedure Y. $^1$H NMR (500 MHz, CD$_3$OD): δ 6.68 (d, J=8.5 Hz, 1H), 6.52 (d, J=7.5 Hz, 1H), 5.69 (s, 1H), 5.68-5.65 (m, 1H), 5.64 (s, 1H), 5.46 (s, 1H), 5.44-5.42 (m, 1H), 3.80 (s, 3H), 3.58-3.55 (m, 1H), 2.75 (d, J=12.5 Hz, 1H), 2.53 (d, J=13.0 Hz, 1H), 2.35-2.29 (m, 2H), 2.08-2.03 (m, 1H), 1.68 (d, J=6.5 Hz, 1H), 0.91 (d, J=7.0 Hz, 3H). HRMS (Positive Mode) m/z 363.2069 [C$_{20}$H$_{23}$FO$_5$+H]$^+$.

Compound 76 (6R,7aR)-7a-((S)-1-(2-fluoro-5-hydroxy-4-methoxyphenyl)propan-2-yl)-6-(2-(methylthio)ethyl)-7,7a-dihydrobenzo[d][1,3]dioxol-5(6H)-one was prepared by general procedure X. $^1$H NMR (500 MHz, CD$_3$OD): δ 6.71 (d, J=11.5 Hz, 1H), 6.63 (d, J=7.5 Hz, 1H), 5.66 (s, 1H), 5.60 (s, 1H), 5.47 (s, 1H), 3.82 (s, 3H), 3.02 (dd, J=14.5, 3.5 Hz, 1H), 2.77-2.70 (m, 2H), 2.65-2.61 (m, 1H), 2.58 (d, J=14.0 Hz, 1H), 2.51-2.46 (m, 1H), 2.27-2.21 (m, 1H), 2.17 (dd, J=13.5, 9.5 Hz, 1H), 2.09 (s, 3H), 2.03-1.99 (m, 1H), 1.80-1.75 (m, 1H), 0.88 (d, J=7.0 Hz, 3H). ESI MS (Positive Mode) m/z 397 [C$_{20}$H$_{25}$FO$_5$S+H]$^+$.

Compound 78 (6S,7aR)-7a-((S)-1-(2-fluoro-5-hydroxy-4-methoxyphenyl)propan-2-yl)-6-(2-methoxyethyl)-7,7a-dihydrobenzo[d][1,3]dioxol-5(6H)-one was prepared by general procedure X. $^1$H NMR (500 MHz, CD$_3$OD): δ 6.70 (d, J=11.5 Hz, 1H), 6.63 (d, J=7.54 Hz, 1H), 5.66 (s, 1H), 5.60 (s, 1H), 5.46 (s, 1H), 3.81 (s, 3H), 3.58-3.56 (m, 2H), 3.35 (s, 3H), 3.02 (dd, J=14.5, 3.5 Hz, 1H), 2.70 (d, J=14.0 Hz, 1H), 2.63-2.60 (m, 1H), 2.51-2.46 (m, 1H), 2.27-2.23 (m, 1H), 2.16 (dd, J=14.0, 9.5 Hz, 1H), 2.00-1.97 (m, 1H), 2.79-2.71 (m, 1H), 0.86 (d, J=7.0 Hz, 3H). ESI MS (Positive Mode) m/z 367 [C$_{20}$H$_{25}$FO$_6$+H]$^+$.

Compound 79 (6R,7aR)-6-(2-chloroallyl)-7a-((S)-1-(2-fluoro-4-methoxyphenyl)propan-2-yl)-7,7a-dihydrobenzo[d][1,3]dioxol-5(6H)-one was prepared by general procedure V. ¹H NMR (500 MHz, CD₃OD): δ 7.14 (t, J=9.0 Hz, 1H), 6.70-6.66 (m, 2H), 5.66 (s, 1H), 5.62 (s, 1H), 5.53 (s, 1H), 5.39 (s, 1H), 5.32 (s, 1H), 3.77 (s, 3H), 3.11-3.05 (m, 2H), 2.97-2.92 (m, 1H), 2.65-2.50 (m, 3H), 2.21 (dd, J=14.0, 10.0 Hz, 1H), 1.95-1.93 (m, 1H), 0.82 (d, J=7.0 Hz, 3H). ESI MS (Positive Mode) m/z 381 [C₂₀H₂₂ClFO₄+H]⁺.

Compound 80 (6S,7aR)-7a-((S)-1-(2-fluoro-5-hydroxy-4-methoxyphenyl)propan-2-yl)-6-(2-methylallyl)-7,7a-dihydrobenzo[d][1,3]dioxol-5(6H)-one was prepared by general procedure V. ¹H NMR (500 MHz, CD₃OD): δ 6.71 (d, J=11.5 Hz, 1H), 6.62 (d, J=7.5 Hz, 1H), 5.65 (s, 1H), 5.60 (s, 1H), 5.51 (s, 1H), 4.91-4.85 (m, 2H), 3.81 (s, 3H), 2.99 (dd, J=14.0, 10.0 Hz, 1H), 2.79-2.73 (m, 2H), 2.64 (d, J=14.0 Hz, 1H), 2.51 (dd, J=14.0, 11.5 Hz, 1H), 2.29 (t, J=12.0 Hz, 1H), 2.14 (dd, J=14.0, 10.5 Hz, 1H), 2.03-1.98 (m, 1H), 1.77 (s, 3H), 0.82 (d, J=7.0 Hz, 3H). ESI MS (Positive Mode) m/z 377 [C₂₁H₂₅FO₅+H]⁺.

Compound 82 (2R,6S,7aR)-6-allyl-7a-((S)-1-(2,5-difluoro-4-methoxyphenyl)propan-2-yl)-2-methyl-7,7a-dihydrobenzo[d][1,3]dioxol-5(6H)-one was prepared by general procedure AB. ¹H NMR (500 MHz, CD₃OD): δ 6.99-6.95 (m, 1H), 6.90-6.87 (m, 1H), 6.00 (q, J=10.0, 5.0 Hz, 1H), 5.92-5.84 (m, 1H), 5.44 (s, 1H), 5.19-5.10 (m, 2H), 3.83 (s, 3H), 3.31 (dd, J=14, 3.5 Hz, 1H), 2.85-2.80 (m, 1H), 2.64 (d, J=14.0 Hz, 1H), 2.60 (dd, J=10.0, 3.5 Hz, 1H), 2.53 (dd, J=11.0, 2.5 Hz, 1H), 2.52-2.18 (m, 1H), 2.10 (dd, J=14.0, 4.0 Hz, 1H), 2.06-1.99 (m, 1H), 1.49 (d, J=5.0 Hz, 3H), 0.86 (d, J=7.0 Hz, 3H). ESI MS (Positive Mode) m/z 379 [C₂₁H₂₄F₂O₄+H]⁺.

Compound 83 ((6S,7aR)-6-allyl-7a-((S)-1-(benzo[d][1,3]dioxol-5-yl)propan-2-yl)-7,7a-dihydrobenzo[d][1,3]dioxol-5(6H)-one was prepared by general procedure A. ¹H NMR (500 MHz, CD₃OD): δ 6.74 (d, J=8.0 Hz, 1H), 6.66-6.63 (m, 2H), 5.92-5.87 (m, 1H), 5.90 (s, 2H), 5.65 (s, 1H), 5.60 (s, 1H), 5.49 (s, 1H), 5.18-5.12 (m, 2H), 3.08 (d, J=12.0 Hz, 1H), 2.88 (dd, J=10.0, 2.0 Hz, 1H), 2.67 (d, J=14.0 Hz, 1H), 2.63-2.61 (m, 1H), 2.44 (dd, J=14.0, 11.5 Hz, 1H), 2.05-1.98 (m, 1H), 2.13 (t, J=9.5 Hz, 1H), 1.95-1.93 (m, 1H), 0.85 (d, J=7.0 Hz, 3H). ESI MS m/z 343 [C₂₀H₂₂O₅+H]⁺.

Compound 84 ((6S,7aR)-6-allyl-7a-((R)-1-(7-methoxybenzofuran-4-yl)propan-2-yl)-7,7a-dihydrobenzo[d][1,3]dioxol-5(6H)-one was prepared by general procedure A. ¹H NMR (500 MHz, CD₃OD): δ 7.67 (s, 1H), 6.86 (d, J=8.0 Hz, 1H), 6.78 (t, J=5.5 Hz, 1H), 6.58 (d, J=8.0 Hz, 1H), 5.75-5.73 (m, 1H), 5.72 (s, 1H), 5.61 (s, 1H), 5.45 (s, 1H), 5.08-5.01 (m, 2H), 3.93 (s, 3H), 3.02 (d, J=14.0 Hz, 1H), 2.75-2.72 (m, 1H), 2.62-2.58 (m, 1H), 2.54-2.51 (m, 2H), 2.10 (dd, J=14.0, 10.0 Hz, 1H), 1.95-1.85 (m, 2H), 0.96 (d, J=7.0 Hz, 3H). ESI MS m/z 369 [C₂₂H₂₄O₅+H]⁺.

Compound 85 ((6S,7aR)-6-allyl-7a-((S)-1-(7-methoxybenzofuran-4-yl)propan-2-yl)-7,7a-dihydrobenzo[d][1,3]dioxol-5(6H)-one was prepared by general procedure A. ¹H NMR (500 MHz, CD₃OD): δ 7.73 (d, J=2.5 Hz, 1H), 6.98 (d, J=8.0 Hz, 1H), 6.85-6.82 (m, 2H), 5.83-5.78 (m, 1H), 5.69 (s, 1H), 5.63 (s, 1H), 5.52 (s, 1H), 5.08-5.01 (m, 2H), 3.95 (s, 3H), 3.19 (dd, J=11.5, 4.0 Hz, 1H), 2.82-2.79 (m, 1H), 2.77 (t, J=11.0 Hz, 1H), 2.66-2.60 (m, 2H), 2.20-2.12 (m, 3H), 0.87 (d, J=8.0 Hz, 3H). ESI MS m/z 369 [C₂₂H₂₄O₅+H]⁺.

Compound 86 ((6S,7aR)-6-allyl-7a-((S)-1-(6-methoxypyridin-3-yl)propan-2-yl)-7,7a-dihydrobenzo[d][1,3]dioxol-5(6H)-one was prepared by general procedure A. ¹H NMR (500 MHz, CD₃OD): δ 7.95 (d, J=2.5 Hz, 1H), 7.54 (d, J=7.5, 2.5 Hz, 1H), 6.77 (d, J=7.5 Hz, 1H), 5.92-5.85 (m, 1H), 5.66 (s, 1H), 5.60 (s, 1H), 5.50 (s, 1H), 5.18-5.13 (m, 2H), 3.87 (s, 3H), 3.07 (dd, J=14.5, 4.0 Hz, 1H), 2.90-2.87 (m, 1H), 2.69 (d, J=14.0 Hz, 1H), 2.67-2.60 (m, 1H), 2.53 (t, J=11.0 Hz, 1H), 2.25-2.20 (m, 1H), 2.16 (dd, J=14.0, 9.5 Hz, 1H), 1.99-1.93 (m, 1H), 0.89 (d, J=8.0 Hz, 3H). ESI MS m/z 330 [C₁₉H₂₃NO₄+H]⁺.

Compound 87 ((6S,7aR)-6-allyl-7a-(1-(3,4-dimethoxyphenyl)butan-2-yl)-7,7a-dihydrobenzo[d][1,3]dioxol-5(6H)-one was prepared by general procedure A. ¹H NMR (500 MHz, CD₃OD): δ 6.88-6.66 (m, 3H), 5.85-5.65 (m, 1H), 5.67 (s, 0.4H), 5.66 (s, 0.6H), 5.61 (s, 0.4H), 5.60 (s, 0.6H), 5.48 (s, 0.6H), 5.43 (s, 0.4H), 5.12-5.08 (m, 2H), 3.82 (s, 3H), 3.80 (s, 3H), 2.95-2.92 (m, 0.6H), 2.83-2.72 (m, 1.4H), 2.63-2.52 (m, 3H), 2.16-2.08 (m, 2H), 1.95-1.85 (m, 1H), 1.62-1.35 (m, 2H), 0.92-0.89 (m, 1.8H), 0.89 (t, J=3.0 Hz, 1.2H). ESI MS m/z 373 [C₂₂H₂₈O₅+H]⁺.

Compound 91 ((6S,7aR)-6-allyl-7a-((S)-1-(4-fluoro-6-methoxy-[1,1'-biphenyl]-3-yl)propan-2-yl)-7,7a-dihydrobenzo[d][1,3]dioxol-5(6H)-one) was prepared by general procedures C and E. ¹H NMR (500 MHz, CD₃OD): δ 7.42 (d, J=3.5 Hz, 2H), 7.36-7.33 (m, 2H), 7.26 (t, J=7.5 Hz, 1H), 7.12 (d, J=7.5 Hz, 1H), 6.86 (d, J=12.0 Hz, 1H), 5.95-5.85 (m, 1H), 5.66 (s, 1H), 5.60 (s, 1H), 5.50 (s, 1H), 5.18-5.11 (m, 2H), 3.77 (s, 3H), 3.12 (dd, J=14.0, 3.5 Hz, 1H), 2.85-2.82 (m, 1H), 2.71 (d, J=14.0 Hz, 1H), 2.63 (t, J=11.5 Hz, 1H), 2.25-2.22 (m, 1H), 2.16 (dd, J=14.0, 9.5 Hz, 1H), 2.05-2.01 (m, 1H), 0.88 (d, J=7.0 Hz, 3H). ESI MS m/z 423 [C₂₆H₂₇FO₄+H]⁺.

Compound 93 (5-((R)-2-((3aR,5S)-5-allyl-6-oxo-3a,4,5,6-tetrahydrobenzo[d][1,3]dioxol-3a-yl)propyl)-4-fluoro-2-methoxy-N,N-dimethylbenzamide) was prepared by procedures C, G, and H. ¹H NMR (500 MHz, CD₃OD): δ 7.02 (d, J=8.0 Hz, 1H), 6.86 (d, J=8.0 Hz, 1H), 5.85-5.78 (m, 1H), 5.68 (s, 1H), 5.62 (s, 1H), 5.53 (s, 1H), 5.08-5.01 (m, 2H), 3.83 (s, 3H), 3.12 (s, 3H), 2.86 (s, 3H), 2.82-2.79 (m, 2H), 2.64-2.58 (m, 1H), 2.55 (d, J=14.0 Hz, 1H), 2.40 (t, J=11.5 Hz, 1H), 2.09-1.95 (m, 3H), 0.98 (d, J=7.0 Hz, 3H). ESI MS m/z 418 [C₂₃H₂₈FO₅+H]⁺.

Compound 94 (5-((S)-2-((3aR,5S)-5-allyl-6-oxo-3a,4,5,6-tetrahydrobenzo[d][1,3]dioxol-3a-yl)propyl)-4-fluoro-2-methoxy-N,N-dimethylbenzamide) was prepared by procedures C, G, and H. ¹H NMR (500 MHz, CD₃OD): δ 7.10 (d, J=8.5 Hz, 1H), 6.89 (d, J=10.0 Hz, 1H), 5.92-5.85 (m, 1H), 5.65 (s, 1H), 5.60 (s, 1H), 5.50 (s, 1H), 5.19-5.10 (m, 2H), 3.83 (s, 3H), 3.08-3.06 (m, 1H), 3.06 (s, 3H), 2.86 (s, 3H), 2.82-2.79 (m, 1H), 2.68-2.55 (m, 3H), 2.22-2.18 (m, 1H), 2.16 (dd, J=14.5, 10.0 Hz, 1H), 2.03-1.95 (m, 1H), 0.85 (d, J=7.0 Hz, 3H). ESI MS m/z 418 [C₂₃H₂₈FO₅+H]⁺.

Compound 97 ((6S,7aR)-6-allyl-7a-((R)-1-(3-(dimethylamino)-4-methoxyphenyl)propan-2-yl)-7,7a-dihydrobenzo[d][1,3]dioxol-5(6H)-one was prepared by general procedures C and F. ¹H NMR (500 MHz, CD₃OD): δ 6.86 (d, J=8.0 Hz, 1H), 6.73 (d, J=8.0 Hz, 1H), 6.68 (s, 1H), 5.85-5.78 (m, 1H), 5.67 (s, 1H), 5.63 (s, 1H), 5.54 (s, 1H), 5.08-5.01 (m, 2H), 3.83 (s, 3H), 2.82-2.78 (m, 2H), 2.68 (s, 6H), 2.64-2.58 (m, 1H), 2.55 (d, J=14.5 Hz, 1H), 2.34 (t, J=11.5 Hz, 1H), 2.10 (dd, J=14.0, 9.5 Hz, 1H), 1.95-1.85 (m, 1H), 0.97 (d, J=6.5 Hz, 3H). ESI MS m/z 372 [C₂₂H₂₉NO₄+H]⁺.

Compound 98 ((6S,7aR)-6-allyl-7a-((S)-1-(2-fluoro-4-methoxy-5-morpholinophenyl)propan-2-yl)-7,7a-dihydrobenzo[d][1,3]dioxol-5(6H)-one) was prepared by general procedures C and F. ¹H NMR (500 MHz, CD₃OD): δ 6.90 (d, J=8.0 Hz, 1H), 6.85 (s, 1H), 6.76 (s, 1H), 5.95-5.90 (m, 1H), 5.67 (s, 1H), 5.60 (s, 1H), 5.49 (s, 1H), 5.18-5.10 (m, 2H), 3.83 (s, 3H), 3.82-3.80 (m, 4H), 3.09 (d, J=14.0 Hz, 1H), 3.02-2.98 (m, 4H), 2.89-2.85 (m, 1H), 2.72 (d, J=14.0 Hz, 1H), 2.64-2.58 (m, 1H), 2.45 (dd, J=13.5, 9.0 Hz, 1H), 2.22-2.20 (m, 1H), 2.15 (t, J=10.0 Hz, 1H), 2.03-1.95 (m, 2H), 0.85 (d, J=7.0 Hz, 3H). ESI MS m/z 414 [$C_{24}H_{31}NO_5$+H]$^+$.

Compound 100 (4-((S)-2-((3aR,5S)-5-allyl-6-oxo-3a,4,5,6-tetrahydrobenzo[d][1,3]dioxol-3a-yl)propyl)phenyl acetate) was prepared by general procedures A and P. $^1$H NMR (500 MHz, CD$_3$OD): δ 7.22 (d, J=7.5 Hz, 2H), 7.03 (d, J=7.5 Hz, 2H), 5.92-5.85 (m, 1H), 5.67 (s, 1H), 5.61 (s, 1H), 5.50 (s, 1H), 5.14-5.11 (m, 2H), 3.16 (dd, J=14.5, 4.0 Hz, 1H), 2.90-2.87 (m, 1H), 2.68 (d, J=14.0 Hz, 1H), 2.67-2.60 (m, 1H), 2.53 (t, J=11.0 Hz, 1H), 2.25 (s, 3H), 2.25-2.20 (m, 1H), 2.16 (t, J=9.5 Hz, 1H), 2.02-1.95 (m, 1H), 0.86 (d, J=7.0 Hz, 3H). ESI MS m/z 357 [$C_{21}H_{24}O_5$+H]$^+$.

Compound 101 ((6S,7aR)-6-allyl-7a-((R)-1-(3-fluoro-4-(2-methoxyethoxy)phenyl)propan-2-yl)-7,7a-dihydrobenzo[d][1,3]dioxol-5(6H)-one) was prepared by general procedures A and N. $^1$H NMR (500 MHz, CD$_3$OD): δ 7.02 (t, J=7.5 Hz, 1H), 6.84-6.79 (m, 2H), 5.85-5.78 (m, 1H), 5.68 (s, 1H), 5.62 (s, 1H), 5.54 (s, 1H), 5.08-5.01 (m, 2H), 4.15 (dd, J=6.5, 4.5 Hz, 2H), 3.74 (dd, J=6.0, 3.0 Hz, 2H), 3.41 (s, 3H), 2.82-2.79 (m, 2H), 2.64-2.58 (m, 1H), 2.55 (d, J=14.0 Hz, 1H), 2.36 (t, J=11.5 Hz, 1H), 2.11 (dd, J=14.0, 10.0 Hz, 1H), 1.95-1.85 (m, 2H), 0.96 (d, J=6.5 Hz, 3H). ESI MS m/z 391 [$C_{22}H_{27}FO_5$+H]$^+$.

Compound 102 (N-(4-((S)-2-((3aR,5S)-5-allyl-6-oxo-3a,4,5,6-tetrahydrobenzo[d][1,3]dioxol-3a-yl)propyl)-2-fluorophenyl)acetamide) was prepared by general procedures D and F. $^1$H NMR (500 MHz, CD$_3$OD): δ 7.77 (t, J=8.0 Hz, 1H), 6.99 (dd, J=5.0, 3.0 Hz, 2H), 5.92-5.85 (m, 1H), 5.66 (s, 1H), 5.60 (s, 1H), 5.50 (s, 1H), 5.17-5.01 (m, 2H), 3.16 (dd, J=14.0, 10.0 Hz, 1H), 2.90 (d, J=9.5 Hz, 1H), 2.67 (d, J=10.5 Hz, 1H), 2.64-2.61 (m, 1H), 2.53 (t, J=11.0 Hz, 1H), 2.25-2.15 (m, 1H), 2.15 (s, 3H), 2.14 (m, 1H), 2.03-1.95 (m, 1H), 0.86 (d, J=6.5 Hz, 3H). ESI MS m/z 374 [$C_{21}H_{24}FNO_4$+H]$^+$.

Compound 103 (N-(4-((S)-2-((3aR,5S)-5-allyl-6-oxo-3a,4,5,6-tetrahydrobenzo[d][1,3]dioxol-3a-yl)propyl)phenyl)-N-methylacetamide) was prepared by general procedure A. $^1$H NMR (500 MHz, CD$_3$OD): δ 7.20 (s, 4H), 5.82-5.78 (m, 1H), 5.71 (s, 1H), 5.64 (s, 1H), 5.54 (s, 1H), 5.09-5.03 (m, 2H), 3.21 (s, 3H), 2.90-2.82 (m, 2H), 2.63-2.61 (m, 1H), 2.57 (d, J=14.0 Hz, 1H), 2.49 (t, J=10.0 Hz, 1H), 2.13 (dd, J=14.0, 10.0 Hz, 1H), 2.08-1.95 (m, 2H), 1.83 (s, 3H), 0.97 (d, J=6.5 Hz, 3H). ESI MS m/z 370 [$C_{22}H_{27}NO_4$+H]$^+$.

Compound 104 ((R)-7a-((S)-1-(2-fluoro-5-hydroxy-4-methoxyphenyl)propan-2-yl)-7,7a-dihydrobenzo[d][1,3]dioxol-5(6H)-one) was prepared by general procedure C. $^1$H NMR (500 MHz, CD$_3$OD): δ 6.72 (d, J=11.5 Hz, 1H), 6.64 (d, J=7.5 Hz, 1H), 5.69 (s, 1H), 5.63 (s, 1H), 5.44 (s, 1H), 3.81 (s, 3H), 3.01 (dd, J=14.0, 3.0 Hz, 1H), 2.67 (d, J=13.5, 5.0 Hz, 1H), 2.48-2.40 (m, 3H), 2.21-2.18 (m, 1H), 2.06-2.03 (m, 1H), 0.92 (d, J=7.0 Hz, 3H). ESI MS m/z 323 [$C_{17}H_{19}FO_5$+H]$^+$.

Compound 112 ((6R,7aR)-6-((R)-but-3-en-2-yl)-7a-((S)-1-(2-fluoro-4-methoxyphenyl)propan-2-yl)-7,7a-dihydrobenzo[d][1,3]dioxol-5(6H)-one) was prepared by general procedures A and AI. $^1$H NMR (500 MHz, CD$_3$OD): δ 7.10 (t, J=9.0 Hz, 1H), 6.69 (dd, J=11.0, 2.0 Hz, 1H), 6.63 (dd, J=12.0, 3.0 Hz, 1H), 5.85-5.75 (m, 1H), 5.57 (s, 1H), 5.56 (s, 1H), 5.53 (s, 1H), 5.13-5.06 (m, 2H), 3.76 (s, 3H), 3.06-3.02 (m, 1H), 2.85 (dd, J=14.0, 3.5 Hz, 1H), 2.63-2.61 (m, 1H), 2.51-2.47 (m, 2H), 2.17 (d, J=11.5 Hz, 1H), 2.11-2.05 (m, 1H), 1.13 (d, J=7.0 Hz, 3H), 0.82 (d, J=7.0 Hz, 3H). ESI MS m/z 361[$C_{21}H_{25}FO_4$+H]$^+$.

Compound 113 ((6S,7aR)-7a-((S)-1-(2-fluoro-5-hydroxy-4-methoxyphenyl)propan-2-yl)-6-(furan-2-ylmethyl)-7,7a-dihydrobenzo[d][1,3]dioxol-5(6H)-one) was prepared by general procedures C and X. $^1$H NMR (500 MHz, CD$_3$OD): δ 7.40 (s, 1H), 6.71 (d, J=11.5 Hz, 1H), 6.65 (d, J=7.0 Hz, 1H), 6.33 (s, 1H), 6.19 (s, 1H), 5.65 (s, 1H), 5.59 (s, 1H), 5.52 (s, 1H), 3.81 (s, 3H), 3.43-3.39 (m, 1H), 3.03 (dd, J=14.0, 4.0 Hz, 1H), 2.93-2.90 (m, 1H), 2.85-2.79 (m, 1H), 2.62 (d, J=14.0 Hz, 1H), 2.48 (t, J=12.0 Hz, 1H), 2.11 (dd, J=14.0, 9.5 Hz, 1H), 2.03-1.99 (m, 1H), 0.84 (d, J=7.0 Hz, 3H). ESI MS m/z 403[$C_{22}H_{23}FO_6$+H]$^+$.

Compound 114 ((6S,7aR)-7a-((S)-1-(2-fluoro-5-hydroxy-4-methoxyphenyl)propan-2-yl)-6-(pyridin-4-ylmethyl)-7,7a-dihydrobenzo[d][1,3]dioxol-5(6H)-one) was prepared by general procedures C and X. $^1$H NMR (500 MHz, CD$_3$OD): δ 8.45 (d, J=5.5 Hz, 2H), 7.38 (d, J=5.5 Hz, 2H), 6.71 (t, J=11.5 Hz, 1H), 6.65 (d, J=7.5 Hz, 1H), 5.65 (s, 1H), 5.60 (s, 1H), 5.51 (s, 1H), 3.81 (s, 3H), 3.50 (dd, J=14.5, 4.0 Hz, 1H), 3.01 (dd, J=8.0, 4.0 Hz, 2H), 2.80 (dd, J=11.0, 3.5 Hz, 1H), 2.47-2.41 (m, 2H), 2.16 (t, J=10.0 Hz, 1H), 2.08-2.03 (m, 1H), 0.88 (d, J=7.0 Hz, 3H). ESI MS m/z 413 [$C_{23}H_{24}FNO_5$+H]$^+$.

Example II

Inhibition Of Cancer Cell Proliferation In Vitro

All of the compounds shown in Table 3-Table 8 below were prepared synthetically as described in EXAMPLE I. The compounds were tested for their ability to inhibit the proliferation of human cancer cells in vitro as described in the following paragraph. Table 3-Table 8 list the IC$_{50}$ values in the M14 and NCI-H460 human cancer cell lines. IC$_{50}$ is defined as the concentration of compound necessary to achieve 50% of the maximum growth inhibition.

For the antiproliferation assay, NCI-H460 (large cell lung carcinoma) or M14 (amelanotic melanoma) cells were grown in RPMI-1640 with 10% FBS supplemented with L-glutamine and HEPES. Cells were seeded into 96-well plates at 5×10$^2$ to 5×10$^4$ cells/well and allowed to adhere overnight; the medium was then removed. A stock solution of test compound in DMSO was diluted in medium to generate a series of working solutions. Aliquots (100 µl) of the working solutions were then added to the appropriate test wells to expose cells to the final concentrations of compound in a total volume of 100 µl. Seven different concentrations were tested, with 2-5 wells per concentration. Camptothecin was used as a positive control; wells containing vehicle without compound were used as negative controls. Plates were kept for 72 h in a 37° C., 5% CO$_2$ incubator. After incubation, viable cells were detected with the CELLTITER 96 AQ$_{ueous}$ Non-Radioactive Cell Proliferation Assay (Promega), and IC$_{50}$ values were determined using GraphPad Prism 5 software.

TABLE 3

Phenethyldihydrobenzodioxolone analogues with $R^3$ = F and their $IC_{50}$ values for inhibition of proliferation of cell lines M14 and NCI-H460.

Chemical Structure

| Compound | $R^2$ | $R^6$ | $R^5$ | ⌇ | M14 $IC_{50}$ (μM) | NCI-H460 $IC_{50}$ (μM) |
|---|---|---|---|---|---|---|
| 2 | —H | —H | —H | ⋯⋯‖‖ | 0.011 | 0.088 |
| 3 | —H | —H | —H | ◀ | 0.013 | 0.077 |
| 8 | —CH₃ | —H | —H | ⋯⋯‖‖ | 0.23 | 0.65 |
| 91 | phenyl | —H | —H | ⋯⋯‖‖ | >20 | >20 |
| 92 | —CH₂C(O)OH | —H | —H | — | >20 | >20 |
| 9 | —CH₂C(O)OCH₃ | —H | —H | ◀ | 0.21 | 0.26 |
| 10 | —CH₂C(O)OCH₃ | —H | —H | ⋯⋯‖‖ | >20 | 2.2 |
| 11 | —CH₂C(O)NH₂ | —H | —H | — | 0.004 | 0.33 |
| 13 | —CH₂C(O)NHCH₃ | —H | —H | ◀ | 0.19 | 0.37 |
| 12 | —CH₂C(O)NHCH₃ | —H | —H | ⋯⋯‖‖ | 0.24 | 0.52 |
| 93 | —CH₂C(O)N(CH₃)₂ | —H | —H | ◀ | >20 | >20 |

TABLE 3-continued

Phenethyldihydrobenzodioxolone analogues with $R^3$ = F and their $IC_{50}$ values for inhibition of proliferation of cell lines M14 and NCI-H460.

Chemical Structure

| Compound | $R^2$ | $R^6$ | $R^5$ | ~~~ | M14 $IC_{50}$ (μM) | NCI-H460 $IC_{50}$ (μM) |
|---|---|---|---|---|---|---|
| 94 | —C(O)N(CH₃)₂ | —H | —H | ·····⁞⁞⁞ | >20 | >20 |
| 14 | —C≡N | —H | —H | ·····⁞⁞⁞ | 0.037 | 0.15 |
| 95 | tetrazole | —H | —H | ·····⁞⁞⁞ | >20 | >20 |
| 5 | —OH | —H | —H | ·····⁞⁞⁞ | 0.009 | 0.033 |
| 4 | —OH | —H | —H | ◢ | 0.011 | 0.015 |
| 15 | —OCH₃ | —H | —H | ·····⁞⁞⁞ | 0.014 | 0.12 |
| 16 | —O-allyl | —H | —H | ◢ | 0.52 | 0.62 |
| 17 | —NH₂ | —H | —H | ·····⁞⁞⁞ | 0.029 | 0.16 |
| 19 | —NHC(O)CH₃ | —H | —H | ◢ | 0.052 | 0.071 |
| 18 | —NHC(O)CH₃ | —H | —H | ·····⁞⁞⁞ | 0.16 | 0.41 |
| 6 | —F | —H | —H | ◢ | 0.010 | 0.035 |
| 7 | —F | —H | —H | ·····⁞⁞⁞ | 0.023 | 0.059 |
| 20 | —H | —OCH₃ | —H | ·····⁞⁞⁞ | 0.71 | |
| 21 | —H | —OCH₃ | —H | ◢ | 2.8 | 3.0 |
| 22 | —H | —F | —H | ◢ | 0.90 | 2.4 |
| 23 | —H | —H | —F | ◢ | 0.27 | 0.72 |

TABLE 4

Phenethyldihydrobenzodioxolone compounds analogues with $R^1 = -OCH_3$ and their $IC_{50}$ values for inhibition of proliferation of cell lines M14 and NCI-H460.

Chemical Structure

| Compound | $R^2$ | ⌇ | M14 $IC_{50}$ (μM) | NCI-H460 $IC_{50}$ (μM) |
|---|---|---|---|---|
| 24 | —$OCH_3$ | ◀ | 0.11 | 0.32 |
| 25 | —H | ⋯⋮⋮ | 0.061 | 0.088 |
| 26 | —H | ◀ | 0.081 | 0.075 |
| 27 | —$CH_3$ | ⋯⋮⋮ | 0.41 | 0.63 |
| 28 | —$CH_2OH$ | ◀ | 10 | 4.2 |
| 96 | —C(O)CH₃ | ⋯⋮⋮ | >20 | >20 |
| 29 | —C(O)NH₂ | ⋯⋮⋮ | 0.012 | 0.066 |
| 30 | —C(O)NHCH₃ | ⋯⋮⋮ | 1.4 | 1.1 |
| 73 | —C(O)N(CH₃)₂ | ⋯⋮⋮ | >20 | >20 |
| 31 | —C≡N | ⋯⋮⋮ | 0.18 | 0.34 |
| 32 | —OH | ⋯⋮⋮ | 0.0079 | 0.083 |
| 33 | —OAc | — | 0.016 | 0.11 |
| 34 | —$NH_2$ | — | 0.049 | 0.18 |
| 97 | —N(CH₃)₂ | ◀ | >20 | >20 |
| 98 | —N-morpholino | ⋯⋮⋮ | >20 | >20 |

TABLE 4-continued

Phenethyldihydrobenzodioxolone compounds analogues with R¹ = —OCH₃ and their IC₅₀ values for inhibition of proliferation of cell lines M14 and NCI-H460.

Chemical Structure

| Compound | R² | ~~~ | M14 IC₅₀ (μM) | NCI-H460 IC₅₀ (μM) |
|---|---|---|---|---|
| 35 | -NH-C(O)CH₃ | ·····IIII | 0.085 | 0.31 |
| 36 | -NH-CH₂CH=CH₂ | — | 0.72 | 1.9 |
| 37 | —F | ·····IIII | 0.008 | 0.085 |
| 38 | —Cl | ·····IIII | 0.24 | 0.64 |
| 39 | —Cl | ◀ | 0.13 | 0.42 |

TABLE 5

Phenethyldihydrobenzodioxolone analogues with R¹ ≠ —OCH₃ and their IC₅₀ values for inhibition of proliferation of cell lines M14 and NCI-H460.

Chemical Structure

| Compound | R¹ | R² | R³ | ~~~ | M14 IC₅₀ (μM) | NCI-H460 IC₅₀ (μM) |
|---|---|---|---|---|---|---|
| 99 | —OH | —H | —H | ·····IIII | >20 | >20 |
| 40 | —OCH₂CH₃ | —H | —H | — | 0.65 | 2 |
| 100 | —OAc | —H | —H | ·····IIII | >20 | >20 |
| 41 | —OCF₃ | —H | —H | ·····IIII | >20 | 3.8 |
| 101 | —OCH₂CH₂OCH₃ | —F | —H | ◀ | >20 | >20 |
| 42 | —NH₂ | —F | —H | ·····IIII | 0.81 | 2.5 |

TABLE 5-continued

Phenethyldihydrobenzodioxolone analogues with R¹ ≠ —OCH₃ and their IC₅₀ values for inhibition of proliferation of cell lines M14 and NCI-H460.

Chemical Structure

| Compound | R¹ | R² | R³ | ⌇ | M14 IC₅₀ (µM) | NCI-H460 IC₅₀ (µM) |
|---|---|---|---|---|---|---|
| 43 | —NH—CH₃ | —F | —H | (wedge) | 0.064 | 0.30 |
| 44 | —NH—CH₃ | —F | —F | (wedge) | 0.016 | 0.068 |
| 45 | —NH—CH₃ | —F | —F | (hashed) | 0.098 | 0.34 |
| 46 | —N(CH₃)₂ | —F | —H | (wedge) | 0.64 | 1.4 |
| 47 | —N(CH₃)₂ | —F | —F | (wedge) | 0.075 | 0.33 |
| 48 | —N(CH₃)₂ | —F | —F | (hashed) | 0.07 | 0.33 |
| 102 | —NHC(O)CH₃ | —F | —H | (hashed) | >20 | >20 |
| 103 | —N(CH₃)C(O)CH₃ | —H | —H | (hashed) | >20 | >20 |
| 116 | —SCH₃ | —F | —F | (hashed) | 0.12 | 0.19 |

TABLE 6

Additional phenethyldihydrobenzodioxolone analogues with substitutions on the aromatic ring, and their IC$_{50}$ values for inhibition of proliferation of cell lines M14 and NCI-H460.

Chemical Structure

| Compound | R$^3$ | R$^6$ | R$^1$ | R$^2$ | ∼∼∼ | M14 IC$_{50}$ (μM) | NCI-H460 IC$_{50}$ (μM) |
|---|---|---|---|---|---|---|---|
| 49 | —H | —H | —H | —H | ·······⫿⫿⫿ | 5.1 | 9.7 |
| 50 | —H | —OCH$_3$ | —H | —H | ·······⫿⫿⫿ | 8.8 | 10.6 |
| 51 | —CH$_3$ | —H | —OCH$_3$ | —H | ◀━━ | 0.28 | 0.78 |
| 52 | —OCH$_3$ | —H | —OCH$_3$ | —H | — | 15 | 15 |
| 53 | —OAc | —H | —OCH$_3$ | —H | ·······⫿⫿⫿ | 0.27 | 2.3 |
| 54 | —Cl | —H | —OCH$_3$ | —H | ◀━━ | 0.045 | 0.32 |
| 55 | —H | —F | —OCH$_3$ | —F | — | 3.3 | 3.8 |

TABLE 7

Phenethyldihydrobenzodioxolone analogues with substitutions at R$^4$, and their IC$_{50}$ values for inhibition of proliferation of cell lines M14 and NCI-H460.

Chemical Structure

| Compound | R$^4$ | R$^2$ | R$^3$ | ∼∼∼ | M14 IC$_{50}$ (μM) | NCI-H460 IC$_{50}$ (μM) |
|---|---|---|---|---|---|---|
| 104 | —H | —OH | —F | ·······⫿⫿⫿ | >20 | >20 |
| 56 | —CH$_3$ | —F | —F | — | 0.14 | 0.43 |
| 57 | —CH$_2$CH$_3$ | —F | —F | ·······⫿⫿⫿ | 0.14 | 0.20 |
| 58 | —CH$_2$CH$_3$ | —F | —F | ◀━━ | 0.29 | 0.44 |
| 70 | —CH$_2$CH$_2$CH$_3$ | —OCH$_3$ | —H | ·······⫿⫿⫿ | 7.4 | >4 |
| 59 | —CH$_2$CH$_2$CH$_3$ | —OH | —F | ·······⫿⫿⫿ | 0.058 | 0.17 |
| 60 | —CH$_2$CH$_2$CH$_3$ | —OH | —F | ◀━━ | 0.0059 | 0.067 |
| 61 | —CH$_2$CH$_2$CH$_3$ | —F | —F | ◀━━ | 0.017 | 0.14 |
| 77 | sec-butyl | —OH | —F | ·······⫿⫿⫿ | 0.11 | 0.55 |

TABLE 7-continued

Phenethyldihydrobenzodioxolone analogues with substitutions at $R^4$, and their $IC_{50}$ values for inhibition of proliferation of cell lines M14 and NCI-H460.

Chemical Structure

| Compound | $R^4$ | $R^2$ | $R^3$ | ⁓ | M14 $IC_{50}$ (μM) | NCI-H460 $IC_{50}$ (μM) |
|---|---|---|---|---|---|---|
| 65 | methoxymethyl | —OH | —F | ┈┈ | 0.64 | 1.2 |
| 78 | methoxyethyl | —OH | —F | ┈┈ | 0.19 | 0.27 |
| 109 | hydroxyisopropyl | —OH | —F | ┈┈ | 0.65 | 1.5 |
| 76 | methylthioethyl | —OH | —F | ┈┈ | 0.30 | 0.45 |
| 115 | ethylthiomethyl | —H | —F | ┈┈ | 11.3 | >20 |
| 74 | propenyl | —OH | —F | ▬ | 0.12 | 0.29 |
| 75 | propenyl | —OH | —F | ┈┈ | 0.51 | 0.86 |
| 80 | methylallyl | —OH | —F | ┈┈ | 0.22 | 0.37 |
| 112 | methylallyl | —H | —F | ┈┈ | 0.044 | 0.068 |
| 90 | dimethylallyl | —OCH₃ | —H | ┈┈ | 7.0 | 8.0 |
| 105 | butenyl | —OCH₃ | —H | ┈┈ | >20 | >20 |

TABLE 7-continued

Phenethyldihydrobenzodioxolone analogues with substitutions at R⁴, and their IC$_{50}$ values for inhibition of proliferation of cell lines M14 and NCI-H460.

| Compound | R⁴ | R² | R³ | ∿∿ | M14 IC$_{50}$ (μM) | NCI-H460 IC$_{50}$ (μM) |
|---|---|---|---|---|---|---|
| 67 | CH₃-CH=CH-CH₂- | —H | —F | ·······ııı | 0.21 | 0.25 |
| 106 | CH₃-C(O)-CH₂- | —OCH₃ | —H | ·······ııı | >20 | >20 |
| 111 | CH₃-C(O)-CH₂- | —OH | —F | ·······ııı | 7.0 | 15 |
| 62 | HC≡C-CH₂- | —H | —F | ·······ııı | 0.20 | 0.073 |
| 110 | HC≡C-CH(CH₃)- | —H | —F | ·······ııı | 0.29 | 0.13 |
| 63 | cyclopropyl-CH₂- | —H | —F | ·······ııı | >20 | 1.7 |
| 66 | Ph-CH₂- | —OH | —F | ·······ııı | 1.6 | 2.6 |
| 113 | furan-2-yl-CH₂- | —OH | —F | ·······ııı | 1.6 | 2.5 |
| 114 | pyridin-4-yl-CH₂- | —OH | —F | ·······ııı | 3.5 | 2.0 |
| 71 | Ph-CH=CH-CH₂- | —OCH₃ | —H | ·······ııı | 6.4 | 14 |

TABLE 7-continued

Phenethyldihydrobenzodioxolone analogues with substitutions at R⁴, and their IC₅₀ values for inhibition of proliferation of cell lines M14 and NCI-H460.

| Compound | R⁴ | R² | R³ | ⌇ | M14 IC$_{50}$ (μM) | NCI-H460 IC$_{50}$ (μM) |
|---|---|---|---|---|---|---|
| 69 | F-CH₂CH₂CH₂- | —OH | —F | ·······‖‖ | 0.57 | 0.51 |
| 107 | F-CH₂CH₂CH₂- | —OCH₃ | —H | — | >20 | >20 |
| 64 | CH₂=CF-CH₂- | —H | —F | ·······‖‖ | 0.14 | 0.22 |
| 79 | CH₂=CCl-CH₂- | —H | —F | ·······‖‖ | 1.3 | 2.5 |
| 68 | F₂C=CH-CH₂- | —H | —F | ·······‖‖ | 0.86 | 0.82 |

TABLE 8

Additional phenethyldihydrobenzodioxolone compounds analogues and their IC₅₀ values for inhibition of proliferation of cell lines M14 and NCI-H460.

| Compound | Chemical Structure | M14 IC$_{50}$ (μM) | NCI-H460 IC$_{50}$ (μM) |
|---|---|---|---|
| 83 | 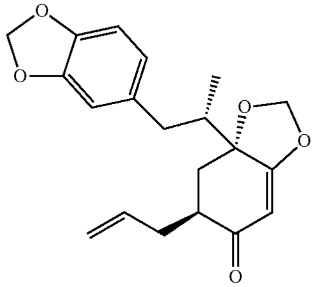 [SMILES: C=CC[C@H]1C[C@]2([C@@H](C)Cc3ccc4c(c3)OCO4)OCOC2=CC1=O] | 0.65 | 0.39 |

TABLE 8-continued

Additional phenethyldihydrobenzodioxolone compounds analogues and their IC$_{50}$ values for inhibition of proliferation of cell lines M14 and NCI-H460.

| Compound | Chemical Structure | M14 IC$_{50}$ (μM) | NCI-H460 IC$_{50}$ (μM) |
| --- | --- | --- | --- |
| 84 | 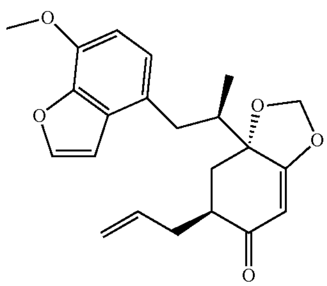 [SMILES: C=CC[C@H]1C[C@]2([C@H](C)Cc3ccc(OC)c4occc34)OCOC2=CC1=O] | >20 | 2.6 |
| 85 | 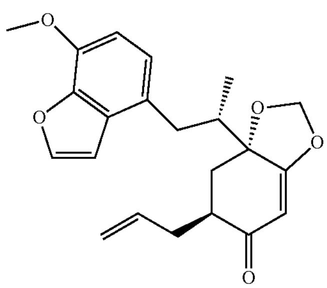 [SMILES: C=CC[C@H]1C[C@]2([C@@H](C)Cc3ccc(OC)c4occc34)OCOC2=CC1=O] | 0.63 | 0.73 |
| 86 | 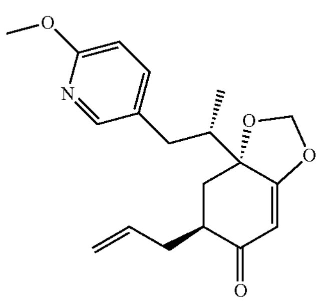 [SMILES: C=CC[C@H]1C[C@]2([C@@H](C)Cc3ccc(OC)nc3)OCOC2=CC1=O] | 0.18 | 0.33 |
| 87 | 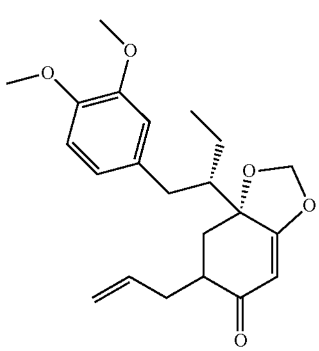 [SMILES: C=CCC1C[C@]2([C@@H](CC)Cc3ccc(OC)c(OC)c3)OCOC2=CC1=O] | 2.6 | 11 |

TABLE 8-continued

Additional phenethyldihydrobenzodioxolone compounds analogues and their IC$_{50}$ values for inhibition of proliferation of cell lines M14 and NCI-H460.

| Compound | Chemical Structure | M14 IC$_{50}$ (μM) | NCI-H460 IC$_{50}$ (μM) |
|---|---|---|---|
| 72 | 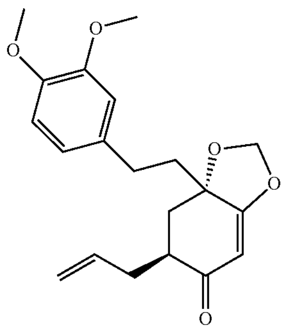 [SMILES: C=CC[C@H]1C[C@]2(CCc3ccc(OC)c(OC)c3)OCOC2=CC1=O] | 2.0 | 3.2 |
| 88 | 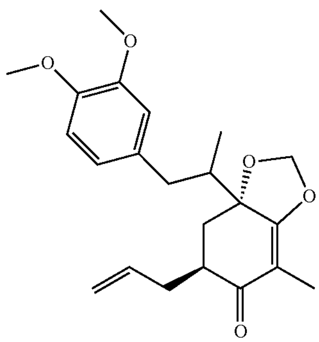 | 4.2 | 4.6 |
| 89 | 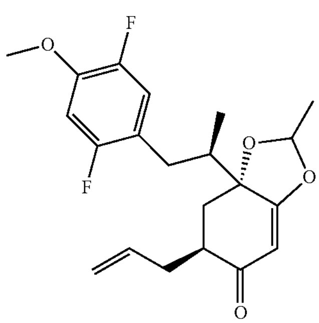 | >20 | 6.9 |
| 82 | 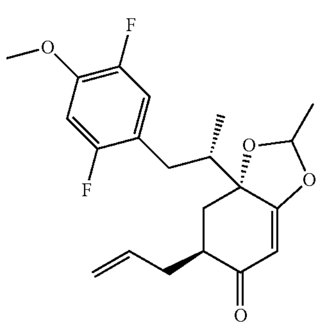 | >20 | 5.2 |

Example III

IC$_{50}$ Values for Selected Analogues in Multiple Cell Lines

Antiproliferation of several of the active compounds was tested against additional cell lines. IC$_{50}$ values in these cell lines are shown in Table 9.

B.-N., Hoch, J. M., Johnson, R. K., Mattern, M. R., Eng, W.-K., Ma, J., Hecht, S. M., Newman, D. J., Kingston, D. G. I., 2000. Use of COMPARE Analysis to Discover New Natural Product Drugs: Isolation of Camptothecin and 9-Methoxycamptothecin from a New Source. Journal of Natural Products 63, 1273-1276.). This analysis suggests without being bound by theory that bifidenone and Compound 37 act on microtubules.

TABLE 9

IC$_{50}$ values of selected compounds against cancer cell lines.
IC$_{50}$ (μM)

| Cell line | A549 | HCT-116 | K-562 | LOX-IMVI | MES-SA/Dx5 | MOLT-4 | NCI/ADR-RES | NCI-H187 | NCI-H441 |
|---|---|---|---|---|---|---|---|---|---|
| 26 | 0.11 | 0.022 | | 0.15 | | | | | |
| 2 | | | 0.076 | 0.056 | 0.052 | 0.11 | 0.045 | 0.091 | |
| 32 | | 0.013 | | 0.012 | | | 0.038 | 0.046 | 0.14 |
| 29 | | | 0.025 | 0.026 | 0.031 | 0.083 | 0.044 | | |
| 61 | | | | 0.053 | 0.084 | 0.12 | 0.063 | | |
| 4 | | | 0.013 | 0.011 | 0.013 | 0.028 | 0.0091 | 0.021 | |
| 6 | | | 0.028 | 0.018 | 0.014 | 0.081 | 0.013 | 0.022 | |

| Cell line | NCI-H526 | OVCAR-3 | OVCAR-4 | PC-3 | SK-Mel-2 | SK-Mel-5 | U-87 MG | UACC-62 |
|---|---|---|---|---|---|---|---|---|
| 26 | | | | 0.066 | 0.11 | 0.034 | 0.10 | 0.096 |
| 2 | | 0.060 | | | | | | |
| 32 | 0.079 | | | | | | | |
| 29 | | 0.057 | | | 0.0092 | | | |
| 61 | | | 0.037 | | | | | |
| 4 | | 0.012 | 0.0064 | | | | | |
| 6 | | 0.038 | | | | | | |

Example IV

Activity Against Drug-Resistant Cell Lines

Compound 4 was tested for antiproliferation activity against several paclitaxel-resistant human cancer cell lines. IC$_{50}$ values are listed in Table 10. Compound 4 is more potent than paclitaxel against at least eight cancer cell lines.

TABLE 10

IC$_{50}$ values of compound 4 against paclitaxel-resistant cancer cell lines.

| | IC$_{50}$ (nM) | |
|---|---|---|
| Cell Line | 4 | paclitaxel |
| NCI/ADR-RES | 9 | 9600 |
| MES-SA/Dx5 | 14 | 5000 |
| UO-31 | 7 | 240 |
| HCT-15 | <5 | 165 |
| EKVX | 7 | 150 |
| DLD-1 | <5 | 90 |
| ACHN | 15 | 90 |
| TK-10 | 7 | 80 |

Example V

NCI-60 Panel and COMPARE Analysis

Bifidenone and Compound 37 were tested for antiproliferation activity against the NCI-60 panel of cancer cell lines. The IC$_{50}$ values are shown in Table 11. COMPARE analysis was then conducted to compare the activity "fingerprint" of bifidenone to those of known classes of compounds (Zhou,

TABLE 11

IC$_{50}$ values for bifidenone and 37 against the NCI 60-cell panel.

| | IC$_{50}$ (μm) | |
|---|---|---|
| Cell Line | bifidenone | 37 |
| A498 | 0.46 | 0.058 |
| A549 | 0.26 | 0.055 |
| ACHN | 0.85 | 0.032 |
| BT-549 | 0.18 | 0.063 |
| Caki-1 | 0.10 | 0.097 |
| CCRF-CEM | 0.15 | 0.060 |
| COLO205 | 0.40 | 0.067 |
| DU-145 | 0.84 | 0.187 |
| EKVX | 0.28 | 0.149 |
| HCC-2998 | 1.41 | 0.129 |
| HCT-15 | 0.23 | 0.056 |
| HCT-116 | 0.49 | 0.115 |
| HL-60 | 0.12 | 0.036 |
| HOP-62 | 0.32 | 0.102 |
| HOP-92 | 0.24 | >10 |
| Hs578T | 0.21 | 0.072 |
| HT29 | 0.31 | 0.088 |
| IGR-OV1 | 0.42 | 0.063 |
| K-562 | 0.18 | 0.043 |
| KM12 | 0.32 | 0.055 |
| LOX IMVI | 0.39 | 0.027 |
| M14 | 0.20 | 0.059 |
| MALME-3M | 0.09 | 0.039 |
| MCF-7 | 0.17 | 0.063 |
| MDA-MB-231 | 0.26 | 0.837 |
| MDA-MB-435 | 0.07 | 0.028 |
| MDA-MB-468 | 0.30 | 0.059 |
| MOLT-4 | 0.17 | 0.097 |
| NCI-ADR/RES | 0.17 | 0.047 |
| NCI-H23 | 0.61 | 0.123 |
| NCI-H226 | 0.81 | 0.141 |
| NCI-H322M | 0.46 | 0.125 |
| NCI-H460 | 0.32 | 0.049 |
| NCI-H522 | 0.15 | 0.061 |
| OVCAR-3 | 0.17 | 0.040 |
| OVCAR-4 | 0.29 | 0.117 |

TABLE 11-continued

IC$_{50}$ values for bifidenone
and 37 against the NCI 60-cell panel.

| Cell Line | IC$_{50}$ (μm) bifidenone | 37 |
|---|---|---|
| OVCAR-5 | 0.52 | 0.119 |
| OVCAR-8 | 0.47 | 0.110 |
| PC-3 | 0.19 | 0.070 |
| RPMI-8226 | 0.25 | 0.074 |
| RXF-393 | 0.78 | 0.095 |
| SF-268 | 0.22 | 0.623 |
| SF-295 | 0.41 | 0.048 |
| SF-539 | 0.26 | 0.074 |
| SK-MEL-2 | 0.13 | 0.051 |
| SK-MEL-5 | 0.25 | 0.060 |
| SK-MEL-28 | 0.13 | 0.037 |
| SK-OV-3 | 0.27 | 0.039 |
| SN12C | 0.33 | 0.35 |
| SNB-19 | 0.30 | 0.073 |
| SNB-75 | 0.27 | 0.049 |
| SR | 0.08 | 0.014 |
| SW-620 | 0.13 | 0.047 |
| T-47D | 0.25 | >10 |
| TK-10 | 0.33 | 0.107 |
| U251 | 0.61 | 0.123 |
| UACC-62 | 0.14 | 0.035 |
| UACC-257 | 0.16 | 0.043 |
| UO-31 | 0.57 | 0.065 |
| 786-0 | 0.32 | 0.12 |

Example VI

Pharmacokinetics

The bioavailabilities of certain compounds were examined in mice. Administration of the compounds was performed by intraperitoneal (IP) injection using a vehicle as known to those skilled in the art. To measure compound concentrations in plasma, blood is collected by cardiac puncture at a specified time after closing. It is then centrifuged in a plasma separator tube with NaEDTA/NaF as the anticoagulant, and the resulting plasma is stored at −80° C. For analysis, an internal standard is added to a 200 μL aliquot of plasma, and the aliquot is extracted with ethyl acetate. The ethyl acetate extract is analyzed by LC/MS and quantitated using a standard curve prepared by adding known amounts of test compound and internal standard to 200 μL aliquots of blank mouse plasma.

Many vehicles can be used to examine bioavailability. Prior to administration, each vehicle was optimized based on compound solubility according to the formulation research conducted by Uckun et at (Uckun, F. M., Tibbles, H., Erbeck, D., Venkatachalam, T. K., Qazi, S., 2007. In vivo pharmacokinetics and toxicity of a novel hydrophilic oral formulation of the potent non-nucleoside reverse transcriptase inhibitor compound N'-[2-(2-thiophene)ethyl]-N'-[2-(5-bromopyridyl)]-thiourea (HI-443). Arzneimittelforschung 57, 218-226.). Based on this publication, vehicles containing approximate ratios of 2:1:1 of propylene glycol:TWEEN-20: PEG400 (TWEEN-20 being a common emulsifier used in formulations and food products) and less than 5% ethanol upon administration exhibit good solubility properties and increase serum bioavailability. During these experiments, PEG400 demonstrated a critical role in serum bioavailability. The concentration of PEG400 is modulated depending upon solubility of the compounds and the amount of water phase added.

Optimization of the vehicle for IP injection of compound 2 began with a vehicle containing 40.5% propylene glycol, 9% TWEEN-20, 24.3% PEG400, 16.2% ethanol, 10% water (v/v). IP injection (40 mg/kg) using this vehicle gave plasma concentrations of compound 2 that were >2 times its IC$_{50}$ against NCI-H460 human lung cancer cells (IC$_{50}$=90 nM) 1 h after injection. Plasma concentrations were increased by decreasing the proportion of TWEEN-20 while increasing the proportion of propylene glycol and PEG400. Using the optimized compound 2 vehicle, consisting of 42.97% propylene glycol, 0.23% TWEEN-20, 31.5% PEG400, 15.3% ethanol, 10% water (v/v), injections of 40 mg/kg resulted in 2 plasma concentrations >6 times the IC$_{50}$ at 30 min and 1 h, and >4 times the IC$_{50}$ at 3 h.

Optimization of the vehicle for IP injection of compound 4 began with a vehicle containing 42.97% propylene glycol, 0.23% TWEEN-20, 31.5% PEG400, 15.3% ethanol, 10% water (v/v). IP injection (40 mg/kg) using this vehicle gave plasma concentrations of compound 4 that were below its IC$_{50}$ against NCI-H460 human lung cancer cells (IC$_{50}$=15 nM) 3-5 h after injection. Plasma concentrations were increased by increasing the proportion of TWEEN-20. Using the optimized compound 2 vehicle, consisting of 40.5% propylene glycol, 9% Tween-20, 24.3% PEG400, 16.2% ethanol, 10% water (v/v), injections of 40 mg/kg resulted in plasma concentrations of compound 4 that were >10 times the IC$_{50}$ at 1-3 h, and >8 times the IC$_{50}$ at 5 h.

Plasma concentrations were measured for several additional compounds. Table 12 lists plasma concentrations (as a multiple of the compound's IC$_{50}$ against NCI-H460 cells) measured for these compounds at different time points after injection, along with the vehicle used. Based on these results, many of the compounds described herein would yield bioavailability. This example demonstrates that the compounds of the invention can be formulated into tablets, capsules, suppositories, and sterile liquids for parenteral administration as known to those skilled in the art.

TABLE 12

Compound concentrations in mouse plasma.

| Compound | Dose (mg/kg) | Vehicle | Plasma concentration/IC$_{50}$[1] |
|---|---|---|---|
| 25 | 40 | 40.5% propylene glycol 9% TWEEN-20 24.3% PEG400 16.2% EtOH 10% water | 30 min: >10 1 h: 1 |
| 37 | 40 | 40.5% propylene glycol 9% TWEEN-20 24.3% PEG400 16.2% EtOH 10% water | 30 min: >6 1 h: >7 3 h: >7 |
| 32 | 40 | 47.75% propylene glycol 0.25% TWEEN-20 35% PEG400 17% EtOH | 30 min: >10 1 h: >10 3 h: >4 |
| 15 | 40 | 47.75% propylene glycol 0.25% TWEEN-20 35% PEG400 17% EtOH | 30 min: >5 1 h: 2 3 h: 1 |
| 33 | 40 | 42.97% propylene glycol 0.23% TWEEN-20 31.5% PEG400 15.3% EtOH 10% water | 30 min: 10 1 h: >4 3 h: 2 |
| 6 | 40 | 42.97% propylene glycol 0.23% TWEEN-20 31.5% PEG400 | 3 h: >8 5 h: >7 |

TABLE 12-continued

Compound concentrations in mouse plasma.

| Compound | Dose (mg/kg) | Vehicle | Plasma concentration/IC$_{50}$[1] |
|---|---|---|---|
| 5 | 40 | 15.3% EtOH<br>10% water<br>40.5% propylene glycol<br>9% TWEEN-20<br>24.3% PEG400<br>16.2% EtOH<br>10% water | 1 h: >10<br>3 h: >7 |
| 7 | 40 | 42.97% propylene glycol<br>0.23% TWEEN-20<br>31.5% PEG400<br>15.3% EtOH<br>10% water | 3 h: >2<br>5 h: >1 |

[1]Concentrations of compound in plasma were normalized by dividing by the compound's IC$_{50}$ against NCI-H460 lung cancer cells.

[1]Concentrations of compound in plasma were normalized by dividing by the compound's IC$_{50}$ against NCI-H460 lung cancer cells.

Accumulation of certain compounds in tumor tissue was also examined in mice. To measure compound concentrations in tumor tissue, mice are prepared with NCI-H460 xenograft tumors as described in EXAMPLE IX. Compounds are administered to mice with tumor volumes between approximately 500 and 4000 mm$^3$. At a specified time after dosing, mice are euthanized and the tumors are excised. Two samples (approximately 200 mg) of each tumor are then weighed, homogenized in 300 µL of 3% SDS, and extracted twice with 600 µL ethyl acetate. The ethyl acetate extract is analyzed by LC/MS and quantitated using a standard curve prepared by adding known amounts of test compound and internal standard to samples of tumor tissue from untreated mice. Concentrations of selected compounds in tumor tissues in individual experiments are listed in Table 13.

TABLE 13

Compound concentration in xenograft tumor tissue.

| Compound | Dose (mg/kg) | Vehicle | Tumor concentration/IC$_{50}$[1] |
|---|---|---|---|
| 2 | 40 | 42.97% propylene glycol<br>0.23% TWEEN-20<br>31.5% PEG400<br>15.3% EtOH<br>10% water | 6 h: >1 |
| 2 | 80 | 42.97% propylene glycol<br>0.23% TWEEN-20<br>31.5% PEG400<br>15.3% EtOH<br>10% water | 3 h: 4<br>6 h: >1<br>10 h: 1 |
| 4 | 40 | 40.5% propylene glycol<br>9% TWEEN-20<br>24.3% PEG400<br>16.2% EtOH<br>10% water | 3 h: >10<br>5 h: >10 |
| 4 | 30 | 40.5% propylene glycol<br>9% TWEEN-20<br>24.3% PEG400<br>16.2% EtOH<br>10% water | 5 h: >10 |
| 4 | 20 | 40.5% propylene glycol<br>9% TWEEN-20<br>24.3% PEG400<br>16.2% EtOH<br>10% water | 5 h: >5 |
| 4 | 10 | 40.5% propylene glycol<br>9% TWEEN-20<br>24.3% PEG400<br>16.2% EtOH<br>10% water | 5 h: >1 |
| 4 | 20 | 41.4% propylene glycol<br>5.4% TWEEN-20<br>27% PEG400<br>16.2% EtOH<br>10% water | 5 h: >3 |
| 4 | 20 | 42.3% propylene glycol<br>1.8% TWEEN-20<br>30.6% PEG400<br>15.3% EtOH<br>10% water | 5 h: >3 |
| 29 | 40 | 40.5% propylene glycol<br>9% TWEEN-20<br>24.3% PEG400<br>16.2% EtOH<br>10% water | 3 h: >9<br>5 h: >2 |
| 6 | 40 | 42.97% propylene glycol<br>0.23% TWEEN-20<br>31.5% PEG400<br>15.3% EtOH<br>10% water | 3 h: >3<br>5 h: >3 |
| 5 | 40 | 40.5% propylene glycol<br>9% TWEEN-20<br>24.3% PEG400<br>16.2% EtOH<br>10% water | 3 h: 2<br>5 h: <1 |
| 7 | 40 | 42.97% propylene glycol<br>0.23% TWEEN-20<br>31.5% PEG400<br>15.3% EtOH<br>10% water | 3 h: >8<br>5 h: 5 |
| 61 | 40 | 42.97% propylene glycol<br>0.23% TWEEN-20<br>31.5% PEG400<br>15.3% EtOH<br>10% water | 3 h: 2<br>5 h: 1 |
| 59 | 40 | 40.5% propylene glycol<br>9% TWEEN-20<br>24.3% PEG400<br>16.2% EtOH<br>10% water | 3 h: >1<br>5 h: 1 |
| 60 | 40 | 40.5% propylene glycol<br>9% TWEEN-20<br>24.3% PEG400<br>16.2% EtOH<br>10% water | 3 h: >2<br>5 h: 2 |
| 3 | 40 | 42.97% propylene glycol<br>0.23% TWEEN-20<br>31.5% PEG400<br>15.3% EtOH<br>10% water | 6 h: >3<br>10 h: >3 |

[1]Concentrations of compound in plasma were normalized by dividing by the compound's IC$_{50}$ against NCI-H460 lung cancer cells.

[1]Concentrations of compound in plasma were normalized by dividing by the compound's IC$_{50}$ against NCI-H460 lung cancer cells.

Example VII

Prodrugs

Several positions may be modified to form a prodrug. One such position is the hydroxyl group at R$^2$. Compounds in this invention have been modified at the R$^2$ position to make derivatives including compounds 33, 73, 81, and 108. Such compounds, upon administration to an animal, are capable of providing active compounds described in this invention.

Compound 33 was administered to mice as described in Exmple IX, and plasma was analyzed after 30 min, 1 h, and 3 h. At each time point, compound 32, but not compound 33 was detected in the plasma. Thus, it appeared that compound 33 had lost an acetate group to provide compound 32. In a similar experiment, compound 108 was administered to mice; after 3 h, compound 5 was detected in the mouse plasma, consistent with loss of the $R^2$ group from compound 108 in the mouse. In a similar experiment, compound 81 was administered to mice; after 3 h, compound 4 was detected in the mouse plasma, consistent with loss of the $R^2$ group from compound 81 in the mouse.

Example VIII

Salts

As stated herein, the invention also includes compounds and their salts. The HCl salt of compound 66 was prepared, and the salt retained activity in the in vitro antiproliferation assay ($IC_{50}$ 5-7 μM).

Example IX

In Vivo Efficacy In Mouse Xenograft Models

Tumor growth inhibition of compound 4 was measured in several murine xenograft models, and the results of individual experiments are listed in Table 14. Tumors were initiated by subcutaneous injection of either tumor cells from cell culture or tumor fragments from continuous in vivo passage. When tumors reached volumes between approximately 100 and 200 $mm^3$, the mice were divided into vehicle and treatment groups. Compound or vehicle was administered by IP injection in a volume of 5-10 mL/kg.

TABLE 14

In vivo efficacy in mouse xenograft models.

| Cell line | Dose (mg/kg) | Days Dosed | Maximum Mean Body Weight Loss (%) | Optimal T/C (%)[a] |
|---|---|---|---|---|
| NCI-H460 (lung) | 60 | 0, 1, 2, 5, 6, 7, 10, 11, 12 | 9 | 40 |
| | 40 | 0, 1, 2, 5, 6, 7, 10, 11, 12 | 7 | 29 |
| | 40 | 0, 1, 2, 5, 6, 7, 10, 11, 12 | 7 | 35 |
| | 30 | 0, 1, 2, 3, 5, 6, 7, 8, 10, 11, 12, 13 | 7 | 42 |
| NCI-H522 (lung) | 40 | 0, 1, 2, 5, 6, 7, 10, 11, 12 | 5 | 13 |
| NCI-H727 | 40 | 0, 1, 2, 5, 6, 7, 10, 11, 12 | 0 | 30 |
| LOX-IMVI (melanoma) | 40 | 0, 1, 2, 5, 6, 7 | 9 | 39 |
| | 30 | 0, 1, 2, 3, 4, 5 | 7 | 31 |
| | 30 | 0, 1, 2, 3, 4, 5, 6 | 6 | 36 |

[a]Changes in tumor weight (delta weights) for each treated (T) and control (C) group are calculated for each day tumors are measured by subtracting the median tumor weight on the first day of treatment (staging day) from the median tumor weight on the specified observation day. These values are used to calculate a percent T/C as follows: % T/C = (delta T/delta C) × 100. The optimal T/C is the minumul value obtained after the first treatment.

Changes in tumor weight (delta weights) for each treated (T) and control (C) group are calculated for each day tumors are measured by subtracting the median tumor weight on the first day of treatment (staging day) from the median tumor weight on the specified observation day. These values are used to calculate a percent T/C as follows: % T/C=(delta T/delta C)×100. The optimal T/C is the minimal value obtained after the first treatment.

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

It is intended that all patentable subject matter disclosed herein be claimed and that no such patentable subject matter be dedicated to the public. Thus, it is intended that the claims be read broadly in light of that intent. In addition, unless it is otherwise clear to the contrary from the context, it is intended that all references to "a" and "an" and subsequent corresponding references to "the" referring back to the antecedent basis denoted by "a" or "an" are to be read broadly in the sense of "at least one." Similarly, unless it is otherwise clear to the contrary from the context, the word "or," when used with respect to alternative named elements is intended to be read broadly to mean, in the alternative, any one of the named elements, any subset of the named elements or all of the named elements.

In view of the above, it will be seen that the several advantages of the invention are achieved and other advantageous results obtained. It should be understood that the aforementioned embodiments are for exemplary purposes only and are merely illustrative of the many possible specific embodiments that can represent applications of the principles of the invention. Thus, as various changes could be made in the above methods and compositions without departing from the scope of the invention, it is intended that all matter contained in the above description as shown in the accompanying drawings shall be interpreted as illustrative and not in a limiting sense.

Moreover, one of ordinary skill in the art can make various changes and modifications to the invention to adapt it to various usages and conditions, including those not specifically laid out herein, without departing from the spirit and scope of this invention. Accordingly, those changes and modifications are properly, equitably, and intended to be, within the full range of equivalents of the invention disclosed and described herein.

What is claimed is:

1. A compound according to formula:

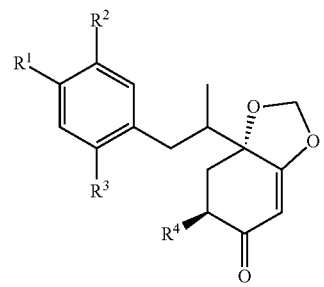

or stereoisomers thereof, wherein $R^1$ is selected from the group consisting of methoxy, ethoxy, —$SCH_3$, —$SCH_2CH_3$, and —$NR^8R^9$; $R^2$ is selected from the group consisting of hydrogen, hydroxyl, alkoxy, amino, aminoalkyl, aminoalkenyl, aminoalkynyl, halide, haloalkyl, hydroxyalkyl, —NHCN, aminocarbonyl, hydroxyaminocarbonyl, alkylaminocarbonyl, acyloxy, nitrile, —CH$_2$CN, lower alkyl, substituted lower alkyl, lower alkenyl, lower alkynyl, —SH, —SCH$_3$, alkoxycarbonyl, alkylcarbonylamino, —NHC(O)—O-lower alkyl, —NHC(O)—O-lower alkenyl, —NHC(O)—O-lower alkynyl, —NHCO-cyclopropyl, —NHCO—haloalkyl, —NHSO$_2$CH$_3$, —NHCSNHCH$_3$, sulfoximine, —CH=NOH, —SOCH$_3$, —SO$_2$CH$_3$, —NHSO$_2$CH$_3$, and —SO$_2$NH$_2$; R$^3$ is selected from the group consisting of hydrogen, halide, haloalkyl, hydroxyl, amino, methylamino, —CH$_2$OH, methoxy, lower alkyl, lower alkenyl, lower alkynyl, acyloxy, alkylcarbonylamino, —C(O)OCH$_3$, nitrile, and —CH$_2$CN; R$^4$ is selected from the group consisting of lower alkyl, substituted lower alkyl, lower alkenyl, substituted lower alkenyl, lower alkynyl, substituted lower alkynyl, alkoxy, alkoxyalkyl, alkoxyalkenyl, alkoxyalkynyl, alkyl ether, alkylthio, alkenylthio, alkynylthio, thioalkyl ether; R$^8$ and R$^9$ are independently selected from the group consisting of hydrogen, lower alkyl, substituted lower alkyl, lower alkenyl, and cycloalkyl, or pharmaceutically acceptable salts, solvates, or prodrugs thereof; provided that R$^2$ is not methoxy when R$^1$ is methoxy, R$^3$ is hydrogen, and R$^4$ is 2-propenyl.

2. A compound as set forth in claim 1 wherein R$^2$ is selected from the group consisting of hydrogen, hydroxyl, alkoxy, amino, aminoalkyl, aminoalkenyl, halide, haloalkyl, aminocarbonyl, hydroxyaminocarbonyl, alkylaminocarbonyl, acyloxy, nitrile, —CH$_2$CN, lower alkyl, lower alkenyl, alkoxycarbonyl, and alkylcarbonylamino; R$^3$ is selected from the group consisting of hydrogen, halide, haloalkyl, lower alkyl, ethenyl, ethynyl, acyloxy, —C(O)OCH$_3$, nitrile, and —CH$_2$CN; R$^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, alkylthio, alkenylthio, alkynylthio, and thioalkyl ether; and R$^8$ and R$^9$ are independently selected from the group consisting of hydrogen and lower alkyl.

3. A compound as set forth in claim 1 wherein R$^1$ is selected from the group consisting of methoxy, —NHCH$_3$, —N(CH$_3$)$_2$; R$^2$ is selected from the group consisting of hydrogen, hydroxyl, alkoxy, amino, aminoalkyl, aminoalkenyl, halide, haloalkyl, aminocarbonyl, hydroxyaminocarbonyl, methylaminocarbonyl, ethylaminocarbonyl, acetoxy, propionyloxy, nitrile, —CH$_2$CN, lower alkyl, ethenyl, ethynyl, alkoxycarbonyl, and alkylcarbonylamino; R$^3$ is selected from the group consisting of hydrogen, halide, haloalkyl, methyl, ethyl, propyl, acetoxy, —C(O)OCH$_3$, nitrile, and —CH$_2$CN; R$^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether and thioalkyl ether.

4. A compound as set forth in claim 3 wherein R$^2$ is selected from the group consisting of hydrogen, hydroxyl, methoxy, ethoxy, amino, —NHCH$_3$, halide, methyl, ethyl, propyl, ethenyl, ethynyl, aminocarbonyl, hydroxyaminocarbonyl, methylaminocarbonyl, acetoxy, propionyloxy, nitrile, —CH$_2$CN, alkoxycarbonyl, and alkylcarbonylamino.

5. A compound as set forth in claim 3 wherein R$^2$ is selected from the group consisting of hydrogen, hydroxyl, amino, fluoro, chloro, methyl, ethyl, aminocarbonyl, hydroxyaminocarbonyl, methylaminocarbonyl, ethylaminocarbonyl, acetoxy, nitrile, methylcarbonylamino, ethylcarbonylamino, and propylcarbonylamino; R$^3$ is selected from the group consisting of hydrogen, fluoro, chloro, methyl, ethyl, acetoxy, —C(O)OCH$_3$, nitrile, and —CH$_2$CN; R$^4$ is selected from the group consisting of substituted lower alkyl, lower alkenyl, substituted lower alkenyl, lower alkynyl, substituted lower alkynyl, and thioalkyl ether.

6. A compound as set forth in claim 3 wherein R$^4$ is selected from the group consisting of substituted lower alkyl, lower alkenyl, substituted lower alkenyl, lower alkynyl, and substituted lower alkynyl.

7. A compound as set forth in claim 3 wherein R$^4$ is selected from the group consisting of lower alkyl, lower alkenyl, and lower alkynyl.

8. A compound as set forth in claim 3 wherein R$^4$ is selected from the group consisting of ethyl, propyl, butyl, 1-methylpropyl, 1-propenyl, 2-propenyl, 1-butenyl, 2-butenyl, 3-butenyl, 1-methyl-2-propenyl, 2-methyl-2-propenyl, 1-propynyl, and 2-propynyl.

9. A compound as set forth in claim 1, or enantiomers thereof, wherein R$^1$ is selected from the group consisting of methoxy; wherein R$^2$ is selected from the group consisting of hydrogen, hydroxyl, amino, fluoro, chloro, methyl, ethyl, propyl, ethenyl, propenyl, haloalkyl, aminoalkyl, aminoalkenyl, alkoxy, aminocarbonyl, methylaminocarbonyl, ethylcarbonylamino, acetoxy, propionyloxy, nitrile, —CH$_2$CN, —C(O)OCH$_3$, ethylcarbonylamino, and methylcarbonylamino; R$^3$ is selected from the group consisting of hydrogen, fluoro, chloro, methyl, ethyl, propyl, haloalkyl, acetoxy, —C(O)OCH$_3$, nitrile, and —CH$_2$CN; R$^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, and thioalkyl ether.

10. A compound as set forth in claim 9 wherein R$^4$ is selected from the group consisting of lower alkyl, substituted lower alkyl, lower alkenyl, substituted lower alkenyl, lower alkynyl, substituted lower alkynyl and thioalkyl ether.

11. A compound as set forth in claim 9 wherein R$^4$ is selected from the group consisting of lower alkyl, lower alkenyl, and lower alkynyl.

12. A compound as set forth in claim 9 wherein R$^4$ is selected from the group consisting ethyl, propyl, butyl, 1-methylpropyl, 1-propenyl, 2-propenyl, 1-butenyl, 2-butenyl, 3-butenyl, 1-methyl-2-propenyl, 2-methyl-2-propenyl, 1-propynyl, and 2-propynyl.

13. A compound according to claim 1 having the formula:

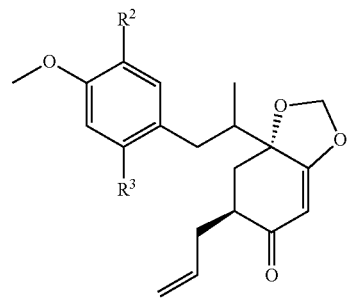

or enantiomers thereof, wherein R$^2$ is selected from the group consisting of hydrogen, hydroxyl, alkoxy, amino, aminoalkyl, aminoalkenyl, halide, haloalkyl, aminocarbonyl, hydroxyaminocarbonyl, alkylaminocarbonyl, acyloxy, nitrile, —CH$_2$CN, lower alkyl, lower alkenyl, alkoxycarbonyl, and alkylcarbonylamino; $R^3$ is selected from the group consisting of hydrogen, halide, haloalkyl, lower alkyl, lower alkenyl, acyloxy, —C(O)OCH$_3$, nitrile, and —CH$_2$CN.

14. A compound as set forth in claim 13 wherein $R^2$ is selected from the group consisting of hydrogen, hydroxyl, amino, fluoro, chloro, methyl, ethyl, propyl, ethenyl, propenyl, haloalkyl, aminoalkyl, aminoalkenyl, alkoxy, aminocarbonyl, methylaminocarbonyl, ethylcarbonylamino, acetoxy, propionyloxy, nitrile, —CH$_2$CN, —C(O)OCH$_3$, ethylcarbonylamino, and methylcarbonylamino; $R^3$ is selected from the group consisting of hydrogen, fluoro, chloro, methyl, ethyl, propyl, acetoxy, —C(O)OCH$_3$, nitrile, and —CH$_2$CN.

15. A compound according to claim 1 having the formula:

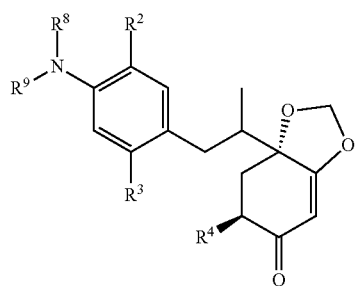

or enantiomers thereof, wherein $R^2$ is selected from the group consisting of hydrogen, fluoro, hydroxyl, chloro, methyl, ethyl, propyl, ethenyl, propenyl, and haloalkyl; $R^3$ is selected from the group consisting of hydrogen, fluoro, chloro, methyl, ethyl, and propyl, and haloalkyl; $R^4$ is selected from the group consisting of lower alkyl, substituted lower alkyl, lower alkenyl, substituted lower alkenyl, lower alkynyl, substituted lower alkynyl and thioalkyl ether; and wherein $R^8$ and $R^9$ are independently selected from the group consisting of hydrogen, methyl, ethyl, propyl, ethenyl, propenyl, and cycloalkyl.

16. A compound as set forth in claim 15 wherein $R^8$ and $R^9$ are independently selected from the group consisting of hydrogen, methyl, and ethyl.

17. A compound according to claim 1 having the formula:

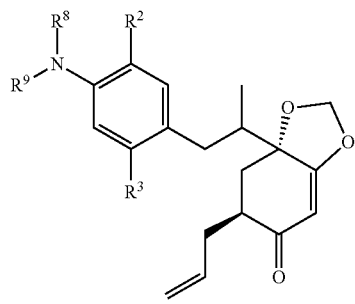

or enantiomers thereof, wherein $R^2$ is selected from the group consisting of hydrogen, methoxy, fluoro, chloro, methyl, ethyl, propyl, aminocarbonyl, methylaminocarbonyl, acetoxy, nitrile, and methylcarbonylamino; $R^3$ is selected from the group consisting of hydrogen, fluoro, chloro, methyl, ethyl, haloalkyl, and acetoxy; and wherein $R^8$ and $R^9$ are independently selected from the group consisting of hydrogen, methyl, ethyl, propyl, ethenyl, propenyl, and cycloalkyl.

18. A compound according to claim 1 having the formula:

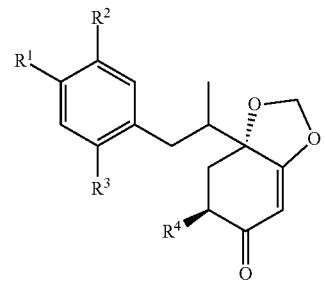

or enantiomers thereof, wherein $R^1$ is selected from the group consisting of methoxy and ethoxy; $R^2$ is selected from the group consisting of hydrogen, hydroxyl, amino, fluoro, chloro, methyl, ethyl, propyl, ethenyl, propenyl, haloalkyl, aminoalkyl, aminoalkenyl, alkoxy, aminocarbonyl, methylaminocarbonyl, ethylaminocarbonyl, acetoxy, propionyloxy, nitrile, —CH$_2$CN, —C(O)OCH$_3$, ethylcarbonylamino, and methylcarbonylamino; $R^3$ is selected from the group consisting of halide, hydroxyl, methoxy, lower alkyl, lower alkenyl, haloalkyl, acetoxy, —C(O)OCH$_3$, nitrile, and —CH$_2$CN; $R^4$ is selected from the group consisting of lower alkyl, substituted lower alkyl, lower alkenyl, and substituted lower alkenyl, lower alkynyl, and substituted lower alkynyl, or pharmaceutically acceptable salts, or solvates thereof.

19. A compound according to claim 1 having the formula:

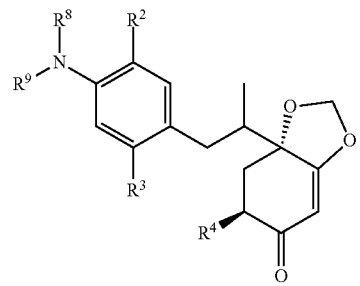

or enantiomers thereof, wherein $R^2$ is selected from the group consisting of hydrogen, fluoro, chloro, methyl, and ethyl; $R^3$ is selected from the group consisting of hydrogen, fluoro, chloro, methyl, ethyl, —CH$_2$Cl, nitrile, and —CH$_2$CN; $R^4$ is selected from the group consisting of lower alkyl, substituted lower alkyl, lower alkenyl, substituted lower alkenyl, lower alkynyl, substituted lower alkynyl, and thioalkyl ether; and wherein $R^8$ and $R^9$ are independently selected from the group consisting of hydrogen, lower alkyl, or pharmaceutically acceptable salts, or solvates thereof.

20. A compound as set forth in claim 19 wherein $R^4$ is selected from the group consisting of lower alkyl, lower alkenyl, and lower alkynyl, and $R^8$ and $R^9$ are independently selected from the group consisting of hydrogen and methyl.

21. A compound according to claim 1 having the formula:

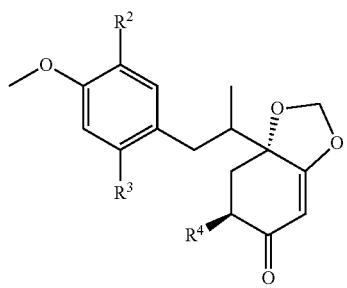

or enantiomers thereof, wherein $R^2$ is selected from the group consisting of hydrogen, hydroxyl, amino, fluoro, chloro, methyl, ethyl, propyl, ethenyl, propenyl, haloalkyl, aminoalkyl, aminoalkenyl, alkoxy, aminocarbonyl, methylaminocarbonyl, ethylcarbonylamino, acetoxy, propionyloxy, nitrile, —CH$_2$CN, —C(O)OCH$_3$, ethylcarbonylamino, and methylcarbonylamino; $R^3$ is selected from the group consisting of fluoro, chloro, methyl, ethyl, —CH$_2$Cl, acetoxy, —C(O)OCH$_3$, nitrile, and —CH$_2$CN; $R^4$ is selected from the group consisting of ethyl, propyl, butyl, 1-methylpropyl, 1-propenyl, 2-propenyl, 1-butenyl, 2-butenyl, 3-butenyl, 1-methyl-2-propenyl, 2-methyl-2-propenyl, 1-propynyl, and 2-propynyl, or pharmaceutically acceptable salts, or solvates thereof.

22. A compound selected from the group consisting of:

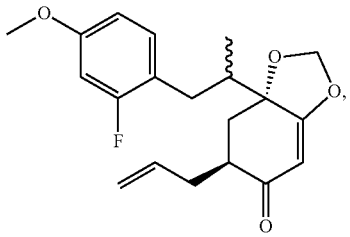

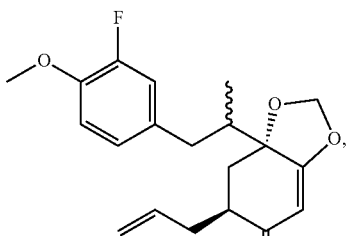

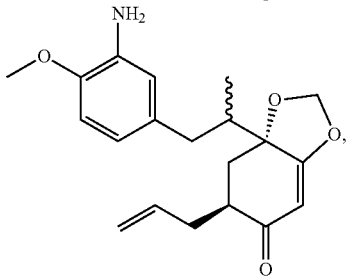

-continued

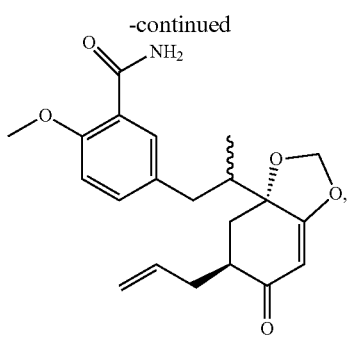

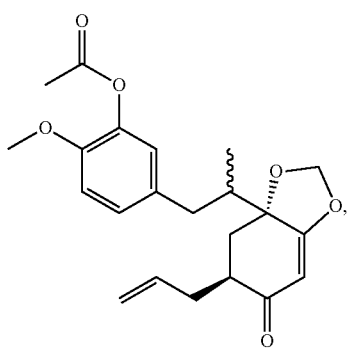

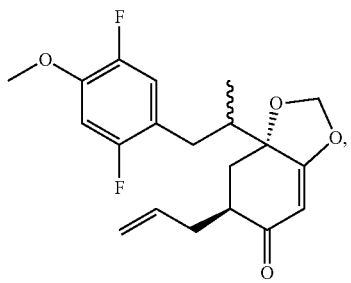

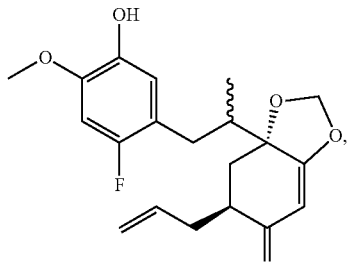

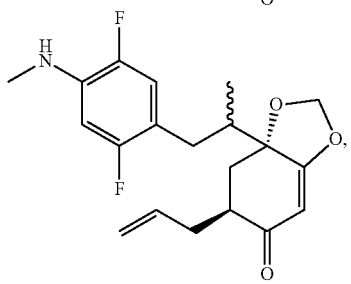

-continued
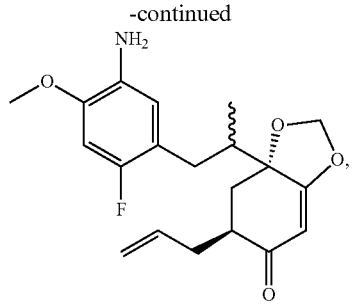
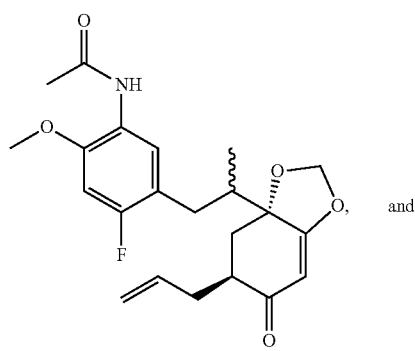
and
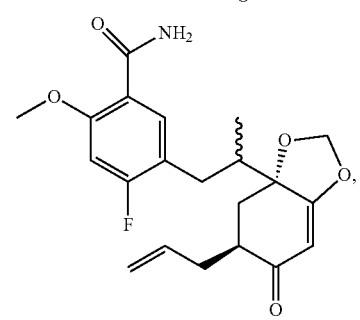
or enantiomers thereof, or pharmaceutically acceptable salts, or solvates thereof.
23. A compound according to claim 22 having the chemical structure:
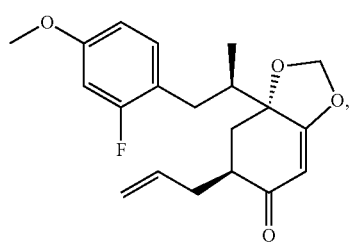
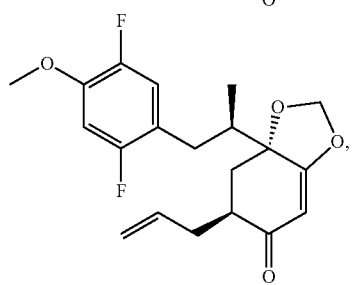
-continued
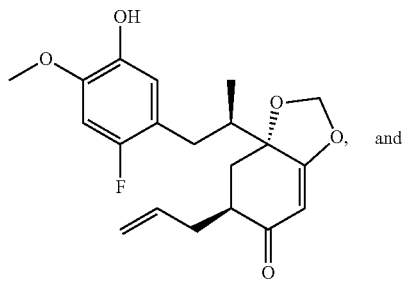
and
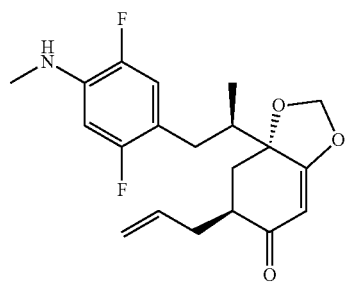
wherein the compound is the (+)-enantiomer.
24. A compound selected from the group consisting of:
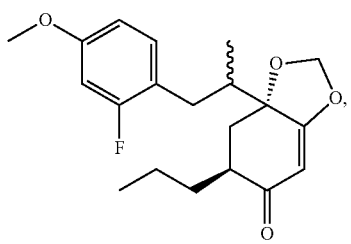
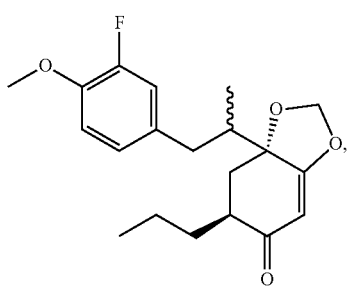
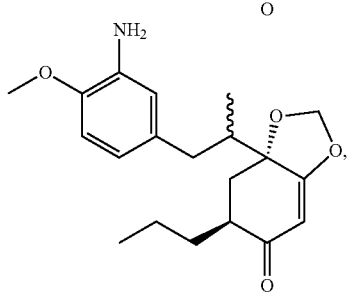

185
-continued
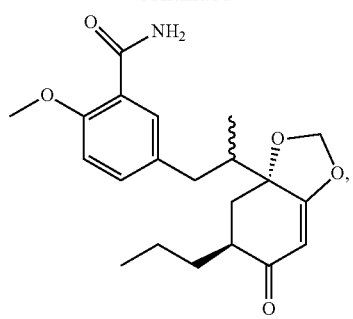
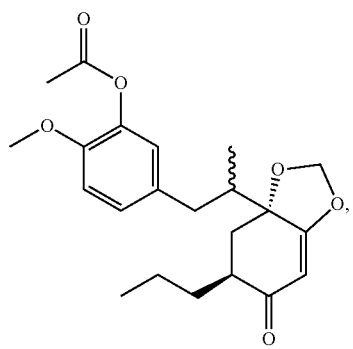
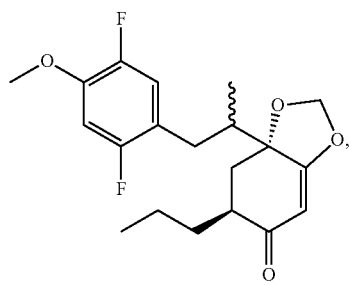
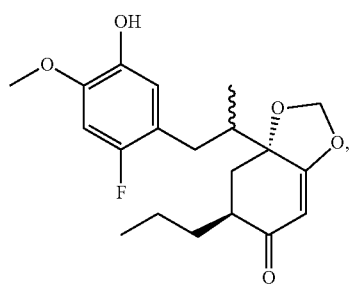
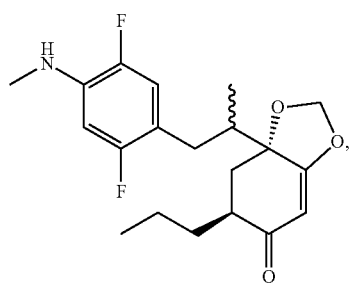
186
-continued
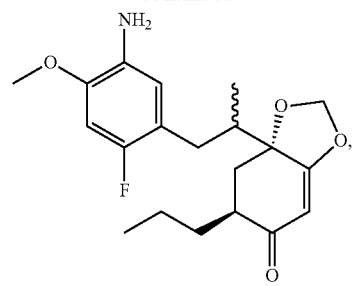
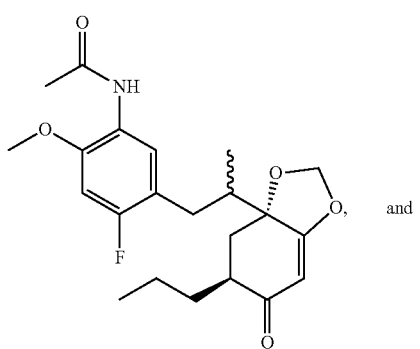
and
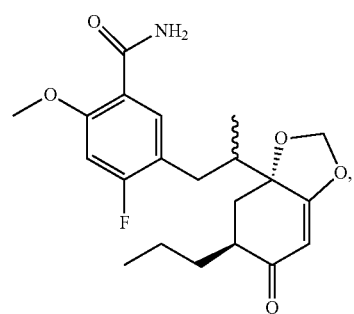
or enantiomers thereof, or pharmaceutically acceptable salts, or solvates thereof.
25. A compound according to claim 24 having the chemical structure:
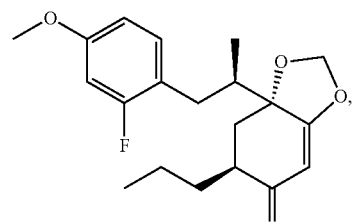
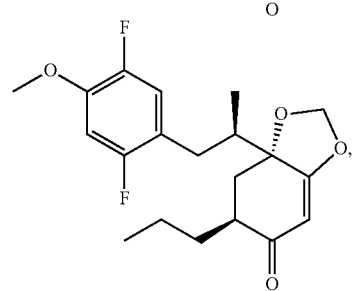

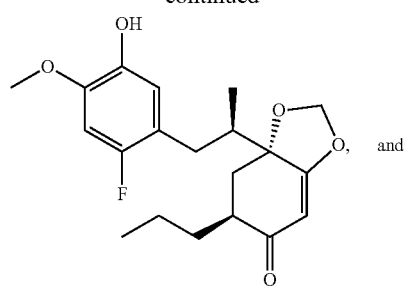
and
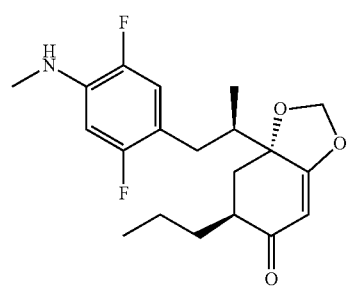
wherein the compound is the (+)-enantiomer.
26. A compound selected from the group consisting of:
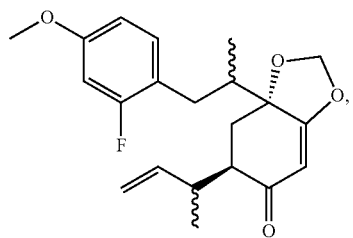
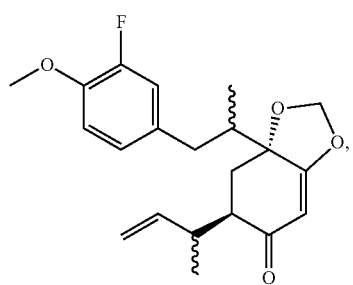
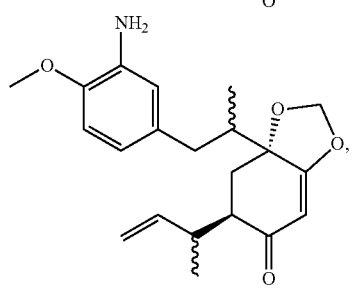
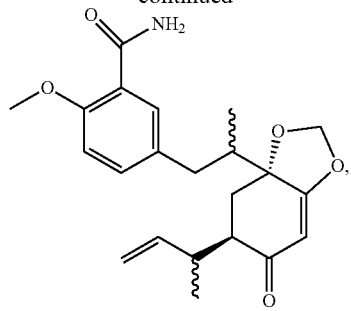
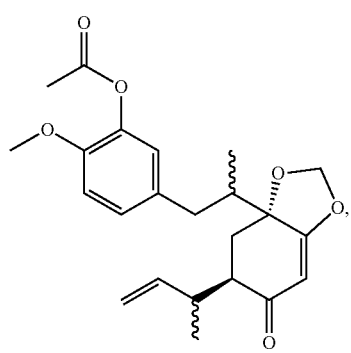
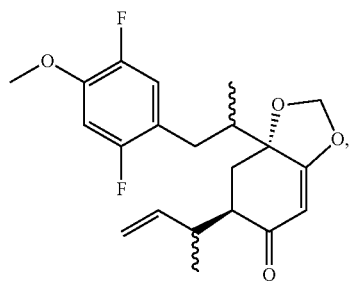
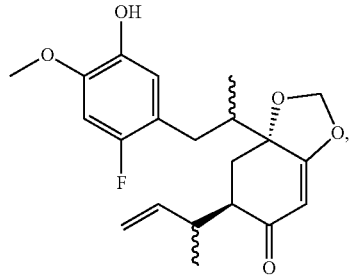
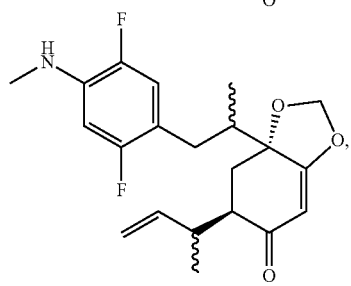

-continued
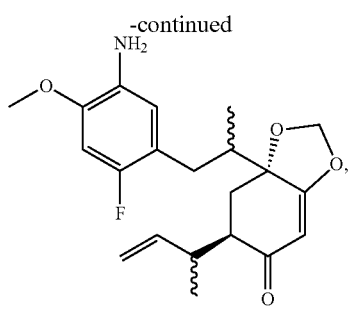
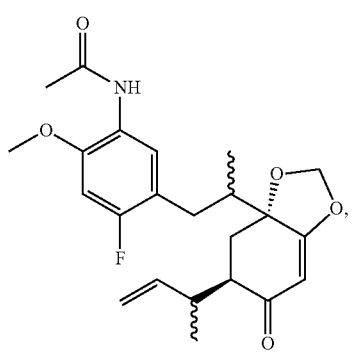
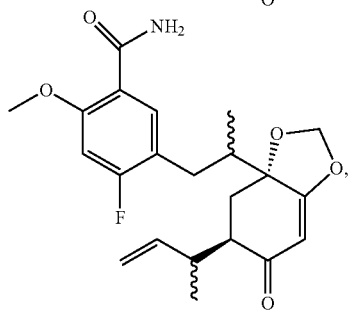
or enantiomers thereof, or pharmaceutically acceptable salts, or solvates thereof.
27. A compound according to claim 26, having the chemical structure:
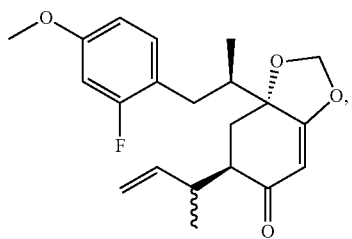
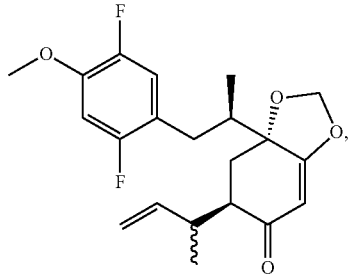
-continued
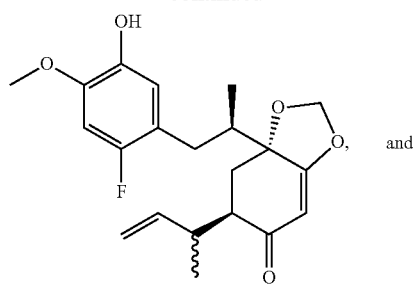 and
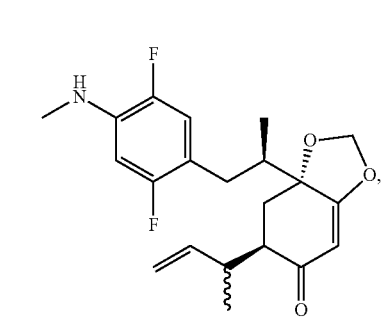
wherein the compound is the (+)-enantiomer.
28. A compound selected from the group consisting of:
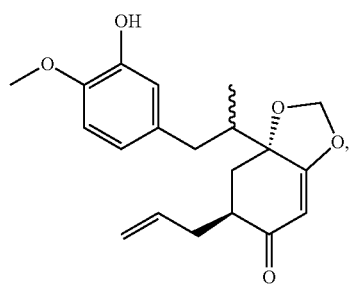
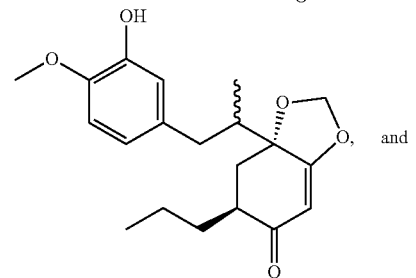 and
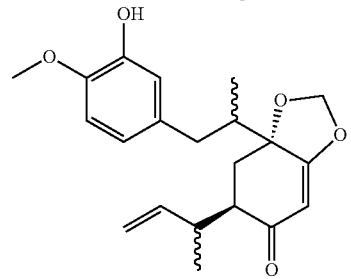
or enantiomers thereof, or pharmaceutically acceptable salts, or solvates thereof.

29. A compound selected from the group consisting of:
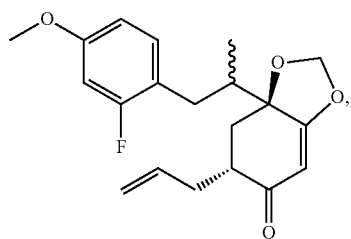
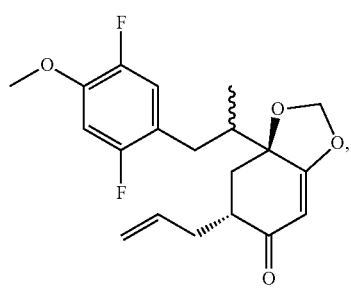
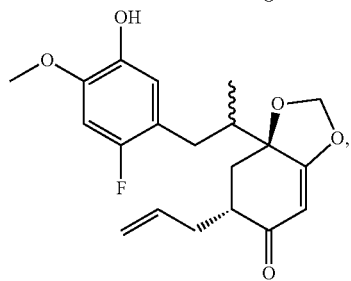
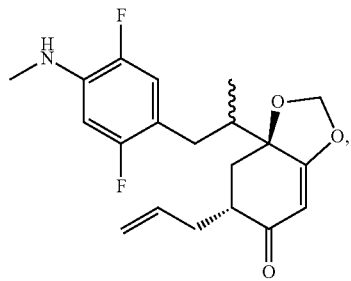
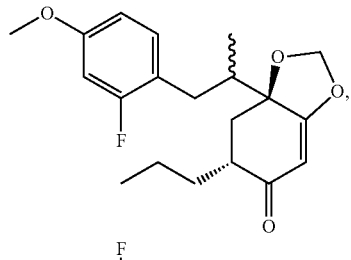
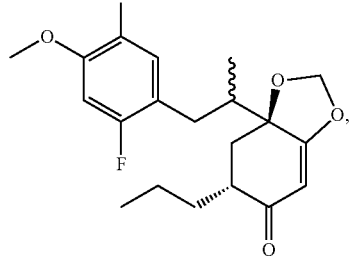
-continued
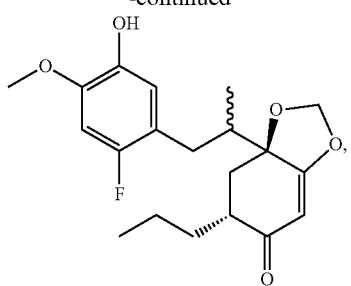
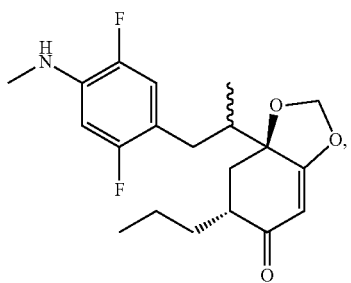
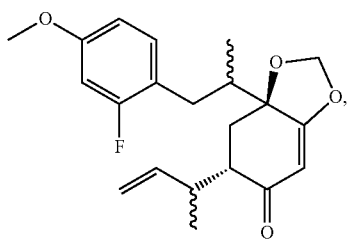
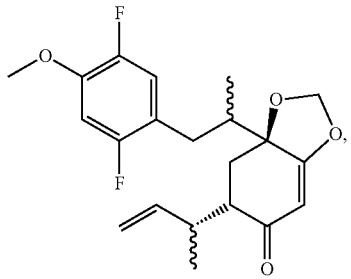
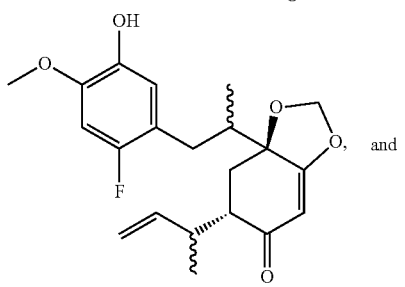 and
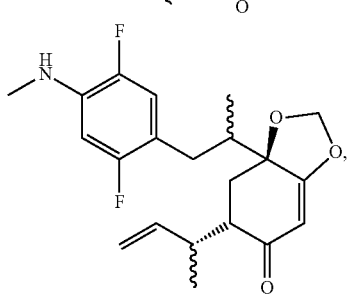
or pharmaceutically acceptable salts, or solvates thereof, wherein the compound is the (+)-enantiomer.

30. A compound selected from the group consisting of:
6-allyl-7a-(1-(2-fluoro-4-methoxyphenyl)propan-2-yl)-7,7a-dihydrobenzo[d][1,3]dioxol-5 (6H)-one,
6-allyl-7a-(1-(2-fluoro-5-hydroxy-4-methoxyphenyl)propan-2-yl)-7,7a-dihydrobenzo[d][1,3]dioxol-5(6H)-one,
6-allyl-7a-(1-(2,5-difluoro-4-methoxyphenyl)propan-2-yl)-7,7a-dihydrobenzo[d][1,3]dioxol-5 (6H)-one,
6-allyl-7a-(1-(2,5-difluoro-4-(methylamino)phenyl)propan-2-yl)-7,7a-dihydrobenzo[d][1,3]dioxol-5(6H)-one,
7a-(1-(2-fluoro-4-methoxyphenyl)propan-2-yl)-7,7a-dihydro-6-propylbenzo[d][1,3]dioxol-5 (6H)-one,
7a-(1-(2-fluoro-5-hydroxy-4-methoxyphenyl)propan-2-yl)-7,7a-dihydro-6-propylbenzo[d][1,3]dioxol-5(6H)-one,
7a-(1-(2,5-difluoro-4-methoxyphenyl)propan-2-yl)-7,7a-dihydro-6-propylbenzo[d][1,3]dioxol-5(6H)-one,
7a-(1-(2,5-difluoro-4-(methylamino)phenyl)propan-2-yl)-7,7a-dihydro-6-propylbenzo[d][1,3]dioxol-5(6H)-one,
6-(but-3-en-2-yl)-7a-(1-(2-fluoro-4-methoxyphenyl)propan-2-yl)-7,7a-dihydrobenzo[d][1,3]dioxol-5(6H)-one,
6-(but-3-en-2-yl)-7a-(1-(2-fluoro-5-hydroxy-4-methoxyphenyl)propan-2-yl)-7,7a-dihydrobenzo[d][1,3]dioxol-5(6H)-one,
6-(but-3-en-2-yl)-7a-(1-(2,5-difluoro-4-methoxyphenyl)propan-2-yl)-7,7a-dihydrobenzo[d][1,3]dioxol-5(6H)-one,
6-(but-3-en-2-yl)-7a-(1-(2,5-difluoro-4-(methylamino)phenyl)propan-2-yl)-7,7a-dihydrobenzo[d][1,3]dioxol-5(6H)-one, or
pharmaceutically acceptable salts, or solvates thereof.

31. A compound according to the formula:

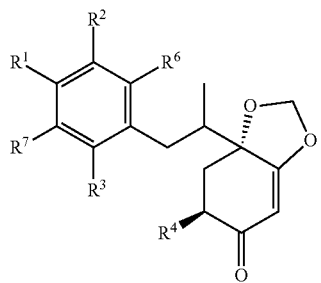

or stereoisomers thereof, wherein $R^1$ is selected from the group consisting of methoxy, ethoxy, —$SCH_3$, —$NHCH_3$, and —$N(CH_3)_2$; $R^2$ is selected from the group consisting of hydrogen, hydroxyl, methoxy, ethoxy, amino, aminoalkyl, aminoalkenyl, fluoro, chloro, aminocarbonyl, hydroxyaminocarbonyl, methylaminocarbonyl, ethylaminocarbonyl, acetoxy, nitrile, lower alkyl, lower alkenyl, lower alkynyl, alkoxycarbonyl, and alkylcarbonylamino; $R^3$ is selected from the group consisting of hydrogen, fluoro, chloro, lower alkyl, lower alkenyl, haloalkyl, acetoxy, —$C(O)OCH_3$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkoxyalkyl, alkoxyalkenyl, alkoxyalkynyl, alkyl ether, and thioalkyl ether; $R^6$ is selected from the group consisting of hydrogen, halide, methoxy, ethoxy, methyl, ethyl, propyl, nitrile, and acetoxy; $R^7$ is selected from the group consisting of hydrogen, halide, hydroxyl, amino, methoxy, ethoxy, methyl, ethyl, propyl, nitrile, and acetoxy, or pharmaceutically acceptable salts, or solvates thereof; provided that when $R^2$ is hydrogen $R^3$ is not hydrogen and only one of either $R^6$ or $R^7$ are hydrogen; $R^2$, $R^3$, $R^6$, and $R^7$ are all not hydrogen; and $R^2$ is not methoxy when $R^1$ is methoxy, $R^3$, $R^5$, and $R^6$ are hydrogen, and $R^4$ is 2-propenyl.

32. A compound as set forth in claim 31, or enantiomers thereof, wherein $R^1$ is selected from the group consisting of methoxy; $R^2$ is selected from the group consisting of hydrogen, hydroxyl, amino, aminoalkyl, aminoalkenyl, fluoro, chloro, aminocarbonyl, hydroxyaminocarbonyl, methylaminocarbonyl, ethylaminocarbonyl, nitrile, methyl, ethyl, propyl, ethenyl, ethynyl, 2-propenyl, 3-propenyl, ethynyl, alkoxycarbonyl, and alkylcarbonylamino; $R^3$ is selected from the group consisting of hydrogen, fluoro, chloro, methyl, ethyl, ethenyl, ethynyl, —$CH_2Cl$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkyl ether, and thioalkyl ether.

33. A compound as set forth in claim 31, or enantiomers thereof, wherein $R^2$ is selected from the group consisting of hydrogen, hydroxyl, fluoro, chloro, methyl, nitrile, and methylcarbonylamino; $R^3$ is selected from the group consisting of hydrogen, fluoro, chloro, methyl, ethyl, —$CH_2Cl$, nitrile, and —$CH_2CN$; $R^4$ is selected from the group consisting of ethyl, propyl, butyl, 1-methylpropyl, 1-propenyl, 2-propenyl, 1-butenyl, 2-butenyl, 3-butenyl, 1-methyl-2-propenyl, 2-methyl-2-propenyl, 1-propynyl, and 2-propynyl, alkoxyalkyl, alkoxyalkenyl, alkoxyalkynyl, and thioalkyl ether.

34. A compound having the chemical structure:

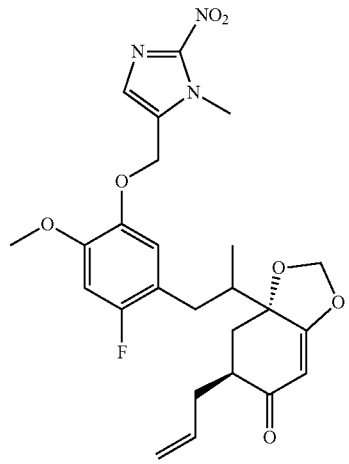 [SMILES: C=CC[C@H]1C[C@]2(C(C)Cc3cc(OCc4cnc([N+](=O)[O-])n4C)c(OC)cc3F)OCOC2=CC1=O]

or stereoisomers thereof, or pharmaceutically acceptable salts and solvates thereof.

35. A compound having the chemical structure:

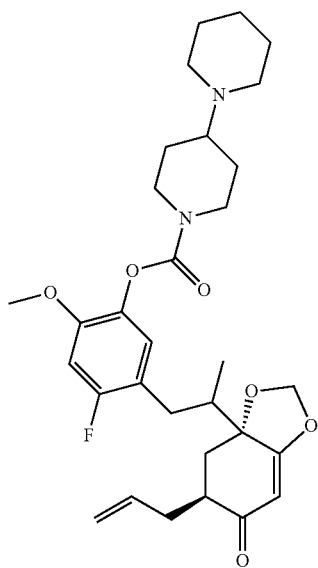 [SMILES: C=CC[C@H]1C[C@]2(C(C)Cc3cc(OC(=O)N4CCC(N5CCCCC5)CC4)c(OC)cc3F)OCOC2=CC1=O]

or stereoisomers thereof, or pharmaceutically acceptable salts and solvates thereof.

36. A compound according to claim 1 having the formula:

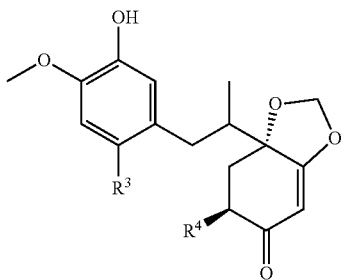

or enantiomers thereof, wherein $R^3$ is selected from the group consisting of hydrogen, fluoro, chloro, methyl, ethyl, propyl, ethenyl, ethynyl, acetoxy, —$CH_2Cl$, —$C(O)OCH_3$, nitrile, and —$CH_2CN$; $R^4$ is selected from the group consisting of lower alkyl, substituted lower alkyl, lower alkenyl, substituted lower alkenyl, lower alkynyl, substituted lower alkynyl, alkyl ether, and thioalkyl ether, or pharmaceutically acceptable salts, solvates, or prodrugs thereof.

37. A compound as set forth in claim 36 wherein $R^3$ is selected from the group consisting of hydrogen, fluoro, chloro, and methyl; $R^4$ is selected from the group consisting of lower alkyl, lower alkenyl, and lower alkynyl.

38. A compound according to claim 1 having the formula:

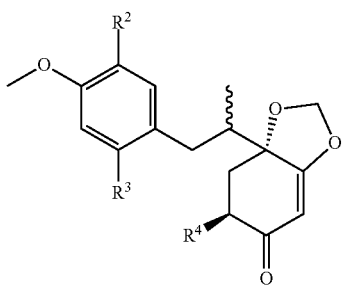

or enantiomers thereof, wherein $R^2$ is selected from the group of hydroxyl and aminocarbonyl; $R^3$ is selected from the group consisting of hydrogen and fluoro; $R^4$ is selected from the group consisting of lower alkyl, substituted lower alkyl, lower alkenyl, substituted lower alkenyl, lower alkynyl, substituted lower alkynyl, alkyl ether, and thioalkyl ether, or pharmaceutically acceptable salts, solvates, or prodrugs thereof.

39. A compound according to the formula:

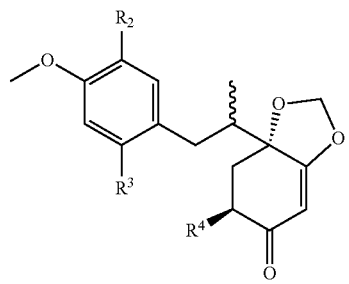

or enantiomers thereof, wherein $R^2$ is selected from the group consisting of —NHCO—$C_1$—$O_5$ alkyl, —NHCO—$C_2$—$O_5$ alkenyl, —NHC(O)—O—$C_1$-$C_5$ alkyl, —NHC(O)—O—$C_2$—$O_5$ alkenyl, and said alkyl and alkenyl groups may be optionally substituted by independent replacement of one, two, or three hydrogen atoms thereon with substituents selected from the group consisting of methoxy, ethoxy, propoxy, isopropoxy, gem-dimethyl, cyclopropyl, oxo, sulfoxide, acetoxy, hydroxyl, halide, $CF_3$, $CCl_3$, nitrile, amino, methylamino, dimethylamino, ethylamino, diethylamino, tert-butylamino, aminocarbonyl, methylaminocarbonyl, methylcarbonylamino, —CH=NOH, —COOH, —$SOCH_3$, —$SO_2CH_3$, —$NHSO_2CH_3$, —$SO_2NH_2$, —$C(O)OCH_3$, —$C(O)CH_3$, —SH, —$SCH_3$, and —$SCH_2CH_3$; $R^3$ is selected from the group consisting of hydrogen and fluoro; $R^4$ is selected from the group consisting of lower alkyl, substituted lower alkyl, lower alkenyl, substituted lower alkenyl, lower alkynyl, substituted lower alkynyl, alkyl ether, and thioalkyl ether, or pharmaceutically acceptable salts, solvates, or prodrugs thereof.

40. A pharmaceutical composition comprising a therapeutically effective amount of at least one compound of claim 1.

41. A method of treating cancer in a patient which comprises providing an effective amount of a compound of claim 1.

42. A method of treating hyperproliferative cellular disease in a patient which comprises providing an effective amount of a compound of claim 1.

43. A method of treating inflammatory disease in a patient which comprises providing an effective amount of a compound of claim 1 to said patient.

\* \* \* \* \*